US011801223B2

(12) United States Patent
Fox et al.

(10) Patent No.: US 11,801,223 B2
(45) Date of Patent: Oct. 31, 2023

(54) SINGLE VIAL VACCINE FORMULATIONS

(71) Applicant: ACCESS TO ADVANCED HEALTH INSTITUTE, Seattle, WA (US)

(72) Inventors: Christopher B. Fox, Sumner, WA (US); Thomas Vedvick, Federal Way, WA (US); Lucien Barnes V., Seattle, WA (US); Ryan M. Kramer, Seattle, WA (US); Steven G. Reed, Bellevue, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

(21) Appl. No.: 15/108,773

(22) PCT Filed: Dec. 29, 2014

(86) PCT No.: PCT/US2014/072615
§ 371 (c)(1),
(2) Date: Jun. 28, 2016

(87) PCT Pub. No.: WO2015/103167
PCT Pub. Date: Jul. 9, 2015

(65) Prior Publication Data
US 2016/0324783 A1 Nov. 10, 2016

Related U.S. Application Data

(60) Provisional application No. 61/922,761, filed on Dec. 31, 2013.

(51) Int. Cl.
| | |
|---|---|
| *A61K 9/19* | (2006.01) |
| *A61K 39/00* | (2006.01) |
| *A61K 47/26* | (2006.01) |
| *A61K 39/04* | (2006.01) |
| *A61K 39/39* | (2006.01) |
| *A61K 47/22* | (2006.01) |
| *A61K 47/10* | (2017.01) |

(52) U.S. Cl.
CPC ............... *A61K 9/19* (2013.01); *A61K 39/00* (2013.01); *A61K 39/04* (2013.01); *A61K 39/39* (2013.01); *A61K 47/10* (2013.01); *A61K 47/22* (2013.01); *A61K 47/26* (2013.01); *A61K 2039/552* (2013.01); *A61K 2039/55511* (2013.01); *A61K 2039/55572* (2013.01)

(58) Field of Classification Search
CPC ........... A61K 9/19; A61K 9/10; A61K 39/39; A61K 47/26
See application file for complete search history.

(56) References Cited

U.S. PATENT DOCUMENTS

| | | | |
|---|---|---|---|
| 3,238,190 A | 3/1966 | Erbring et al. | |
| 4,420,461 A | 12/1983 | Reckel et al. | |
| 4,420,558 A | 12/1983 | De Mey et al. | |
| 4,436,727 A | 3/1984 | Ribi | |
| 4,595,654 A | 6/1986 | Reckel et al. | |
| 4,614,722 A | 9/1986 | Pasula | |
| 4,659,659 A | 4/1987 | Dwek et al. | |
| 4,683,195 A | 7/1987 | Mullis et al. | |
| 4,743,540 A | 5/1988 | Ralph et al. | |
| 4,912,094 A | 3/1990 | Myers | |
| 4,981,684 A | 1/1991 | MacKenzie et al. | |
| 5,057,540 A | 10/1991 | Kensil et al. | |
| 5,124,141 A | 6/1992 | Makler | |
| 5,147,785 A | 9/1992 | Pasula | |
| 5,162,990 A | 11/1992 | Odeyale et al. | |
| 5,231,168 A | 7/1993 | Dziegiel et al. | |
| 5,278,302 A | 1/1994 | Caruthers et al. | |
| 5,298,396 A | 3/1994 | Kotzin et al. | |
| 5,411,865 A | 5/1995 | Reed | |
| 5,422,109 A | 6/1995 | Brancq et al. | |
| 5,424,067 A | 6/1995 | Brancq et al. | |
| 5,565,209 A | 10/1996 | Rijke | |
| 5,576,016 A * | 11/1996 | Amselem | A61K 9/5123 424/450 |
| 5,635,491 A | 6/1997 | Seki et al. | |
| 5,654,140 A | 8/1997 | Persico et al. | |
| 5,666,153 A | 9/1997 | Copeland | |
| 5,709,879 A | 1/1998 | Barchfeld et al. | |
| 5,719,263 A | 2/1998 | Reed | |
| 5,786,148 A | 7/1998 | Bandman et al. | |
| 5,840,871 A | 11/1998 | Hillman et al. | |
| 5,843,464 A | 12/1998 | Bakaletz et al. | |

(Continued)

FOREIGN PATENT DOCUMENTS

| | | |
|---|---|---|
| EP | 0198474 A1 | 10/1986 |
| EP | 0304578 A1 | 3/1989 |

(Continued)

OTHER PUBLICATIONS

Orr et al., Journal of Controlled Release, 177: 20-26 (2014, epub. Dec. 29, 2013).*
Fox et al., AAPS PharmaSciTech, 13: 498-506 (2012). (Year: 2012).*
Moral et al. Eur J Pharm Biopharm, 78/2, 2011, 264-270.*
Abu-Raddad, L.J. et al. (Aug. 18, 2009). "Epidemiological Benefits Of More-Effective Tuberculosis Vaccines, Drugs, And Diagnostics," *PNAS* 106(33):13980-13985.
Ad Hoc Committee of the Scientific Assembly On Clinical Problems. (Nov. 1995). "Standards for the diagnosis and care of patients with chronic obstructive pulmonary disease. American Thoracic Society." *Am. J. Respir. Crit. Care Med.* 152(5Pt2):S77-121.

(Continued)

*Primary Examiner* — Kyle A Purdy
(74) *Attorney, Agent, or Firm* — Benjamin Keim; Newport IP, LLC

(57) ABSTRACT

The invention provides for thermostable lyophilized formulations, including vaccines and pharmaceutical compositions for inducing or enhancing an immune response, and methods of use thereof. The lyophilized formulations generally comprise an antigen and/or an adjuvant, a metabolizable oil, and a cake-forming excipient.

44 Claims, 40 Drawing Sheets
Specification includes a Sequence Listing.

(56) References Cited

U.S. PATENT DOCUMENTS

| | | | |
|---|---|---|---|
| 5,846,758 A | 12/1998 | Medenica | |
| 5,912,166 A | 6/1999 | Reed et al. | |
| 5,955,306 A | 9/1999 | Gimeno et al. | |
| 5,981,215 A | 11/1999 | Meissner et al. | |
| 6,027,732 A | 2/2000 | Morein et al. | |
| 6,231,861 B1 | 5/2001 | Barnwell | |
| 6,261,762 B1 | 7/2001 | Alizon et al. | |
| 6,316,183 B1 | 11/2001 | Alizon et al. | |
| 6,512,102 B1 | 1/2003 | Xu et al. | |
| 6,544,518 B1 | 4/2003 | Friede et al. | |
| 6,544,728 B1 | 4/2003 | Alizon et al. | |
| 6,555,653 B2 | 4/2003 | Alderson et al. | |
| 6,587,792 B1 | 7/2003 | Thomas | |
| 6,596,501 B2 | 7/2003 | Roth | |
| 6,630,169 B1* | 10/2003 | Bot | A61K 9/0043 424/489 |
| 6,660,487 B2 | 12/2003 | Faustman | |
| 6,682,901 B2 | 1/2004 | Blaschuk et al. | |
| 6,706,872 B1 | 3/2004 | Barnwell | |
| 6,734,172 B2 | 3/2004 | Scholler et al. | |
| 6,770,445 B1 | 8/2004 | Scholler et al. | |
| 6,846,489 B1 | 1/2005 | Garcon et al. | |
| 6,846,648 B2 | 1/2005 | Maes | |
| 6,855,322 B2 | 2/2005 | Lyon et al. | |
| 6,869,607 B1 | 3/2005 | Buschle et al. | |
| 6,893,820 B1 | 5/2005 | Plass | |
| 6,919,078 B2 | 7/2005 | Ni et al. | |
| 6,919,210 B1 | 7/2005 | Okamoto | |
| 6,929,796 B1 | 8/2005 | Conti-Fine | |
| 6,932,972 B2 | 8/2005 | Stephenne et al. | |
| 6,933,123 B2 | 8/2005 | Hu et al. | |
| 6,936,255 B1 | 8/2005 | Wettendorff | |
| 6,949,246 B2 | 9/2005 | Reed et al. | |
| 6,979,535 B2 | 12/2005 | Alizon et al. | |
| 6,979,730 B2 | 12/2005 | Reiter et al. | |
| 7,008,774 B2 | 3/2006 | Ryan et al. | |
| 7,012,134 B2 | 3/2006 | Steven et al. | |
| 7,029,678 B2 | 4/2006 | Momin et al. | |
| 7,029,685 B2 | 4/2006 | Lanar et al. | |
| 7,030,232 B1 | 4/2006 | Reiter et al. | |
| 7,070,931 B2 | 4/2006 | Fujinaga et al. | |
| 7,060,276 B2 | 6/2006 | Lanar et al. | |
| 7,060,802 B1 | 6/2006 | Trakht et al. | |
| 7,078,180 B2 | 7/2006 | Genetta | |
| 7,078,231 B2 | 8/2006 | Guerin-Marchand et al. | |
| 7,087,713 B2 | 8/2006 | Campos-Neto et al. | |
| 8,231,881 B2 | 7/2012 | Bhatia et al. | |
| 8,410,258 B2 | 4/2013 | Goto et al. | |
| 8,486,414 B2 | 7/2013 | Reed et al. | |
| 8,703,095 B2 | 4/2014 | Klucker et al. | |
| 9,504,659 B2 | 11/2016 | Klucker et al. | |
| 2007/0021017 A1 | 1/2007 | Derin-holzapfel | |
| 2007/0191314 A1* | 8/2007 | Klucker | A61K 31/047 514/102 |
| 2008/0131466 A1* | 6/2008 | Reed | A61P 35/00 424/282.1 |
| 2009/0041798 A1 | 2/2009 | Reed et al. | |
| 2009/0045033 A1 | 2/2009 | Hausladen | |
| 2009/0060906 A1* | 3/2009 | Barry | A61K 47/20 424/131.1 |
| 2009/0291099 A1 | 11/2009 | Goto et al. | |
| 2010/0037466 A1 | 2/2010 | Rowlay et al. | |
| 2010/0129391 A1 | 5/2010 | Reed et al. | |
| 2010/0310602 A1 | 6/2010 | Reed et al. | |
| 2012/0114688 A1 | 5/2012 | Bhatia et al. | |
| 2015/0335752 A1* | 11/2015 | Look | A61K 39/07 424/190.1 |
| 2016/0324783 A1 | 11/2016 | Fox et al. | |

FOREIGN PATENT DOCUMENTS

| | | |
|---|---|---|
| EP | 0362279 B1 | 1/1990 |
| EP | 0366412 A2 | 5/1990 |
| EP | 0414374 A2 | 2/1991 |
| EP | 0109942 B1 | 3/1991 |
| EP | 0468520 A2 | 1/1992 |
| EP | 0468520 A3 | 1/1992 |
| EP | 0480981 B1 | 10/1993 |
| EP | 0480982 B1 | 10/1993 |
| EP | 0399843 B1 | 7/1994 |
| EP | 0480982 B2 | 11/1997 |
| EP | 3089754 A1 | 11/2016 |
| JP | 5328975 B2 | 10/2013 |
| WO | WO-90/01496 A1 | 2/1990 |
| WO | WO-90/06951 A1 | 6/1990 |
| WO | 1991/00106 | 10/1991 |
| WO | 1991/00107 | 10/1991 |
| WO | WO-93/02184 A1 | 2/1993 |
| WO | WO-93/10152 A1 | 5/1993 |
| WO | WO-94/00152 A1 | 1/1994 |
| WO | WO-94/05792 A1 | 3/1994 |
| WO | WO-94/20137 A1 | 9/1994 |
| WO | WO-95/17210 A1 | 6/1995 |
| WO | WO-95/26204 A1 | 10/1995 |
| WO | WO-96/02555 A1 | 2/1996 |
| WO | WO-96/11272 A2 | 4/1996 |
| WO | WO-96/11711 A1 | 4/1996 |
| WO | WO-96/26277 A1 | 8/1996 |
| WO | WO-96/33739 A1 | 10/1996 |
| WO | WO-98/12302 A1 | 3/1998 |
| WO | WO-98/16247 A1 | 4/1998 |
| WO | WO-98/20117 A1 | 5/1998 |
| WO | WO-98/37418 A2 | 8/1998 |
| WO | WO-98/56414 A1 | 12/1998 |
| WO | WO-99/03884 A2 | 1/1999 |
| WO | WO-99/10008 A1 | 3/1999 |
| WO | WO-99/10375 A2 | 3/1999 |
| WO | WO-99/11241 A1 | 3/1999 |
| WO | WO-99/12565 A1 | 3/1999 |
| WO | WO-99/17741 A1 | 4/1999 |
| WO | WO-99/28475 A2 | 6/1999 |
| WO | WO-99/40188 A2 | 8/1999 |
| WO | WO-99/51748 A2 | 10/1999 |
| WO | WO-99/53061 A2 | 10/1999 |
| WO | WO-00/04149 A2 | 1/2000 |
| WO | WO-2008/124647 A2 | 10/2008 |
| WO | WO-2009/045033 A2 | 4/2009 |
| WO | WO-2009/045033 A3 | 4/2009 |
| WO | 2011129120 A1 | 10/2011 |
| WO | WO-2011/129120 A1 | 10/2011 |
| WO | WO-2012/064659 A1 | 5/2012 |
| WO | 2012085872 A2 | 6/2012 |
| WO | WO-2012/085872 A2 | 6/2012 |
| WO | 2013006837 A1 | 1/2013 |
| WO | WO-2013/006837 A1 | 1/2013 |
| WO | WO 2013119856 A1 * | 8/2013 ........... A61K 39/015 |
| WO | WO-2013/177444 A2 | 11/2013 |
| WO | WO-2015/103167 A2 | 7/2015 |
| WO | 2015103167 A3 | 11/2015 |

OTHER PUBLICATIONS

Andaloussi, A. et al. (2006, e-pub. Aug. 11, 2006). "Stimulation of TLR9 with CpG ODN Enhances Apoptosis of Glioma and Prolongs the Survival of Mice with Experimental Brain Tumors," *Glia* 54:526-535.

Anderson, P. et al. (Aug. 2005). "The Success And Failure Of BCG—Implications For A Novel Tuberculosis Vaccine," *Nat Rev Microbiol.* 3(8):656-662.

Anderson, R.C. et al. (Jan. 1, 2010; e-published on Aug. 20, 2009). "Physicochemical Characterization And Biological Activity Of Synthetic TLR4 Agonist Formulations," *Colloids Surf B: Biointerfaces* 75(1):123-132.

Armant, M. A. et al. (Jul. 29, 2002). "Toll-like Receptors: A Family of Pattern-recognition Receptors in Mammals," *Genome Biol.* 3(8):reviews3011.1-3011.6; six pages.

Bachmann, M.F. et al. (Nov. 2010; e-published on Oct. 15, 2010), "Vaccine Delivery: A Matter Of Size, Geometry, Kinetics And Molecular Patterns" *Nature Rev Immunol* 10(11):787-796.

Badaró, R. et al. (Jan. 1986). "Evaluation of the Micro Enzyme-Linked Immunosorbent Assay (ELISA) for Antibodies in American

(56) References Cited

OTHER PUBLICATIONS

Visceral Leishmaniasis: Antigen Selection for Detection of Infection-Specific Responses," *Am. J. Trop. Med. Hyg.* 35(1):72-78.
Badaró, R. et al. (1996). rK39: A Cloned Antigen of *Leishmania chagasi* Predicts Active Visceral Leishmaniasis, *J. Inf. Dis.* 173:758-761.
Baheti, A. et al. (2010). "Excipients Used in Lyophilization of Small Molecules," *J. Excipients and Food Chem.* 1(1):41-54.
Barouch, D.H. (Oct. 2, 2008). "Challenges in the Development of an HIV-1 Vaccine," *Nature* 455(7213):613-619.
Bayés, M. et al. (Apr. 2005). "Gateways to Clinical Trials," *Methods Find. Exp. Clin. Pharmacol.* 27(3):193-219.
Bedu-Addo, F.K. (2004), "Understanding Lyophilization Formulation Development," *Pharmaceutical Technology* 2004(Supplement 2):10-18.
Bertholet, S. et al. (Dec. 1, 2008). "Identification Of Human T Cell Antigens For The Development Of Vaccines Against *Mycobacterium tuberculosis*," *J Immunol* 181(11):7948-7957.
Bertholet, S. et al. (Oct. 13, 2010). "A Defined Tuberculosis Vaccine Candidate Boosts BCG And Protects Against Multidrug-Resistant *Mycobacterium tuberculosis*," *Sci Transl Med* 2(53):53ra74; 18 pages.
Bomford, R. et al. (1992). "Adjuvanticity and ISCOM Formation by Structurally Diverse Saponins," *Vaccine* 10(9):572-577.
Bray, R. S., et al. (1966). "The Immunology and Serology of Leishmanisis—Results of Ouchterlony Double Diffusion Tests," *Trans. R. Soc. Trop. Med. Hyg.* 60:605-609.
Brazolot-Millan, C.L. et al. (Dec. 1998). "CpG DNA Can Induce Strong Th1 Humoral and Cell-Mediated Immune Responses Against Hepatitis B Surface Antigen in Young Mice," *Proc. Natl. Acad. Sci.* 95(26):15553-15558.
Center for Disease Control (Sep. 2013). "Vaccine Excipient & Media Summary. Excipients Included in U.S. Vaccines, by Vaccine," located at <www.cdc.gov/vaccines/pubs/pinkbook/downloads/appendices/B/excipient-table-2.pdf>, last visited on Apr. 13, 2017, 4 pages.
Checkley, A.M. et al. (Oct. 2011). "Tuberculosis vaccines: progress and challenges," *Trends Pharmacol Sci* 32(10):601-606.
Chen, L. et al. (2006). "Distinct Responses of Lung and Spleen Dendritic Cells to the TLR9 Agonist CpG Oligodeoxynucleotide," *J. Immunol.* 177:2373-2383.
Choudhry, A. et al. (1990). "Enzyme-Linked Immunosorbent Assay in the Diagnosis of Kala-Azar in Bhodohi (Varanasi), India," *Trans. R. Soc. Trop. Med. Hyg.* 84(3):363-366.
Choudhry, A. et al. (Mar. 1992). "An Indirect Fluorescent Antibody (IFA) Test for the Serodiagnosis of Kala-Azar," *J. Comm. Dis.* 24(1):32-36.
Clausi, A. et al. (2008). "Inhibition of Aggregation of Aluminum Hydroxide Adjuvant During Freezing and Drying," *J Pharm Sci.* 97(6):2049-2061.
Cole, S.T. et al. (Nov. 1998). "Deciphering the Biology of *Mycobacterium tuberculosis* From the Complete Genome Sequence," *Nature* 393:537-544.
Coler, R.N. et al. (Jan. 26, 2011). "Development And Characterization Of Synthetic Glucopyranosyl Lipid Adjuvant System as a Vaccine Adjuvant," *PLoS One* 6(1):e16333, twelve pages.
Cooper, A.M. (2009). "Cell-Mediated Immune Responses In Tuberculosis," *Annu Rev Immunol.* 27:393-422.
Cooper, C. et al. (2005). "CPG 7909 Adjuvant Improves Hepatitis B Virus Vaccine Seroprotection In Antiretroviral-Treated HIV-Infected Adults," *AIDS* 19(14):1473-1479.
Correale, P. et al. (1997). "In Vitro Generation of Human Cytotoxic T Lymphocytes Specific for Peptides Derived From Prostate-Specific Antigen," *Journal of the National Cancer Institute* 89(4):293-300.
Datta, S.K. et al. (2003). "A Subset of Toll-Like Receptor Ligands Induces Cross-presentation by Bone Marrow-Derived Dendritic Cells," *J. Immunol.* 170:4102-4110.

Davis, H.L. et al. (1998). "CpG DNA is a Potent Enhancer of Specific Immunity in Mice Immunized with Recombinant Hepatitis B Surface Antigen," *J. Immunol* 160(2):870-876.
Deng, J.C. et al. (2004). CpG Oligodeoxynucleotides Stimulate Protective Innate Immunity Against Pulmonary Klebsiella Infection, *J. Immunol._* 173:5148-5155.
Edelman, R. (May-Jun. 1980). "Vaccine Adjuvants," *Rev. Infect. Dis.* 2(3):370-383.
Edelman, R. (2002). "The Development and Use of Vaccine Adjuvants," *Mol. Biotechnol.* 21:129-148.
El-On, J. et al. (1979). "Leishmania Donovani: Physicochemical, Immunological, and Biological Characterization of Excreted Factor from Promastigotes," *Exper. Parasitol.* 47:254 269.
Fearon, D.T. et al. (Apr. 5, 1996). "The Instructive Role of Innate Immunity in the Acquired Immune Response," *Science* 272:50-54.
Feuillet, V. et al. (Aug. 15, 2006). "Involvement of Toll-Like Receptor 5 In the Recognition of Flagellated Bacteria," *Proc. Nat. Acad. Sci.* 103(33):12487-12492.
Fiedler, U. (1953). "Zum Nachweis von Aesculus-Inhaltsstoffen," *Arzneimittel-Forschung* 4:213-216, with Machine Translation, sixteen pages.
Flynn, J.L. et al. (2001). "Immunology of Tuberculosis," *Annu Rev Immunol* 19:93-129.
Fox, C.B. et al. (Aug. 1, 2008, e-pub Mar. 22, 2008). "Monitoring the Effects of Component Structure and Source on Formulation Stability and Adjuvant Activity of Oil-In-Water Emulsions," *Colloids Surf B. Biointerfaces* 65(1):98-105.
Fox, C.B. et al. (2011). "Effects Of Emulsifier Concentration, Composition, and Order of Addition In Squalene-Phosphatidylcholine Oil-In-Water Emulsions," *Pharmaceutical Development and Technology*16(5):511-519.
Frentsch, M. et al. (Oct. 2005, e-pub Sep. 25, 2005). "Direct access to $CD4^+$ T Cells Specific For Defined Antigens According To CD154 Expression," *Nat Med* 11(10):1118:1124.
Gao, Z. et al. (Jun. 10, 2013). "WH1fungin a Surfactin Cyclic Lipopeptide is a Novel Oral Immunoadjuvant," *Vaccine* 31(26):2796-2803, English Abstract only, three pages.
Gibson, S. et al. (Jul./Aug. 2002). "Plasmacytoid Dendritic Cells Produce Cytokines and Mature in Response to the TLR7 Agonists, Imiquimod and Resiquimod," *Cell. Immunol.* 218(1/2):74-86.
Gisvold, O. et al. (Jul. 1934). "Digitonin and Phytosterol From the Seed of Digitalis Purpurea," *J. Am. Pharm.Assoc.* 23(7):664-666.
Glück, R. (1992). "Immunopotentiating Reconstituted Influenza Virosomes (IRIVs) and Other Adjuvants for Improved Presentation of Small Antigens," *Vaccine* 10(13): 915-919.
Gorden, K.B. et al. (2005). "Synthetic TLR Agonists Reveal Functional Differences Between Human TLR7 and TLR8," *J. Immunol.* 174:1259-1268.
Grabenstein, JD. (2011; List Updated on Feb. 2012). "Vaccine Excipient & Media Summary," A table listing vaccine excipients in *ImmunoFacts: Vaccines and Immunologic Drugs*, 37th revision, St Louis, MO: Wolters Kluwer Health, 3 pages.
Harrison's Principles of Internal Medicine, $16^{th}$ Edition, vol. 1, pp. 1004-1014 and 1019-1020.
Hedhli, D. et al. (Apr. 6, 2009, e-published on Jan. 31, 2009). "Protective Immunity Against *Toxoplasma* Challenge in Mice by Coadministration of *T. Gondii* Antigens and *Eimeria* Profilin-Like Protein as an Adjuvant," *Vaccine* 27(16):2274-2281.
Hemmi, H. et al. (Feb. 2002). "Small Anti-Viral Compounds Activate Immune Cells Via the TLR7 MyD88-Dependent Signaling Pathway," *Nat. Immunol.* 3(2):196-200.
Horsmans, Y. et al. (2005). "Isatoribine, an Agonist of TLR7, Reduces Plasma Virus Concentration in Chronic Hepatitis C Infection," *Hepatol.* 42:724-731.
Hubert, R.S. et al. (Dec. 7, 1999). "STEAP: A Prostate-Specific Cell-Surface Antigen Highly Expressed in Human Prostate Tumors," *Proc. Natl. Acad. Sci.* 96(25):14523-14528.
Ivins, B. et al. (Dec. 1995). "Experimental Anthrax Vaccines: Efficacy Of Adjuvants Combined With Protective Antigen Against An Aerosol *Bacillus anthracis* Spore Challenge In Guinea Pigs," *Vaccine* 13(18):1779-1784.

(56) References Cited

OTHER PUBLICATIONS

Jacobson, D.L. et al (Sep. 1997). "Epidemiology and Estimated Population Burden of Selected Autoimmune Diseases in the United States," *Clinical Immunology and Immunopathology* 84(3):223-243.
Johansen, P. et al. (2005). "Toll-like Receptor Ligands as Adjuvants in Allergen-Specific Immunotherapy," *Clin. Exp. Allerg.* 35:1591-1598.
Kaisho, T. et al. (2004, e-pub. Nov. 5, 2004). "Pleiotropic Function of Toll-like Receptors," *Microbes Infect.* 6:1388-1394.
Kasper, J.C. et al. (Oct. 2013; e-published on Jun. 7, 2013). "Recent Advances and Further Challenges in Lyophilization," *Eur J Pharm Biopharm.* 85(2):162-169.
Kensil, C. et al. (Jan. 15, 1991). "Separation and Characterization of Saponins With Adjuvant Activity From *Quillajas saponaria* Molina Cortex," *J. Immunology* 146(2):431-437.
Kensil, C. (1996). "Saponins as Vaccine Adjuvants," in *Critical Reviews™ in Therapeutic Drug Carrier Systems*, Begell House, Inc., New York 13(1-2):1-55.
Krieg, A.M. et al. (Apr. 6, 1995). "CpG Motifs in Bacterial DNA Trigger Direct B-Cell Activation," *Nature* 374(6522):546-549.
Lacaille-Dubois, M. et al. (1996). "A Review of the Biological and Pharmacological Activities of Saponins," *Phytomedicine* 2(4):363-386.
Lee, J. et al. (Feb. 7, 2006). "Activation of Anti-Hepatitis C Virus Responses Via Toll-like Receptor 7," *Proc. Nat. Acad. Sci.* USA 103(6):1828-1833.
Lien, E. et al. (Dec. 2003). "Adjuvants and Their Signaling Pathways: Beyond TLR's," *Nat. Immunol.* 4(12):1162-1164.
Lin, W. et al. (2005). "Implication of Toll-Like Receptors and Tumor Necrosis Factor α Signaling in Septic Shock," *Shock* 24(3):206-209.
Lu, P.J. et al. (May 28, 1999). "A Novel Gene (PLU-1) Containing Highly Conserved Putative DNA/Chromatin Binding Motifs is Specifically Up-Regulated in Breast Cancer," *J. Biol. Chem.* 274(22):15633-15645.
Luster, A.D. (Feb. 2002). "The Role of Chemokines in Linking Innate and Adaptive Immunity," *Curr. Opin. Immunol.* 14(1):129-135.
McCluskie, M.J. et al. (Nov. 1, 1998). "Cutting Edge: CpG DNA is a Potent Enhancer of Systemic and Mucosal Immune Response Against Hepatitis B Surface Antigen with Intranasal Administration to Mice," *J. Immunol.* 161(9):4463-4466.
McGeary, R.P. et al. (Jul. 2003). "Lipid and Carbohydrate Based Adjuvant/Carriers in Immunology," *J Pept Sci.* 9(7):405-418.
Medzhitov, R. et al. (Feb. 1997). "Innate Immunity: Impact on the Adaptive Immune Response," *Curr. Opin. Immunol.* 9(1):4-9.
Medzhitov, R. (Nov. 2001). "Toll-Like Receptors and Innate Immunity," *Nat. Rev. Immunol.* 1:135-145.
Mitchell, T.J. (Jan. 23, 1989). "Expression of the Pneumolysin Gene In *Escherichia Coli*: Rapid Purification and Biological Properties," *Biochim Biophys Acta.* 1007(1):67-72.
Mologen AG, (2005) "Company Profile", located at <https://web.archive.org/web/20061119083957/http://www.mologen.com/English/01.10-Company.shtml>, last visited on May 2, 2017, 2 pages.
Morrow, M.P. et al. (Jan. 30, 2008). "Cytokines as Adjuvants for Improving Anti-HIV Responses," *AIDS* 22(3):333-338.
Nakao, Y. et al. (2005). "Surface-Expressed TLR6 participates in the Recognition of Diacylated Lipopeptide and Peptidoglycan in Human Cells," *J. Immunol.* 174:1566-1573.
Nelson, P.S. et al. (Mar. 16, 1999). "Molecular Cloning and Characterization of Prostase, An Androgen-Regulated Serine Protease With Prostate-Restricted Expression," *Proc. Natl. Acad. Sci.* 96(6):3114-3119.
Orr, M.T. et al. (Nov. 28, 2013; e-published on Aug. 9, 2013). "Adjuvant Formulation Structure And Composition are Critical for the Development of an Effective Vaccine Against Tuberculosis," *J Control Release* 172(1):190-200.
Orr, M.T. et al. (Sep. 2013, e-published on Jul. 3, 2013). "Cooperative intracellular interactions between MyD88 and TRIF are required for CD4 T cell $T_H1$ polarization with a synthetic TLR4 agonist adjuvant," *Eur J Immunol.* 43(9):2398-2408, (original version).
Orr, M.T. et al. (Sep. 2013; e-published on Jul. 3, 2013). "MyD88 and TRIF Synergistic Interaction Is Required For TH1-Cell Polarization With A Synthetic TLR4 Agonist Adjuvant," *Eur J Immunol.* 43(9):2398-2408, (edited version).
Path, and Working in Tandem Ltd. (Nov. 29, 2012). "Summary of stability data for licensed vaccines," Seattle, WA, located at <https://www.path.org/publications/files/TS_vaccine_stability_table.pdf>, last visited on Apr. 13, 2017, 17 pages.
Powell, M. (ed.) et al. (1995). *Vaccine design—The Subunit and Adjuvant Approach*, Plenum Press, New York, Table of Contents, twenty three pages.
Radbruch and Lipsky, P.E. (Eds.) (2006). *Current Concepts in Autoimmunity and Chronic Inflammation*, Springer, NY, pp. 1-276, two hundred and eighty seven total pages.
Reed, S.G. et al. (1990). "An Improved Serodiagnostic Procedure for Visceral Leishmaniasis," *Am. J. Trop. Med. Hyg.* 43(6):632-639.
Reed, S. et al. (Jan. 2009; e-published on Dec. 6, 2008). "New Horizons in Adjuvants for Vaccine Development," *Trends Immunol.* 30(1):23-32.
Reiter, R. et al. (Feb. 17, 1998). "Prostate Stem Cell Antigen: A Cell Surface Marker Overexpressed in Prostate Cancer," *Proc. Nat. Acad. Sci.* USA 95(4):1735-1740.
Robbins, P. and Kawakami, Y. (1996). "Human Tumor Antigens Recognized by T Cells," *Current Opinions in Immunology* 8(5):628-636.
Rossi, J. et al. (2007). "Principles in the Development of Intravenous Lipid Emulsions," Chapter 4 in *Role of Lipid Excipients in Modifying Oral and Parenteral Drug Delivery*. Kishor M. Wasan (ed.), John Wiley & Sons, Inc., Hoboken, NJ, pp. 88-123.
Rowland, R. et al. (May 2011). "Tuberculosis Vaccines In Clinical Trials," *Expert Rev. Vaccines* 10(5):645-658.
Rubins, J. et al. (1998). "Pneumolysin in Penumococcal Adherence and Colonization," *Microbial Pathogenesis* 25:337-342.
Ruhenstroth-Bauer, G. et al. (Nov. 25, 1955). "Purification of Digitonin," *Hoppe Seyler's Z Physiol. Chem.* 302(2-3):111-118, (English Translation of Summary only).
Salem, M.L. et al. (2006, e-pub. May 2, 2006). "The Adjuvant Effects of the Toll-Like Receptor 3 Ligand Polyinosinic-Cytidylic Acid Poly (I:C) on Antigen-Specific CD8+ T Cell Responses are Partially Dependent on NK Cells with the Induction of a Beneficial Cytokine Milieu," *Vaccine* 24:5119-5132.
Salomon, D.S. et al. (1999). "Cripto: A Novel Epidermal Growth Factor (EGF)-Related Peptide in Mammary Gland Development and Neoplasia," *BioEssays* 21.1:61-70.
Schirmbeck, R. et al. (2003). "Antigenic Epitopes Fused to Cationic Peptide Bound to Oligonucleotides Facilitate Toll-Like Receptor 9-Dependent, but $CD4^+$ T Cell Help-Independent, Priming of the $CD8^+$ T Cells," *J. Immunol.* 171:5198-5207.
Schmidt, M. et al. (2006). "Cytokine and Ig-Production by CG-Containing Sequences With Phosphorodiester Backbone and Dumbell-Shape," *Allergy* 61:56-63.
Schmidt, M. et al. (Aug. 25, 2005). "MIDGE Vectors and dSLIM Immunomodulators: DNA-based Molecules for Gene Therapeutic Strategies," Chapter 7 in *Modern Biopharmaceuticals: Design, Development and Optimization*, Knablein, J. (ed.), Wiley-VCH Verlag GmbH, Weinheim, Germany, pp. 183-211.
Schneider, C.A. et al. (Jul. 2012). "NIH Image to ImageJ: 25 Years of Image Analysis," *Nat Methods* 9(7):671-675.
Schnur, L.F. et al. (Jul. 1972). "Leishmanial Serotypes as Distinguished by the Gel Diffusion of Factors Excreted In Vitro and In Vivo," *Israel. J. Med. Sci.* 8(7):932-942.
Schweneker, K. et al. (Apr. 2013). "The Mycobacterial Cord Factor Adjuvant Analogue Trehalsoe-6,6'-Dibehenate (TDB) Activates the Nlrp3 Inflammasome," *Immunobiology* 218(4):664-673.
Senaldi, G. et al. (1996). "Serological Diagnosis of Visceral Leishmaniasis by a Dot-Enzyme Immunoassay for the Detection of a *Leishmania donovani*-Related Circulating Antigen," *J. Immunol. Methods* 193:9-15.

(56) References Cited

OTHER PUBLICATIONS

Sergeiev, V. et al. (1969). "Meditsinskaia Parazitoclogiiai Parazitarknye Bolezni," *Med. Parasitol.* 38:208-212. (English Translation of Summary only).

Sethi, S. et al. (Apr. 2001). "Bacterial Infection in Chronic Obstructive Pulmonary Disease In 2000: A State-Of-The-Art Review," *Clin Microbiol Rev.* 14(2):336-363.

Shiow, L.R. et al. (Mar. 23, 2006, e-pub. Mar. 8, 2006). "CD69 Acts Downstream of Interferon-α/β To Inhibit $S1P_1$ And Lymphocyte Egress From Lymphoid Organs," *Nature* 440(7083):540-544.

Soboll, G. et al. (2006, e-pub. Jul. 1, 2006). "Expression of Toll-Like Receptors (TLR) and Responsiveness to TLR Agonists by Polarized Mouse Uterine Epithelial Cells in Culture," *Biol. Reprod.* 75:131-139.

Takeda, K. et al. (2003, e-pub. Jan. 9, 2003). "Toll-Like Receptors," *Ann Rev Immunol.* 21:335-376.

Takeda, K. et al. (2005). "Toll-Like Receptors in Innate Immunity," *Int. Immunol.* 17(1):1-14.

The Merck Index: An Encyclopedia of Chemicals Drugs, and Biologicals, 10th Ed., entry No. 8619, (1983), 3 pages.

The Merck Index: An Encyclopedia of Chemicals Drugs, and Biologicals, 12th Ed., entry 3737, (1996), 4 pages.

The Merck Index: An Encyclopedia of Chemicals Drugs, and Biologicals, 12th Ed., entry 3204, (1996) 3 pages.

Triozzi, P. et al. (Dec. 1997). "Effects of a β-Human Chorionic Gonadotropin Subunit Immunogen Administered in Aqueous Solution with a Novel Nonionic Block Copolymer Adjuvant in Patients with Advanced Cancer," *Clin. Canc. Res.* 3:2355-2362.

Tsan, M. et al. (2004). "Cytokine Function of Heat Shock Proteins," *Am. J. Physiol.* Cell Physiol. 286:C739-C744.

Tsan, M. et al. (Sep. 2004). "Endogenous Ligands of Toll-Like Receptors," *J. Leuk. Biol.* 76:514-519.

U.S. Food and Drug Administration (Nov. 14-15, 2012). "2012 Meeting Materials, Vaccines and Related Biological Products Advisory Committee," located at <https://www.fda.gov/AdvisoryCommittees/CommitteesMeetingMaterials/BloodVaccinesandOtherBiologics/VaccinesandRelatedBiologicalProductsAdvisoryCommittee/ucm288695.html>, last visited on Apr. 18, 2017.

Van Den Eynde, B. et al. (1997). "Tumor Antigens Recoginzed by T Lymphocytes," *International Journal of Clinical & Laboratory Research* 27:81-16.

Vollmer J. et al. (Jun. 2004). "Immunopharmacology of CpG Oligodeoxynucleotides and Ribavirin," *Antimicrob. Agents Chemother.* 48(6):2314-2317.

Vollmer J. (May 2005). "Progress In Drug Development Of Immunostimulatory CpG Oligodeoxynucleotide Ligands For TLR9," *Expert Opinion on Biological Therapy* 5(5):673-682.

Wang, W. (Aug. 10, 2000). "Lyophilization and Development of Solid Protein Pharmaceuticals," *Int. J. Pharm.* 203(1-2):1-60.

Wasylyk, B. et al. (Jan. 15, 1993). "The Ets Family of Transcription Factors," *Eur. J Bioch.* 211(1-2):7-18.

Weeratna, R.D. et al. (2005, e-pub. Jul. 18, 2005). "TLR Agonists as Vaccine Adjuvants: Comparison of CpG ODN and Resiquimod (R-848)," *Vaccine* 23:5263-5270.

Weihrauch, M.R. et al. (Aug. 15, 2005). "Phase I/II Combined Chemoimmunotherapy with Carcinoembryonic Antigen-Derived HLA-A2-Restricted CAP-1 Peptide and Irinotecan, 5-Fluorouracil, and Leucovorin in Patients with Primary Metastatic Colorectal Cancer," *Clin Cancer Res.* 11(16):5993-6001.

Yeh, M. et al. (1996). "Improving Protein Delivery from Microparticles Using Blends of Poly(DL Lactide Co-Glycolide) and Poly(Ethylene Oxide)-Poly(Propylene Oxide) Copolymers," *Pharm. Res.* 13(11):1693-1698.

Yoshikawa M, et al. (Aug. 1996). "Bioactive Saponins and Glycosides. III. Horse Chestnut. (1): The Structures, Inhibitory Effects on Ethanol Absorption, and Hypolglycemic Activity of Escins, Ia, Ib, IIa, IIb, and IIIa From the Seeds of *Aesculus Hippocastanum* L," *Chem Pharm Bull.* 44(8):1454-1464.

Zijlstra, E. et al. (1997). "The Direct Agglutination Test for Diagnosis of Visceral Leishmaniasis Under Field conditions in Sudan: comparison of Aqueous and Freeze-Dried Antigens," *Trans. R. Soc. Trop. Med. Hyg.* 91:671-673.

European Supplementary Search Report dated Jul. 5, 2017, for EP Patent Application No. 14876449.1 filed on Jul. 8, 2016, twelve pages.

International Preliminary Report On Patentability dated Jul. 5, 2016, for PCT/US2014/072615, Internationally filed on Dec. 29, 2014, ten pages.

International Search Report dated May 21, 2015, for PCT/US2014/072615, Internationally filed on Dec. 29, 2014, four pages.

Written Opinion mailed dated May 21, 2015, for PCT/US2014/072615, Internationally filed on Dec. 29, 2014, nine pages.

Fox, C. B., "Squalene Emulsions for Parenteral Vaccine and Drug Delivery" Molecules 2009, 14, pp. 3286-3312.

Fox, et al., "Adjuvanted pandemic influenza vaccine: variation of emulsion components affects stability, antigen structure, and vaccine efficacy," DOI:10.1111/irv.12031, www.influenzajournal.com, Nov. 5, 2012, 12 pages.

Office Action dated Dec. 16, 2019 for co-pending EA patent application No. 201691348, English translation, 4 pages.

Office Action dated Sep. 9, 2020 for co-pending EA Patent Application No. 20169348, English translation, 2 pages.

Office Action dated Apr. 3, 2020 for co-pending Chinese patent application No. 201480076620.01, English translation, 6 pages.

Office Action dated Nov. 4, 2019 for co-pending Chinese patent application No. 201480076620.01, English translation, 6 pages.

Office Action dated Mar. 27, 2019 for co-pending Chinese patent application No. 201480076620.1, English translation, 5 pages.

Orr, et al., "Elimination of the cold-chain dependence of a nanoemulsion adjuvanted vaccine against tuberculosis by lyophilization," J Control Release. Mar. 10, 2014; 177: 20, 26doi:10.1016/j.jconrel.2013.12.025, 17 pages.

Summons to attend oral proceedings for EP application No. 14876449.1 dated Jul. 13, 2020, 10 pages.

CA Application No. 2,935,620—Office Action, dated Jan. 8, 2021, 5 pages.

EA Application No. 201691348—Office Action, dated Feb. 9, 2021, 6 pages.

CA 2,935,620—Office Action and Search Report, dated Nov. 17, 2021, 3 pages.

EA 201691348—Office Action, dated Oct. 27, 2021, 4 pages, (with English translation).

IL 246456—Office Action, dated Oct. 27, 2021, 6 pages, (with English translation).

EP 211 601 58.8—Extended European Search Report, dated Nov. 2, 2021, 13 pages.

MX MX/a/2016/008640—Office Action, dated Oct. 6, 2021, 9 pages, (with English translation).

KR 10-2016-7020820—Office Action, dated Dec. 22, 2021, 5 pages, (with English translation).

KR Application No. 10-2016-7020820—Office Action dated Jun. 19, 2021, 20 pages, (with English translation).

DA 2,935,620—Office Action dated Oct. 21, 2022, 3 pages.

Office Action from the Koran Intellectual Property Office Preliminary Rejection dated Feb. 17, 2023 for Application No. 10-2022-7020632, 12 pages.

Office Action from the United States Patent and Trademark Office for U.S. Appl. No. 18/180,801, dated Jul. 26, 2023, 20 pages.

\* cited by examiner

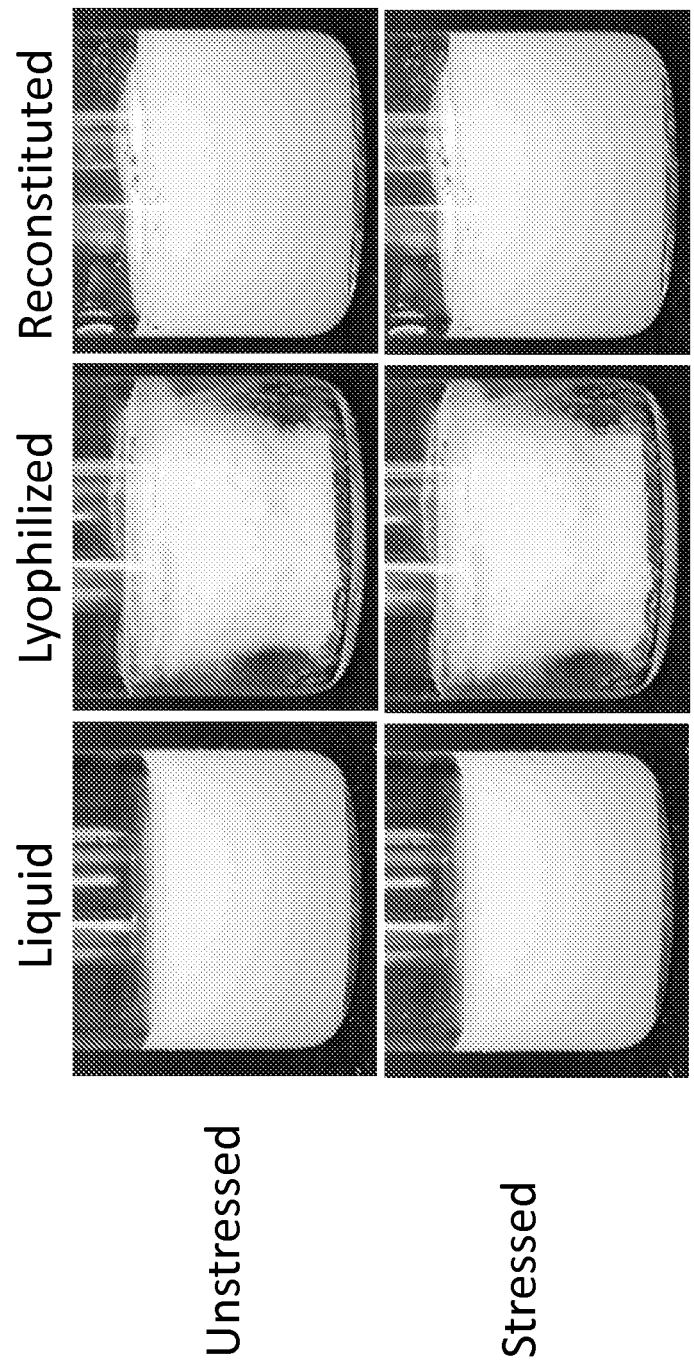

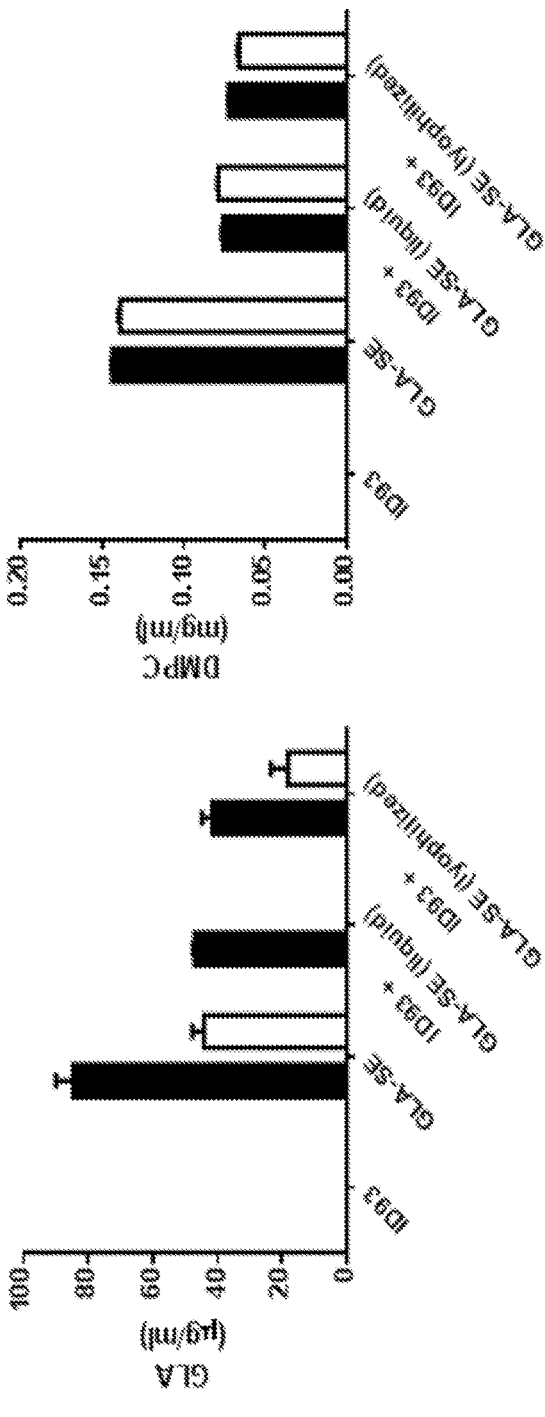
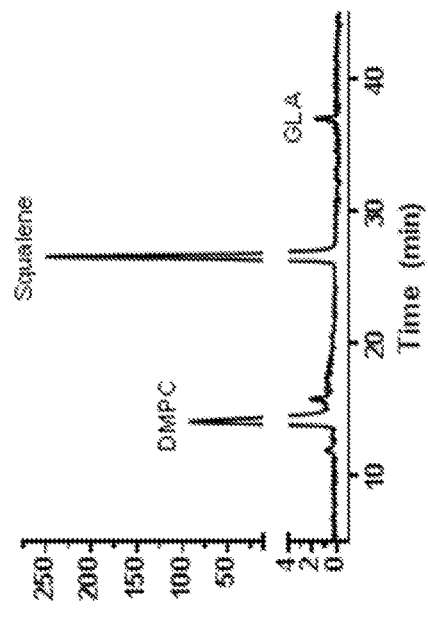
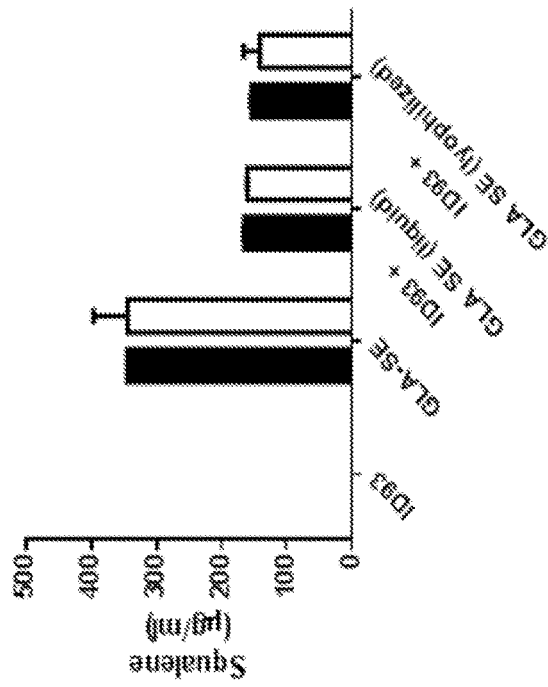
FIG. 12A  FIG. 12B  FIG. 12C  FIG. 12D

FIG. 15
| Sample | 0 Days, A | 0 Days, B | 30 Days, A | 30 Days, B |
|---|---|---|---|---|
| Cake Image | 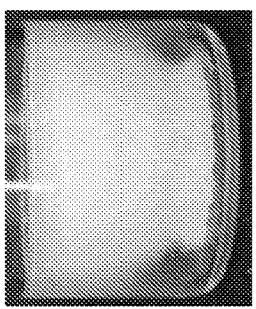 | 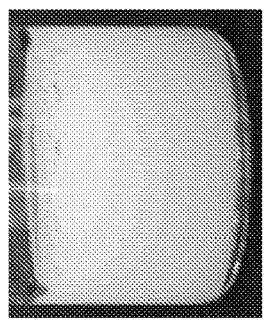 | 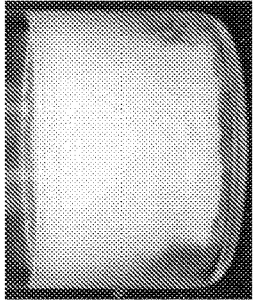 | 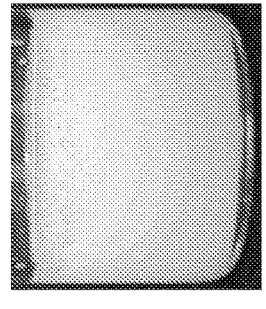 |
| Solution Image | 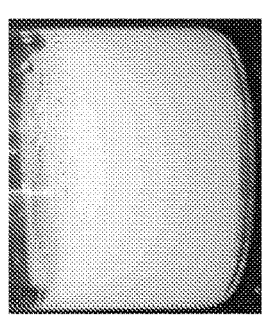 | 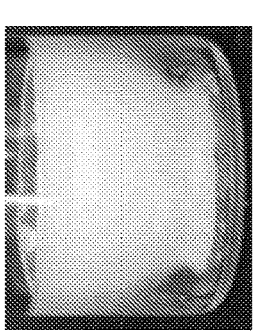 | 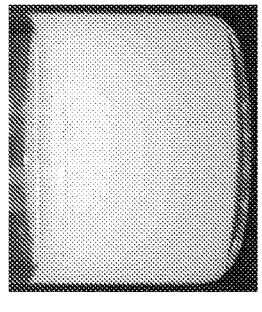 | 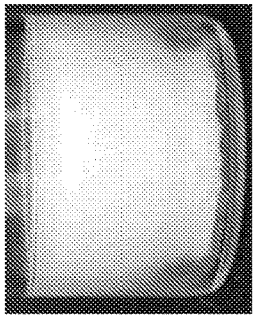 |
| Creaming (1 Hour) | Negative | Negative | Negative | Negative |
| Creaming (24 Hours) | Negative | Negative | Negative | Negative |
| Solution pH | 7.47 | 7.48 | 7.19 | 7.19 |

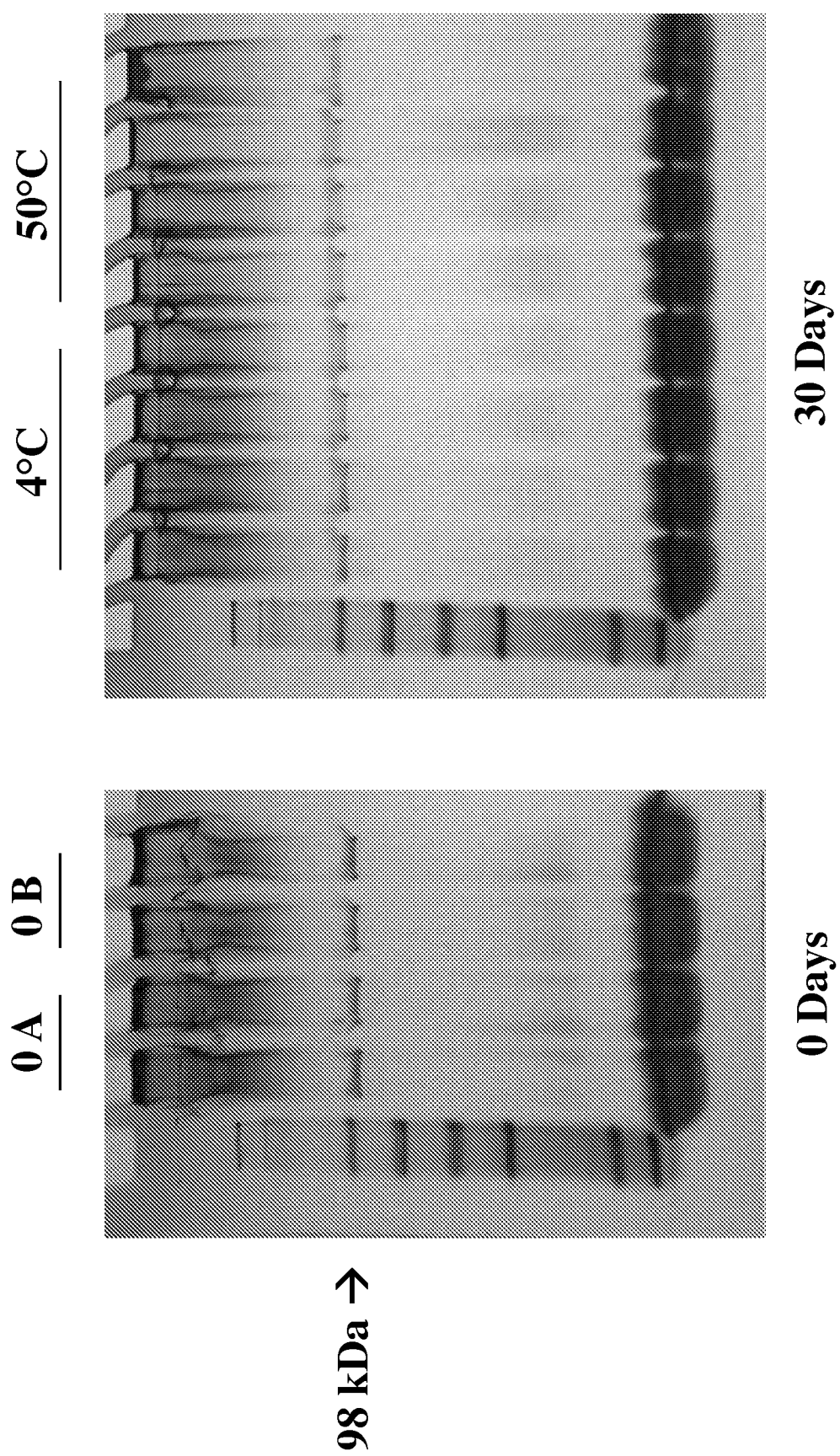

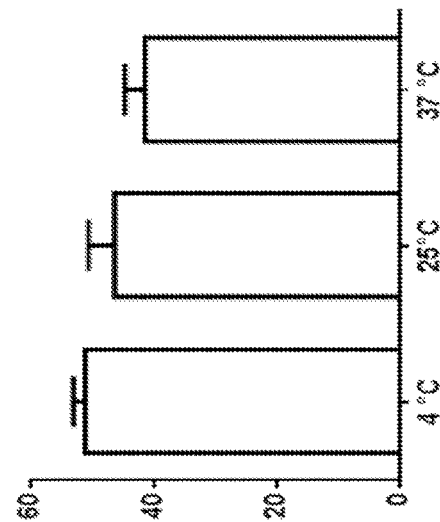
FIG. 21A
FIG. 21B
|  | 4 °C | 25 °C | 37 °C |
|---|---|---|---|
| Cake | Pass | Pass | Pass |
| Creaming (1 hr) | Neg | Neg | Neg |
| Creaming (24 hrs) | Neg | Neg | Neg |
| Z-Aved (nm) | 104.9 ± 0.1 | 105 ± 0.6 | 117.8 ± 0.2 |
| PDI | 0.072 ± 0.008 | 0.0675 ± 0.0005 | 0.096 ± 0.05 |
| pH | 7.48 ± 0.01 | 7.46 ± 0.01 | 7.32 ± 0.01 |
| GLA (μg/mL) | 51 ± 2 | 46 ± 4 | 42 ± 3 |
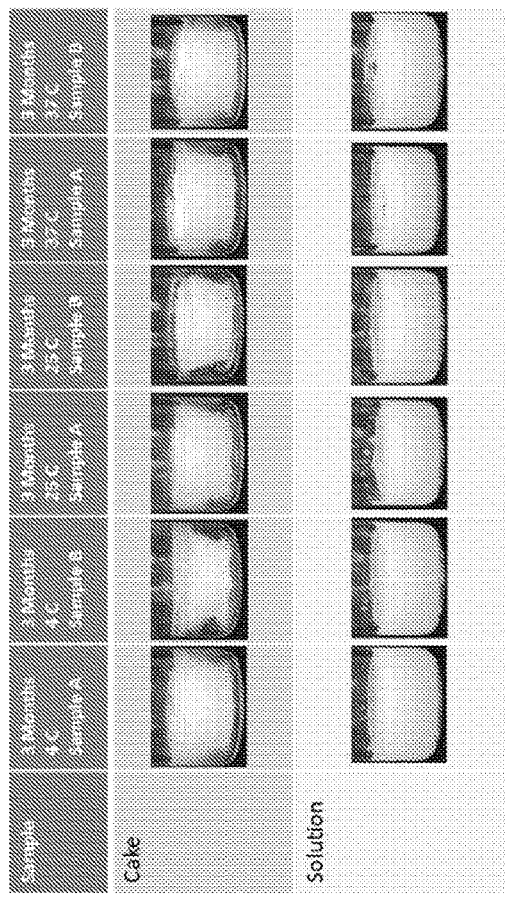
FIG. 21C
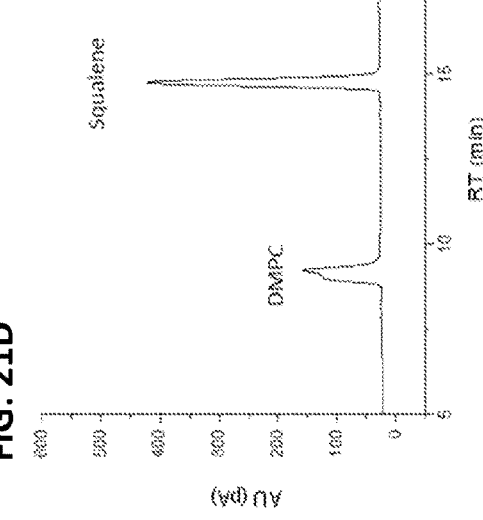
FIG. 21D
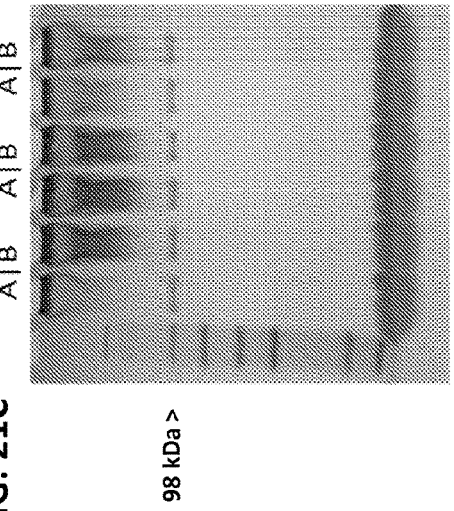
FIG. 21E

FIG. 22B
|  | 4 °C | 25 °C | 37 °C |
|---|---|---|---|
| Cake | Pass | Pass | Pass |
| Creaming (1 hr) | Neg | Neg | Neg |
| Creaming (24 hrs) | Neg | Neg | Neg |
| Z-Aved (nm) | 103.4 ± 0.4 | 103.2 ± 0.1 | 117.4 ± 0.6 |
| PDI | 0.069 ± 0.006 | 0.0675 ± 0.005 | 0.10 ± 0.08 |
| pH | 7.49 ± 0.00 | 7.45 ± 0.02 | 7.21 ± 0.02 |
| GLA (µg/mL) | 47 ± 2 | 42 ± 2 | 25 ± 2 |
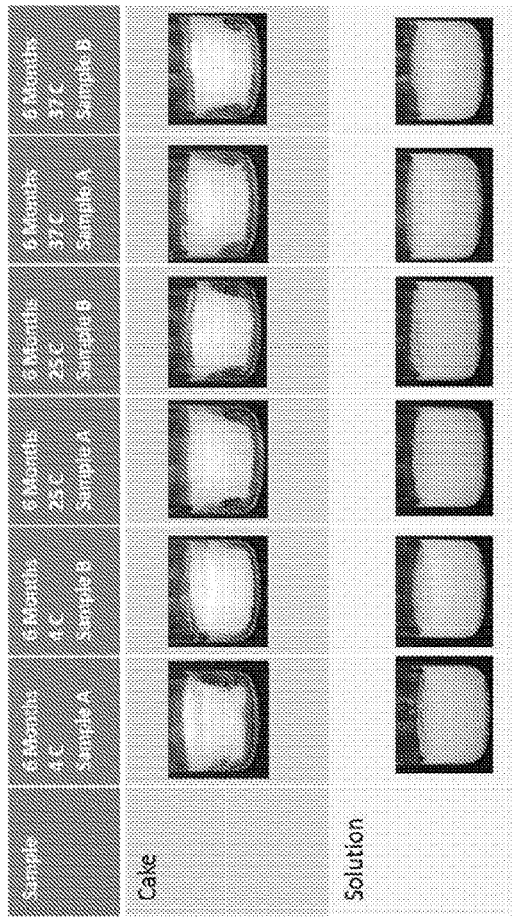
FIG. 22A
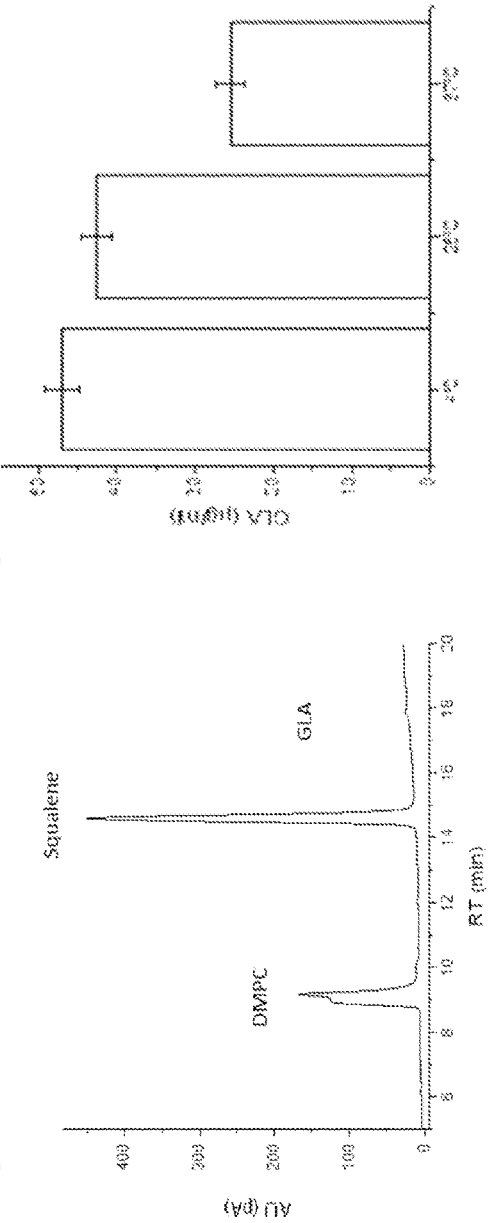
FIG. 22E
FIG. 22D
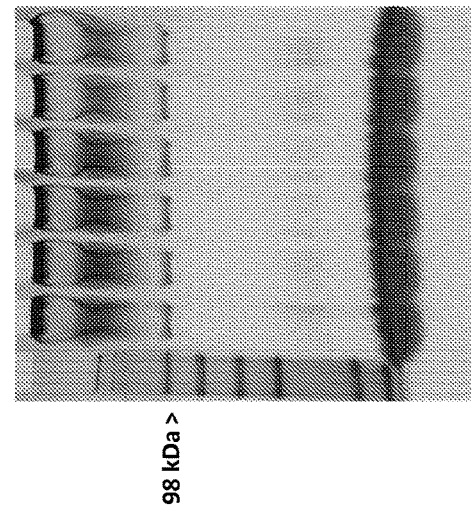
FIG. 22C
98 kDa >

FIG. 23A
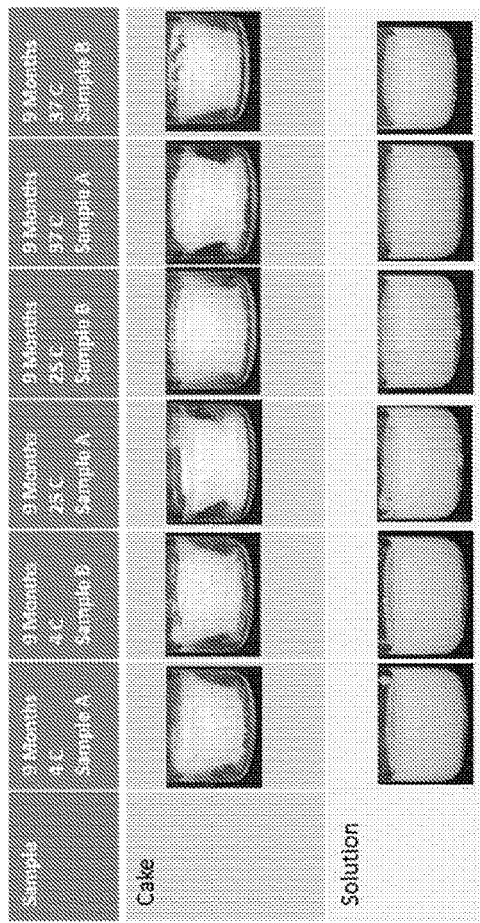
FIG. 23B
| | 4 °C | 25 °C | 37 °C |
|---|---|---|---|
| Cake | Pass | Pass | Pass |
| Reconstitution | Pass | Pass | Pass |
| Creaming (1 hr) | Neg | Neg | Neg |
| Creaming (24 hrs) | Neg | Neg | Neg |
| Z-Aved (nm) | 105.3 ± 0.3 | 105.8 ± 0.5 | 128 ± 2 |
| PDI | 0.060 ± 0.009 | 0.054 ± 0.005 | 0.141 ± 0.008 |
| pH | 7.525 ± 0.007 | 7.43 ± 0.04 | 7.195 ± 0.007 |
| GLA (µg/mL) | 40.9 ± 0.4 | 40 ± 1 | 15.8 ± 0.9 |
FIG. 23C
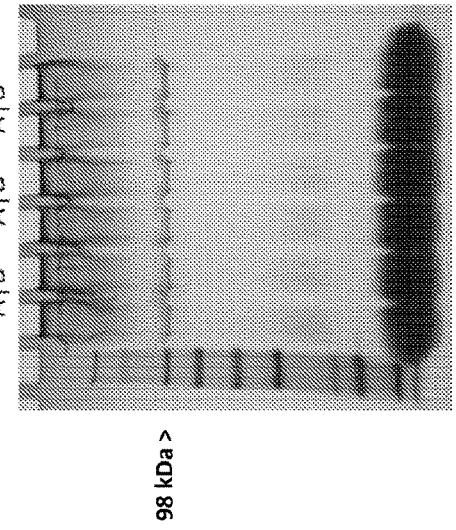
FIG. 23D
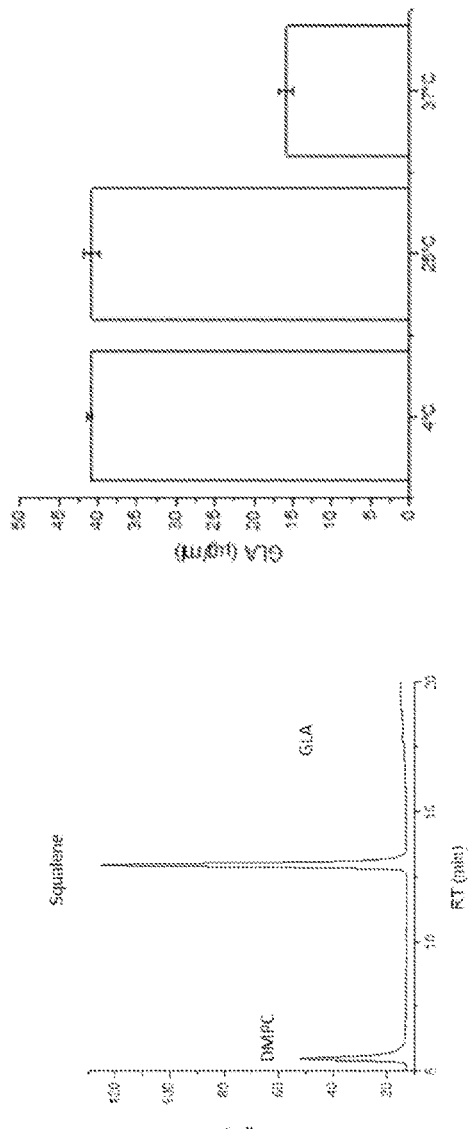
FIG. 23E

FIG. 24A
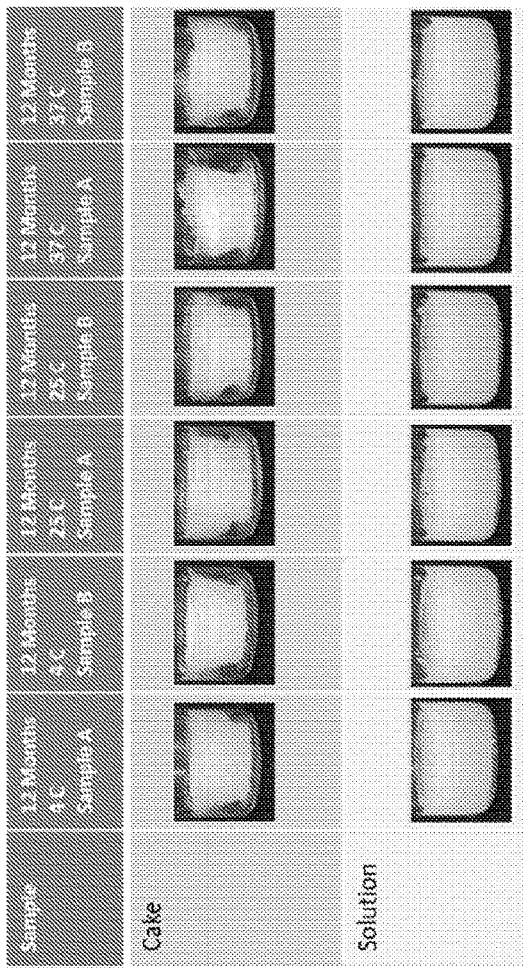
FIG. 24B
| | 4 °C | 25 °C | 37 °C |
|---|---|---|---|
| Cake | Pass | Pass | Pass |
| Creaming (1 hr) | Neg | Neg | Neg |
| Creaming (24 hrs) | Neg | Neg | Neg |
| Z-Aved (nm) | 106.6 ± 0.6 | 109 ± 1 | 127 ± 2 |
| PDI | 0.06 ± 0.01 | 0.08 ± 0.010 | 0.134 ± 0.000 |
| pH | 7.485 ± 0.007 | 7.407 ± 0.005 | 7.155 ± 0.007 |
| GLA (µg/mL) | 40.9 ± 0.4 | 40 ± 1 | 15.8 ± 0.9 |
FIG. 24C
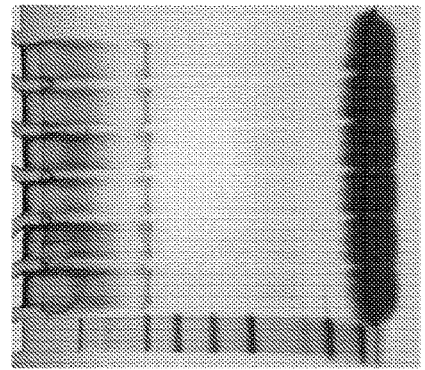
98 kDa >

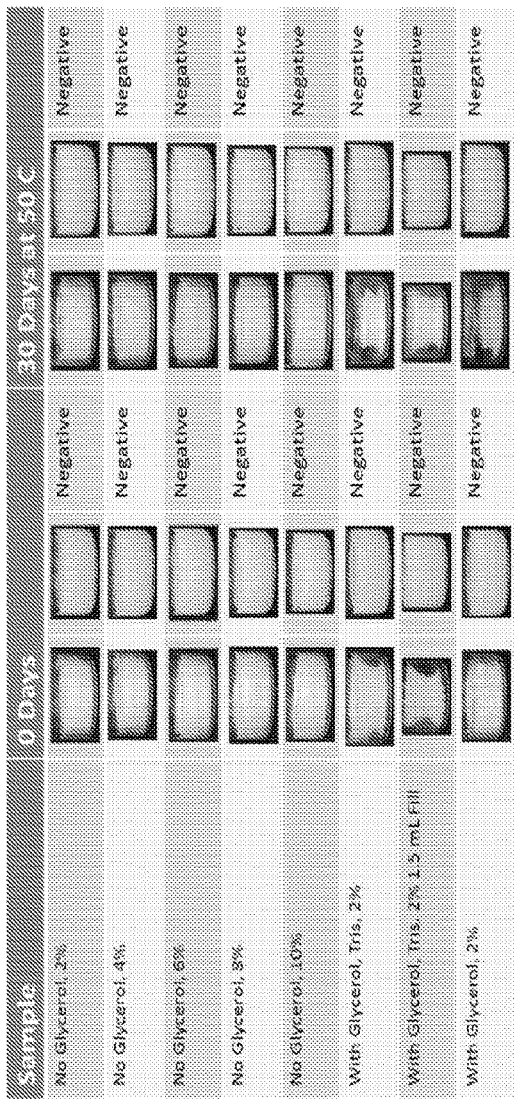
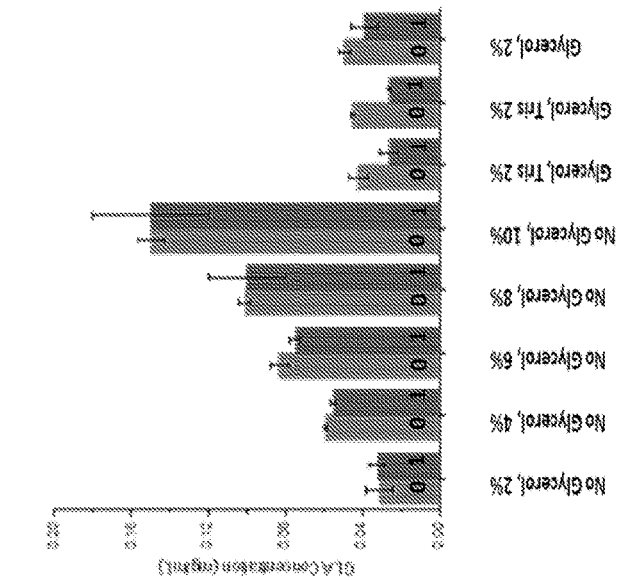
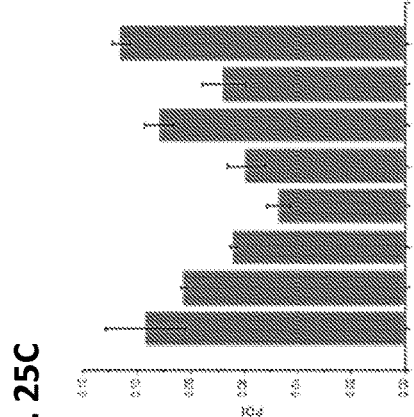
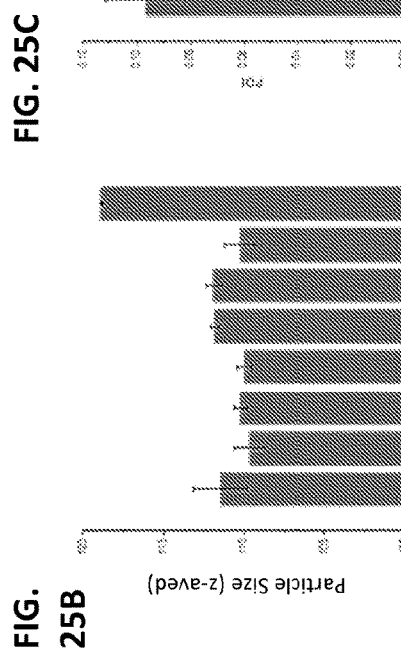
FIG. 25A
FIG. 25B
FIG. 25C
FIG. 25D

FIG. 26A  5% w/v Trehalose

FIG. 26B

5% w/v Trehalose, 0.1% w/v Mannitol

| Temp | Post | t0 | 1Wk | 2Wk | 1mo | 3mo |
|---|---|---|---|---|---|---|
| 4°C | | | | | | |
| Creaming | Negative | Negative | Negative | | Negative | Negative |
| 25°C | | | | | | |
| Creaming | Negative | Negative | Negative | | Negative | Negative |
| 37°C | | | | | | |
| Creaming | Negative | Negative | Negative | Negative | Negative | Negative |
| 50°C | | | | | | |
| Creaming | Negative | Negative | Negative | Negative | Negative | Negative |

FIG. 26C  2.5% w/v Trehalose, 2.5% w/v Mannitol
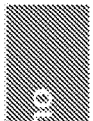

FIG. 26D  10% w/v Trehalose

| Temp | Post | 0 | 1 wk | 2 wk | 1 mo | 3 mo |
|---|---|---|---|---|---|---|
| 4 °C | | | | | | |
| Creaming | Negative | Negative | Negative | | Negative | Negative |
| 25 °C | | | | | | |
| Creaming | Negative | Negative | Negative | | Negative | Negative |
| 37 °C | | | | | | |
| Creaming | Negative | Negative | Negative | Negative | Negative | Negative |
| 50 °C | | | | | | |
| Creaming | Negative | Negative | Negative | Negative | Negative | Negative |

FIG. 27 Initial Formulation Characterization

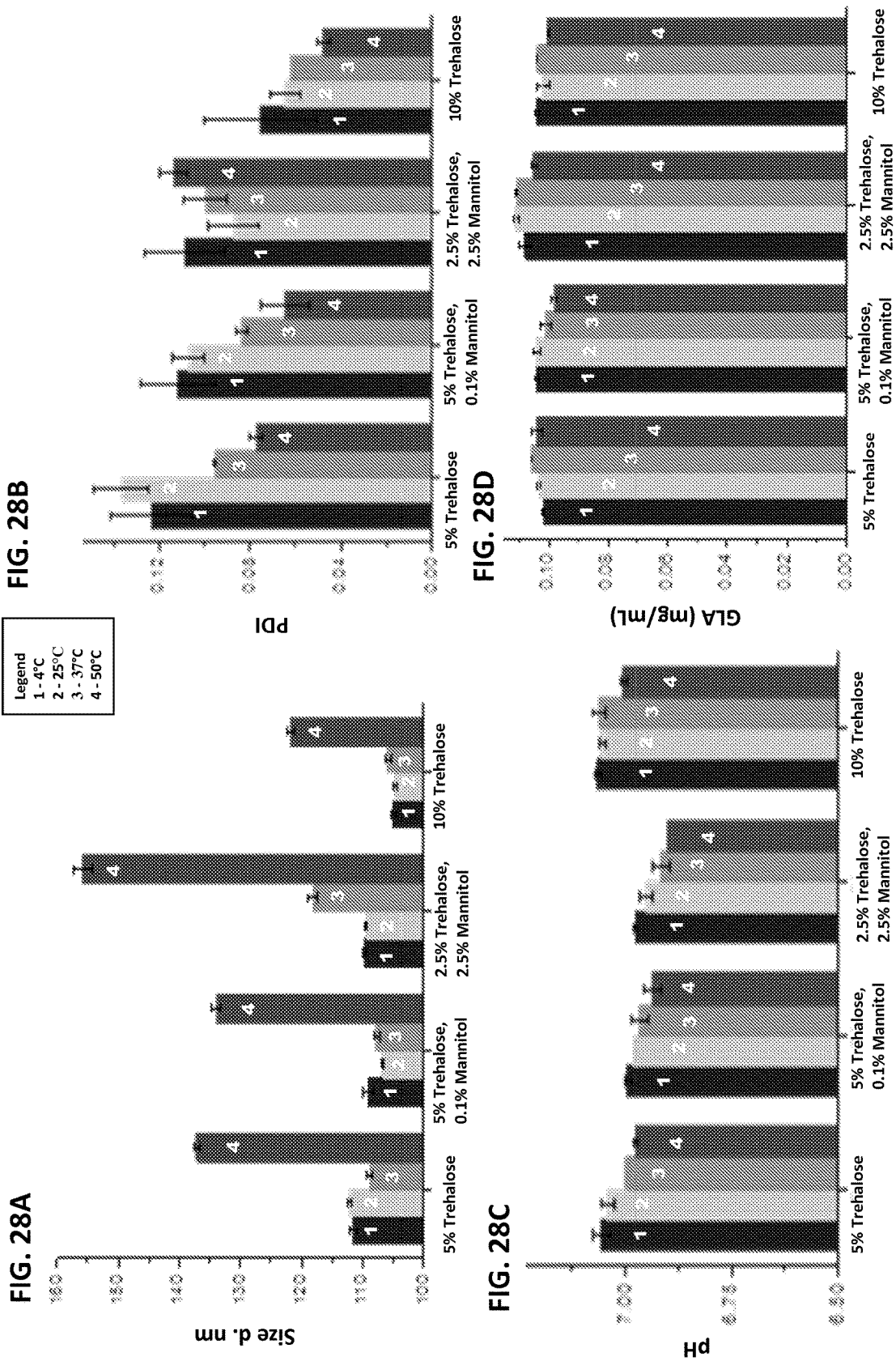

FIG. 29 Characterization Week 2
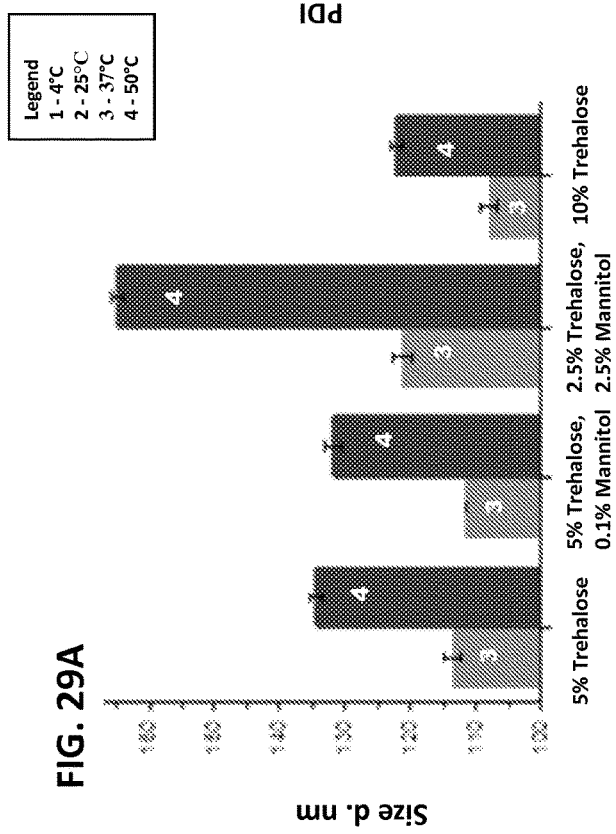
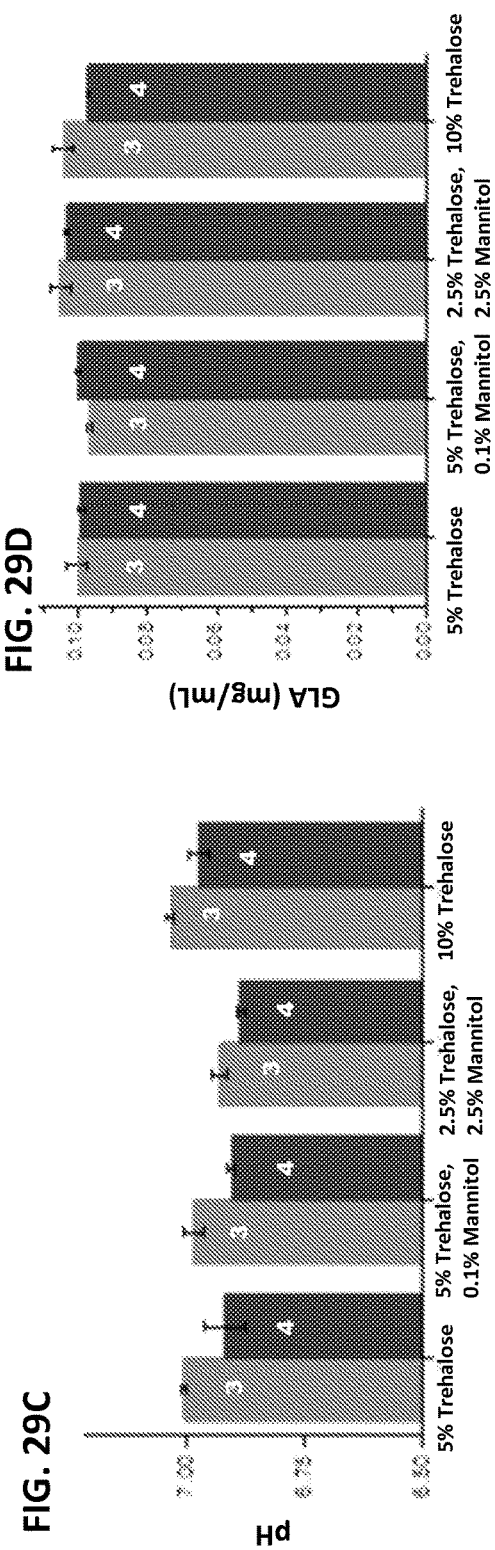

FIG. 30 Characterization Week 4

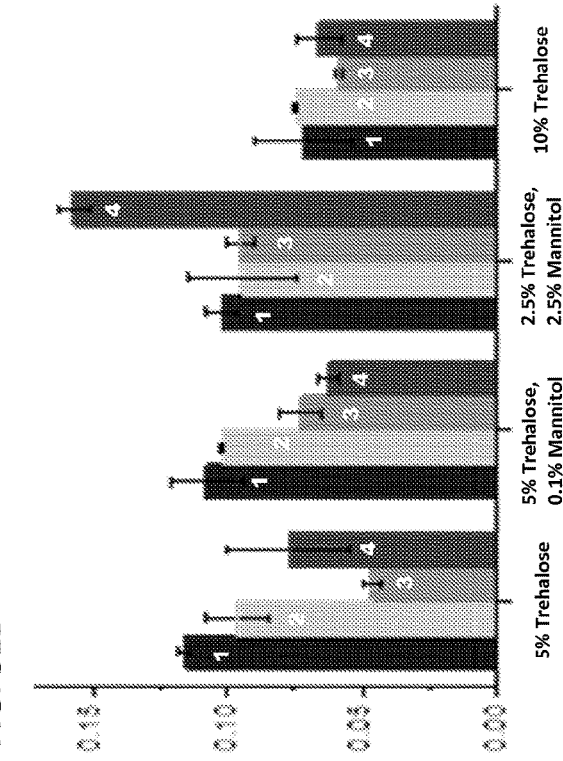
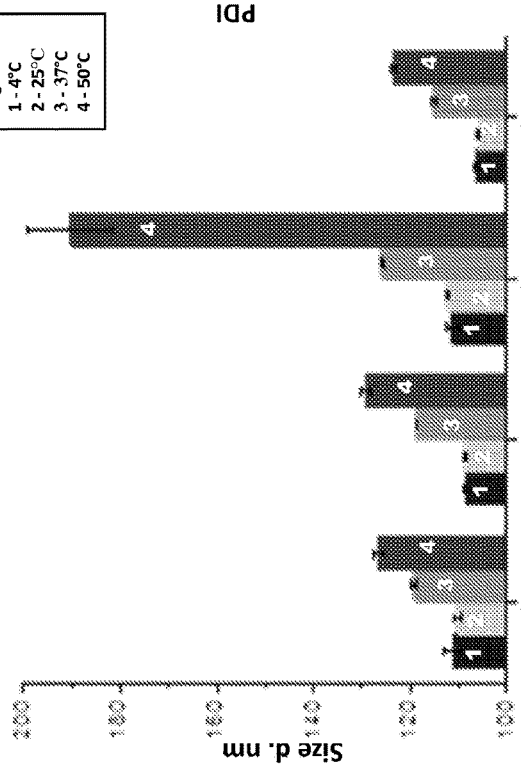
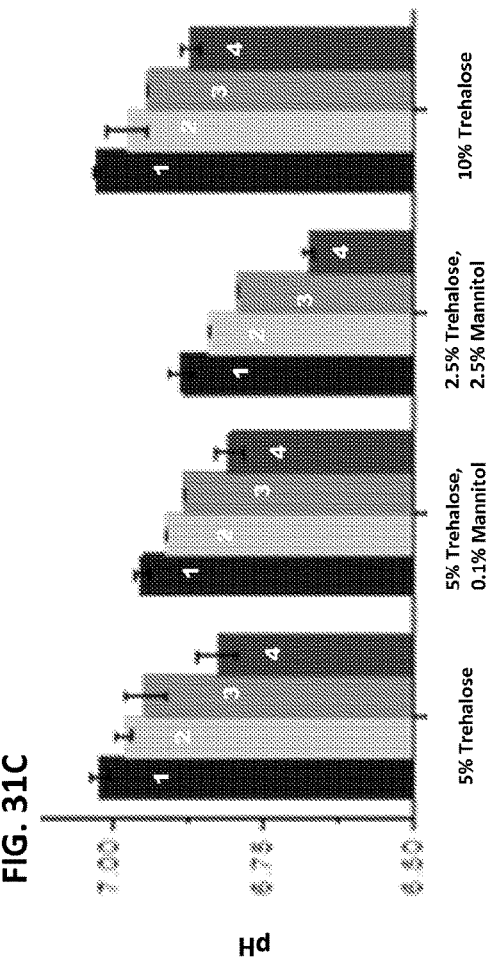
FIG. 31 Characterization 3 Month

SEQUENCE LISTING

```
<160> NUMBER OF SEQ ID NOS: 8

<210> SEQ ID NO 1
<211> LENGTH: 911
<212> TYPE: PRT
<213> ORGANISM: Artificial Sequence
<220> FEATURE:
<223> OTHER INFORMATION: Synthetic Construct

<400> SEQUENCE: 1

Met Gly Ser Ser His His His His His His Ser Ser Gly Leu Val Pro
1               5                   10                  15

Arg Gly Ser His Met Thr Ile Asn Tyr Gln Phe Gly Asp Val Asp Ala
            20                  25                  30

His Gly Ala Met Ile Arg Ala Gln Ala Gly Ser Leu Glu Ala Glu His
        35                  40                  45

Gln Ala Ile Ile Ser Asp Val Leu Thr Ala Ser Asp Phe Trp Gly Gly
    50                  55                  60

Ala Gly Ser Ala Ala Cys Gln Gly Phe Ile Thr Gln Leu Gly Arg Asn
65                  70                  75                  80

Phe Gln Val Ile Tyr Glu Gln Ala Asn Ala His Gly Gln Lys Val Gln
                85                  90                  95

Ala Ala Gly Asn Asn Met Ala Gln Thr Asp Ser Ala Val Gly Ser Ser
            100                 105                 110

Trp Ala Gly Thr His Leu Ala Asn Gly Ser Met Ser Glu Val Met Met
        115                 120                 125

Ser Glu Ile Ala Gly Leu Pro Ile Pro Pro Ile Ile His Tyr Gly Ala
    130                 135                 140

Ile Ala Tyr Ala Pro Ser Gly Ala Ser Gly Lys Ala Trp His Gln Arg
145                 150                 155                 160

Thr Pro Ala Arg Ala Glu Gln Val Ala Leu Glu Lys Cys Gly Asp Lys
                165                 170                 175

Thr Cys Lys Val Val Ser Arg Phe Thr Arg Cys Gly Ala Val Ala Tyr
            180                 185                 190

Asn Gly Ser Lys Tyr Gln Gly Gly Thr Gly Leu Thr Arg Arg Ala Ala
        195                 200                 205
```

Glu Asp Ala Val Asn Arg Leu Glu Gly Gly Arg Ile Val Asn Trp
210                 215                 220

Ala Cys Asn Glu Leu Met Thr Ser Arg Phe Met Thr Asp Pro His Ala
225                 230                 235                 240

Met Arg Asp Met Ala Gly Arg Phe Glu Val His Ala Gln Thr Val Glu
            245                 250                 255

Asp Glu Ala Arg Arg Met Trp Ala Ser Ala Gln Asn Ile Ser Gly Ala
            260                 265                 270

Gly Trp Ser Gly Met Ala Glu Ala Thr Ser Leu Asp Thr Met Thr Gln
            275                 280                 285

Met Asn Gln Ala Phe Arg Asn Ile Val Asn Met Leu His Gly Val Arg
290                 295                 300

Asp Gly Leu Val Arg Asp Ala Asn Asn Tyr Glu Gln Gln Glu Gln Ala
305                 310                 315                 320

Ser Gln Gln Ile Leu Ser Ser Val Asp Ile Asn Phe Ala Val Leu Pro
                325                 330                 335

Pro Glu Val Asn Ser Ala Arg Ile Phe Ala Gly Ala Gly Leu Gly Pro
            340                 345                 350

Met Leu Ala Ala Ala Ser Ala Trp Asp Gly Leu Ala Glu Glu Leu His
            355                 360                 365

Ala Ala Ala Gly Ser Phe Ala Ser Val Thr Thr Gly Leu Ala Gly Asp
370                 375                 380

Ala Trp His Gly Pro Ala Ser Leu Ala Met Thr Arg Ala Ala Ser Pro
385                 390                 395                 400

Tyr Val Gly Trp Leu Asn Thr Ala Ala Gly Gln Ala Ala Gln Ala Ala
                405                 410                 415

Gly Gln Ala Arg Leu Ala Ala Ser Ala Phe Glu Ala Thr Leu Ala Ala
            420                 425                 430

Thr Val Ser Pro Ala Met Val Ala Ala Asn Arg Thr Arg Leu Ala Ser
            435                 440                 445

Leu Val Ala Ala Asn Leu Leu Gly Gln Asn Ala Pro Ala Ile Ala Ala
450                 455                 460

Ala Glu Ala Glu Tyr Glu Gln Ile Trp Ala Gln Asp Val Ala Ala Met
465                 470                 475                 480

Phe Gly Tyr His Ser Ala Ala Ser Ala Val Ala Thr Gln Leu Ala Pro
                485                 490                 495

Ile Gln Glu Gly Leu Gln Gln Leu Gln Asn Val Leu Ala Gln Leu
            500                 505                 510

Ala Ser Gly Asn Leu Gly Ser Gly Asn Val Gly Val Gly Asn Ile Gly
            515                 520                 525

Asn Asp Asn Ile Gly Asn Ala Asn Ile Gly Phe Gly Asn Arg Gly Asp
530                 535                 540

Ala Asn Ile Gly Ile Gly Asn Ile Gly Asp Arg Asn Leu Gly Ile Gly
545                 550                 555                 560

Asn Thr Gly Asn Trp Asn Ile Gly Ile Gly Ile Thr Gly Asn Gly Gln
                565                 570                 575

Ile Gly Phe Gly Lys Pro Ala Asn Pro Asp Val Leu Val Gly Asn
            580                 585                 590

Gly Gly Pro Gly Val Thr Ala Leu Val Met Gly Gly Thr Asp Ser Leu
            595                 600                 605

Leu Pro Leu Pro Asn Ile Pro Leu Leu Glu Tyr Ala Ala Arg Phe Ile
610                 615                 620

Thr Pro Val His Pro Gly Tyr Thr Ala Thr Phe Leu Glu Thr Pro Ser
625                 630                 635                 640

Gln Phe Phe Pro Phe Thr Gly Leu Asn Ser Leu Thr Tyr Asp Val Ser
            645                 650                 655

Val Ala Gln Gly Val Thr Asn Leu His Thr Ala Ile Met Ala Gln Leu
        660                 665                 670

Ala Ala Gly Asn Glu Val Val Phe Gly Thr Ser Gln Ser Ala Thr
    675                 680                 685

Ile Ala Thr Phe Glu Met Arg Tyr Leu Gln Ser Leu Pro Ala His Leu
690                 695                 700

Arg Pro Gly Leu Asp Glu Leu Ser Phe Thr Leu Thr Gly Asn Pro Asn
705                 710                 715                 720

Arg Pro Asp Gly Gly Ile Leu Thr Arg Phe Gly Phe Ser Ile Pro Gln
            725                 730                 735

Leu Gly Phe Thr Leu Ser Gly Ala Thr Pro Ala Asp Ala Tyr Pro Thr
        740                 745                 750

Val Asp Tyr Ala Phe Gln Tyr Asp Gly Val Asn Asp Phe Pro Lys Tyr
    755                 760                 765

Pro Leu Asn Val Phe Ala Thr Ala Asn Ala Ile Ala Gly Ile Leu Phe
770                 775                 780

Leu His Ser Gly Leu Ile Ala Leu Pro Pro Asp Leu Ala Ser Gly Val
785                 790                 795                 800

Val Gln Pro Val Ser Ser Pro Asp Val Leu Thr Thr Tyr Ile Leu Leu
            805                 810                 815

Pro Ser Gln Asp Leu Pro Leu Leu Val Pro Leu Arg Ala Ile Pro Leu
        820                 825                 830

Leu Gly Asn Pro Leu Ala Asp Leu Ile Gln Pro Asp Leu Arg Val Leu
    835                 840                 845

Val Glu Leu Gly Tyr Asp Arg Thr Ala His Gln Asp Val Pro Ser Pro
850                 855                 860

Phe Gly Leu Phe Pro Asp Val Asp Trp Ala Glu Val Ala Ala Asp Leu
865                 870                 875                 880

Gln Gln Gly Ala Val Gln Gly Val Asn Asp Ala Leu Ser Gly Leu Gly
            885                 890                 895

Leu Pro Pro Pro Trp Gln Pro Ala Leu Pro Arg Leu Phe Ser Thr
        900                 905                 910

<210> SEQ ID NO 2
<211> LENGTH: 891
<212> TYPE: PRT
<213> ORGANISM: Artificial Sequence
<220> FEATURE:
<223> OTHER INFORMATION: Synthetic Construct

<400> SEQUENCE: 2

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

-continued

```
Asn Met Ala Gln Thr Asp Ser Ala Val Gly Ser Ser Trp Ala Gly Thr
                85                  90                  95
His Leu Ala Asn Gly Ser Met Ser Glu Val Met Met Ser Glu Ile Ala
            100                 105                 110
Gly Leu Pro Ile Pro Pro Ile Ile His Tyr Gly Ala Ile Ala Tyr Ala
            115                 120                 125
Pro Ser Gly Ala Ser Gly Lys Ala Trp His Gln Arg Thr Pro Ala Arg
            130                 135                 140
Ala Glu Gln Val Ala Leu Glu Lys Cys Gly Asp Lys Thr Cys Lys Val
145                 150                 155                 160
Val Ser Arg Phe Thr Arg Cys Gly Ala Val Ala Tyr Asn Gly Ser Lys
                165                 170                 175
Tyr Gln Gly Gly Thr Gly Leu Thr Arg Arg Ala Ala Glu Asp Asp Ala
            180                 185                 190
Val Asn Arg Leu Glu Gly Gly Arg Ile Val Asn Trp Ala Cys Asn Glu
            195                 200                 205
Leu Met Thr Ser Arg Phe Met Thr Asp Pro His Ala Met Arg Asp Met
            210                 215                 220
Ala Gly Arg Phe Glu Val His Ala Gln Thr Val Glu Asp Glu Ala Arg
225                 230                 235                 240
Arg Met Trp Ala Ser Ala Gln Asn Ile Ser Gly Ala Gly Trp Ser Gly
                245                 250                 255
Met Ala Glu Ala Thr Ser Leu Asp Thr Met Thr Gln Met Asn Gln Ala
            260                 265                 270
Phe Arg Asn Ile Val Asn Met Leu His Gly Val Arg Asp Gly Leu Val
            275                 280                 285
Arg Asp Ala Asn Asn Tyr Glu Gln Gln Glu Gln Ala Ser Gln Gln Ile
            290                 295                 300
Leu Ser Ser Val Asp Ile Asn Phe Ala Val Leu Pro Pro Glu Val Asn
305                 310                 315                 320
Ser Ala Arg Ile Phe Ala Gly Ala Gly Leu Gly Pro Met Leu Ala Ala
                325                 330                 335
Ala Ser Ala Trp Asp Gly Leu Ala Glu Glu Leu His Ala Ala Ala Gly
            340                 345                 350
Ser Phe Ala Ser Val Thr Thr Gly Leu Ala Gly Asp Ala Trp His Gly
            355                 360                 365
Pro Ala Ser Leu Ala Met Thr Arg Ala Ala Ser Pro Tyr Val Gly Trp
            370                 375                 380
Leu Asn Thr Ala Ala Gly Gln Ala Ala Gln Ala Gly Gln Ala Arg
385                 390                 395                 400
Leu Ala Ala Ser Ala Phe Glu Ala Thr Leu Ala Ala Thr Val Ser Pro
                405                 410                 415
Ala Met Val Ala Ala Asn Arg Thr Arg Leu Ala Ser Leu Val Ala Ala
            420                 425                 430
Asn Leu Leu Gly Gln Asn Ala Pro Ala Ile Ala Ala Glu Ala Glu
            435                 440                 445
Tyr Glu Gln Ile Trp Ala Gln Asp Val Ala Ala Met Phe Gly Tyr His
            450                 455                 460
Ser Ala Ala Ser Ala Val Ala Thr Gln Leu Ala Pro Ile Gln Glu Gly
465                 470                 475                 480
Leu Gln Gln Gln Leu Gln Asn Val Leu Ala Gln Leu Ala Ser Gly Asn
                485                 490                 495
```

```
Leu Gly Ser Gly Asn Val Gly Val Gly Asn Ile Gly Asn Asp Asn Ile
                500                 505                 510

Gly Asn Ala Asn Ile Gly Phe Gly Asn Arg Gly Asp Ala Asn Ile Gly
            515                 520                 525

Ile Gly Asn Ile Gly Asp Arg Asn Leu Gly Ile Gly Asn Thr Gly Asn
        530                 535                 540

Trp Asn Ile Gly Ile Gly Ile Thr Gly Asn Gly Gln Ile Gly Phe Gly
545                 550                 555                 560

Lys Pro Ala Asn Pro Asp Val Leu Val Val Gly Asn Gly Gly Pro Gly
                565                 570                 575

Val Thr Ala Leu Val Met Gly Gly Thr Asp Ser Leu Leu Pro Leu Pro
            580                 585                 590

Asn Ile Pro Leu Leu Glu Tyr Ala Ala Arg Phe Ile Thr Pro Val His
        595                 600                 605

Pro Gly Tyr Thr Ala Thr Phe Leu Glu Thr Pro Ser Gln Phe Phe Pro
    610                 615                 620

Phe Thr Gly Leu Asn Ser Leu Thr Tyr Asp Val Ser Val Ala Gln Gly
625                 630                 635                 640

Val Thr Asn Leu His Thr Ala Ile Met Ala Gln Leu Ala Ala Gly Asn
                645                 650                 655

Glu Val Val Phe Gly Thr Ser Gln Ser Ala Thr Ile Ala Thr Phe
            660                 665                 670

Glu Met Arg Tyr Leu Gln Ser Leu Pro Ala His Leu Arg Pro Gly Leu
        675                 680                 685

Asp Glu Leu Ser Phe Thr Leu Thr Gly Asn Pro Asn Arg Pro Asp Gly
    690                 695                 700

Gly Ile Leu Thr Arg Phe Gly Phe Ser Ile Pro Gln Leu Gly Phe Thr
705                 710                 715                 720

Leu Ser Gly Ala Thr Pro Ala Asp Ala Tyr Pro Thr Val Asp Tyr Ala
                725                 730                 735

Phe Gln Tyr Asp Gly Val Asn Asp Phe Pro Lys Tyr Pro Leu Asn Val
            740                 745                 750

Phe Ala Thr Ala Asn Ala Ile Ala Gly Ile Leu Phe Leu His Ser Gly
        755                 760                 765

Leu Ile Ala Leu Pro Pro Asp Leu Ala Ser Gly Val Val Gln Pro Val
    770                 775                 780

Ser Ser Pro Asp Val Leu Thr Thr Tyr Ile Leu Leu Pro Ser Gln Asp
785                 790                 795                 800

Leu Pro Leu Leu Val Pro Leu Arg Ala Ile Pro Leu Leu Gly Asn Pro
                805                 810                 815

Leu Ala Asp Leu Ile Gln Pro Asp Leu Arg Val Leu Val Glu Leu Gly
            820                 825                 830

Tyr Asp Arg Thr Ala His Gln Asp Val Pro Ser Pro Phe Gly Leu Phe
        835                 840                 845

Pro Asp Val Asp Trp Ala Glu Val Ala Ala Asp Leu Gln Gln Gly Ala
    850                 855                 860

Val Gln Gly Val Asn Asp Ala Leu Ser Gly Leu Gly Leu Pro Pro
865                 870                 875                 880

Trp Gln Pro Ala Leu Pro Arg Leu Phe Ser Thr
                885                 890

<210> SEQ ID NO 3
<211> LENGTH: 818
<212> TYPE: PRT
```

<213> ORGANISM: Artificial Sequence
<220> FEATURE:
<223> OTHER INFORMATION: Synthetic Construct

<400> SEQUENCE: 3

```
Met Gly Ser Ser His His His His His His Ser Ser Gly Leu Val Pro
1               5                   10                  15

Arg Gly Ser His Met Gly Thr His Leu Ala Asn Gly Ser Met Ser Glu
            20                  25                  30

Val Met Met Ser Glu Ile Ala Gly Leu Pro Ile Pro Ile Ile His
        35                  40                  45

Tyr Gly Ala Ile Ala Tyr Ala Pro Ser Gly Ala Ser Gly Lys Ala Trp
    50                  55                  60

His Gln Arg Thr Pro Ala Arg Ala Glu Gln Val Ala Leu Glu Lys Cys
65              70                  75                  80

Gly Asp Lys Thr Cys Lys Val Val Ser Arg Phe Thr Arg Cys Gly Ala
                85                  90                  95

Val Ala Tyr Asn Gly Ser Lys Tyr Gln Gly Gly Thr Gly Leu Thr Arg
            100                 105                 110

Arg Ala Ala Glu Asp Asp Ala Val Asn Arg Leu Glu Gly Gly Arg Ile
            115                 120                 125

Val Asn Trp Ala Cys Asn Glu Leu Met Thr Ser Arg Phe Met Thr Asp
130                 135                 140

Pro His Ala Met Arg Asp Met Ala Gly Arg Phe Glu Val His Ala Gln
145                 150                 155                 160

Thr Val Glu Asp Glu Ala Arg Arg Met Trp Ala Ser Ala Gln Asn Ile
                165                 170                 175

Ser Gly Ala Gly Trp Ser Gly Met Ala Glu Ala Thr Ser Leu Asp Thr
            180                 185                 190

Met Thr Gln Met Asn Gln Ala Phe Arg Asn Ile Val Asn Met Leu His
            195                 200                 205

Gly Val Arg Asp Gly Leu Val Arg Asp Ala Asn Asn Tyr Glu Gln Gln
            210                 215                 220

Glu Gln Ala Ser Gln Gln Ile Leu Ser Ser Val Asp Ile Asn Phe Ala
225                 230                 235                 240

Val Leu Pro Pro Glu Val Asn Ser Ala Arg Ile Phe Ala Gly Ala Gly
                245                 250                 255

Leu Gly Pro Met Leu Ala Ala Ala Ser Ala Trp Asp Gly Leu Ala Glu
            260                 265                 270

Glu Leu His Ala Ala Gly Ser Phe Ala Ser Val Thr Thr Gly Leu
            275                 280                 285

Ala Gly Asp Ala Trp His Gly Pro Ala Ser Leu Ala Met Thr Arg Ala
            290                 295                 300

Ala Ser Pro Tyr Val Gly Trp Leu Asn Thr Ala Ala Gly Gln Ala Ala
305                 310                 315                 320

Gln Ala Ala Gly Gln Ala Arg Leu Ala Ala Ser Ala Phe Glu Ala Thr
                325                 330                 335

Leu Ala Ala Thr Val Ser Pro Ala Met Val Ala Ala Asn Arg Thr Arg
            340                 345                 350

Leu Ala Ser Leu Val Ala Ala Asn Leu Leu Gly Gln Asn Ala Pro Ala
            355                 360                 365

Ile Ala Ala Ala Glu Ala Glu Tyr Glu Gln Ile Trp Ala Gln Asp Val
            370                 375                 380
```

```
Ala Ala Met Phe Gly Tyr His Ser Ala Ala Ser Ala Val Ala Thr Gln
385                 390                 395                 400

Leu Ala Pro Ile Gln Glu Gly Leu Gln Gln Gln Leu Gln Asn Val Leu
            405                 410                 415

Ala Gln Leu Ala Ser Gly Asn Leu Gly Ser Gly Asn Val Gly Val Gly
        420                 425                 430

Asn Ile Gly Asn Asp Asn Ile Gly Asn Ala Asn Ile Gly Phe Gly Asn
            435                 440                 445

Arg Gly Asp Ala Asn Ile Gly Ile Gly Asn Ile Gly Asp Arg Asn Leu
        450                 455                 460

Gly Ile Gly Asn Thr Gly Asn Trp Asn Ile Gly Ile Gly Ile Thr Gly
465                 470                 475                 480

Asn Gly Gln Ile Gly Phe Gly Lys Pro Ala Asn Pro Asp Val Leu Val
            485                 490                 495

Val Gly Asn Gly Gly Pro Gly Val Thr Ala Leu Val Met Gly Gly Thr
        500                 505                 510

Asp Ser Leu Leu Pro Leu Pro Asn Ile Pro Leu Leu Glu Tyr Ala Ala
        515                 520                 525

Arg Phe Ile Thr Pro Val His Pro Gly Tyr Thr Ala Thr Phe Leu Glu
        530                 535                 540

Thr Pro Ser Gln Phe Phe Pro Phe Thr Gly Leu Asn Ser Leu Thr Tyr
545                 550                 555                 560

Asp Val Ser Val Ala Gln Gly Val Thr Asn Leu His Thr Ala Ile Met
            565                 570                 575

Ala Gln Leu Ala Ala Gly Asn Glu Val Val Phe Gly Thr Ser Gln
        580                 585                 590

Ser Ala Thr Ile Ala Thr Phe Glu Met Arg Tyr Leu Gln Ser Leu Pro
        595                 600                 605

Ala His Leu Arg Pro Gly Leu Asp Glu Leu Ser Phe Thr Leu Thr Gly
        610                 615                 620

Asn Pro Asn Arg Pro Asp Gly Gly Ile Leu Thr Arg Phe Gly Phe Ser
625                 630                 635                 640

Ile Pro Gln Leu Gly Phe Thr Leu Ser Gly Ala Thr Pro Ala Asp Ala
            645                 650                 655

Tyr Pro Thr Val Asp Tyr Ala Phe Gln Tyr Asp Gly Val Asn Asp Phe
            660                 665                 670

Pro Lys Tyr Pro Leu Asn Val Phe Ala Thr Ala Asn Ala Ile Ala Gly
        675                 680                 685

Ile Leu Phe Leu His Ser Gly Leu Ile Ala Leu Pro Pro Asp Leu Ala
        690                 695                 700

Ser Gly Val Val Gln Pro Val Ser Ser Pro Asp Val Leu Thr Thr Tyr
705                 710                 715                 720

Ile Leu Leu Pro Ser Gln Asp Leu Pro Leu Leu Val Pro Leu Arg Ala
            725                 730                 735

Ile Pro Leu Leu Gly Asn Pro Leu Ala Asp Leu Ile Gln Pro Asp Leu
            740                 745                 750

Arg Val Leu Val Glu Leu Gly Tyr Asp Arg Thr Ala His Gln Asp Val
        755                 760                 765

Pro Ser Pro Phe Gly Leu Phe Pro Asp Val Asp Trp Ala Glu Val Ala
        770                 775                 780

Ala Asp Leu Gln Gln Gly Ala Val Gln Gly Val Asn Asp Ala Leu Ser
785                 790                 795                 800
```

-continued

Gly Leu Gly Leu Pro Pro Trp Gln Pro Ala Leu Pro Arg Leu Phe
                805                 810                 815

Ser Thr

<210> SEQ ID NO 4
<211> LENGTH: 795
<212> TYPE: PRT
<213> ORGANISM: Artificial Sequence
<220> FEATURE:
<223> OTHER INFORMATION: Synthetic Construct

<400> SEQUENCE: 4

His Leu Ala Asn Gly Ser Met Ser Glu Val Met Met Ser Glu Ile Ala
1               5                   10                  15

Gly Leu Pro Ile Pro Pro Ile Ile His Tyr Gly Ala Ile Ala Tyr Ala
            20                  25                  30

Pro Ser Gly Ala Ser Gly Lys Ala Trp His Gln Arg Thr Pro Ala Arg
        35                  40                  45

Ala Glu Gln Val Ala Leu Glu Lys Cys Gly Asp Lys Thr Cys Lys Val
    50                  55                  60

Val Ser Arg Phe Thr Arg Cys Gly Ala Val Ala Tyr Asn Gly Ser Lys
65                  70                  75                  80

Tyr Gln Gly Gly Thr Gly Leu Thr Arg Arg Ala Ala Glu Asp Asp Ala
                85                  90                  95

Val Asn Arg Leu Glu Gly Gly Arg Ile Val Asn Trp Ala Cys Asn Glu
            100                 105                 110

Leu Met Thr Ser Arg Phe Met Thr Asp Pro His Ala Met Arg Asp Met
        115                 120                 125

Ala Gly Arg Phe Glu Val His Ala Gln Thr Val Glu Asp Glu Ala Arg
    130                 135                 140

Arg Met Trp Ala Ser Ala Gln Asn Ile Ser Gly Ala Gly Trp Ser Gly
145                 150                 155                 160

Met Ala Glu Ala Thr Ser Leu Asp Thr Met Thr Gln Met Asn Gln Ala
                165                 170                 175

Phe Arg Asn Ile Val Asn Met Leu His Gly Val Arg Asp Gly Leu Val
            180                 185                 190

Arg Asp Ala Asn Asn Tyr Glu Gln Gln Glu Gln Ala Ser Gln Gln Ile
        195                 200                 205

Leu Ser Ser Val Asp Ile Asn Phe Ala Val Leu Pro Pro Glu Val Asn
    210                 215                 220

Ser Ala Arg Ile Phe Ala Gly Ala Gly Leu Gly Pro Met Leu Ala Ala
225                 230                 235                 240

Ala Ser Ala Trp Asp Gly Leu Ala Glu Glu Leu His Ala Ala Ala Gly
                245                 250                 255

Ser Phe Ala Ser Val Thr Thr Gly Leu Ala Gly Asp Ala Trp His Gly
            260                 265                 270

Pro Ala Ser Leu Ala Met Thr Arg Ala Ala Ser Pro Tyr Val Gly Trp
        275                 280                 285

Leu Asn Thr Ala Ala Gly Gln Ala Ala Gln Ala Gly Gln Ala Arg
    290                 295                 300

Leu Ala Ala Ser Ala Phe Glu Ala Thr Leu Ala Ala Thr Val Ser Pro
305                 310                 315                 320

Ala Met Val Ala Ala Asn Arg Thr Arg Leu Ala Ser Leu Val Ala Ala
                325                 330                 335

-continued

Asn Leu Leu Gly Gln Asn Ala Pro Ala Ile Ala Ala Glu Ala Glu
                340                 345                 350

Tyr Glu Gln Ile Trp Ala Gln Asp Val Ala Ala Met Phe Gly Tyr His
                355                 360                 365

Ser Ala Ala Ser Ala Val Ala Thr Gln Leu Ala Pro Ile Gln Glu Gly
                370                 375                 380

Leu Gln Gln Gln Leu Gln Asn Val Leu Ala Gln Leu Ala Ser Gly Asn
385                 390                 395                 400

Leu Gly Ser Gly Asn Val Gly Val Gly Asn Ile Gly Asn Asp Asn Ile
                405                 410                 415

Gly Asn Ala Asn Ile Gly Phe Gly Asn Arg Gly Asp Ala Asn Ile Gly
                420                 425                 430

Ile Gly Asn Ile Gly Asp Arg Asn Leu Gly Ile Gly Asn Thr Gly Asn
                435                 440                 445

Trp Asn Ile Gly Ile Gly Ile Thr Gly Asn Gly Gln Ile Gly Phe Gly
                450                 455                 460

Lys Pro Ala Asn Pro Asp Val Leu Val Val Gly Asn Gly Gly Pro Gly
465                 470                 475                 480

Val Thr Ala Leu Val Met Gly Gly Thr Asp Ser Leu Leu Pro Leu Pro
                485                 490                 495

Asn Ile Pro Leu Leu Glu Tyr Ala Ala Arg Phe Ile Thr Pro Val His
                500                 505                 510

Pro Gly Tyr Thr Ala Thr Phe Leu Glu Thr Pro Ser Gln Phe Phe Pro
                515                 520                 525

Phe Thr Gly Leu Asn Ser Leu Thr Tyr Asp Val Ser Val Ala Gln Gly
                530                 535                 540

Val Thr Asn Leu His Thr Ala Ile Met Ala Gln Leu Ala Ala Gly Asn
545                 550                 555                 560

Glu Val Val Phe Gly Thr Ser Gln Ser Ala Thr Ile Ala Thr Phe
                565                 570                 575

Glu Met Arg Tyr Leu Gln Ser Leu Pro Ala His Leu Arg Pro Gly Leu
                580                 585                 590

Asp Glu Leu Ser Phe Thr Leu Thr Gly Asn Pro Asn Arg Pro Asp Gly
                595                 600                 605

Gly Ile Leu Thr Arg Phe Gly Phe Ser Ile Pro Gln Leu Gly Phe Thr
                610                 615                 620

Leu Ser Gly Ala Thr Pro Ala Asp Ala Tyr Pro Thr Val Asp Tyr Ala
625                 630                 635                 640

Phe Gln Tyr Asp Gly Val Asn Asp Phe Pro Lys Tyr Pro Leu Asn Val
                645                 650                 655

Phe Ala Thr Ala Asn Ala Ile Ala Gly Ile Leu Phe Leu His Ser Gly
                660                 665                 670

Leu Ile Ala Leu Pro Pro Asp Leu Ala Ser Gly Val Val Gln Pro Val
                675                 680                 685

Ser Ser Pro Asp Val Leu Thr Thr Tyr Ile Leu Leu Pro Ser Gln Asp
                690                 695                 700

Leu Pro Leu Leu Val Pro Leu Arg Ala Ile Pro Leu Leu Gly Asn Pro
705                 710                 715                 720

Leu Ala Asp Leu Ile Gln Pro Asp Leu Arg Val Leu Val Glu Leu Gly
                725                 730                 735

Tyr Asp Arg Thr Ala His Gln Asp Val Pro Ser Pro Phe Gly Leu Phe
                740                 745                 750

```
Pro Asp Val Asp Trp Ala Glu Val Ala Ala Asp Leu Gln Gly Ala
            755                 760                 765

Val Gln Gly Val Asn Asp Ala Leu Ser Gly Leu Gly Leu Pro Pro
        770                 775                 780

Trp Gln Pro Ala Leu Pro Arg Leu Phe Ser Thr
785                 790                 795

<210> SEQ ID NO 5
<211> LENGTH: 143
<212> TYPE: PRT
<213> ORGANISM: Mycobacterium tuberculosis

<400> SEQUENCE: 5

Met Ile Thr Asn Leu Arg Arg Arg Thr Ala Met Ala Ala Ala Gly Leu
1               5                   10                  15

Gly Ala Ala Leu Gly Leu Gly Ile Leu Leu Val Pro Thr Val Asp Ala
            20                  25                  30

His Leu Ala Asn Gly Ser Met Ser Glu Val Met Met Ser Glu Ile Ala
        35                  40                  45

Gly Leu Pro Ile Pro Pro Ile Ile His Tyr Gly Ala Ile Ala Tyr Ala
    50                  55                  60

Pro Ser Gly Ala Ser Gly Lys Ala Trp His Gln Arg Thr Pro Ala Arg
65                  70                  75                  80

Ala Glu Gln Val Ala Leu Glu Lys Cys Gly Asp Lys Thr Cys Lys Val
                85                  90                  95

Val Ser Arg Phe Thr Arg Cys Gly Ala Val Ala Tyr Asn Gly Ser Lys
            100                 105                 110

Tyr Gln Gly Gly Thr Gly Leu Thr Arg Arg Ala Ala Glu Asp Asp Ala
        115                 120                 125

Val Asn Arg Leu Glu Gly Gly Arg Ile Val Asn Trp Ala Cys Asn
    130                 135                 140

<210> SEQ ID NO 6
<211> LENGTH: 98
<212> TYPE: PRT
<213> ORGANISM: Mycobacterium tuberculosis

<400> SEQUENCE: 6

Met Thr Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 7
<211> LENGTH: 580
<212> TYPE: PRT
<213> ORGANISM: Mycobacterium tuberculosis
```

<400> SEQUENCE: 7

| | | | | | | | | | | | | | | |
|---|---|---|---|---|---|---|---|---|---|---|---|---|---|---|
|Met|Asn|Phe|Ala|Val|Leu|Pro|Pro|Glu|Val|Asn|Ser|Ala|Arg|Ile|Phe|
|1| | | |5| | | | |10| | | | |15| |

Ala Gly Ala Gly Leu Gly Pro Met Leu Ala Ala Ala Ser Ala Trp Asp
            20              25              30

Gly Leu Ala Glu Glu Leu His Ala Ala Gly Ser Phe Ala Ser Val
            35              40              45

Thr Thr Gly Leu Ala Gly Asp Ala Trp His Pro Ala Ser Leu Ala
50                55              60

Met Thr Arg Ala Ala Ser Pro Tyr Val Gly Trp Leu Asn Thr Ala Ala
65              70              75            80

Gly Gln Ala Ala Gln Ala Ala Gly Gln Ala Arg Leu Ala Ala Ser Ala
            85              90              95

Phe Glu Ala Thr Leu Ala Ala Thr Val Ser Pro Ala Met Val Ala Ala
            100           105          110

Asn Arg Thr Arg Leu Ala Ser Leu Val Ala Ala Asn Leu Leu Gly Gln
            115           120          125

Asn Ala Pro Ala Ile Ala Ala Ala Glu Ala Glu Tyr Glu Gln Ile Trp
130               135          140

Ala Gln Asp Val Ala Ala Met Phe Gly Tyr His Ser Ala Ala Ser Ala
145               150          155          160

Val Ala Thr Gln Leu Ala Pro Ile Gln Glu Gly Leu Gln Gln Leu
            165           170          175

Gln Asn Val Leu Ala Gln Leu Ala Ser Gly Asn Leu Gly Ser Gly Asn
            180           185          190

Val Gly Val Gly Asn Ile Gly Asn Asp Asn Ile Gly Asn Ala Asn Ile
            195           200          205

Gly Phe Gly Asn Arg Gly Asp Ala Asn Ile Gly Ile Gly Asn Ile Gly
            210           215          220

Asp Arg Asn Leu Gly Ile Gly Asn Thr Gly Asn Trp Asn Ile Gly Ile
225               230          235          240

Gly Ile Thr Gly Asn Gly Gln Ile Gly Phe Gly Lys Pro Ala Asn Pro
            245           250          255

Asp Val Leu Val Val Gly Asn Gly Gly Pro Gly Val Thr Ala Leu Val
            260           265          270

Met Gly Gly Thr Asp Ser Leu Leu Pro Leu Pro Asn Ile Pro Leu Leu
            275           280          285

Glu Tyr Ala Ala Arg Phe Ile Thr Pro Val His Pro Gly Tyr Thr Ala
            290           295          300

Thr Phe Leu Glu Thr Pro Ser Gln Phe Phe Pro Phe Thr Gly Leu Asn
305               310          315          320

Ser Leu Thr Tyr Asp Val Ser Val Ala Gln Gly Val Thr Asn Leu His
            325           330          335

Thr Ala Ile Met Ala Gln Leu Ala Ala Gly Asn Glu Val Val Phe
            340           345          350

Gly Thr Ser Gln Ser Ala Thr Ile Ala Thr Phe Glu Met Arg Tyr Leu
            355           360          365

```
                                                -continued

Gln Ser Leu Pro Ala His Leu Arg Pro Gly Leu Asp Glu Leu Ser Phe
        370                 375                 380

Thr Leu Thr Gly Asn Pro Asn Arg Pro Asp Gly Ile Leu Thr Arg
385                 390                 395                 400

Phe Gly Phe Ser Ile Pro Gln Leu Gly Phe Thr Leu Ser Gly Ala Thr
                405                 410                 415

Pro Ala Asp Ala Tyr Pro Thr Val Asp Tyr Ala Phe Gln Tyr Asp Gly
            420                 425                 430

Val Asn Asp Phe Pro Lys Tyr Pro Leu Asn Val Phe Ala Thr Ala Asn
            435                 440                 445

Ala Ile Ala Gly Ile Leu Phe Leu His Ser Gly Leu Ile Ala Leu Pro
        450                 455                 460

Pro Asp Leu Ala Ser Gly Val Val Gln Pro Val Ser Ser Pro Asp Val
465                 470                 475                 480

Leu Thr Thr Tyr Ile Leu Leu Pro Ser Gln Asp Leu Pro Leu Leu Val
                485                 490                 495

Pro Leu Arg Ala Ile Pro Leu Leu Gly Asn Pro Leu Ala Asp Leu Ile
            500                 505                 510

Gln Pro Asp Leu Arg Val Leu Val Glu Leu Gly Tyr Asp Arg Thr Ala
        515                 520                 525

His Gln Asp Val Pro Ser Pro Phe Gly Leu Phe Pro Asp Val Asp Trp
        530                 535                 540

Ala Glu Val Ala Ala Asp Leu Gln Gln Gly Ala Val Gln Gly Val Asn
545                 550                 555                 560

Asp Ala Leu Ser Gly Leu Gly Leu Pro Pro Pro Trp Gln Pro Ala Leu
                565                 570                 575

Pro Arg Leu Phe
            580

<210> SEQ ID NO 8
<211> LENGTH: 94
<212> TYPE: PRT
<213> ORGANISM: Mycobacterium tuberculosis

<400> SEQUENCE: 8

Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

SINGLE VIAL VACCINE FORMULATIONS

CROSS-REFERENCE TO RELATED PATENT APPLICATIONS

This application is a National Phase filing under 35 U.S.C. § 371 of International Application No. Application No.: PCT/US2014/072615, filed Dec. 29, 2014, which claims the priority benefit of U.S. Provisional Application Ser. No. 61/922,761, filed Dec. 31, 2013, which are incorporated herein by reference in their; entirety.

SEQUENCE LISTING

The Sequence Listing associated with this application is provided in text format in lieu of a paper copy and is hereby incorporated by reference into the specification. The name of the text file containing the Sequence Listing is 30-11S-00_Sequence_Listing_ST 25.txt. The text file is 36,625 bytes, was created on Mar. 9, 2023, and is submitted through the USPTO electronic filing system.

FIELD OF THE INVENTION

The present invention relates generally to the fields of pharmaceutical and vaccine formulations.

BACKGROUND OF THE INVENTION

Next-generation rationally-designed vaccine adjuvants represent a significant breakthrough in the development of vaccines against challenging diseases including tuberculosis, HIV, and malaria. However these new adjuvants also require maintenance of a cold-chain process to ensure long-term stability. This presents a significant financial and technological barrier to worldwide implementation of such vaccines. Additionally, cold-chain maintenance cannot be ensured during natural disasters when power supplies may be compromised. Lyophilization of protein-containing pharmaceuticals such as vaccines is a commonly employed method to prolong shelf-life and increase resistance to thermal stress (Kasper et al., 2013, Eur J Pharm Biopharm. 2013 October; 85(2):162-9; Wang et al, Int J Pharm, 203: 1-60), and multiple marketed vaccines are distributed as lyophilized products (PATH, and Working in Tandem Ltd, 2012, Summary of stability data for licensed vaccines, Seattle, Wash.). New vaccines under development for complex cell immunity-mediated diseases such as malaria or tuberculosis may require adjuvant components in order to enhance and shape immune responses effectively (Reed et al., 2009, Trends Immunol, 30:23-32). However, the addition of adjuvant(s) to a vaccine antigen results in a more complex formulation with the potential for multiple interactions among components. Thus, maintaining long-term stability in adjuvanted vaccines can present a significant challenge to vaccine developers. For this reason, some adjuvanted vaccines are administered following bedside-mixing with a separate adjuvant vial (US Food and Drug Administration, 2012, Vaccines and Related Biological Products Advisory Committee Meeting). Moreover, none of the existing marketed lyophilized vaccines contain adjuvant in the lyophilized formulation (PATH, and Working in Tandem Ltd, 2012, Summary of stability data for licensed vaccines, Seattle, Wash.). Indeed, adjuvant formulations already used in approved human vaccines such as aluminum salts or oil-in-water emulsions may be particularly challenging to lyophilize (Clausi et al, 2008, J Pharm Sci, 97:2049-2061; Rossi et al., 2007, Role of Lipid Excipients in Modifying Oral and Parenteral Drug Delivery: Basic Principles and Biological Examples, pp 88-123, John Wiley & Sons, Inc., Hoboken N.J.). Although lyophilization of protein, live-attenuated or inactivated virus or bacteria-containing vaccines is a routine practice, to date there have been no reports of successful lyophilization and thermostability characterization of an adjuvanted clinical vaccine candidate (PATH, and Working in Tandem Ltd, 2012, Summary of stability data for licensed vaccines, Seattle, Wash.). Lyophilization of protective antigen of anthrax in a squalene emulsion has been reported; however, a description of the thermostability and a biophysical characterization of the reconstituted system were not included (Ivins et al., 1995, Vaccine, 13:1779-1784). The complex nature of clinical approved vaccine adjuvants (e.g., alum, oil-in-water emulsions and/or monophosphoryl lipid A (MPLA) present a substantial hurdle to developing lyophilized adjuvanted vaccines.

Development of adjuvanted vaccines that do not require cold-chain maintenance would significantly reduce the cost and technological hurdles of implementation of new vaccines worldwide, especially in low resource settings. Accordingly, there is a need for thermostable adjuvanted vaccines that are chemically stable at sustained temperatures and that retain the ability to elicit an immune response against the vaccine antigen. As described herein, the present invention meets these needs and offers other related advantages.

All publications, patents, and patent applications cited herein are hereby incorporated by reference in their entirety for all purposes.

BRIEF SUMMARY OF THE INVENTION

In one aspect, provided herein is a thermostable lyophilized vaccine composition comprising a metabolizable oil and a cake-forming excipient, wherein the composition is in the form of a cake and forms an oil-in-water emulsion upon reconstitution, and wherein the cake-forming excipient is (1) a combination of mannitol and a saccharide selected from the group consisting of trehalose, dextrose, lactose, maltose, sucrose, raffinose, mannose, fructose, and lactulose; or (2) a saccharide selected from the group consisting of trehalose, lactose, raffinose, and lactulose. In some embodiments, the composition further comprises an antigen and/or an adjuvant.

In one aspect, provided herein is a thermostable lyophilized vaccine composition comprising an effective amount of an antigen, a metabolizable oil, and a cake-forming excipient, wherein the composition is in the form of a cake and forms an oil-in-water emulsion upon reconstitution, and wherein the cake-forming excipient is (1) a combination of mannitol and a saccharide selected from the group consisting of trehalose, dextrose, lactose, maltose, sucrose, raffinose, mannose, fructose, and lactulose; or (2) a saccharide selected from the group consisting of trehalose, lactose, raffinose, and lactulose. In some embodiments, the composition further comprises an adjuvant.

In another aspect, provided herein is a thermostable lyophilized vaccine composition comprising an effective amount of an adjuvant, a metabolizable oil, and a cake-forming excipient, wherein the composition is in the form of a cake and forms an oil-in-water emulsion upon reconstitution, and wherein the cake-forming excipient is (1) a combination of mannitol and a saccharide selected from the group consisting of trehalose, dextrose, lactose, maltose, sucrose, raffinose, mannose, fructose, and lactulose; or (2) a saccharide selected from the group consisting of trehalose, lactose, raffinose, and lactulose. In some embodiments, the composition further comprises an antigen.

In some embodiments of the compositions described herein, the cake-forming excipient is a saccharide selected from the group consisting of lactose, raffinose, and lactulose.

In some embodiments of the compositions described herein, the cake-forming excipient is a combination of mannitol and a saccharide selected from the group consisting of trehalose, dextrose, lactose, maltose, sucrose, raffinose, mannose, fructose, and lactulose.

In some embodiments of the compositions described herein, the composition is formed by lyophilization of an oil-in water emulsion formulation, and the oil-in water emulsion formulation comprises less than or about 1% (w/v) glycerol.

In some embodiments of the compositions described herein, the oil-in water emulsion formulation comprises less than or about 0.5% (w/v) glycerol.

In some embodiments of the compositions described herein, the oil-in water emulsion formulation does not comprise glycerol.

In some embodiments of the compositions described herein, the composition is formed by lyophilization of an oil-in water emulsion formulation, and wherein the cake-forming excipient is trehalose which is at a concentration of about 10% (w/v) in the oil-in water emulsion formulation.

In some embodiments of the compositions described herein, the composition is formed by lyophilization of an oil-in water emulsion formulation, and wherein the cake-forming excipient is trehalose which is at a concentration of about 5% (w/v) in the oil-in water emulsion formulation.

In some embodiments of the compositions described herein, the composition is formed by lyophilization of an oil-in water emulsion formulation, wherein the cake-forming excipient is a combination of mannitol and trehalose, wherein the mannitol in the oil-in water emulsion formulation is at a concentration of about 0.1% (w/v) and trehalose in the oil-in water emulsion formulation is at a concentration of about 5% (w/v) in the oil-in water emulsion formulation.

In some embodiments of the compositions described herein, the composition is formed by lyophilization of an oil-in water emulsion formulation, wherein the cake-forming excipient is a combination of mannitol and trehalose, and wherein the mannitol in the oil-in water emulsion formulation is at a concentration of about 2.5% (w/v) and trehalose in the oil-in water emulsion formulation is at a concentration of about 2.5% (w/v).

In some embodiments of the compositions described herein, the oil-in water emulsion formulation does not comprise glycerol.

In some embodiments of the compositions described herein, the composition is thermostable at a temperature between about 8° C. to about 60° C. for at least 1 month.

In some embodiments of the compositions described herein, the composition is thermostable at a temperature between about 8° C. to about 60° C. for at least 3 months.

In some embodiments of the compositions described herein, the composition is thermostable at a temperature between about 8° C. to about 60° C. for at least 6 months.

In some embodiments of the compositions described herein, the composition is thermostable at a temperature between about 8° C. to about 60° C. for at least 12 months.

In some embodiments of the compositions described herein, the composition is thermostable at about 25° C. for at least 1 day.

In some embodiments of the compositions described herein, the composition is thermostable at about 25° C. for at least 1 week.

In some embodiments of the compositions described herein, the composition is thermostable at about 25° C. for at least 1 month.

In some embodiments of the compositions described herein, the composition is thermostable at about 37° C. for at least 1 day.

In some embodiments of the compositions described herein, the composition is thermostable at about 37° C. for at least 1 week.

In some embodiments of the compositions described herein, the composition is thermostable at about 37° C. for at least 1 month.

In some embodiments of the compositions described herein, the composition is thermostable at about 50° C. for at least 1 day.

In some embodiments of the compositions described herein, the composition is thermostable at about 50° C. for at least 1 week.

In some embodiments of the compositions described herein, the composition is thermostable at about 50° C. for at least 1 month.

In some embodiments of the compositions described herein, the composition is thermostable at about 30° C. to about 50° C. for at least 1 day, at least 1 week, or at least 1 month.

In some embodiments of the compositions described herein, the composition is in the form of an elegant cake.

In some embodiments of the compositions described herein, the composition is in the form of a cake that does not exhibit browning by visual inspection when stored at any of the temperature and duration conditions described herein.

In some embodiments of the compositions described herein, the thermostability of the composition is determined prior to reconstitution of the lyophilized composition.

In some embodiments of the compositions described herein, the form of a cake and wherein the thermostability is determined by observation of the cake for shrinking, cracking and/or browning.

In some embodiments of the compositions described herein, the thermostability is determined following reconstitution of the lyophilized composition.

In some embodiments of the compositions described herein, the thermostability is determined by inspection of the oil-in-water emulsion formed upon reconstitution for creaming.

In some embodiments of the compositions described herein, the composition is formed by lyophilization of an oil-in water emulsion formulation, and the antigen or adjuvant concentration in the oil-in-water emulsion formed upon reconstitution exhibits no more than or about 25% breakdown of the antigen or adjuvant concentration in the oil-in-water emulsion formulation prior to lyophilization.

In some embodiments of the compositions described herein, thermostability is determined by assay of the components of the oil-in-water emulsion formed upon reconstitution.

In some embodiments of the compositions described herein, the reconstituted emulsion has particle size with Z-average diameter of less than about 200 nm.

In some embodiments of the compositions described herein, the antigen is a polypeptide, a nucleic acid encoding a polypeptide, or a pathogen.

In some embodiments of the compositions described herein, the adjuvant is a metabolizable oil. In some embodiments, the metabolizable oil is squalene, synthetic squalene, grape seed oil, olive oil or a synthetic isoprenoid.

In some embodiments of the compositions described herein, the adjuvant is a TLR4 agonist. In some embodiments, the TLR4 agonist is MPL, 3d-MPL, or synthetic GLA. In some embodiments, the synthetic GLA adjuvant has the following structure:

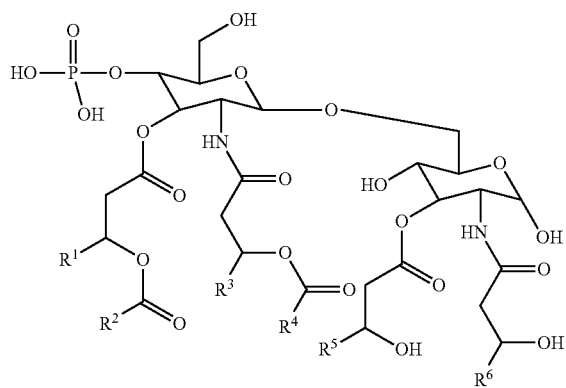

wherein $R^1$, $R^3$, $R^5$ and $R^6$ are $C_{11}$-$C_{20}$ alkyl; and $R^2$ and $R^4$ are $C_9$-$C_{20}$ alkyl. In some embodiments, $R^1$, $R^3$, $R^5$ and $R^6$ are $C_{11}$ alkyl; and $R^2$ and $R^4$ are $C_9$ alkyl.

In some embodiments of the compositions described herein, the metabolizable oil is squalene, mineral oil, grape seed oil, synthetic squalene, or synthetic isoprenoid.

In some embodiments, the composition further comprises 1,2-dimyristoyl-sn-glycero-3-phosphocholine(DMPC), 1-palmitoyl-2-oleoyl-sn-glycerol-3-phsphocholine (POPC), 1,2-dioleoyl-sn-glycero-3-phosphocholine (DOPC), egg PC, lecithin, TWEEN®, or a combination thereof.

In some embodiments, the compositions described herein further comprise a surfactant. In some embodiments, the surfactant is PLURONIC® F68. In some embodiments, the composition further comprises an antioxidant. In some embodiments, the antioxidant is vitamin E.

In another aspect, provided herein is a single vial comprising the thermostable lyophilized vaccine compositions described herein, wherein the composition is contained in the vial.

In another aspect, provided herein is a method of storing the thermostable vaccine compositions described herein comprising storing the compositions at between about 8° C. to about 60° C. or at between about 25° C. to about 60° C. for at least 1 month, wherein the vaccine formulation is thermostable.

In another aspect, provided herein is a method for generating a thermostable lyophilized vaccine composition, comprising the step of lyophilizing an oil-in-water emulsion to form a thermostable lyophilized vaccine composition, wherein the oil-in-water emulsion comprises (1) an antigen, (2) a metabolizable oil, and (3) a cake-forming excipient, wherein the cake-forming excipient is (a) a combination of mannitol and a saccharide selected from the group consisting of trehalose, dextrose, lactose, maltose, sucrose, raffinose, mannose, fructose, and lactulose; or (b) a saccharide selected from the group consisting of trehalose, lactose, raffinose, and lactulose, and wherein the vaccine composition is in the form of a cake and forms an oil-in-water emulsion upon reconstitution.

In another aspect, provided herein is a method for generating a thermostable lyophilized vaccine composition, comprising the step of lyophilizing an oil-in-water emulsion to form a thermostable lyophilized vaccine composition, wherein the oil-in-water emulsion comprises (1) an adjuvant, (2) a metabolizable oil, and (3) a cake-forming excipient, wherein the cake-forming excipient is (1) a combination of mannitol and a saccharide selected from the group consisting of trehalose, dextrose, lactose, maltose, sucrose, raffinose, mannose, fructose, and lactulose; or (2) a saccharide selected from the group consisting of trehalose, lactose, raffinose, and lactulose, and wherein the vaccine composition is in the form of a cake and forms an oil-in-water emulsion upon reconstitution.

In some embodiments of the methods described herein, the cake-forming excipient is a saccharide selected from the group consisting of lactose, raffinose, and lactulose.

In some embodiments of the methods described herein, the cake-forming excipient is a combination of mannitol and a saccharide selected from the group consisting of trehalose, dextrose, lactose, maltose, sucrose, raffinose, mannose, fructose, and lactulose.

In some embodiments of the methods described herein, the oil-in-water emulsion prior to lyophilization comprises less than or about 1% (w/v) glycerol.

In some embodiments of the methods described herein, the oil-in-water emulsion prior to lyophilization comprises less than or about 0.5% (w/v) glycerol.

In some embodiments of the methods described herein, the oil-in-water emulsion prior to lyophilization does not comprise glycerol.

In some embodiments of the methods described herein, the cake-forming excipient is trehalose at a concentration of about 10% (w/v) in the oil-in-water emulsion prior to lyophilization.

In some embodiments of the methods described herein, the cake-forming excipient is 5% (w/v) trehalose at a concentration of about 5% (w/v) in the oil-in-water emulsion prior to lyophilization.

In some embodiments of the methods described herein, the cake-forming excipient is a combination of mannitol and trehalose, and wherein the mannitol in the oil-in-water emulsion prior to lyophilization is about 0.1% (w/v) and trehalose in the oil-in-water emulsion prior to lyophilization is about 5% (w/v).

In some embodiments of the methods described herein, the cake-forming excipient in the oil-in-water emulsion prior to lyophilization is a combination of mannitol and trehalose, and wherein the mannitol in the oil-in-water emulsion prior to lyophilization is about 2.5% (w/v) and trehalose in the oil-in-water emulsion prior to lyophilization is about 2.5% (w/v).

In some embodiments of the methods described herein, the oil-in-water emulsion prior to lyophilization does not comprise glycerol.

In some embodiments of the methods described herein, the composition is thermostable at a temperature between about 8° C. to about 60° C. for at least 1 month.

In some embodiments of the methods described herein, the composition is thermostable for at least 3 months.

In some embodiments of the methods described herein, the composition is thermostable for at least 6 months.

In some embodiments of the methods described herein, the composition is thermostable for at least 12 months.

In some embodiments of the methods described herein, the composition is thermostable at about 25° C. for at least 1 month.

In some embodiments of the methods described herein, the composition is thermostable at about 37° C. for at least 1 month.

In some embodiments of the methods described herein, the composition is thermostable at about 50° C. for at least 1 month.

In some embodiments of the methods described herein, the step of lyophilizing is performed in a single vial.

In some embodiments of the methods described herein, the oil-in-water emulsion upon reconstitution has a particle size with a Z-average diameter of less than about 200 nm.

In some embodiments of the methods described herein, the oil-in-water emulsion upon reconstitution has a particle size with a Z-average diameter of less than about 100 nm.

In some embodiments of the methods described herein, the concentration of the antigen and/or adjuvant in the oil-in-water emulsion upon reconstitution exhibits no more than or about 25% breakdown compared to the concentration of the antigen and/or adjuvant in the oil-in-water emulsion prior to lyophilization.

In some embodiments of the methods described herein, the lyophilized composition is in the form of a cake.

In some embodiments of the methods described herein, the thermostability is determined prior to reconstitution of the lyophilized composition.

In some embodiments of the methods described herein, the lyophilized composition is in the form of a cake and wherein the thermostability is determined by observation of the cake for shrinking or browning.

In some embodiments of the methods described herein, the thermostability is determined following reconstitution of the lyophilized composition.

In some embodiments of the methods described herein, the thermostability is determined by inspection of the oil-in-water emulsion upon reconstitution for creaming.

In some embodiments of the methods described herein, the thermostability is determined visually.

In some embodiments of the methods described herein, the thermostability is determined by assay of the components of the oil-in-water emulsion upon reconstitution.

In some embodiments of the methods described herein, the emulsion is lyophilized in a single vial.

In some embodiments of the methods described herein, the reconstituted emulsion has particle size with Z-average diameter of less than about 200 nm.

In some embodiments of the methods described herein, the oil-in-water emulsion prior to lyophilization comprises an antigen and an adjuvant.

In some embodiments of the methods described herein, the antigen is a polypeptide, a nucleic acid encoding a polypeptide, or a pathogen.

In some embodiments of the methods described herein, the adjuvant is a metabolizable oil. In some embodiments of the methods described herein, the metabolizable oil adjuvant is squalene, synthetic squalene, grape seed oil, olive oil or a synthetic isoprenoid.

In some embodiments of the methods described herein, the antigen is a polypeptide, a nucleic acid encoding a polypeptide, or a pathogen.

In some embodiments of the methods described herein, the adjuvant is a TLR4 agonist. In some embodiments, the TLR4 agonist is MPL, 3d-MPL, or synthetic GLA. In some embodiments, the synthetic GLA adjuvant has the following structure:

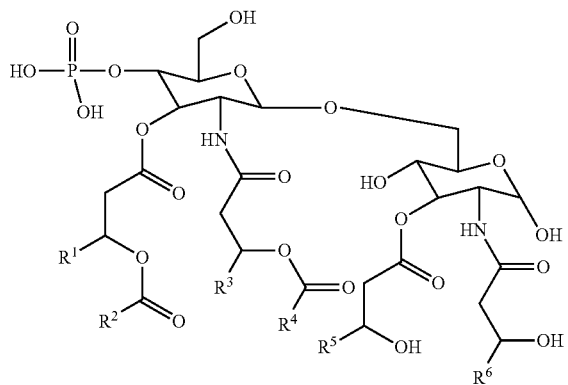

wherein $R^1$, $R^3$, $R^5$ and $R^6$ are $C_{11}$-$C_{20}$ alkyl; and $R^2$ and $R^4$ are $C_9$-$C_{20}$ alkyl. In some embodiments, $R^1$, $R^3$, $R^5$ and $R^6$ are $C_{11}$ alkyl; and $R^2$ and $R^4$ are $C_9$ alkyl.

In some embodiments of the methods described herein, the metabolizable oil is squalene, mineral oil, grape seed oil, synthetic squalene, or synthetic isoprenoid.

In some embodiments, the vaccine composition further comprises 1,2-dimyristoyl-sn-glycero-3-phosphocholine (DMPC), 1-palmitoyl-2-oleoyl-sn-glycerol-3-phsphocholine (POPC), 1,2-dioleoyl-sn-glycero-3-phosphocholine (DOPC), egg PC, lethicin, TWEEN®, or a combination thereof.

In some embodiments, the vaccine composition further comprises a surfactant. In some embodiments, the surfactant is PLURONIC® F68. In some embodiments, the vaccine composition further comprises an antioxidant (e.g., vitamin E).

In another aspect, provided herein is a method of stimulating an immune response in a subject comprising: (a) reconstituting any one of the thermostable lyophilized vaccine compositions described herein into an oil-in-water emulsion; and (b) administering the emulsion to the subject, thereby stimulating an immune response in the subject. In some embodiments, the immune response is a non-specific immune response. In some embodiments, the immune response is an antigen-specific immune response. In some embodiments, the oil-in-water emulsion is administered intradermally or orally. In some embodiments, the composition comprises GLA. In some embodiments the mammal is a human, a dog, or a cow.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 1 shows that lyophilization of 2% v/v SE in 5% w/v trehalose retained emulsion characteristics.

FIG. 2 shows that lyophilization significantly improved physical and pH stability of the emulsion at 37° C. and chemical stability at 90° C.

FIG. 3 shows physicochemical changes of lyophilized emulsion during storage at 25° C., 37° C., 50° C., 60° C., and 90° C. that was reconstituted periodically over 1500 hours.

FIG. 4 shows that excipient selection impacts emulsion maintenance following reconstitution.

FIG. 5 shows formulation and cake characteristics of reconstituted 2% (v/v) oil SE in 5% (w/v) trehalose, ribose, mannitol, or proline.

FIG. 6 shows that excipient selection and chemical structure impacts cake thermostability.

FIG. 7 shows that emulsion size stability depends on cake morphology and susceptibility to thermally induced melt-back.

FIG. 9 shows representative images of liquid (left), lyophilized (center), and reconstituted (right) vials of ID93+GLA-SE. Vials were unstressed (top row) or stressed (bottom row) at 50° C. for 30 days.

FIG. 12 shows liquid and reconstituted lyophilized samples containing ID93 and/or GLA-SE. FIG. 12A) GLA, FIG. 12B) DMPC, and FIG. 12C) squalene concentrations were determined from standard curves of reverse-phase HPLC analysis. FIG. 12D) A representative chromatogram showing components DMPC, squalene, and GLA. Filled bars represent unstressed samples and open bars represent samples stressed at 50° C. for 30 days.

FIG. 13 shows that lyophilization of ID93+GLA-SE prevented loss of biological activity due to heat stress. Mice were immunized with saline or liquid, liquid covial, or lyophilized covial ID93+GLA-SE exposed to 4° C. or 50° C. for one month.

FIG. 15 shows lyophilized and reconstituted ID93+SLA-SE co-lyophilized formulations following 30 days of stress at 50° C. Duplicate samples shown for the 0 day and 30 day time points.

FIG. 16 shows Coomassie stained reducing SDS-PAGE gel images of reconstituted ID93+SLA-SE co-lyophilized formulations. 1 μg ID93+SLA-SE was loaded per lane.

FIG. 17 shows DLS particle size of reconstituted ID93+SLA-SE co-lyophilized formulations.

FIG. 21 shows the stability characteristics of the duplicate lyophilized ID93+GLA-SE formulations after 3 months of storage at 4° C., 25° C., and 37° C. FIG. 21A) The cake does not show any further signs of collapse or discoloration, and reconstituted samples maintained the appearance of an emulsion with no creaming up to 24 hours after reconstitution. FIG. 21B) The table show the Z-average diameter from DLS experiments. polydispersity index from DLS experiments, pH and GLA concentration of the reconstituted emulsions. Error bars represent 1 SD about the mean of 2 vials for pH and 2 vials×3 dilutions×3 runs for DLS size and PDI measurements. HPLC-derived GLA concentrations (μg/mL) in reconstituted ID93+GLA-SE co-lyophilized formulations. Error bars represent 1 standard deviation about the mean, n=3. The data demonstrates no appreciable increase in the particle size, polydispersity, or pH of the reconstituted emulsion following reconstitution of any of the storage temperatures. FIG. 21C) shows Coomassie stained reducing SDS-PAGE gel images of reconstituted ID93+SLA-SE co-lyophilized formulations. 1 μg ID93+SLA-SE was loaded per lane. The presence of the 98 kD band demonstrates no appreciable degradation of the ID93 polypeptide. FIG. 21D). HPLC tracing of emulsion components squalene and DMPC. HPLC analysis demonstrates no appreciable degradation at any temperature tested of the DMPC emulsion component or squalene as demonstrated by no appearance of additional peaks or broadening of the peaks. FIG. 21E) shows HPLC-derived GLA concentrations (μg/mL) in reconstituted ID93+GLA-SE co-lyophilized formulations. Error bars represent 1 standard deviation about the mean, n=3 runs. At three months the reconstituted emulsion samples demonstrate little appreciable loss of GLA at 4° C. and 25° C. (GLA at 51 μg/ml (102%) in the 4° C. sample and 46 μg/ml (92%). in the 25° C. sample) The 37° C. sample may show a trending of some loss of GLA concentration at 42 μg/ml (84%) at 3 months.

FIG. 22 shows the stability characteristics of the duplicate lyophilized ID93+GLA-SE formulations after 6 months of storage at 4° C., 25° C., and 37° C. The sample stored at 4° C. represents the control lyophilized emulsion kept under normal cold chain storage conditions of 2°-8° C. FIG. 22A) The cake does not show any further signs of collapse or discoloration, and reconstituted samples maintained the appearance of an emulsion with no creaming up to 24 hours after reconstitution. FIG. 22B) The table show the Z-Average diameter from DLS experiments and polydispersity index from DLS experiments, pH and GLA concentration of the reconstituted emulsions. Error bars represent 1 SD about the mean of 2 vials for pH and 2 vials×3 dilutions×3 runs for DLS size and PDI measurements. HPLC-derived GLA concentrations (μg/mL) in reconstituted ID93+GLA-SE co-lyophilized formulations. Error bars represent 1 standard deviation about the mean, n=3. The table demonstrates that the pH is maintained within physiologic ranges at 7.21-7.49 for the samples reconstituted and stored over the six months. FIG. 22C) shows Coomassie stained reducing SDS-PAGE gel images of reconstituted ID93+SLA-SE co-lyophilized formulations. 1 μg ID93+GLA-SE was loaded per lane. The presence of the 98 kD band demonstrates no appreciable degradation of the ID93 polypeptide at six months as demonstrated by no appearance of additional bands or broadening of the 98 kD band. FIG. 22D). HPLC tracing of emulsion components squalene and DMPC. HPLC analysis demonstrates no appreciable degradation at any temperature tested of these emulsion components as demonstrated by no appearance of additional peaks or broadening of the peaks. FIG. 22E) shows HPLC-derived GLA concentrations (μg/mL) in reconstituted ID93+GLA-SE co-lyophilized formulations. Error bars represent 1 standard deviation about the mean, n=3 runs. At six months the 4° C. and 25° C. samples demonstrate no appreciable loss of GLA, (GLA at 47 μg/ml (94%) in the 4° C. sample and 42 μg/ml (84%). in the 25° C. sample), but the 37° C. stored sample shows a loss of approximately 50% of the initial GLA concentration, 25 μg/ml (84%).

FIG. 23 shows the stability characteristics of the duplicate lyophilized ID93+GLA-SE formulations after 9 months of storage at 4° C., 25° C., and 37° C. The sample stored at 4° C. represents the control lyophilized emulsion kept under normal cold chain storage conditions of 2°-8° C. FIG. 23A) The cake does not show any further signs of collapse or discoloration, and reconstituted samples maintained the appearance of an emulsion with no creaming up to 24 hours after reconstitution. FIG. 23B) The table shows the Z-Average diameter from DLS experiments and polydispersity index from DLS experiments, pH and GLA concentration. Error bars represent 1 SD about the mean of 2 vials for pH and 2 vials×3 dilutions×3 runs for DLS size and PDI measurements. HPLC-derived GLA concentrations (μg/mL) in reconstituted ID93+GLA-SE co-lyophilized formulations. Error bars represent 1 standard deviation about the mean, n=3. The table demonstrates that the pH is maintained within physiologic ranges at 7.19-7.53 for the samples reconstituted and stored over the nine months. FIG. 23C) shows Coomassie stained reducing SDS-PAGE gel images of reconstituted ID93+SLA-SE co-lyophilized formulations. 1 μg ID93+GLA-SE was loaded per lane. The presence of the 98 kD band demonstrates no appreciable degradation of the ID93 polypeptide at nine months as demonstrated by no appearance of additional bands or broadening of the 98 kD band. FIG. 23D). HPLC tracing of emulsion components squalene and DMPC. HPLC analysis demonstrates no appreciable degradation at any temperature tested of the emulsion components as demonstrated by no appearance of additional peaks or broadening of the peaks. FIG. 23E) shows HPLC-derived GLA concentrations (μg/mL) in reconstituted ID93+GLA-SE co-lyophilized formulations. Error bars represent 1 standard deviation about the mean, n=3 runs. At nine months the 4° C. and 25° C. samples demonstrate no appreciable loss of GLA (GLA at 40 μg/ml (80%) in the 4° C. sample and 40 μg/ml (80%). in the 25° C. sample), but the 37° C. stored sample shows a loss of approximately 69% (15 μg/ml) of the initial GLA concentration flowing nine months of storage.

FIG. 24 shows the stability characteristics of the duplicate lyophilized ID93+GLA-SE formulations after 12 months of storage at 4° C., 25° C., and 37° C. The sample stored at 4°

C. represents the control lyophilized emulsion kept under normal cold chain storage conditions of 2°-8° C. FIG. 24A) The cake does not show any further signs of collapse or discoloration, and reconstituted samples maintained the appearance of an emulsion with no creaming up to 24 hours after reconstitution. FIG. 24B) The table shows the Z-Average diameter from DLS experiments and polydispersity index from DLS experiments, pH and GLA concentration. Error bars represent 1 SD about the mean of 2 vials for pH and 2 vials×3 dilutions×3 runs for DLS size and PDI measurements. HPLC-derived GLA concentrations (μg/mL) in reconstituted ID93+GLA-SE co-lyophilized formulations. Error bars represent 1 standard deviation about the mean, n=3. The table demonstrates that the pH is maintained within physiologic ranges at 7.15-7.48 for the samples reconstituted and stored over the 12 months. FIG. 24C) shows Coomassie stained reducing SDS-PAGE gel images of reconstituted ID93+GLA-SE co-lyophilized formulations. 1 μg ID93+GLA-SE was loaded per lane. The presence of the 98 kD band demonstrates no appreciable degradation of the ID93 polypeptide at twelve months as demonstrated by no appearance of additional bands or broadening of the 98 kD band.

FIG. 25 shows the effect on the lyophilized emulsions of the addition or removal of glycerol as a cake forming excipient, the variation in the percentage of oil in the emulsion, the inclusion of 2% Tris as tonicity agent over a range of GLA concentrations (ng/ml) tested immediately after lyophilization (0 Days) or after 30 days stored at 50° C. FIG. 25A shows that the lyophilized emulsion formulations with increasing concentrations of the biodegradable oil, squalene, (2-10% v/v) and lacking the 0.5% glycerol (labeled as No Glycerol) all formed elegant cakes upon lyophilization with no further shrinking of the cake or discoloration visible even after 30 days at 50° C. when compared to the formulations containing the 0.0.5% glycerol v\v (labeled as With Glycerol). Cakes containing glycerol are slightly shrunken and depressed both immediately post lyophilization (time 0 days and 30 days after storage at 50° C.) with samples stored at 50° C. demonstrating further (shrinking) or collapse of cake structure 30 days after storage at 50° C. FIG. 25B and FIG. 25C) demonstrate that there is no appreciable difference in the either the particle size (Z-Average nm) FIG. 25B, and polydispersity (PDI) FIG. 25C for any of the formulations after storage at 50° C. for 30 days with all formulations displaying particle sizes about or below 200 nm following reconstitution of the cake. FIG. 25D) shows that the presence of 0.5% v/v glycerol affects the stability of the GLA adjuvant in the lyophilization formulation. The lyophilization formulations containing varying concentrations of squalene (2%-10% v/v) contained varying concentration of GLA adjuvant. The concentration at time zero was compared to the concentration of GLA obtained after storage of the lyophilization formulation for 30 days at 50° C. The data show that the lyophilization formulations that did not contain any glycerol (depicted as NO Glycerol) all demonstrated greater than 85% percent of the initial concentration of GLA while the lyophilization formulations containing glycerol demonstrate greater than 80% loss of GLA concentration after storage at 50° C. for one month.

FIG. 26 shows four lyophilization formulations evaluated for their ability to thermoprotect the GLA-SE emulsion, all lyophilization formulations evaluated lack glycerol. For the FIG. 26-31 the concentration of the adjuvant, GLA, was increased in the GLA-SE emulsion to 100 ng/ml to allow for more reproducible quantitation of GLA concentration after reconstitution of the lyophilized cake. Formulations were evaluated for cake formation and appearance, and creaming following reconstitution a time 0 (immediately following lyophilization), one week (1 wk), 2 weeks (2 wk), 1 month (1 mo) and 3 months (3 mo) following lyophilization for samples stored the indicated time at 4° C., 25° C., 37° C., and 50° C. FIG. 26A) 5% Trehalose alone (no glycerol), FIG. 26B) 5% Trehalose w/v, 0.1% w/v Mannitol, FIG. 26C) 2.5% w/v Trehalose, 2.5% w/v Mannitol, FIG. 26D) 10% w/v Trehalose. The data demonstrates that all the lyophilization formulations tested that lack or have no glycerol demonstrated good to elegant cake formation with no discoloration or browning of the lyophilized cake at any of the times (post lyophilization, at least about 1 week, at least about 2 weeks, at least about 1 month, or at least about 3 months) or temperature tested (at least about 4° C., at least about 25° C., at least about 37° C., and at least about 50° C.). The cakes all also showed little or no collapse or shrinking or discoloration and formed emulsions that did not cream upon reconstitution.

FIG. 28 shows the various single vial GLA-SE lyophilization formulations (the emulsion containing the cake forming excipients) as indicated below each set of bars as 5% Trehalose alone (no glycerol), 5% Trehalose w/v, 0.1% w/v Mannitol, 2.5% w/v Trehalose, 2.5% w/v Mannitol, 2.5% w/v Trehalose, 2.5% w/v Mannitol stored at 4° C. (bar 1), 25° C. (bar 2), 37° C. (bar 3), and 50° C. (bar 4) for a particular formulation) for one week (1 wk). Samples were reconstituted and analyzed for particle size (Z-average diameter, nm), polydispersity (PDI) as a function of aggregation, pH, and concentration of GLA (mg/ml). FIG. 28A) all 4 lyophilization formulations when stored at temperatures ranging from 4° C.-50° C. displayed the desired size particle size of less than about 200 nm, FIG. 28B) all 4 lyophilization formulations when stored at temperature ranging from 4° C.-50° C. displayed the desired lack of appreciable aggregates as measured by polydispersity, FIG. 28C) all 4 lyophilization formulations when stored at temperature ranging from 4° C.-50° C. displayed the desired physiologic pH. FIG. 28D) all show no appreciable loss of GLA (values ranging between approximately 105%-95%) when stored as the lyophilized cake and reconstituted as the GLA-SE emulsion compared to the original concentration of GLA.

FIG. 29 shows the various single vial GLA-SE lyophilization formulations (the emulsion containing the cake forming excipients) as indicated below each set of bars as 5% Trehalose alone (no glycerol), 5% Trehalose w/v, 0.1% w/v Mannitol, 2.5% w/v Trehalose, 2.5% w/v Mannitol, 2.5% w/v Trehalose, 2.5% w/v Mannitol stored at 37° C. (bar 3) and 50° C. (bar 4) for a particular lyophilization formulation) for two weeks (2 wk). Samples were reconstituted and analyzed for particle size (Z-average diameter, nm), polydispersity (PDI) as a function of aggregation, pH, and concentration of GLA (mg/ml). FIG. 29A) demonstrates that all 4 lyophilization formulations when stored at temperatures of 37° C. and 50° C. for 2 weeks when reconstituted formed GLA-SE emulsions that displayed the desired size particle size of less than about 200 nm, FIG. 29B) demonstrates that all 4 lyophilization formulations when stored at temperatures 37° C. and 50° C. for 2 weeks when reconstitute formed GLA-SE emulsions that displayed the desired lack of appreciable aggregates as measured by polydispersity, FIG. 29C) demonstrates that all 4 lyophilization formulations when stored at temperatures 37° C. and 50° C. for 2 weeks when reconstitute formed GLA-SE emulsions that displayed the desired physiologic pH of about pH 7.0. FIG. 29D) all lyophilization formulations for GLA-SE show no appreciable loss of GLA (values ranging between approximately 105%-95%) of the original concentration of GLA when stored as the lyophilized cake at 37° C. or 50° C. for 2 weeks and reconstituted to form the GLA-SE emulsion.

FIG. 31 shows the various single vial GLA-SE lyophilization formulations (the emulsion containing the cake forming excipients) as indicated below each set of bars as 5% Trehalose alone (no glycerol), 5% Trehalose w/v, 0.1% w/v Mannitol, 2.5% w/v Trehalose, 2.5% w/v Mannitol, 2.5% w/v Trehalose, 2.5% w/v Mannitol stored at 4° C. (bar 1), 25° C. (bar 2), 37° C. (bar 3), and 50° C. (bar 4) for a particular lyophilization formulation) for one month (1 mo). Samples were reconstituted and analyzed for particle size (Z-average diameter, nm), polydispersity (PDI) as a function of aggregation, pH, and concentration of GLA (mg/ml). FIG. 31A) demonstrates that all 4 lyophilization formulations when stored at temperature ranging from 4° C.-50° C. displayed the desired size particle size of less than about 200 nm, FIG. 31B) demonstrates that all 4 lyophilization formulations when stored at temperature ranging from 4° C.-50° C. displayed the desired lack of appreciable aggregates as measured by polydispersity, and FIG. 31C) demonstrates that all 4 lyophilization formulations when stored at temperature ranging from 4° C.-50° C. displayed the desired physiologic pH of at least about pH 7.0.

DETAILED DESCRIPTION OF THE INVENTION

Figure 1A:
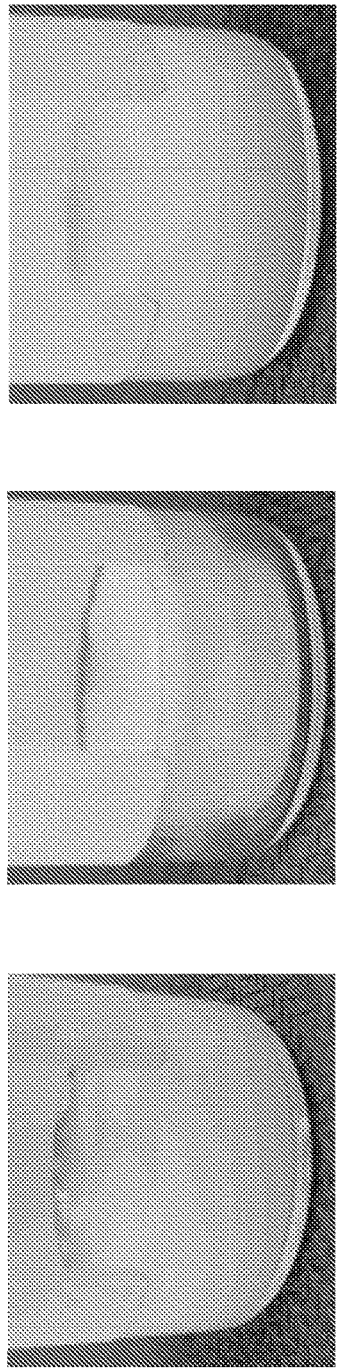
FIG. 1A) Appearance of emulsion before lyophilization (left), as lyophilized cake (middle), and after reconstitution of lyophilized cake (right).

In one aspect, the invention provides thermostable lyophilized vaccine compositions comprising (1) a metabolizable oil, and (2) a cake-forming excipient. The thermostable lyophilized vaccine compositions further optionally include an antigen and/or an adjuvant. In some embodiments, the cake-forming excipient is a combination of mannitol and a saccharide selected from the group consisting of trehalose, dextrose, lactose, maltose, sucrose, raffinose, mannose, fructose, and lactulose. In some embodiments, the cake-forming excipient is a saccharide selected from the group consisting of trehalose, lactose, raffinose, and lactulose. In some embodiments, the cake-forming excipient is a saccharide selected from the group consisting of lactose, raffinose, and lactulose. In some embodiments the composition is formed by the lyophilization of an oil-in water emulsion formulation and the oil-in-water formulation prior to lyophilization or upon reconstitution contains less than or about 1% (w/v) glycerol, less than or about 0.5% (w/v) glycerol, or no glycerol. In some embodiments, the composition is in the form of a cake and forms an oil-in-water emulsion upon reconstitution. In some embodiments, the composition is stored in a single vial.

As one of ordinary skill in the art will appreciate, the terms, thermostable lyophilized vaccine composition, lyophilized vaccine composition, lyophilized thermostable cake, and lyophilized cake are used interchangeably herein. This term generally refers to an lyophilized oil-in-water stable emulsion comprising a biodegradable oil or metabolizable oil, and/or one or more antigens, and/or and one or more adjuvants as well as cake forming excipients used to produce the cake of the invention. Upon reconstitution of the thermostable lyophilized vaccine composition, a liquid oil-in water emulsion forms that possesses the desired characteristics of the invention: an average particle size of less than or about 200 nm, a physiologic pH of about 7.4, and no loss of concentration of each active ingredient (such as the antigen, or the adjuvant) greater than or about 25% of the concentration of each active ingredient in the initial oil-in-water formulation prior to lyophilization, or any significant degradation or alteration of each active ingredient (for example the antigen, the adjuvant) which is suitable to induce or stimulate an immune response in a subject.

As provided herein, the lyophilized vaccine composition is thermostable. For example, the composition is stable from between about 8° C. to about 60° C. Such compositions may further comprise suitable excipients, such as pharmaceutically acceptable excipients (carriers) including buffers, acids, bases, sugars, diluents, preservatives, and the like, which are well known in the art and are described herein. In yet another aspect, the invention provides methods for generating a thermostable lyophilized vaccine composition described herein.

In some aspects, the invention provides methods for stimulating an immune response in a subject comprising reconstituting a thermostable lyophilized vaccine composition described herein into an emulsion and administering the emulsion to the subject. In some embodiments, the emulsion is an oil-in-water emulsion. In some embodiments, the immune response is a non-specific immune response. In some embodiments, the immune response is an antigen-specific immune response. A method described herein for stimulating an immune response, or a reconstituted thermostable lyophilized vaccine composition described herein, can be used alone or in combination with other conventional methods of treatment (e.g., chemotherapeutic agents).

In some embodiments, reference to "about" a value or parameter herein includes (and describes) variations that are directed to that value or parameter per se. For example, description referring to "about X" includes description of "X".

Definitions

It is understood that aspects and embodiments of the invention described herein include "comprising," "consisting," and "consisting essentially of" aspects and embodiments.

An "individual" or a "subject" is a mammal, more preferably a human. Mammals also include, but are not limited to farm animals, sport animals, pets (such as cats, dogs, horses), primates, mice and rats.

As used herein and in the appended claims, the singular forms "a," "an," and "the" include plural reference unless the context clearly indicates otherwise.

Cake-forming excipient and cake-forming bulking agent are used herein interchangeably. A cake-forming excipient refers to a substance added to a liquid stable oil-in-water emulsion formulation prior to lyophilization which yields a cake following lyophilization. Upon reconstitution of the lyophilized cake, a stable emulsion forms, that is suitable for delivery of a pharmacologically active drug including the vaccines of the present invention. As used herein, cake-forming excipients are those substances which do not disrupt an emulsion upon reconstitution of the lyophilized cake.

Excipients as used herein refers to substances other than the pharmacologically active drugs, which are included in the manufacturing process, or fill-finish process for storage or shipment of the pharmacologically active drug including, without limitation, lyophilization, and are contained in a finished pharmaceutical process.

Lyophilization excipients, as used herein, may refer to substances other than the pharmacologically active drug which are included in the lyophilization process to contribute to the form or formulation of a suitable cake structure. Lyophilization excipients may include bulking agents, buffering agents, or solubilizing agents.

General Techniques

The practice of the present invention will employ, unless otherwise indicated, conventional techniques of molecular biology, recombinant DNA, biochemistry, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Md. (1989).

Characteristics of the Lyophilized Vaccine Compositions

Provided herein are thermostable lyophilized vaccine compositions comprising an antigen and/or an adjuvant. The present invention describes that oil-in water emulsion formulations can be lyophilized and stored, maintained, or exposed to temperatures between about 8° C. to about 60° C., that when reconstituted, form emulsions may have one or more of the following characteristics: (1) that do not demonstrate creaming, (2) maintain a desirable pH around physiologic 7.4, (3) maintain a particle with a Z-average diameter of less than about 200 nm, with little or no aggregation, (4) exhibit no loss of concentration of the active ingredient greater than or about 25% of the initial oil-in-water emulsion formulation prior to lyophilization, or any significant degradation or alteration of each active ingredient (for example the antigen, the adjuvant), and (5) are suitable to induce or stimulate an immune response in a subject.

These lyophilized formulations comprise cake-forming excipients including (a) a combination of mannitol and a saccharide selected from the group consisting of trehalose, dextrose, lactose, maltose, sucrose, raffinose, mannose, fructose, and lactulose; (b) a saccharide selected from the group consisting of trehalose, lactose, raffinose, and lactulose; or (c) a saccharide selected from the group consisting of, lactose, raffinose, and lactulose. These thermostable formulations are an improvement over the art and may significantly reduce the over 50% loss of vaccine formulations annually due to failures in maintenance of cold chain storage in much of the developed world. Cold chain storage is described by the Centers for Disease Control, CDC, and the US Food and Drug Administration (USFDA) in vac-storagecdcpDF.pdf. Furthermore, in many regions in the developing world, ambient temperatures of greater than 25° C. occur, thus the thermostable vaccine formulations described herein can be stored at, exposed to, or maintained at temperatures higher than the ambient temperature of 25° C.

In one aspect, the desired thermostability characteristics of the thermostable lyophilized vaccine composition is that the lyophilized composition should possess certain desirable characteristics including: long term stability; short reconstitution time; maintenance of the cake appearance after storage equivalent to the cake appearance immediately after lyophilization; maintenance of the characteristics of the original dosage form upon reconstitution, including solution properties, structure or conformation of proteins; and particle size and distribution of particles. (Frank Kofi Bedu-Addo in Understanding Lyophilization Development. Pharmaceutical Technology). Additional desired characteristics of a thermostable lyophilized vaccine composition may include one or more of the following characteristics including: long term stability at temperatures above 8° C. typical of cold chain storage products; short reconstitution time; maintenance of substantially similar cake appearance after storage, exposure or maintenance at about or above 8° C. to the cake appearance immediately after lyophilization; maintenance of the characteristics of the original dosage form (plus or minus 25% of original concentration or function) of the active ingredients of the vaccine (active ingredients include but are not limited to antigen concentration and or conformation and adjuvants concentration) and which upon reconstitution maintains solution properties, structure or conformation of proteins if included; and particle size and distribution of particles no greater than at least or about an average particle size of 200 nm.

In one embodiment, a thermostable cake as used herein refers to a cake produced from a single vial lyophilization of an oil-in-water stable emulsion (SE) of the invention that may comprise additional active ingredients of the invention including antigens and/or adjuvants in the presence of suitable cake-forming excipients of the invention that when stored or exposed through storage or transport to temperatures above the typical cold chain storage temperature of 2°-8° C., and demonstrates the desirable characteristics of a vaccine oil-in water emulsion.

In one embodiment, thermostable vaccine as used herein refers to a vaccine composition that is produced from the reconstitution of a thermostable cake/thermostable lyophilized vaccine composition of the invention. Also, as used herein, a thermostable vaccine may also refer to the thermostable lyophilized/cake composition to be reconstituted into the thermostable vaccine.

Assessment of Thermostability

Thermostability of the lyophilized vaccine compositions provided herein can be assessed in the lyophilized state, prior to reconstitution or following reconstitution. Thermostability of the lyophilized vaccine compositions provided herein can be assessed by visual observation, and/or with the aid of one or more assays provided herein. These assays can provide an estimate of the integrity of the emulsion, antigen, and/or adjuvant following lyophilization and reconstitution.

The thermostability assays and observations described herein can be carried out upon lyophilization, 1 hour following lyophilization, 6 hours following lyophilization, 12 hours following lyophilization, 24 hours following lyophilization, 36 hours following lyophilization, 48 hours following lyophilization, 1 week following lyophilization, 2 weeks following lyophilization, 1 month following lyophilization, 2 months following lyophilization, 3 months following lyophilization, 4 months following lyophilization, 6 months following lyophilization, 12 months following lyophilization, or beyond. Prior to carrying out the assays and observations, the lyophilized composition can be maintained, stored at, or exposed to temperatures greater than or about 8° C., for example, greater than or about 25° C., greater than or about 37° C., or greater than or about 50° C., or about 60° C.

The thermostability assays and observations described herein can be carried out upon reconstitution of the lyophilized composition, immediately upon reconstitution, 1 hour following reconstitution, 6 hours following reconstitution, 12 hours following reconstitution, 24 hours following reconstitution, 36 hours following reconstitution, 48 hours following reconstitution, or 1 week following reconstitution. Prior to reconstitution, and carrying out the assays and observations, the lyophilized composition can be maintained, stored or exposed to temperatures greater than or about 8° C., for example, greater than or about 25° C., greater than or about 37° C., greater than or about 50° C., or at about 60° C.

One of ordinary skill in the art would understand that the present invention is designed to provide lyophilized vaccine compositions that can be stored and or shipped at temperatures more closely approaching ambient temperatures in the developed or developing world therefore in some embodiments the lyophilized composition is maintained, stored, or exposed to more than one temperature or a combination of temperatures greater than or about 8° C., for example, greater than or about 25° C., greater than or about 37° C., greater than or about 50° C., or about 60° C.

In some embodiments, the thermostability of the lyophilized vaccine compositions provided herein is assessed by visual observation, prior to reconstitution. In other embodiments, the thermostability of the lyophilized vaccine compositions provided herein is assessed following reconstitution by the aid of one or more assays, for example biophysical and biochemical assays.

In some embodiments, the thermostability of the lyophilized vaccine compositions provided herein is assessed by visual observation, following reconstitution. In other embodiments, the thermostability of the lyophilized vaccine compositions provided herein is assessed following reconstitution by the aid of one or more assays, for example biophysical and biochemical assays.

In one embodiment, the lyophilized cake resulting upon lyophilization of the oil-in-water emulsion formulation, can be observed for color and consistency. In some embodiments, the cake referred to herein is a porous and spongy structure-like material resulting from the lyophilization process; or the cake is the solid content remaining after the freeze drying process. In some embodiments, the cake's appearance can be described as a spongiform cake, lovely cake and elegant cake. In some embodiments, a cake can be visually inspected for lack of cracking, collapse (also can be described as shrinking or pulling away from the sides of the vial, depression or slight indentation of the top of cake, or a decrease in total volume of the cake), and/or a change in coloration or discoloration or browning of the cake. In some embodiments the cake can be classified as an elegant cake, a white cake, an elegant white cake, a spongiform white cake, a white cake with increased volume, a brown cake, a browning cake or a shrinking/shrunk cake. In some embodiments, discoloration or browning as used herein refers to a formulation which contains reducing sugars (for example lactose and maltose) which upon lyophilization and storage of the cake at a temperature at or above 8°, for example, at 25° C., 37° C. and or 60° C. can undergo a Maillard reaction or reduction of the sugars resulting in a discoloration of the original cake resulting in visually a yellow-to-brown-to tint to the cake. In some embodiments, if no cake forms upon lyophilization, the resulting composition can be characterized as a clear film, a think film, a thick white film, or solidified bubbles. In some embodiments, desired cakes of the invention refers to cakes that after exposure, storage, or maintenance of the cake at temperatures described above the typical cold chain storage of 2°-8° C., or above or at about 8° C. display desired characteristics of a lyophilized vaccine formulation. ("Excipients used in lyophilization of small molecules" Ankit Bahetia, Lokesh Kumarb, Arvind K. Bansal, J. Excipients and Food Chem. 1 (1) 2010; 41-54.)

In some embodiments, the melting temperature (Tm) of the cake resulting from lyophilization is measured.

In some embodiments, the emulsion particle size is evaluated following reconstitution of the lyophilized composition. For example, dynamic light scattering (DLS) can be used to evaluate emulsion particle size. In some embodiments, this is compared to the emulsion particle size prior to lyophilization, for example in the liquid stable emulsion state prior to lyophilization. In some embodiments the emulsion particle size is not compared to the particles size prior to lyophilization. In some embodiments herein, the particle size is determined by measuring the Z-average diameter (Z-Aved) of the liquid lyophilized composition. In particular embodiments, a thermostable composition is indicated when the reconstituted liquid emulsion of the lyophilized composition maintained, stored, or exposed at a temperature greater than or about 8° C. has a particle size with a Z-average diameter of less than about 200 nM, less than about 190 nM, less than about 180 nM, less than about 170 nM, less than about 160 nM, less than about 150 nM, less than about 140 nM, less than about 130 nM, less than about 120 nM, less than about 110 nM, less than about 100 nM, or less than about 90 nM, less than about 80 nM, less than about 70 nM, or less than about 60 nm. In particular embodiments, the reconstituted emulsion has a particle size with a Z-average diameter range of about 100 nM to about 200 nM.

In some embodiments, the polydispersity index (PdI) is evaluated following reconstitution of the lyophilized composition. For example, dynamic light scattering (DLS) can be used to evaluate the PdI. In some embodiments, this is compared to the PDI of the liquid emulsion prior to lyophilization, for example in the liquid stable emulsion state prior to lyophilization.

In one embodiment, the zeta potential is evaluated following reconstitution of the lyophilized composition. For example, dynamic light scattering (DLS) can be used to evaluate the zeta potential. In some embodiments, this is compared to the zeta potential prior to lyophilization, for example in the liquid stable emulsion state prior to lyophilization.

In some embodiments, the pH of the emulsion is evaluated following reconstitution of the lyophilized composition. In some embodiments, this is compared to the pH prior to lyophilization, for example in the liquid stable emulsion state prior to lyophilization.

In some embodiments, creaming of the emulsion is evaluated following reconstitution of the lyophilized composition.

In some embodiments, the % deterioration or % breakdown of the antigen, adjuvant, and/or other components of the lyophilized composition is evaluated, upon reconstitution of the lyophilized composition. In some embodiments, reverse phase high performance liquid chromatography (RP-HPLC) is used to evaluate the chemical degradation, if any, of the components. In one exemplary embodiment, the chemical degradation of squalene, DMPC, and GLA, is monitored by RP-HPLC. In other embodiments gel-based Coomassie staining is used to evaluate the degradation of the protein antigen of vaccine, if any, of the lyophilized composition, upon reconstitution. A thermostable composition as provided herein is one exhibits no more than or about 25%, 20%, 15%, 10%, 9%, 8%, 7%, 6%, 5%, 4%, 3%, 2%, 1% antigen and/or adjuvant, or other component degradation, loss or breakdown after reconstitution of the thermostable lyophilized composition which was maintained at a temperature greater than or at about 8° C.

Thermostability Characteristics

In one aspect, the lyophilized vaccine compositions provided herein are thermostable at greater than or at about 8° C. In some embodiments the lyophilized vaccine compositions provided herein are thermostable at about or greater 9° C., at about or greater than 10° C., at about or greater than 11° C., at about or greater than 12° C., at about or greater than 13° C., at about or greater than 14° C., at about or greater than 15° C., at about or greater than 16° C., at about or greater than 17° C., at about or greater than 18° C., at about or greater than 19° C., at about or greater than 20° C., at about or greater than 25° C., at about or greater than 30° C., at about or greater than 32° C., at about or greater than 35° C., at about or greater than 37° C., at about or greater than 40° C., at about or greater than 42° C., at about or greater than 45° C., at about or greater than 50° C., and at about or greater than 60° C. In other embodiments, the lyophilized vaccine compositions provided herein are thermostable at about 8° C. to about 25° C., at about 25° C. to about 37° C., at about 37° C. to about 50° C., at about 25° C. to about 50° C., at about 8° C. to about 37° C., at about 8° C. to about 50° C., or at about 8° C. to about 60° C. In one exemplary embodiment, the lyophilized vaccine compositions provided herein are thermostable at or about 25° C. In another exemplary embodiment, the lyophilized vaccine compositions provided herein are thermostable at or about 37° C. In another exemplary embodiment, the lyophilized vaccine compositions provided herein are thermostable at or about 50° C. In another exemplary embodiment, the lyophilized vaccine compositions provided herein are thermostable at or about 60° C.

In some embodiments the lyophilized vaccine compositions provided herein are thermostable at greater than or at about 8° C. for at least 1 hour, at least 12 hours, at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years, at least 4 years, and at least 5 years. In one exemplary embodiment, the lyophilized vaccine compositions provided herein are thermostable at greater than or at about 8° C. In another exemplary embodiment, the lyophilized vaccine compositions provided herein are thermostable at greater than or at about 8° C. for at least three months. In another exemplary embodiment, the lyophilized vaccine compositions provided herein are thermostable at greater than or at about 8° C. for at least six months. In another exemplary embodiment, the lyophilized vaccine compositions provided herein are thermostable at greater than or at about 8° C. for at least twelve months. In one embodiment, the lyophilized vaccine compositions provided herein are thermostable at greater than or at about 8° C. indefinitely.

In some embodiments the lyophilized vaccine compositions provided herein are thermostable at about or greater than 25° C. for at least 1 hour, at least 12 hours, at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years, at least 4 years, and at least 5 years. In one exemplary embodiment, the lyophilized vaccine compositions provided herein are thermostable at greater than 25° C. for at least one month. In another exemplary embodiment, the lyophilized vaccine compositions provided herein are thermostable at greater than 25° C. for at least three months. In another exemplary embodiment, the lyophilized vaccine compositions provided herein are thermostable at greater than 25° C. for at least six months. In another exemplary embodiment, the lyophilized vaccine compositions provided herein are thermostable at greater than 25° C. for at least twelve months. In one embodiment, the lyophilized vaccine compositions provided herein are thermostable at greater than 25° C. indefinitely.

In some embodiments the lyophilized vaccine compositions provided herein are thermostable at about or greater than 37° C. for at least 1 hour, at least 12 hours, at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years, at least 4 years, and at least 5 years. In one exemplary embodiment, the lyophilized vaccine compositions provided herein are thermostable at greater than 37° C. for at least one month. In another exemplary embodiment, the lyophilized vaccine compositions provided herein are thermostable at greater than 37° C. for at least three months. In another exemplary embodiment, the lyophilized vaccine compositions provided herein are thermostable at greater than 37° C. for at least six months. In another exemplary embodiment, the lyophilized vaccine compositions provided herein are thermostable at greater than 37° C. for at least twelve months. In one embodiment, the lyophilized vaccine compositions provided herein are thermostable at greater than 37° C. indefinitely.

In some embodiments the lyophilized vaccine compositions provided herein are thermostable at about or greater than 50° C. for at least 1 hour, at least 12 hours, at least 1 day, at least 2 days, at least 3 days, at least 4 days, at least 5 days, at least 6 days, at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 1.5 years, at least 2 years, at least 3 years, at least 4 years, and at least 5 years. In one exemplary embodiment, the lyophilized vaccine compositions provided herein are thermostable at greater than 50° C. for at least one month. In another exemplary embodiment, the lyophilized vaccine compositions provided herein are thermostable at greater than 50° C. for at least three months. In another exemplary embodiment, the lyophilized vaccine compositions provided herein are thermostable at greater than 50° C. for at least six months. In another exemplary embodiment, the lyophilized vaccine compositions provided herein are thermostable at greater than 50° C. for at least twelve months. In one embodiment, the lyophilized vaccine compositions provided herein are thermostable at greater than 50° C. indefinitely.

Excipients and Agents for Use in Thermostable Vaccine Compositions

Provided herein are thermostable lyophilized vaccine compositions comprising an antigen and/or an adjuvant. In some embodiments, the compositions comprise further agents and/or excipients such as cake-forming excipients, cake-forming bulking agents, buffering agents, solubilizing agents, isotonicity agents, surfactants, and/or emulsifiers.

Excipients

Excipients of the invention may be used singly or in combination with other excipients which include, but are not limited to, cake-forming excipients, cake-forming bulking agents, bulking agents, buffering agents, solubilizing agents, isotonicity agents, tonicifying agents, surfactants, emulsifiers, antimicrobial agents, and/or collapse temperature modifiers.

In some embodiments the excipients are substances other than the pharmacologically active drug, which are included in the manufacturing process, or fill-finish process for storage or shipment of the pharmacologically active drug including, without limitation, lyophilization, and are contained in a finished pharmaceutical process.

In some embodiments, an excipient is a substance added to a liquid stable oil-in-water emulsion formulation prior to lyophilization which yields a cake following lyophilization.

Excipients suitable for vaccine formulations and/or lyophilization are known in the art (See, e.g. Bahetia et. al., 2010: J. Excipients and Food Chem.:1 (1)41-54, Grabenstein J D. ImmunoFacts: Vaccines and Immunologic Drugs—2012 (37th revision). St Louis, Mo.: Wolters Kluwer Health, 2011 and, by Vaccine) and include cake-forming excipients, cake-forming bulking agents, bulking agents, buffering agents, solubilizing agents, isotonicity agents, tonicifying agents, surfactants, emulsifiers, antimicrobial agents, and/or collapse temperature modifiers. A list of excipients in currently approved vaccines can be found via the Centers for Disease Control (see worldwide web at cdc.gov/vaccines/pubs/pinkbook/downloads/appendices/B/ excipient-table-2.pdf., September 2013, "Vaccine Excipient & Media Summary. Excipients Included in U.S. Vaccines, by Vaccine") and include without limitation sucrose, D-mannose, D-fructose, dextrose, potassium phosphate, plasdone C, anhydrous lactose, micro crystalline cellulose, polacrilin potassium, magnesium stearate, cellulose acetate phthalate, alcohol, acetone, castor oil, FD&C Yellow #6 aluminum lake dye, human serum albumin, fetal bovine serum, sodium bicarbonate, human-diploid fibroblast cell cultures (WI-38), Dulbecco's Modified Eagle's Medium, aluminum hydroxide, benzethonium chloride, formaldehyde, gluteraldehyde, amino acids, vitamins, inorganic salts, sugars, glycerin, asparagine, citric acid, potassium phosphate, magnesium sulfate, iron ammonium citrate, lactose, aluminum potassium sulfate, aluminum hydroxyphosphate, potassium aluminum sulfate, peptone, bovine extract, thimerosal (trace), modified Mueller and Miller medium, beta-propiolactone, thimerosol (multi-dose vials only), monobasic sodium phosphate, dibasic sodium phosphate, monobasic potassium phosphate, potassium chloride, potassium glutamate, calcium chloride, sodium taurodeoxycholate, neomycin sulfate, polymyxin B, egg protein, lactalbumin hydrolysate, and neomycin sulfate.

Cake-Forming Excipients/Cake-Forming Bulking Agents

In some embodiments, a cake-forming excipient is a substance added to a liquid stable oil-in-water emulsion formulation prior to lyophilization which yields a cake following lyophilization. Upon reconstitution of the lyophilized cake, a oil-in-water stable emulsion forms which is suitable for delivery of a pharmacologically active drug including the vaccines of the present invention.

In some embodiments, cake-forming excipients are those substances which do not disrupt an emulsion upon reconstitution of the cake.

In some embodiments the agents useful as cake-forming excipients, also referred to as bulking agents, for the present invention include sugars/saccharides or sugars/saccharides in combination with sugar alcohols. In some embodiments disclosed herein, the sugars/saccharides or sugars/saccharides in combination with sugar alcohols are useful as bulking agents or cake-forming excipients include. These include, but are not limited to, trehalose, dextrose, lactose, maltose, sucrose, raffinose, mannose, stachyose, fructose, lactulose, glucose, and optionally glycerol, sorbitol, and/or mannitol.

In some embodiments, the cake-forming excipient is a combination of mannitol and a saccharide selected from the group consisting of trehalose, dextrose, lactose, maltose, sucrose, raffinose, mannose, stachyose, fructose, and lactulose.

In some embodiments, the cake-forming excipient is a combination of sorbitol and a saccharide selected from the group consisting of trehalose, dextrose, lactose, maltose, sucrose, raffinose, mannose, stachyose, fructose, and lactulose.

In some embodiments, the cake-forming excipient is a saccharide selected from the group consisting of trehalose, lactose, raffinose, and lactulose.

In some embodiments, the cake-forming excipient is a saccharide selected from the group consisting of lactose, raffinose, and lactulose.

In some embodiments the cake-forming excipient is a saccharide, or a saccharide in combination with a sugar alcohol in the presence of no glycerol. In other embodiments the cake-forming excipient is a saccharide, or a saccharide in combination with a sugar alcohol in the presence of less than about 1% w/v glycerol, less than about 0.5% glycerol, or less than about 0.1% glycerol.

In some embodiments, the cake-forming excipient is a saccharide and the saccharide is present in the oil-in-water emulsion formulation prior to lyophilization or in the oil-in-water emulsion upon reconstitution at a concentration range of about 0.01% w/v to about 20% w/v, about 0.05% w/v to about 10% w/v, about 0.05% w/v to about 5% w/v, about 0.5% w/v to about 10% w/v, about 0.5% w/v to about 7.5% w/v, about 0.5% w/v to about 5% w/v, about 0.5% w/v to about 2.5% w/v, about 0.5% w/v to about 1% w/v, about 2.5% w/v to about 10% w/v, about 2.5% w/v to about 7.5% w/v, about 2.5% w/v to about 5% w/v, about 1% w/v to about 2.5% w/v, about 5% w/v to about 10% w/v, or at a concentration range of about 5% w/v to about 7.5% w/v. In some embodiments, the cake-forming excipient is present in the oil-in-water emulsion formulation prior to lyophilization or in the oil-in-water emulsion upon reconstitution at a concentration of about 5% w/v. In some embodiments, the cake-forming excipient is present at a concentration of about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 7.5% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In some embodiments the cake-forming excipient is provided in the presence of less than about 1% w/v glycerol, less than about 0.5% glycerol, less than about 0.1% glycerol, or is provided with no glycerol present (the % glycerol refers to the concentration of glycerol in the oil-in-water emulsion formulation prior to lyophilization).

In some exemplary embodiments, the cake-forming excipient is trehalose and the trehalose is present in the oil-in-water emulsion formulation prior to lyophilization or in the oil-in-water emulsion upon reconstitution at a concentration range of about 0.01% w/v to about 20% w/v, about 0.05% w/v to about 10% w/v, about 0.05% w/v to about 5% w/v, about 0.5% w/v to about 10% w/v, about 0.5% w/v to about 7.5% w/v, about 0.5% w/v to about 5% w/v, about 0.5% w/v to about 2.5% w/v, about 0.5% w/v to about 1% w/v, about 2.5% w/v to about 10% w/v, about 2.5% w/v to about 7.5% w/v, about 2.5% w/v to about 5% w/v, about 1% w/v to about 2.5% w/v, about 5% w/v to about 10% w/v, or at a concentration range of about 5% w/v to about 7.5% w/v. In some embodiments, the trehalose is present in the oil-in-water emulsion formulation prior to lyophilization or in the oil-in-water emulsion upon reconstitution at a concentration of about 5% w/v. In some embodiments, the trehalose is present at a concentration of about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 7.5% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In some embodiments where the cake-forming excipient is trehalose, the trehalose is provided in the presence of less than about 1% w/v glycerol, less than about 0.5% glycerol, less than about 0.1% glycerol, or is provided with no glycerol present (the % glycerol refers to the concentration of glycerol in the oil-in-water emulsion formulation prior to lyophilization).

In some exemplary embodiments, the cake-forming excipient is a saccharide in combination with a sugar alcohol. In such embodiments, the saccharide is present in the oil-in-water emulsion formulation prior to lyophilization or in the oil-in-water emulsion upon reconstitution at a concentration range of about 0.01% w/v to about 20% w/v, and the sugar alcohol is present at a concentration range of about 0.01% w/v to about 20% w/v. In some embodiments, the saccharide is present in combination with a sugar alcohol, and the saccharide is present in the oil-in-water emulsion formulation prior to lyophilization or in the oil-in-water emulsion upon reconstitution at a concentration range of about 0.5% w/v to about 10% w/v, about 0.5% w/v to about 7.5% w/v, about 0.5% w/v to about 5% w/v, about 0.5% w/v to about 2.5% w/v, about 0.5% w/v to about 1% w/v, about 2.5% w/v to about 10% w/v, about 2.5% w/v to about 7.5% w/v, about 2.5% w/v to about 5% w/v, about 1% w/v to about 2.5% w/v, about 5% w/v to about 10% w/v, about 5% w/v to about 7.5% w/v, or at about 5% w/v in and the sugar alcohol is present at a concentration range of about 0.01% w/v to about 10% w/v, about 0.01% w/v to about 7.5% w/v, about 0.01% w/v to about 5% w/v, about 0.01% w/v to about 2.5% w/v, about 0.01% w/v to about 1% w/v, about 0.01% w/v to about 0.1% w/v, about 0.01% w/v to about 0.05% w/v, about 0.05% w/v to about 10% w/v, about 0.05% w/v to about 7.5% w/v, about 0.05% w/v to about 5% w/v, about 0.05% w/v to about 2.5% w/v, about 0.05% w/v to about 1% w/v, about 0.05% w/v to about 0.1% w/v, about 0.1% w/v to about 10% w/v, about 0.1% w/v to about 7.5% w/v, about 0.1% w/v to about 5% w/v, about 0.1% w/v to about 2.5% w/v, about 0.1% w/v to about 1% w/v, about 0.5% w/v to about 10% w/v, about 0.5% w/v to about 7.5% w/v, about 0.5% w/v to about 5% w/v, about 0.5% w/v to about 2.5% w/v, about 0.5% w/v to about 1% w/v, about 1% w/v to about 10% w/v, about 1% w/v to about 7.5% w/v, about 1% w/v to about 5% w/v, about 1% w/v to about 2.5% w/v or at about 0.1% w/v. In some embodiments, the saccharide is present in combination with a sugar alcohol where the saccharide is present at a concentration of about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 7.5% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v, and the sugar alcohol is present at a concentration of about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5%, about 2% w/v, about 2.5%, about 3% w/v, about 4% w/v, about 5% w/v, about 6% w/v, about 7% w/v, about 7.5% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In some embodiments the saccharide in combination with a sugar alcohol is provided in the presence of less than about 1% w/v glycerol, less than about 0.5% glycerol, less than about 0.1% glycerol, or is provided with no glycerol present (the % glycerol refers to the concentration of glycerol in the oil-in-water emulsion formulation prior to lyophilization).

In some exemplary embodiments, the cake-forming excipient is trehalose in combination with mannitol. In such embodiments, the trehalose in the oil-in-water emulsion formulation prior to lyophilization is present at a concentration range of about 0.01% w/v to about 20% w/v, and the mannitol is present in the oil-in-water emulsion formulation prior to lyophilization or in the oil-in-water emulsion upon reconstitution at a concentration range of about 0.01% w/v to about 20% w/v. In some embodiments, the trehalose is present in combination with mannitol, and the trehalose is present in the oil-in-water emulsion formulation prior to lyophilization or in the oil-in-water emulsion upon reconstitution at a concentration range of about 0.5% w/v to about 10% w/v, about 0.5% w/v to about 7.5% w/v, about 0.5% w/v to about 5% w/v, about 0.5% w/v to about 2.5% w/v, about 0.5% w/v to about 1% w/v, about 2.5% w/v to about 10% w/v, about 2.5% w/v to about 7.5% w/v, about 2.5% w/v to about 5% w/v, about 1% w/v to about 2.5% w/v, about 5% w/v to about 10% w/v, about 5% w/v to about 7.5% w/v, or at about 5% w/v in and the mannitol is present in the oil-in-water emulsion formulation prior to lyophilization or in the oil-in-water emulsion upon reconstitution at a concentration range of about 0.01% w/v to about 10% w/v, about 0.01% w/v to about 7.5% w/v, about 0.01% w/v to about 5% w/v, about 0.01% w/v to about 2.5% w/v, about 0.01% w/v to about 1% w/v, about 0.01% w/v to about 0.1% w/v, about 0.01% w/v to about 0.05% w/v, about 0.05% w/v to about 10% w/v, about 0.05% w/v to about 7.5% w/v, about 0.05% w/v to about 5% w/v, about 0.05% w/v to about 2.5% w/v, about 0.05% w/v to about 1% w/v, about 0.05% w/v to about 0.1% w/v, about 0.1% w/v to about 10% w/v, about 0.1% w/v to about 7.5% w/v, about 0.1% w/v to about 5% w/v, about 0.1% w/v to about 2.5% w/v, about 0.1% w/v to about 1% w/v, about 0.5% w/v to about 10% w/v, about 0.5% w/v to about 7.5% w/v, about 0.5% w/v to about 5% w/v, about 0.5% w/v to about 2.5% w/v, about 0.5% w/v to about 1% w/v, about 1% w/v to about 10% w/v, about 1% w/v to about 7.5% w/v, about 1% w/v to about 5% w/v, about 1% w/v to about 2.5% w/v or at about 0.1% w/v. In some embodiments, the trehalose is present in combination with mannitol where the trehalose is present in the oil-in-water emulsion formulation prior to lyophilization or in the oil-in-water emulsion upon reconstitution at a concentration of about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 7.5% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v, and the mannitol is present in the oil-in-water emulsion formulation prior to lyophilization or in the oil-in-water emulsion upon reconstitution at a concentration of about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5%, about 2% w/v, about 2.5%, about 3% w/v, about 4% w/v, about 5% w/v, about 6% w/v, about 7% w/v, about 7.5% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In some embodiments the trehalose in combination with the mannitol is provided in the presence of less than about 1% w/v glycerol, less than about 0.5% glycerol, less than about 0.1% glycerol, or is provided with no glycerol present (the % glycerol refers to the concentration of glycerol in the oil-in-water emulsion formulation prior to lyophilization).

In other embodiments the agents useful as cake-forming excipients, for the present invention include any amino acid. Exemplary amino acids useful as bulking agents in the present invention include arginine, glycine, proline, glutamic acid, methionine, cysteine, proline and histidine alone, or in combination, either as pure molecules or formulated.

In other embodiments bulking agents include polymers such as dextran and polyethylene glycol.

Buffering Agents

In some embodiments, the compositions of the present invention comprise a buffering agent. Buffering agents useful as excipients in the present invention include Tris acetate, Tris base, Tris HCl, Ammonium phosphate, Citric Acid, Sodium Citrate, Potassium citrate, Tartic Acid, Sodium Phosphate, Zinc Chloride, Arginine, and Histidine. In some embodiments buffering agents include pH adjusting agents such as hydrochloric acid, sodium hydroxide, and meglumine.

Solubilizing Agents

In some embodiments suitable solubilizing agents include complexing excipients such as ethylenediaminetetraacetic acid (EDTA), Alpha cyclodextrin, Hydroxypropyl-β-cyclodextrin (HP-β-CD). Surfactants may also be included as solubilizing excipients including polysorbate 80 and Tween. Other Co-Solvents known in the art as solubilizing agents may be used and include tert-butyl alcohol, isopropyl alcohol, dichloromethane, ethanol and acetone.

Tonicifying agents for use as excipients in the present invention include glycerol, sodium chloride, sucrose, mannitol, and dextrose. Collapse temperature modifiers include dextran, Hydroxyethyl starch, ficoll, and gelatin. Antimicrobial agents include benzyl alcohol, phenol, m-cresol, methyl paraben, ethyl paraben, thimerosol.

Isotonicity Agents

In some embodiments, the compositions of the present invention comprise an isotonicity agent. In some embodiments, the isotonicity agent is glycerol. In one particular embodiment, the isotonicity agent is present at a concentration of about 0.36% v/v in the oil-in-water emulsion formulation prior to lyophilization or in the oil-in-water emulsion upon reconstitution.

Surfactants

In some embodiments, the compositions of the present invention comprise a surfactant. In some embodiments, the surfactant is PLURONIC® F68. In some embodiments, the surfactant is present at a ratio of about 100: 1 (oil:surfactant). In some embodiments, the surfactant is present at a concentration of about 0.018% w/v. In some embodiments, the surfactant is present at a concentration of about 0.0001% w/v, about 0.0005% w/v, about 0.001% w/v, about 0.005% w/v, about 0.01% w/v, about 0.011% w/v, about 0.012% w/v, about 0.013% w/v, about 0.014% w/v, about 0.015% w/v, about 0.016% w/v, about 0.017% w/v, about 0.018% w/v, about 0.019% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, or about 1% w/v. The percentages and ratios described herein refer to the ratios and percentages in either the oil-in-water emulsion formulation prior to lyophilization or in the oil-in-water emulsion upon reconstitution.

Emulsifiers

In some embodiments, the compositions of the present invention comprise an emulsifier. In some embodiments, the emulsifier is 1,2-dimyristoyl-sn-glycero-3-phosphocholine (DMPC). In some embodiments, the emulsifier is lecithin. In some embodiments, the emulsifier is present at a ratio of about 1:5 (emulsifier:oil). In some embodiments, the emulsifier is present at a concentration of about 0.38% w/v. In some embodiments, the emulsifier is present at a concentration of about 0.002% w/v, about 0.005% w/v, about 0.010% w/v, about 0.015% w/v, about 0.020% w/v, about 0.025% w/v, about 0.030% w/v, about 0.035% w/v, about 0.040% w/v, about 0.045% w/v, about 0.050% w/v, about 0.055% w/v, about 0.060% w/v, about 0.065% w/v, about 0.070% w/v, about 0.075% w/v, about 0.080% w/v, about 0.085% w/v, about 0.090% w/v, about 0.095% w/v, about 0.10% w/v, about 0.15% w/v, about 0.20% w/v, about 0.25% w/v, about 0.30% w/v, about 0.35% w/v, about 0.40% w/v, about 0.45% w/v, about 0.50% w/v, about 0.55% w/v, about 0.60% w/v, about 0.65% w/v, about 0.70% w/v, about 0.75% w/v, about 0.80% w/v, about 0.85% w/v, about 0.90% w/v, about 0.95% w/v, about 1% w/v, about 2% w/v, about 3% w/v, about 4% w/v, about 5% w/v, about 6% w/v, about 7% w/v, about 7.5% w/v, about 8% w/v, about 9% w/v, or about 10% w/v. The percentages and ratios described herein refer to the ratios and percentages in either the oil-in-water emulsion formulation prior to lyophilization or in the oil-in-water emulsion upon reconstitution.

Adjuvants for Use in Thermostable Lyophilized Vaccine Compositions

In some aspects of the invention provided herein, a composition described herein (e.g., thermostable lyophilized vaccine) comprises an adjuvant. In some embodiments the adjuvant is provided alone, for example, for use a therapeutic agent. In other embodiments, the adjuvant is provided in combination with an antigen. Adjuvants for use in compositions that modify the immune response are well known in the art. For example, adjuvants for use in compositions described herein may comprise one or more of an immunostimulatory adjuvant, a delivery adjuvant, an inorganic adjuvant, or an organic adjuvant. Non-limiting examples of adjuvants for use in compositions described herein can be found, inter alia, in Barouch D. H., 2008, Nature, 455(7213): 613-9; Morrow et al., 2008, AIDS, 22(3):333-8; and McGeary et al., 2003, Peptide Sci., 9(7):405-181.

In some embodiments, an adjuvant used in a composition described herein (e.g., thermostable lyophilized vaccine) is an immunostimulatory adjuvant. Immunostimulatory adjuvants can be adjuvants that directly act on the immune system such as, for example, a cytokine, a TLR ligand or a microbial toxin. In some embodiments herein, the adjuvant is a cytokine adjuvant. One or more cytokine can be suitable as an adjuvant alone or in a combination with one or more additional adjuvant in a composition described herein. Suitable cytokines include an interferon (IFN), an interleukin (IL), a chemokine, a colony-stimulating factor, or a tumor necrosis factor. In some embodiments, the interferon is a Type I IFN, a Type II IFN, or a Type III IFN. In some embodiments, the interferon is IFN-α, IFN-β, IFN-γ, or IFN-λ and subtypes from among these (e.g., IFN-λ, IFN-λ2, and IFN-λ3). In some embodiments, the cytokine is an interleukin. Non-limiting examples of interleukins that can be used as an adjuvant in a composition described herein include IL-1, IL-2, IL-3, IL-4, IL-5, IL-6, IL-7, IL-8, IL-9, IL-10, IL-11, IL-12, IL-13, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35 and IL-36. In some embodiments, the cytokine is a chemokine. In some embodiments, the chemokine is a CC chemokine, a CXC chemokine, a C chemokine, or a CX3C chemokine. Non-limiting examples of CC chemokines that can be used as an adjuvant in a composition described herein include CCL1, CCL2, CCL3, CCL4, CCL5, CCL6, CCL7, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. Non-limiting examples of CXC chemokines that can be used in a composition described herein include CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. In some embodiments, the cytokine is a colony-stimulating factor. In some embodiments, the colony-stimulatory factor is granulocyte macrophage colony-stimulating factor (GM-CSF), granulocyte colony-stimulating factor (G-CSF), or macrophage colony-stimulating factor (M-CSF). In some embodiments, the cytokine is a tumor necrosis factor. Non-limiting examples of a tumor necrosis factor family protein that can be used as an adjuvant in a composition described herein include TNF-α and 4-1BBL.

In some embodiments, the immunostimulatory adjuvant is a Toll-like receptor (TLR) ligand (e.g., a TLR agonist). One or more TLR ligand can be suitable as an adjuvant alone or in a combination with one or more additional adjuvant in a composition described herein. TLRs include cell surface transmembrane receptors of the innate immune system that confer early-phase recognition capability to host cells for a variety of conserved microbial molecular structures such as may be present in or on a large number of infectious pathogens. (e.g., Armant et al., 2002 Genome Biol. 3(8): reviews3011.1-3011.6; Fearon et al., 1996 Science 272:50; Medzhitov et al., 1997 Curr. Opin. Immunol. 9:4; Luster 2002 Curr. Opin. Immunol. 14:129; Lien et al. 2003 Nat. Immunol. 4:1162; Medzhitov, 2001 Nat. Rev. Immunol. 1:135; Takeda et al., 2003 Ann Rev Immunol. 21:335; Takeda et al. 2005 Int. Immunol. 17:1; Kaisho et al., 2004 Microbes Infect. 6:1388; Datta et al., 2003 J. Immunol. 170:4102).

Induction of TLR-mediated signal transduction to potentiate the initiation of immune responses via the innate immune system may be effected by TLR agonists (i.e., a TLR ligand), which engage cell surface TLR. For example, lipopolysaccharide (LPS) may be a TLR agonist through TLR2 or TLR4 (Tsan et al., 2004 J. Leuk. Biol. 76:514; Tsan et al., 2004 Am. J. Physiol. Cell Phsiol. 286:C739; Lin et al., 2005 Shock 24:206); poly(inosine-cytidine) (polyI:C) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG 10101 Bayes et al. Methods Find Exp Clin Pharmacol 27:193; Vollmer et al. Expert Opinion on Biological Therapy 5:673; Vollmer et al., 2004 Antimicrob. Agents Chemother. 48:2314; Deng et al., 2004 J. Immunol. 173:5148) may be TLR agonists through TLR9 (Andaloussi et a., 2006 Glia 54:526; Chen et al., 2006 J. Immunol. 177:2373); peptidoglycans may be TLR2 and/or TLR6 agonists (Soboll et al., 2006 Biol. Reprod. 75:131; Nakao et al., 2005 J. Immunol. 174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 J. Immunol. 174:1259) may be a TLR7 agonist (Johansen 2005 Clin. Exp. Allerg. 35:1591) and/or a TLR8 agonist (Johansen 2005); flagellin may be a TLR5 agonist (Feuillet et al., 2006 Proc. Nat. Acad. Sci. USA 103:12487); a profilin may be a TLR11 agonist (Hedhli et al., 2009, Vaccine, 27(16): 2274-87); a lipopeptide may be a TLR1, TLR2, and/or TLR6 agonist (Gao et al., 2013, Vaccine, 31(26):2796-803); and hepatitis C antigens may act as TLR agonists through TLR7 and/or TLR9 (Lee et al., 2006 Proc. Nat. Acad. Sci. USA 103:1828; Horsmans et al., 2005 Hepatol. 42:724). Other TLR agonists are known (e.g., Schirmbeck et al., 2003 J. Immunol. 171:5198) and may be used according to certain of the presently described embodiments.

For example, and by way of background (see, e.g., U.S. Pat. No. 6,544,518) immunostimulatory oligonucleotides containing ummethylated CpG dinucleotides ("CpG") are known as being adjuvants when administered by both systemic and mucosal routes (WO 96/02555, EP 468520, Davis et al., J. Immunol, 1998. 160(2):870-876; McCluskie and Davis, J. Immunol., 1998, 161(9):4463-6). CpG is an abbreviation for cytosine-guanosine dinucleotide motifs present in DNA. The central role of the CG motif in immuno stimulation was elucidated by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., Proc. Natl. Acad. Sci., USA, 1998, 95(26), 15553-8).

In some embodiments, the oligonucleotides for use as an adjuvant of the present invention contain two or more dinucleotide CpG motifs separated by at least three, more preferably at least six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Examples of preferred oligonucleotides have sequences that are disclosed in the following publications; for certain herein disclosed embodiments the sequences preferably contain phosphorothioate modified internucleotide linkages: (1) CPG 7909: Cooper et al., "CPG 7909 adjuvant improves hepatitis B virus vaccine seroprotection in antiretroviral-treated HIV-infected adults." AIDS, 2005 Sep. 23; 19(14): 1473-9; (2) CpG 10101: Bayes et al., "Gateways to clinical trials." Methods Find. Exp. Clin. Pharmacol. 2005 April; 27(3):193-219; and (3) Vollmer J., "Progress in drug development of immunostimulatory CpG oligodeoxynucleotide ligands for TLR9." Expert Opinion on Biological Therapy. 2005 May; 5(5): 673-682.

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilizing an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phosphodiesters. Other internucleotide bonds which stabilize the oligonucleotide may also be used.

In certain embodiments, the adjuvant is a TLR4 agonist. In some embodiments, the TLR4 agonist used in a composition of the invention comprises a glucopyranosyl lipid adjuvant (GLA), such as those described in U.S. Patent Publication Nos. US2007/021017, US2009/045033, US2010/037466, and US 2010/0310602, the contents of which are incorporated herein by reference in their entireties.

For example, in certain embodiments, the TLR4 agonist is a synthetic GLA adjuvant having the following structure:

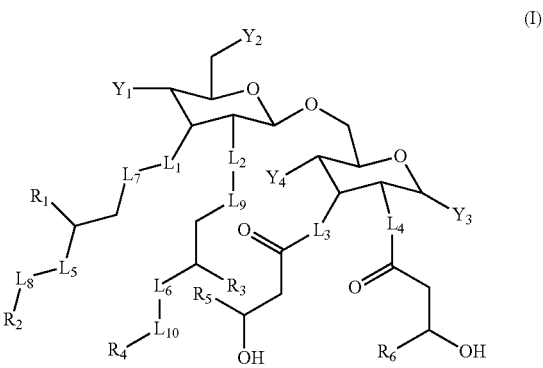

or a pharmaceutically acceptable salt thereof, wherein:
$L_1$, $L_2$, $L_3$, $L_4$, $L_5$ and $L_6$ are the same or different and independently —O—, —NH— or —(CH$_2$)—;
$L_7$, $L_8$, $L_9$, and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1$, $R_3$, $R_5$ and $R_6$ are the same or different and independently $C_{8-13}$ alkyl; and
$R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl. In certain embodiments, $R^1$, $R^3$, $R^5$ and $R^6$ are $C_{11}$ alkyl; and $R^2$ and $R^4$ are $C_9$ alkyl.

For example, in certain embodiments, the TLR4 agonist is a synthetic GLA adjuvant having the following structure:

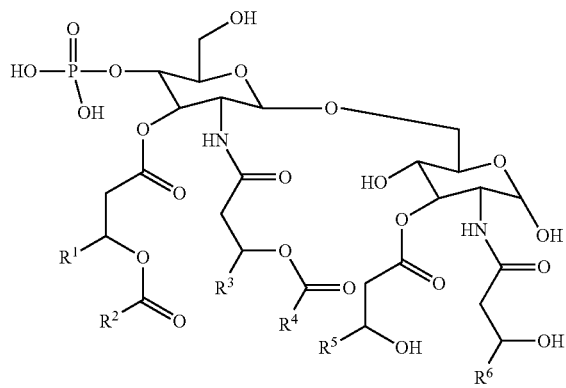

In a specific embodiment, $R^1$, $R^3$, $R^5$ and $R^6$ are $C_{11}$-$C_{20}$ alkyl; and $R^2$ and $R^4$ are $C_{12}$-$C_{20}$ alkyl.

In another specific embodiment, the GLA has the formula set forth above wherein $R^1$, $R^3$, $R^5$ and $R^6$ are $C_{11}$ alkyl; and $R^2$ and $R^4$ are $C_{13}$ alkyl.

In another specific embodiment, the GLA has the formula set forth above wherein $R^1$, $R^3$, $R^5$ and $R^6$ are $C_{10}$ alkyl; and $R^2$ and $R^4$ are $C_8$ alkyl.

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

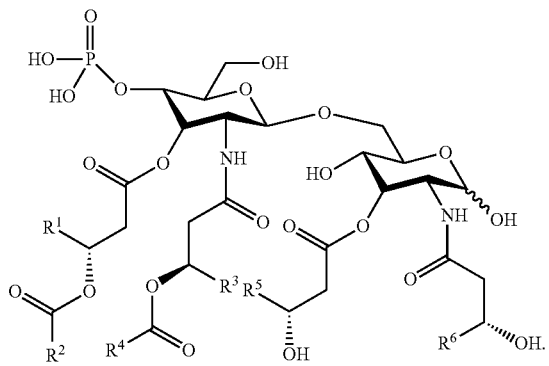

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

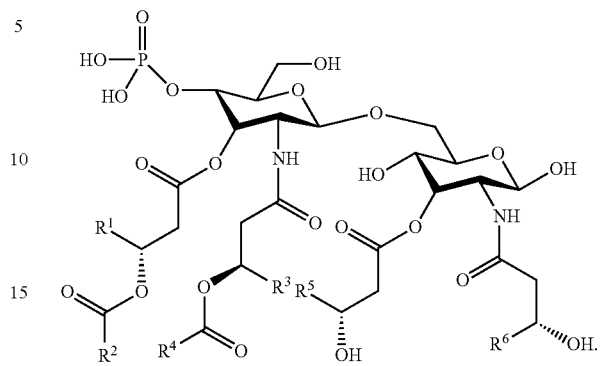

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

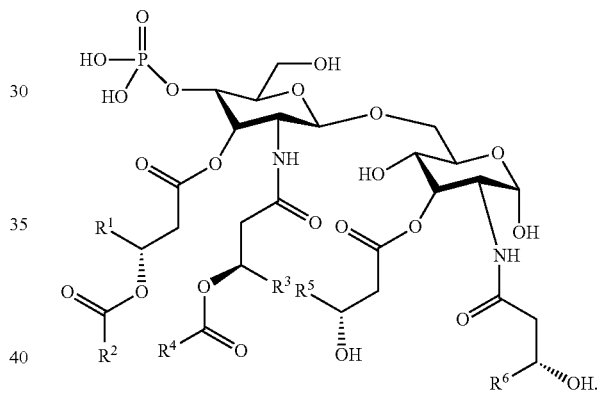

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the TLR4 agonist is a synthetic GLA adjuvant having the following structure:

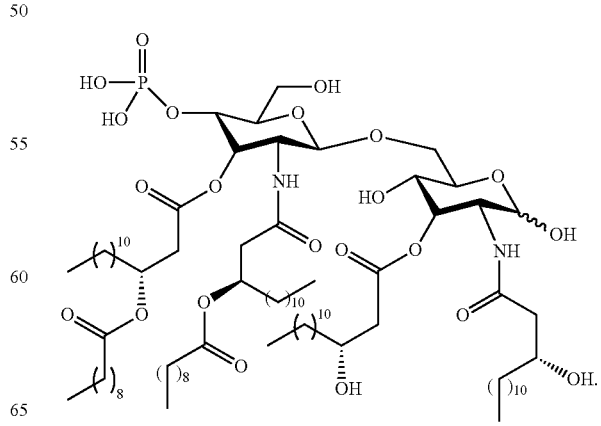

In certain embodiments, the TLR4 agonist is a synthetic GLA adjuvant having the following structure:

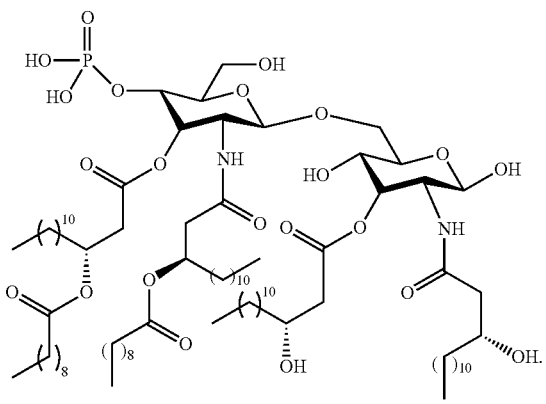

In certain embodiments, the TLR4 agonist is a synthetic GLA adjuvant having the following structure:

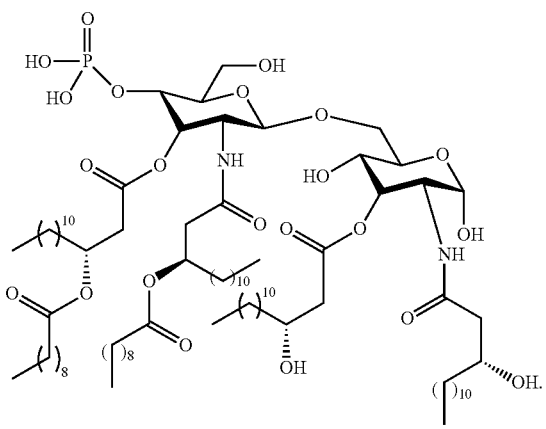

In another embodiment, the adjuvant used in a composition of the invention herein is an attenuated lipid A derivative (ALD). ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay (CELD50) ALDs useful according to the subject invention include monophosphoryl lipid A (MLA) and 3-deacylated monophosphoryl lipid A (3D-MLA). MLA and 3D-MLA are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 U.S. Pat. No. 4,912,094 to Myers, et al., also assigned to Ribi ImmunoChem Research, Inc., embodies 3-deacylated monophosphoryl lipid A and a method for its manufacture.

In some embodiments, response modifiers such as imidazoquinoline and other immune response modifiers known in the art and may also be included as adjuvants in certain presently disclosed embodiments. Certain preferred imidazoquinoline immune response modifiers include, by way of non-limiting example, resiquimod (R848), imiquimod and gardiquimod (Hemmi et al., 2002 Nat. Immunol. 3:196; Gibson et al., 2002 Cell. Immunol. 218:74; Gorden et al., 2005 J. Immunol. 174:1259); these and other imidazoquinoline immune response modifiers may, under appropriate conditions, also have TLR agonist activity as described herein. Other immune response modifiers are the nucleic acid-based double stem loop immune modifiers (dSLIM). Specific examples of dSLIM that are contemplated for use in certain of the presently disclosed embodiments can be found in Schmidt et al., 2006 Allergy 61:56; Weihrauch et al. 2005 Clin Cancer Res. 11(16):5993-6001; Modern Biopharmaceuticals, J. Knäblein (Editor). John Wiley & Sons, Dec. 6, 2005. (dSLIM discussed on pages 183 to ~200), and from Mologen AG (Berlin, FRG: [retrieved online on Aug. 18, 2006, see worldwide web at mologen.com/English/04.20-dSLIM.shtml]).

In some embodiments, an adjuvant used in a composition described herein is a polysaccharide derived from bacteria or plants. Non-limiting examples of polysaccharide-based adjuvants that can be used alone or in combination with one or more additional adjuvant in a composition described herein include glucans (e.g., beta glucans), dextrans (e.g., sulfated and diethylaminoethyl-dextrans), glucomannans, galactomannans, levans, xylans, fructans (e.g., inulin), chitosan, endotoxins (e.g., lipopolysaccharide), biobran MGN-3, polysaccharides from *Actinidia eriantha*, eldexomer, and variations thereof.

In some embodiments, an adjuvant used in a composition described herein is a proteosome or subunit thereof. In some embodiments, an adjuvant used in a composition described herein comprises identical or different antigenic peptide sequences assembled around a lysine core. In some embodiments, an adjuvant used in a composition described herein is a toxin (e.g., a bacterial toxin). In some embodiments, the toxin is from one or more bacteria selected from the group consisting of *Escherichia coli*, *Vibrio cholera*, *Bordetella pertussis*, and *Bordetella parapertussis*.

In some embodiments, an adjuvant used in a composition described herein (e.g., themostable lyophilized vaccine) is a delivery adjuvant. A delivery adjuvant can serve as an adjuvant and/or can deliver an antigen. Non-limiting examples of an adjuvant that can be used alone or in combination with one or more additional adjuvant in a composition described herein includes mineral salts (e.g., calcium phosphate), emulsions (e.g., squalene in water), liposomes (e.g., DPPC:cholesterol liposomes), virosomes (e.g., immunopotentiating reconstituted influenza virosomes), and microspheres.

Other adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a composition described herein include PLURONIC® L121 (BASF Corp., Mount Olive, N.J.; see, e.g., Yeh et al., 1996 Pharm. Res. 13:1693; U.S. Pat. No. 5,565,209), CRL1005 (e.g., Triozzi et al., 1997 Clin Canc. Res. 3:2355), poly(lactic-co-glycolic acid) (PLGA), poly(lactic acid) (PLA), poly-(D,L-lactide-co-glycolide) (PLG), and polyI:C. (See, e.g., Powell and Newman, "Vaccine design—The Subunit and Adjuvant Approach", 1995, Plenum Press, New York), In some embodiments, an adjuvant used in a composition described herein (e.g., thermostable lyophilized vaccine) is an organic adjuvant. Organic adjuvants can be adjuvants that are derived from living organisms or chemically contain carbon. In some embodiment, the adjuvant is a peptide derived from a microbial cell wall (e.g., muramyl dipeptide and variants thereof). In some embodiments, the adjuvant is trehalose 6,6'-dimycolate or variants thereof. See Schweneker et al., 2013, Immunobiology, 218(4):664-73. In some embodiments, the adjuvant is stearyl tyrosine.

Saponins and saponin mimetics, including QS21 and structurally related compounds conferring similar effects and referred to herein as QS21 mimetics. (see, e.g., U.S. Pat. No. 5,057,540; EP 0 362 279 B1; WO 95/17210), plant alkaloids such as tomatine, detergents such as (but not limited to) saponin, polysorbate 80, SPAN® 85 and stearyl tyrosine, an imidazoquinoline immune response modifier, and a double stem loop immune modifier (dSLIM, e.g., Weeratna et al., 2005 Vaccine 23:5263) may be used as an adjuvant according to certain of the presently described embodiments.

In some embodiments, the adjuvant used in a composition described herein is a saponin or a saponin mimetic. Detergents including saponins are taught in, e.g., U.S. Pat. No. 6,544,518; Lacaille-Dubois, M and Wagner H. (1996 Phytomedicine 2:363-386), U.S. Pat. No. 5,057,540, Kensil, Crit Rev Ther Drug Carrier Syst, 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. QS21 may comprise an HPLC purified non-toxic fraction derived from the bark of *Quillaja Saponaria* Molina. The production of QS21 is disclosed in U.S. Pat. No. 5,057,540. (See also U.S. Pat. Nos. 6,936,255, 7,029,678 and 6,932,972.) Also described in these references is the use of QS7 (a non-haemolytic fraction of Quil-A) which acts as a potent adjuvant for systemic vaccines. Use of QS21 is further described in Kensil et al. (1991. J. Immunology 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., Vaccine, 10(9):572-577, 1992).

In some embodiments, the adjuvant is an "immunostimulatory complexes" known as ISCOMS (e.g., U.S. Pat. Nos. 6,869,607, 6,846,489, 6,027,732, 4,981,684), including saponin-derived ISCOMATRIX®, which is commercially available, for example, from Iscotec (Stockholm, Sweden) and CSL Ltd. (Parkville, Victoria, Australia).

Escin is another detergent related to the saponins for use in the adjuvant compositions of the embodiments herein disclosed. Escin is described in the Merck index (12th Ed.: entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin (also known as aescin) have been purified and shown to be biologically active (Yoshikawa M, et al. (Chem Pharm Bull (Tokyo) 1996 August; 44(8): 1454-1464)). Digitonin is another detergent, also being described in the Merck index (12th Ed., entry 3204) as a saponin, being derived from the seeds of *Digitalis purpurea* and purified according to the procedure described by Gisvold et al., J. Am. Pharm. Assoc., 1934, 23, 664; and Rubenstroth-Bauer, Physiol. Chem., 1955, 301, 621.

In some embodiments, an adjuvant used in a composition described herein (e.g., thermostable lyophilized vaccine) is an inorganic adjuvant. Inorganic adjuvants can be adjuvants that are generally not carbon-based such as, for example, mineral salts, emulsions, and calcium phosphates. Mineral salts adjuvants contemplated herein include, but are not limited to, aluminum-based compounds such as aluminum phosphate and aluminum hydroxide. As used herein, calcium phosphate adjuvants include, but are not limited to, calcium ions ($Ca^{2+}$) together with orthophosphates ($PO_4^{3-}$), metaphosphates ($PO_3^{-}$), or pyrophosphates ($P_2O_7^{4-}$).

As also noted above, one type of adjuvant for use in a composition as described herein may be the aluminum adjuvants, which are generally referred to as "alum." Alum adjuvants are based on the following: aluminum oxy-hydroxide; aluminum hydroxyphosphate; or various proprietary salts. Vaccines that use alum adjuvants may include vaccines for tetanus strains, HPV, hepatitis A, inactivated polio virus, and other antigens as described herein. Alum adjuvants are advantageous because they have a good safety record, augment antibody responses, stabilize antigens, and are relatively simple for large-scale production. (Edelman 2002 Mol. Biotechnol. 21:129-148; Edelman, R. 1980 Rev. Infect. Dis. 2:370-383.).

In some embodiments, the compositions of the present invention comprise an adjuvant. In some embodiments, the adjuvant is a TLR4 agonist. In some embodiments, the adjuvant is present at a concentration of about 0.5 μg/mL to about 12 mg/mL. In some embodiments, the adjuvant is present at a concentration of about 0.5 μg/mL, about 1 μg/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 20 μg/mL, about 30 μg/mL, about 40 μg/mL, about 50 μg/mL, about 60 μg/mL, about 70 μg/mL, about 80 μg/mL, about 90 μg/mL, or about 100 μg/mL. In some embodiments, the adjuvant is an MPL or GLA described herein. In some embodiments, the adjuvant is present at a concentration of about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, or about 12 mg/mL.

Suitable adjuvants for use in certain compositions described herein (e.g., a thermostable lyophilized vaccine composition) include commercially available adjuvants such as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); AddaVax (InvivoGen); MF59 (Norvartis); AS03 (GlaxoSmithKline); AS01B (GlaxoSmithKline); AS02A (GlaxoSmithKline).

Some embodiments as provided herein include compositions (e.g., thermostable lyophilized vaccine compositions), that contain one adjuvant and at least one more adjuvant that is different from the first adjuvant. For example, a composition provided herein may comprise GLA and a second adjuvant other than GLA. In some embodiments, a composition provided herein comprises two, three, four or five adjuvants. In some embodiments, a composition provided herein comprises two adjuvants.

An adjuvant as described herein includes an adjuvant that, when administered to a subject such as a human (e.g., a human patient), a non-human primate, a mammal or another higher eukaryotic organism having a recognized immune system, is capable of altering (i.e., increasing or decreasing in a statistically significant manner, and in certain embodiments, enhancing or increasing) the potency and/or longevity of an immune response. (See, e.g., Powell and Newman, "Vaccine design—The Subunit and Adjuvant Approach", 1995, Plenum Press, New York) In certain embodiments disclosed herein GLA and a desired antigen, and optionally one or more adjuvant, may so alter, e.g., elicit or enhance, an immune response that is directed against the desired antigen.

Antigens for Use in Thermostable Lyophilized Vaccine Compositions

In some embodiments the thermostable vaccine composition is used to elicit or enhance the immunoreactivity or an immune response in a host to an antigen.

In some embodiments the antigen may be already present in the host such as an autoimmune antigen, allergen, or cancer antigen and the vaccine composition may only include the stable emulsion and optionally an adjuvant that when administered elicits or enhances the immunoreactivity to the antigen already present in a subject. This administration of a vaccine composition comprising the thermostable lyophilized emulsion and an adjuvant for eliciting an immune response to an antigen already present in a host as used herein is a monotherapy.

In some embodiments, a vaccine composition described herein comprises one or more antigens.

An antigen, for use in certain embodiments of the herein described compositions and methods for generating and using such compositions, may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

In some embodiments, an antigen may be present at any concentration sufficient to elicit or enhance immunoreactivity in a subject at a desired level. In some embodiments, an antigen may be present at a concentration range of about 0.1 µg/mL to about 50 µg/mL, about 1 µg/mL to about 50 µg/mL, about 2.5 µg/mL to about 50 µg/mL, about 5 µg/mL to about 50 µg/mL, about 10 µg/mL to about 50 µg/mL, 0.1 µg/mL to about 25 µg/mL, about 1 µg/mL to about 25 µg/mL, about 2.5 µg/mL to about 25 µg/mL, about 5 µg/mL to about 25 µg/mL, about 10 µg/mL to about 25 µg/mL, 0.1 µg/mL to about 10 µg/mL, about 1 µg/mL to about 10 µg/mL, about 2.5 µg/mL to about 10 µg/mL, about 5 µg/mL to about 10 µg/mL, 0.1 µg/mL to about 5 µg/mL, about 1 µg/mL to about 5 µg/mL, about 2.5 µg/mL to about 5 µg/mL, 0.1 µg/mL to about 2.5 µg/mL, about 1 µg/mL to about 2.5 µg/mL, or about 0.1 µg/mL to about 1 µg/mL. The concentrations provided refer to the concentrations of the antigen in either the oil-in-water emulsion formulation prior to lyophilization or in the oil-in-water emulsion upon reconstitution.

In certain embodiments the compositions described herein (e.g., a thermostable lyophilized vaccine composition) comprise an antigen or antigenic composition capable of eliciting an immune response against a human or other mammalian pathogen, which antigen or antigenic composition may include a composition derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gp1, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tickborne encephalitis virus, Japanese Encephalitis Virus) or Influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, or M proteins, or combinations thereof).

In some embodiments the compositions described herein (e.g., a thermostable lyophilized vaccine composition) comprise an antigen or antigenic composition capable of eliciting an immune response against a human or other mammalian pathogen, which antigen or antigenic composition may include a composition derived from one or more bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, —B or —C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example *clostridium* toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii*; *Ehrlichia* spp., including *E. equi* and the agent of the Human Granulocytic Ehrlichiosis; *Rickettsia* spp, including *R. rickettsii*; *Chlamydia* spp. including *C. trachomatis* (for example MOMP, heparin-binding proteins), *C. pneumoniae* (for example MOMP, heparin-binding proteins), *C. psittaci*; *Leptospira* spp., including *L. interrogans*; *Treponema* spp., including *T. pallidum* (for example the rare outer membrane proteins), *T. denticola*, T. hyodysenteriae; or other bacterial pathogens.

In certain embodiments the compositions described herein (e.g., a thermostable lyophilized vaccine composition) comprise an antigen or antigenic composition capable of eliciting an immune response against a human or other mammalian pathogen, which antigen or antigenic composition may include a composition derived from one or more parasites (See, e.g., John, D. T. and Petri, W. A., Markell and Voge's Medical Parasitology—9th Ed., 2006, WB Saunders, Philadelphia; Bowman, D. D., Georgis' Parasitology for Veterinarians-8th Ed., 2002, WB Saunders, Philadelphia) such as *Plasmodium* spp., including *P. falciparum*; *Toxoplasma* spp., including *T. gondii* (for example SAG2, SAGS, Tg34); *Entamoeba* spp., including *E. histolytica*; *Babesia* spp., including *B. microti*; *Trypanosoma* spp., including *T. cruzi*; *Giardia* spp., including *G. lamblia*; Leshmania spp., including *L. major*; *Pneumocystis* spp., including *P. carinii*; *Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis*, and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). Certain embodiments may therefore contemplate vaccine compositions that include an antigen derived from *Schisostoma* spp., *Schistosoma mansonii, Schistosoma haematobium*, and/or *Schistosoma japonicum*, or derived from yeast such as *Candida* spp., including *C. albicans*; *Cryptococcus* spp., including *C. neoformans*.

In some embodiments, a composition described herein comprises at least two heterologous polypeptides of a *Mycobacterium* species of the tuberculosis complex. A *Mycobacterium* species of the tuberculosis complex includes those species traditionally considered as causing the disease tuberculosis, as well as *Mycobacterium* environmental and opportunistic species that cause tuberculosis and lung disease in immune compromised patients, such as patients with AIDS, e.g., *Mycobacterium tuberculosis* (Mtb), *Mycobacterium bovis*, or *Mycobacterium africanum*, BCG, *Mycobacterium avium, Mycobacterium intracellulare, Mycobacterium celatum, Mycobacterium genavense, Mycobacterium haemophilum, Mycobacterium kansasii, Mycobacterium simiae, Mycobacterium vaccae, Mycobacterium fortuitum*, and *Mycobacterium scrofulaceum* (see, e.g., Harrison's Principles of Internal Medicine, volume 1, pp. 1004-1014 and 1019-1020). The sequences of antigens from *Mycobacterium* species are readily available. For example, *Mycobacterium tuberculosis* sequences can be found in Cole et al., Nature 393:537 (1998) and can be found at websites such as those maintained by the Wellcome Trust, Sanger Institute and Institut Pasteur.

Other specific antigens for *M. tuberculosis* that may be used in a composition described herein are for example Th Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. In certain embodiments, fusion proteins include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647.

In certain embodiments, a composition described herein comprises an isolated fusion protein comprising a combination of two or more covalently linked *M. tuberculosis* antigens, or immunogenic fragments thereof, wherein the antigens are selected from the group consisting of Rv0164, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv3872, Rv3873, Rv151 1 and Rv3875, and antigens having at least 90% identity to any of the foregoing sequences.

In certain embodiments, a composition described herein comprises the ID93 fusion protein, which comprises the antigens Rv2608, Rv3619, Rv3620 and Rv1813 or a sequence having at least 90% identity to the combination of antigens. In another embodiment, the composition comprises the ID93 fusion protein, which comprises the antigens Rv2608, Rv3619, Rv3620 and Rv1813, wherein the sequences of the antigens are from *M. tuberculosis*. In another embodiment, the ID93 fusion protein comprises a sequence set forth in SEQ ID NO: 1, or a sequence having at least 90% identity thereto. In some embodiments, the fusion protein comprises a sequence set forth in SEQ ID NO:2, or a sequence having at least 90% identity thereto. In some embodiments, the therapeutic vaccine comprises a fusion protein comprising a combination of *Mycobacterium* antigens Rv2608, Rv3620 and Rv1813, or a sequence having at least 90% identity the combination of antigens. In some embodiments, the *Mycobacterium* antigens Rv2608, Rv3620 and Rv1813 are *M. tuberculosis* antigens Rv2608, Rv3620 and Rv1813. In some embodiments, the fusion protein comprises a sequence set forth in SEQ ID NO:3 or 4, or a sequence having at least 90% identity to SEQ ID NO:3 or SEQ ID NO:4. In some embodiments, antigen Rv1813 comprises the amino acid sequence of SEQ ID NO:5. In some embodiments, antigen Rv3620 comprises the amino acid sequence of SEQ ID NO:6. In some embodiments, antigen Rv2608 comprises the amino acid sequence of SEQ ID NO:7. In some embodiments, antigen Rv3619 comprises the amino acid sequence of SEQ ID NO:8. One skilled in the art would understand that one or more N-terminal amino acids (such as signal sequences) may be removed. These sequences are described in U.S. Pat. No. 8,486,414 which is incorporated herein by reference.

In some embodiments, the composition comprises the ID93 fusion protein, or a polynucleotide encoding the same, which comprises four antigens belonging to families of Mtb proteins associated with virulence (Rv2608, Rv3619, Rv3620) or latency (Rv1813), as described in US Patent Application Publication No. 2010/0129391 (specifically incorporated herein by reference in its entirety).

In some embodiments, a composition described herein comprises an antigen for *Chlamydia*. Antigens for *Chlamydia* include for example the High Molecular Weight Protein (HWMP) (WO 99/17741), ORF3 (EP 366 412), and putative membrane proteins (Pmps). Other *Chlamydia* antigens of the composition can be selected from the group described in WO 99128475. In some embodiments, a composition described herein comprises antigens derived from *Streptococcus* spp., including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other bacterial antigens are derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Derivatives of Hepatitis B Surface antigen are well known in the art and include, inter alia, those PreS1, Pars2 S antigens set forth described in European Patent applications EP-A414 374; EP-A-0304 578, and EP 198474. In some embodiments, a composition described herein comprises the HIV-1 antigen, gp120, especially when expressed in CHO cells. In a further embodiment, the composition comprises gD2t as hereinabove defined.

In some embodiments, a composition described herein comprises an antigen derived from the Human Papilloma Virus (HPV) considered to be responsible for genital warts (HPV 6 or HPV 11 and others), and the HPV viruses responsible for cervical cancer (HPV16, HPV18 and others). In some embodiments, the composition is a genital wart prophylactic, or therapeutic, vaccine comprising L1 particles or capsomers, and fusion proteins comprising one or more antigens selected from the HPV 6 and HPV 11 proteins E6, E7, L1, and L2. Certain forms of fusion protein include L2E7 as disclosed in WO 96/26277, and proteinD(⅓)-E7 disclosed in GB 9717953.5 (PCT/EP98/05285). In some embodiments, the composition is an HPV cervical infection or cancer, prophylaxis or therapeutic vaccine, comprising HPV 16 or 18 antigens. For example, L1 or L2 antigen monomers, or L1 or L2 antigens presented together as a virus like particle (VLP) or the L1 alone protein presented alone in a VLP or caposmer structure. Such antigens, virus like particles and capsomer are per se known. See for example WO94/00152, WO94/20137, WO94/05792, and WO93/02184.

Additional early proteins may be included alone or as fusion proteins such as E7, E2 or preferably F5 for example; some embodiments include a VLP comprising L1E7 fusion proteins (WO 96/11272). In some embodiments, HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such a composition (e.g., a thermostable lyophilized vaccine composition) may optionally contain either or both E6 and E7 proteins front HPV 18, preferably in the form of a Protein D-E6 or Protein D-E7 fusion protein or Protein D E6/E7 fusion protein. A composition of the present invention may additionally comprise antigens from other HPV strains, preferably from strains HPV 31 or 33.

Compositions of the present invention may further comprise antigens derived from parasites that cause Malaria. For example, antigens from Plasmodia *falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. An embodiment of the present invention is a Malaria vaccine wherein the antigenic preparation comprises a combination of the RTS,S and TRAP antigens. Other plasmodia antigens that are likely candidates to be components of a multistage Malaria vaccine are *P. falciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

Certain herein disclosed embodiments contemplate an antigen that is derived from at least one infectious pathogen such as a bacterium, a virus or a fungus, including an Actinobacterium such as *M. tuberculosis* or *M. leprae* or another *mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus, Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti,* Giardia, and *Leishmania*.

For example, in embodiments of compositions containing antigens derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Compositions and methods are known in the art for identifying subjects having, or suspected of being at risk for having, an infection with an infectious pathogen as described herein.

For example, the bacterium *Mycobacterium tuberculosis* cases tuberculosis (TB). The bacteria usually attack the lungs but can also attack the kidney, spine, and brain. If not treated properly, TB disease can be fatal. The disease is spread from one person to another in the air when an infected person sneezes or coughs. In 2003, more than 14,000 cases of TB were reported in the United States.

Although tuberculosis can generally be controlled using extended antibiotic therapy, such treatment is not sufficient to prevent the spread of the disease and concerns exist regarding the potential selection for antibiotic-resistant strains. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance. (e.g., U.S. Pat. No. 7,087,713)

Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48 72 hours after injection, which indicates exposure to Mycobacterial antigens. Sensitivity and specificity have, however, been a problem with this test, and individuals vaccinated with BCG cannot be distinguished from infected individuals. (e.g., U.S. Pat. No. 7,087,713)

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-gamma), which, in turn, has been shown to trigger the anti-mycobacterial effects of macrophages in mice. While the role of IFN-gamma in humans is less clear, studies have shown that 1,25-dihydroxy-vitamin D3, either alone or in combination with IFN-gamma or tumor necrosis factor-alpha, activates human macrophages to inhibit *M. tuberculosis* infection. Furthermore, it is known that IFN-gamma stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection, see Chan and Kaufmann, in Tuberculosis: Pathogenesis, Protection and Control, Bloom (ed.), ASM Press. Washington, D.C. (1994).

Existing compounds and methods for diagnosing tuberculosis or for inducing protective immunity against tuberculosis include the use of polypeptides that contain at least one immunogenic portion of one or more *Mycobacterium* proteins and DNA molecules encoding such polypeptides. Diagnostic kits containing such polypeptides or DNA sequences and a suitable detection reagent may be used for the detection of *Mycobacterium* infection in patients and biological samples. Antibodies directed against such polypeptides are also provided. In addition, such compounds may be formulated into compositions described herein for immunization against *Mycobacterium* infection. (U.S. Pat. Nos. 6,949,246 and 6,555,653).

Malaria was eliminated in many parts of the world in the 1960s, but the disease still persists and new strains of the disease are emerging that are resistant to existing drugs. Malaria is a major public health problem in more than 90 countries. Nine out of ten cases of malaria occur in sub-Saharan Africa. More than one third of the world's population is at risk, and between 350 and 500 million people are infected with malaria each year. Forty-five million pregnant women are at risk of contracting malaria this year. Of those individuals already infected, more than 1 million of those infected die each year from what is a preventable disease. The majority of those deaths are children in Africa.

Malaria is usually transmitted when a person is bitten by an infected female *Anopheles* mosquito. To transmit the disease, the mosquito must have been infected by having drawn blood from a person already infected with malaria. Malaria is caused by a parasite and the clinical symptoms of the disease include fever and flu-like illness, such as chills, headache, muscle aches, and tiredness. These symptoms may be accompanied by nausea, vomiting, and diarrhea. Malaria can also cause anemia and jaundice because of the loss of red blood cells. Infection with one type of malaria, *Plasmodium falciparum*, if not promptly treated, may cause kidney failure, seizures, mental confusion, coma, and death.

An in vitro diagnostic method for malaria in an individual is known, comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed (see, e.g., U.S. Pat. No. 7,087,231).

Expression and purification of a recombinant *Plasmodium falciparum* (3D7) AMA-1 ectodomain have been described. Previous methods have produced a highly purified protein which retains folding and disulfide bridging of the native molecule. The recombinant AMA-1 is useful as a diagnostic reagent as well as in antibody production, and as a protein for use alone, or as part of, a vaccine to prevent malaria. (U.S. Pat. No. 7,029,685)

Polynucleotides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection. (U.S. Pat. No. 6,706,872) Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection (see, e.g., U.S. Pat. No. 6,231,861).

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. (U.S. Pat. No. 7,060,276) Similarly known are the expression and purification of a recombinant *Plasmodium falciparum* (3D7) MSP-1$_{42}$, which retains folding and disulfide bridging of the native molecule. The recombinant MSP-1$_{42}$ is useful as a diagnostic reagent, for use in antibody production, and as a vaccine. (U.S. Pat. No. 6,855,322).

Diagnostic methods for the detection of human malaria infections to identify a subject having or suspected of being at risk for having an infection with a malaria infectious pathogen are thus known according to these and related disclosures. Specifically, for example, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the above-described reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis. Detection of the reduced APAD in the foregoing manner provides a positive indication of malaria infection (e.g., U.S. Pat. No. 5,124,141). In another methodology for diagnosing malaria, a polypeptide comprising a characteristic amino acid sequence derived from the *Plasmodium falciparum* antigen GLURP, is recognized in a test sample by a specific antibody raised against or reactive with the polypeptide. (U.S. Pat. No. 5,231,168).

Leishmaniasis is a widespread parasitic disease with frequent epidemics in the Indian subcontinent, Africa, and Latin America and is a World Health Organization priority for vaccine development. A complex of different diseases, *Leishmania* parasites cause fatal infections of internal organs, as well as serious skin disease. One of the most devastating forms of leishmaniasis is a disfiguring infection of the nose and mouth. The number of cases of leishmaniasis are increasing, and it is now out of control in many areas. Leishmaniasis is also on the rise in some developed countries, specifically southern Europe as a result of HIV infection. Available drugs are toxic, expensive, and require long-term daily injections.

*Leishmania* are protozoan parasites that inhabit macrophages or the white blood cells of the immune system. The parasites are transmitted by the bite of small blood sucking insects (sand flies), which are difficult to control, as they inhabit vast areas of the planet.

Visceral leishmaniasis is the most dangerous of the three manifestations of the disease. It is estimated that about 500,000 new cases of the visceral form (kala-azar or "the killing disease") occur each year. More than 200 million people are currently at risk for contracting visceral leishmaniasis. Over 90 percent of visceral leishmaniasis cases occur in India, Bangladesh, Sudan, Brazil, and Nepal. Most of the deaths occur in children. Those with the cutaneous forms are often left permanently disfigured.

*Leishmania* infections are difficult to diagnose and typically involve histopathologic analysis of tissue biopsy specimens. Several serological and immunological diagnostic assays have, however, been developed. (U.S. Pat. No. 7,008,774; Senaldi et al., (1996) J. Immunol. Methods 193:9 5; Zijlstra, et al., (1997) Trans. R. Soc. Trop. Med. Hyg. 91:671 673; Badaro, et al., (1996) J. Inf. Dis. 173:758 761; Choudhary, S., et al., (1992) J. Comm. Dis. 24:32 36; Badaro, R., et al., (1986) Am. J. Trop. Med. Hyg. 35:72 78; Choudhary, A., et al., (1990) Trans. R. Soc. Trop. Med. Hyg. 84:363 366; and Reed, S. G., et al., (1990) Am. J. Trop. Med. Hyg. 43:632 639). The promastigotes release metabolic products into the culture medium to produce conditioned medium. These metabolic products are immunogenic to the host. See Schnur, L. F., et al., (1972) lsrl. J. Med. Sci. 8:932 942; Sergeiev, V. P., et al., (1969) Med. Parasitol. 38:208 212; El-On, J., et al., (1979) Exper. Parasitol. 47:254 269; and Bray, R. S., et al., (1966) Trans. R. Soc. Trop. Med. Hyg. 60:605 609; U.S. Pat. Nos. 6,846,648, 5,912,166; 5,719,263; 5,411,865).

In some embodiments, an antigen is *Leishmania* antigen described in US 2009/0041798, US 2009/0291099, U.S. Pat. Nos. 8,410,258, 8,231,881, and WO 2012/064659, which are incorporated herein by reference. In some embodiments, the antigen is a fusion polypeptide comprising at least a *Leishmania* sterol 24-c-methyltransferase (SMT) polypeptide sequence and a *Leishmania* non-specific nucleoside hydrolase (NH) polypeptide sequence. In some embodiments, the *Leishmania* NH polypeptide sequence comprises at least an immunogenic portion of a sequence having at least 90% identity to a *Leishmania* NH sequence of *L. donovani*, *L. infantum* and *L. major*. In some embodiments, the *Leishmania* NH polypeptide sequence comprises at least an immunogenic portion of a sequence selected from the group consisting of SEQ ID NOs: 1, 3 and 5, or a sequence having at least 90% identity thereto. In some embodiments, the *Leishmania* SMT polypeptide sequence comprises at least an immunogenic portion of a sequence having at least 90% identity to a *Leishmania* SMT sequence of *L. donovani*, *L. infantum* and *L. major*. In some embodiments, the *Leishmania* SMT polypeptide sequence comprises at least an immunogenic portion of a sequence selected from the group consisting of SEQ ID NOs: 7, 9 and 11, or a sequence having at least 90% identity thereto. In some embodiments, the fusion polypeptide comprises an amino acid sequence set forth in SEQ ID NO: 13, or a sequence having at least 90% identity thereto. The sequences of SEQ ID NO:1, 3, 5, 7, 9, 11 and 13 are provided in WO 2012/064659 and US 20120114688, which are incorporated herein by reference.

About 40 million people around the world are infected with HIV, the virus that causes AIDS. Around 3 million people die of the disease each year, 95 percent of them in the developing world. Each year, close to 5 million people become infected with HIV. Currently, sub-Saharan African carries the highest burden of disease, but it is quickly spreading to other countries such as India, China, and Russia. The epidemic is growing most rapidly among minority populations. In the United States there have been more than 950,000 cases of AIDS reported since 1981. AIDS hits people during their most productive years. Women, for both biological and social reasons, have an increased risk for HIV/AIDS.

AIDS is caused by human immunodeficiency virus (HIV), which kills and damages cells of the body's immune system and progressively destroys the body's ability to fight infections and certain cancers. HIV is spread most commonly by having unprotected sex with an infected partner. The most robust solution to the problem is preventing the virus from spreading. Making a safe, effective, and affordable HIV vaccine is one way to reach this goal. Across the world, fewer than one in five people at high risk for HIV infection have access to effective prevention.

Methods for diagnosing HIV infections are known, including by virus culture, PCR of definitive nucleic acid sequences from patient specimens, and antibody tests for the presence of anti-HIV antibodies in patient sera, (see e.g., U.S. Pat. Nos. 6,979,535, 6,544,728, 6,316,183, 6,261,762, 4,743,540.).

According to certain other embodiments as disclosed herein, the compositions and methods of use may include an antigen that is derived from a cancer cell, as may be useful for the immunotherapeutic treatment of cancers. For example, the composition may find utility with tumor rejection antigens such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 Current Opinions in Immunology 8, pps 628-636; Van den Eynde et al., International Journal of Clinical & Laboratory Research (1997 & 1998); Correale et al. (1997), Journal of the National Cancer Institute 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens are suitable for use in compositions described herein include, but are not restricted to, tumor-specific or tumor-associated gangliosides such as $GM_2$, and $GM_3$ or conjugates thereof to carrier proteins; or an antigen for use in a GLA vaccine composition for eliciting or enhancing an anti-cancer immune response may be a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., Proc. Nat. Acad. Sci. USA 95(4) 1735-1740 1998), PSMA or, in a preferred embodiment an antigen known as Prostase. (e.g., Nelson, et al., Proc. Natl. Acad. Sci. USA (1999) 96: 3114-3119; Ferguson, et al. Proc. Natl. Acad. Sci. USA 1999. 96, 3114-3119; WO 98/12302; U.S. Pat. No. 5,955,306; WO 98/20117; U.S. Pat. Nos. 5,840,871 and 5,786,148; WO 00/04149. Other prostate specific antigens are known from WO 98/137418, and WO/004149. Another is STEAP (PNAS 96 14523 14528 7-12 1999).

Other tumor associated antigens useful in the context of the present invention include: Plu-1 (J Biol. Chem 274 (22) 15633-15645, 1999), HASH-1, HasH-2, Cripto (Salomon et al Bioessays 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

The herein disclosed embodiments pertaining to compositions comprising a cancer antigen may be useful against any cancer characterized by tumor associated antigen expression, such as HER-2/neu expression or other cancer-specific or cancer-associated antigens.

Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohistocytochemical and immunohistopathological examination of patient samples (e.g., blood, skin biopsy, other tissue biopsy, surgical specimens, etc.), PCR tests for defined genetic (e.g., nucleic acid) markers, serological tests for circulating cancer-associated antigens or cells bearing such antigens, or for antibodies of defined specificity, or other methodologies with which those skilled in the art will be familiar. See, e.g., U.S. Pat. Nos. 6,734,172; 6,770,445; 6,893,820; 6,979,730; 7,060,802; 7,030,232; 6,933,123; 6,682,901; 6,587,792; 6,512,102; 7,078,180; 7,070,931; JP5-328975; Waslylyk et al., 1993 Eur. J Bioch. 211(7):18.

Compositions and methods according to certain embodiments of the present invention may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells (Akamizu et al., 1996; Kellerman et al., 1995; Raju et al., 1997; and Texier et al., 1992); pemphigus is cadherin-like pemphigus antigens such as desmoglein 3 and other adhesion molecules (Memar et al., 1996: Stanley, 1995; Plott et al., 1994; and Hashimoto, 1993); and thrombic thrombocytopenic purpura is antigens of platelets. (See, e.g., U.S. Pat. No. 6,929,796; Gorski et al. (Eds.), Autoimmunity, 2001, Kluwer Academic Publishers, Norwell, Mass.; Radbruch and Lipsky, P. E. (Eds.) Current Concepts in Autoimmunity and Chronic Inflammation (Curr. Top. Microbiol. and Immunol.) 2001, Springer, N.Y.)

Autoimmunity plays a role in more than 80 different diseases, including type 1 diabetes, multiple sclerosis, lupus, rheumatoid arthritis, scleroderma, and thyroid diseases. Vigorous quantitative estimates of morbidity for most autoimmune diseases are lacking. Most recent studies done in the late 1990s reveal that autoimmune diseases are the third most common major illness in the United States; and the most common autoimmune diseases affect more than 8.5 million Americans. Current estimates of the prevalence of the disease range from 5 to 8 percent of the United States population. Most autoimmune diseases disproportionately affect women. Women are 2.7 times more likely than men to acquire an autoimmune disease. Women are more susceptible to autoimmune diseases; men appear to have higher levels of natural killer cell activity than do women. (Jacobsen et al, Clinical Immunology and Immunopathology, 84:223-243, 1997.)

Autoimmune diseases occur when the immune system mistakes self tissues for nonself and mounts an inappropriate attack. The body can be affected in different ways from autoimmune diseases, including, for example, the gut (Crohn's disease) and the brain (multiple sclerosis). It is known that an autoantibody attacks self-cells or self-tissues to injure their function and as a result causes autoimmune diseases, and that the autoantibody may be detected in the patient's serum prior to the actual occurrence of an autoimmune disease (e.g., appearance of clinical signs and symptoms). Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests (e.g., U.S. Pat. Nos. 6,919,210, 6,596, 501, 7,012,134, 6,919,078) while other autoimmune diagnostics may involve detection of a relevant metabolite (e.g., U.S. Pat. No. 4,659,659) or immunological reactivity (e.g., U.S. Pat. Nos. 4,614,722 and 5,147,785, 4,420,558, 5,298, 396, 5,162,990, 4,420,461, 4,595,654, 5,846,758, 6,660, 487).

In certain embodiments, the compositions of the invention will be particularly applicable in treatment of the elderly and/or the immunosuppressed, including subjects on kidney dialysis, subjects on chemotherapy and/or radiation therapy, transplant recipients, and the like. Such individuals generally exhibit diminished immune responses to vaccines and therefore use of the compositions of the invention can enhance the immune responses achieved in these subjects.

In other embodiments, the antigen or antigens used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):577-121). Exacerbations of COPD are often caused by bacterial (e.g. pneumococcal) infection (Clin Microbiol Rev. 2001 April; 14(2):336-63).

Oils for Use in the Thermostable Compositions

Certain embodiments contemplate compositions described herein that include an oil, which in some such embodiments may contribute adjuvant activity and in other such embodiments may additionally or alternatively provide a pharmaceutically acceptable carrier or excipient. Any number of suitable oils are known and may be selected for inclusion in the compositions based on the present disclosure. Examples of such oils, by way of illustration and not limitation, include squalene, synthetic squalene, mineral oil, grape seed oil, a synthetic isoprenoid, olive oil, cholesterol, and a mannide monooleate.

An oil contemplated herein can be used in an emulsion system and such emulsion systems are referred to as an emulsion adjuvant. Emulsion adjuvants include oil-in-water, water-in-oil, or water-in-oil-in-water mixtures. Without being bound by theory, such emulsion adjuvants can function by enabling slow release of antigens to provide continued stimulation of the immune system. Certain emulsion adjuvants can also be used as a delivery system for other adjuvants including immunostimulatory adjuvants such as, but not limited to, CpG oligodeoxynucleotides (CpG ODN), glucopyranosyl lipid adjuvant (GLA), monophosphoryl lipid A (MLA), and 3-deacylated monophosphoryl lipid A (3D-MLA). Certain emulsion systems for formulating adjuvant compositions have been described, including single or multiphase emulsion systems. Oil-in-water emulsion adjuvants per se have been suggested to be useful as an adjuvant composition (EP 0 399 843B), also combinations of oil-in-water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil-in-water emulsions (U.S. Pat. No. 5,424,067; EP 0 480 981 B).

The oil emulsion adjuvants for use in the present invention may be natural or synthetic, and may be mineral or organic. Examples of mineral and organic oils will be readily apparent to the man skilled in the art. In a particular embodiment, a composition of the invention (e.g., a themostable lyophilized vaccine) comprises an emulsion of oil-in-water wherein the adjuvant is incorporated in the oil phase. In order for an oil-in-water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any plant oil, vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used.

Squalene (2,6,10,15,19,23-Hexamethyl-2,6,10,14,18,22-tetracosahexaene), for example, is an unsaturated oil which is found in large quantities in shark-liver oil, and in lower quantities in olive oil, wheat germ nil, rice bran oil, and yeast, and is a particularly preferred oil for use in this invention. Squalene is a metabolizable oil virtue of the fact that it is an intermediate in the biosynthesis of cholesterol (Merck index, 10th Edition, entry no. 8619). Illustrative metabolizable oils useful according to the subject invention include, but are not limited to, squalene, soybean oil, sesame oil and caprylic/capric acid triglycerides (MIGLYCOL 810 oil). In one embodiment, the metabolizable oil comprises squalene. In another embodiment, the metabolizable oil comprises one or more yeast-derived isoprenoids, such as yeast-derived squalene or related isoprenoid structure derived from yeast.

In some embodiments, the compositions of the present invention comprise a metabolizable oil that is present at a concentration of about 0.01%-5% v/v, about 0.01%-4% v/v, about 0.01%-3% v/v, about 0.01%-2% v/v, about 0.01%-1% v/v, or about 0.01%-0.5% v/v. In some embodiments, the metabolizable oil is present at a concentration of about 0.01% v/v, about 0.05% v/v, about 0.1% v/v, about 0.5% v/v, about 1% v/v, about 1.5% v/v, about 2% v/v, about 2.5% v/v, about 3% v/v, about 3.5% v/v, about 4% v/v, about 4.5% v/v, about 5% v/v, about 6% v/v, about 7% v/v, about 8% v/v, about 9% v/v, about 10% v/v, about 11% v/v, about 12% v/v, about 13% v/v, about 14% v/v, about 15% v/v, about 16% v/v, about 17% v/v, about 18% v/v, about 19% v/v, or about 20% v/v. In some embodiments, the metabolizable oil is present at a concentration of about 2% v/v. In some embodiments, the metabolizable oil is present at a concentration below 1% v/v. The percentages described refer to the percentages in either the oil-in-water emulsion formulation prior to lyophilization or in the oil-in-water emulsion upon reconstitution.

The size of the oil droplets found within the stable oil-in-water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges.

The hydrophilic-lipophilic balance (HLB) of an emulsion allows for the estimation of the hydrophilic or lipophilic force of a surfactant. The HLB of an amphiphilic molecule is generally calculated as follows:

$$HLB=(20\times\text{Weight of the hydrophilic part})/(\text{Weight of the amphiphilic molecule})$$

The HLB may have a value ranging from 0 (for the most lipophilic molecule) to 20 (for the most hydrophilic molecule). According to the chemical composition of the surfactant (notably for example the addition of ethoxyl groups or of alkene oxides), this estimation may change and the domain of HLB value may increase (for example, the LUTROL F68® has a HLB of 29). With a mixture of surfactants, the HLB of the mixture is the addition of the HLB of each surfactant, balanced by its Weight ratio:

$$HLB=(HLB \text{ surfactant } X\times\text{Weight surfactant } X) + (HLB \text{ surfactant } Y\times\text{Weight surfactant } Y)/(\text{Weight surfactant } X+\text{Weight surfactant } Y)$$

In one embodiment of an emulsion made according to the present invention, the final HLB of the emulsion is from about 9 to about 12, preferably from about 9.5 to about 11.5 and more preferably from about 10 to about 11.5. In some embodiments the HLB of the emulsion is from about 10.5 to about 11.0. The method of producing oil-in-water emulsions is well known to the person skilled in the art. Commonly, the method comprises the mixing the oil phase with a suitable surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar) could be adapted to produce smaller or larger volumes of emulsion. This adaptation could be achieved by routine experimentation comprising the measurement of the resultant emulsion until a preparation was achieved with oil droplets of the required diameter.

Use of Pharmaceutical Thermostable Compositions

In another aspect, provided herein are methods for stimulating an immune response in a subject comprising administering a reconstituted thermostable vaccine composition described herein to the subject. The method may further comprise a step of reconstituting the thermostable lyophilized vaccine composition into an oil-in-water emulsion before administration.

Accordingly, the present invention is useful for enhancing or eliciting, in a host, a patient or a subject, or in cell culture, an immune response. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

Routes of Administration

The present invention is directed to methods and compositions for vaccination, treatment and prevention of conditions such as an infectious disease, cancer, or an autoimmune disease. The methods of the present invention comprise routes of administration that include parenteral and non-parenteral administration. Non-parenteral routes of administration include, but are not limited to, oral, buccal, sublingual, topical, transdermal, ophthalmic, otic, nasal, rectal, and vaginal routes. Injectable methods include, but are not limited to, parenteral routes of administration, intravenous, intramuscular, subcutaneous, intraperitoneal, intraspinal, intrathecal, intracerebroventricular, intraarterial and other routes of injection. These inventions contemplate compositions that can provide controlled, slow release, or sustained release of the antigen and/or adjuvant over a predetermined period of time.

Formulations

Formulations are known to those skilled in the art and include but are not limited to formulations such as tablets, coated tablets, chewable tablets, effervescent tablets, pellets, capsules, syrups, suppositories, injectable formulations, and dispersion of the active agent in a medium that is insoluble in physiologic fluids or where the release of the antigen and/or adjuvant is released after degradation of the formulation due to mechanical, chemical or enzymatic activity.

It is to be understood that this invention is not limited to the particular formulations, process steps, and materials disclosed herein as such formulations, process steps, and materials may vary somewhat.

Kits and Pharmaceutical Packs

Also contemplated in certain embodiments are kits comprising the herein described vaccine compositions, which may be provided in one or more containers. In one embodiment all components of the vaccine compositions are present together in a single container, but the invention embodiments are not intended to be so limited and also contemplate two or more containers.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Preferred examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

The invention will be more fully understood by reference to the following examples. They should not, however, be construed as limiting the scope of the invention. It is understood that the examples and embodiments described herein are for illustrative purposes only. The various embodiments described above can be combined to provide further embodiments. Various modifications or changes in light thereof will become apparent to those skilled in the art from the foregoing description and are to be included within the spirit and purview of this application, and are to fall within the scope of the appended claims.

EXAMPLES

Example 1: Lyophilized Vaccine Emulsion Formulation and Stability in Single and Multi-Excipient Systems Lyophilization of an oil-in-water stable emulsion (SE) for use in vaccines was desired. The capacity of an excipient to form a thermally stable elegant cake upon lyophilization and/or preserve emulsion integrity upon reconstitution was investigated in order to develop thermally-stable vaccine systems that reduced or eliminated the need for cold chain maintenance at all terrestrially relevant temperatures.
Materials and Methods
Formulation and Lyophilization A squalene-containing stable emulsion (SE) previously described (EM001; Fox et al., 2012, Influenza and Other Respiratory Viruses, in press) was lyophilized at a final concentration of 2.0% squalene (v/v) (diluted to a target final injection concentration from an initial 10% formulation), with a total fill volume of 1.0 mL. Excipient concentrations were reported as mass percentage (% w/v) and emulsion concentrations as volume percentage (% v/v) of the squalene oil phase. Maltose, D-(−)-ribose, D-(−)-fructose, lactose, polyethylene glycol (PEG; mw 3,350 Da), lactulose, nicotinic acid, D(+)-rafinose pentahydrate, 2,6-pyridinedicarboxylic acid, and L-proline were purchased from Sigma-Aldrich (St. Louis, Mo.). USP grade D(+)-mannitol and D(+)-trehalose dihydrate, NF grade sucrose and lactose monohydrate, and dextran (mw 40,000 Da) were purchased from Spectrum Chemical (New Brunswick, N.J.). D(+)-Mannose, stachyose hydrate, and USP grade dextrose monohydrate were purchased from Thermo Scientific (Waltham, Mass.). Samples were formulated using the above excipients at various concentrations dissolved in water that had been de-ionized and filtered through a Barnstead/Thermolyne (Dubuque Iowa) E-Pure D4631 filtration system followed by a 20 nm Whatman (Maidstone, Kent, UK) Anotop plus filter. Formulations resulting in extreme pH shifts (below 5.0 or above 7.0) upon reconstitution were re-formulated to pH 5.5 before lyophilization using NaCl and NaOH. Lyophilization was performed using a VirTis (Gardiner, N.Y.) AdVantage 2.0 EL-85 benchtop freeze dryer. The lyophilization recipe utilized a thermal treatment schedule including a 10-hour freezing step from 4 to −40° C., and an annealing step at −15° C. The primary drying phase (at 100 mTorr) lasted 18.3 hours from −40° C. to 25° C. Finally, a secondary drying phase at 50 mTorr was employed at 25° C. for 9 hours. All samples were stoppered in atmospheric gas at 500 mTorr, sealed using aluminum caps, and stored at 4° C. until use.
Reconstitution Prior to reconstitution, cakes were visually characterized as either an elegant white cake (meaning the cake was white, approximately the same volume as was filled, and appeared to have a uniform lattice), a film, or anything different from an elegant white cake. All samples were reconstituted using 20 nm filtered water (described above) and gently swirled by hand until either all components had solubilized, or until three minutes had elapsed, whichever came first. Following reconstitution, formulations were described as either a milky white emulsion (appearing similar to the pre-lyophilized formulation), or otherwise, noting any differences from a milky white emulsion. Aliquots of each formulation were then allowed to rest at room temperature for 1 hour, and visually evaluated for evidence of a thick, white phase on the surface which was referred to as creaming. The pH of each formulation was also tested, using a Mettler-Toledo (Columbus, Ohio) MP225 pH meter.
Melting Point Determination The melting points of each lyophilized formulation were evaluated in triplicate using a Stanford Research Systems (Sunnyvale, Calif.) OptiMelt automated melting point system. Each melting capillary was probed once into the cake and tamped down until the material settled to the bottom. Melting was performed from 27° C. to 200° C., (typically truncated once melting had completed) with a ramp rate of 1° C. per minute.

An alternative metric for melting point involved the use of an imaging melting point apparatus. Vials of lyophilized SE with various excipients were melted in triplicate as described above. The melting transition was observed as an opaque cake melting into a clear liquid which decreased the light intensity of the sample in the image. Onset points were visually estimated as the first noticeable reduction in cake volume at the beginning of the melting transition (the start of cake changes immediately before melting), and the cake's midpoint melting point ($T_m$) was determined as the temperature at which the cakes had lost half of the pixel intensity between a fully solid and a fully melted cake. Similarly, the temperatures at which the cake had lost 25 and 75 percent of intensity (normalized to the beginning and end of the transition) were calculated as a metric of melting range.
Moisture Determination Moisture contents of 5% trehalose-containing lyophilized cakes were characterized using a Denver Instruments (Bohemia, NT) Coulometric Karl Fischer Titrator, (Model 270) using duplicate vials of lyophilized SE (5% trehalose with 2% oil SE) following 2 independent lyophilization runs. Titration measurements were taken at a medium stirring speed, with an endpoint persistence time of 15 seconds and endpoint slope of 0.05. Samples were reconstituted using Riedel-de-Haens Hydranal AG Solution (Sigma-Aldrich, St. Louis, Mo.) and the weighed solution was injected into the titrator. Following mass determination of water content using the instrument, the water percentage was calculated as % w/w.

Particle Size and Zeta Potential

Emulsion particle size, polydispersity (PdI), and zeta potential were evaluated using dynamic light scattering (DLS) on a Malvern (Worcestershire, UK) Nano-ZS. Measurements were performed generally as previously described (Fox et al., 2011, Pharmaceutical Development and Technology, 16(5):511-519). Briefly, all DLS size measurements were performed in $10^{-2}$ dilutions into 20 nm filtered water (described above) and evaluated in triplicate on single aliquots. For zeta-potential measurements, the same aliquot was evaluated using triplicate measurements and an automatic software determination of the measurement duration between 20 and 40 runs.

High-Performance Liquid Chromatography

Chemical degradation of squalene, DMPC, and GLA, was monitored by Reverse-Phase High-Performance Liquid Chromatography (RP-HPLC). An Agilent 1200 (Santa Clara, Calif.) and an ESA Biosciences Corona Charged Aerosol Detector (CAD; Chelmsford, Mass.) were used with a Waters Atlantics C18 μm column (4.6 mm×250 mm; Milford, Mass.). See Fox et al., 2008, Colloids and Sufaces B: Biointerfaces, 65:98-105. Mobile phase A contained 75:15:10 (v/v/v) methanol:chloroform:water and 20 mM ammonium acetate with 1% acetic acid and mobile phase B contained 50:50 (v/v) methanol:chloroform with 20 mM ammonium acetate and 1% acetic acid. Samples were prepared by dilution of reconstituted samples 1:20 into mobile phase B. A 9 μl injection was used with a linear gradient from 100% to 10% mobile phase A over 45 minutes, and column temperature of 30° C. All solvents used were HPLC grade.

Reconstitution Screen

Formulations containing 2% SE and each of 5% trehalose, dextrose, lactose, maltose, sucrose, raffinose, mannose, fructose, lactulose, ribose, dextran, PEG, mannitol, stachyose, sorbitol, and proline were generated as described in 3.1. Formulations with dipicolinic acid and nicotinic acid were also generated, but were formulated at 0.5% due to solubility constraints. Each formulation was reconstituted as described above. Samples were characterized according to cake appearance, creaming, particle size, zeta potential, PdI, and pH as described above.

Cake Stability Screen

The melting points of a subset of compounds at 5% were evaluated as described above. These compounds included trehalose, dextrose, lactose, maltose, sucrose, mannose, fructose, lactulose, raffinose, ribose, stachyose, mannitol, and proline. As a follow-up study, formulations containing trehalose, dextrose, lactose, maltose, or sucrose at 5% were generated with 0.2 or 5% mannitol and 2% SE. These formulations were evaluated according to cake melting, creaming, pH, PdI and particle size, as described above.

Accelerated Stability Characterization

Vials of lyophilized SE in 5% trehalose were stored at 25, 37, 50, 60, and 90° C. and reconstituted periodically over 1500 hours or until complete failure was observed. Samples were characterized by DLS, pH, HPLC, and cake appearance at each time point. A non-lyophilized SE was similarly characterized for comparison. Formulations identified as having high cake melting temperatures were selected for additional accelerated stability characterization to develop a more stable system. Formulations included 5% dextrose, maltose, sucrose and trehalose. An experimental formulation containing 15% lactose was also included. The accelerated stability of these formulations was characterized as described above at 90° C. to capture changes in all of these formulations.

Results

Lyophilization of SE in Trehalose

Figure 1B:
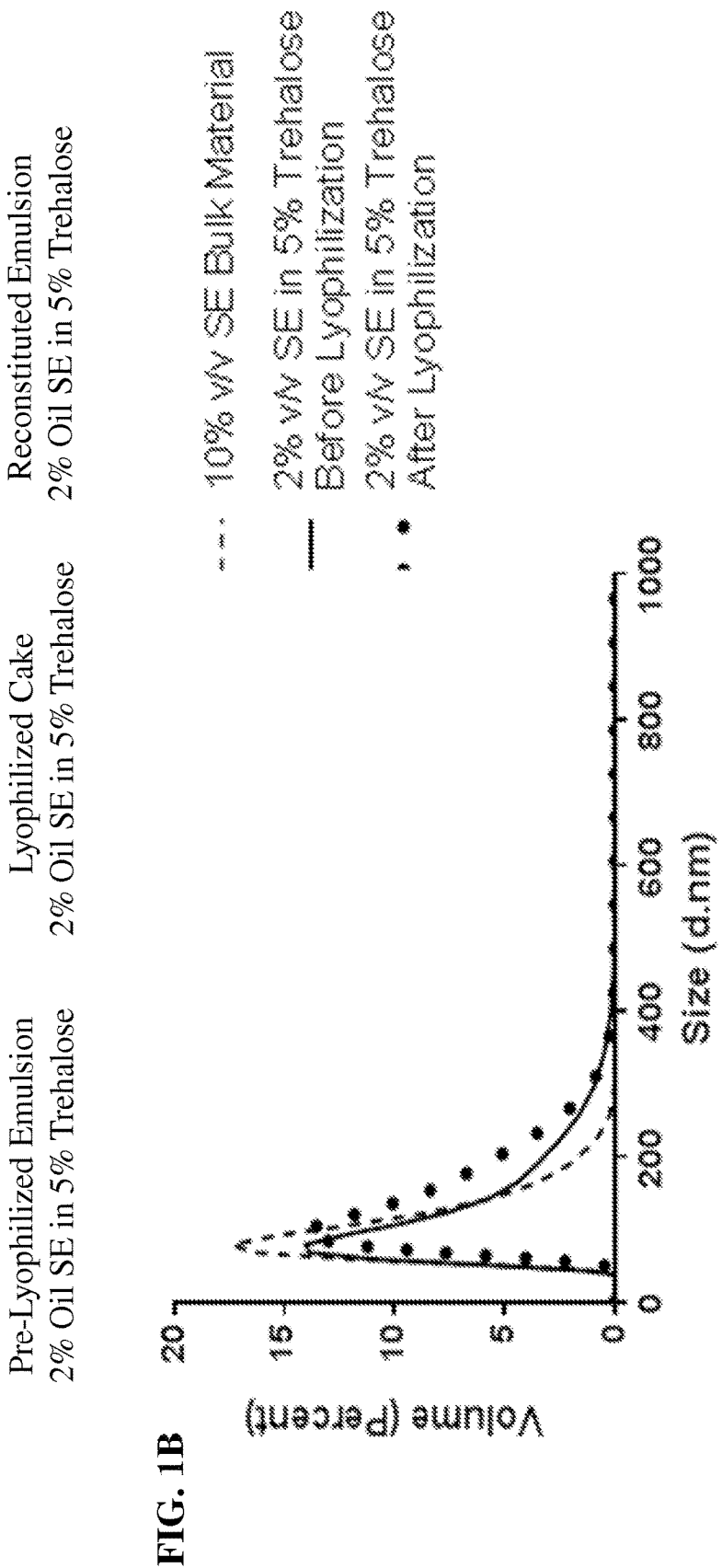
FIG. 1B) Particle size volume distributions were measured by dynamic light scattering (DLS).

Due to the wide use of trehalose in lyophilized formulations, a trehalose containing formulation was evaluated to investigate the feasibility of emulsion lyophilization. Following lyophilization, cakes containing 5% trehalose and 2% v/v squalene SE yielded a slightly shrunken white cake with a moisture content of 0.3% w/w and good reconstitution solubility (FIG. 1A). Reconstituted emulsion appeared visually similar to the non-lyophilized formulation. Upon reconstitution a 21 nm increase in average particle diameter was observed (FIG. 1B), along with a PdI increase of 0.02. Lyophilization and reconstitution did not change the pH. These results provided an initial estimate that the emulsion was maintained following lyophilization and reconstitution.

Accelerated Stability Characterization of SE in Trehalose

Figure 2A:
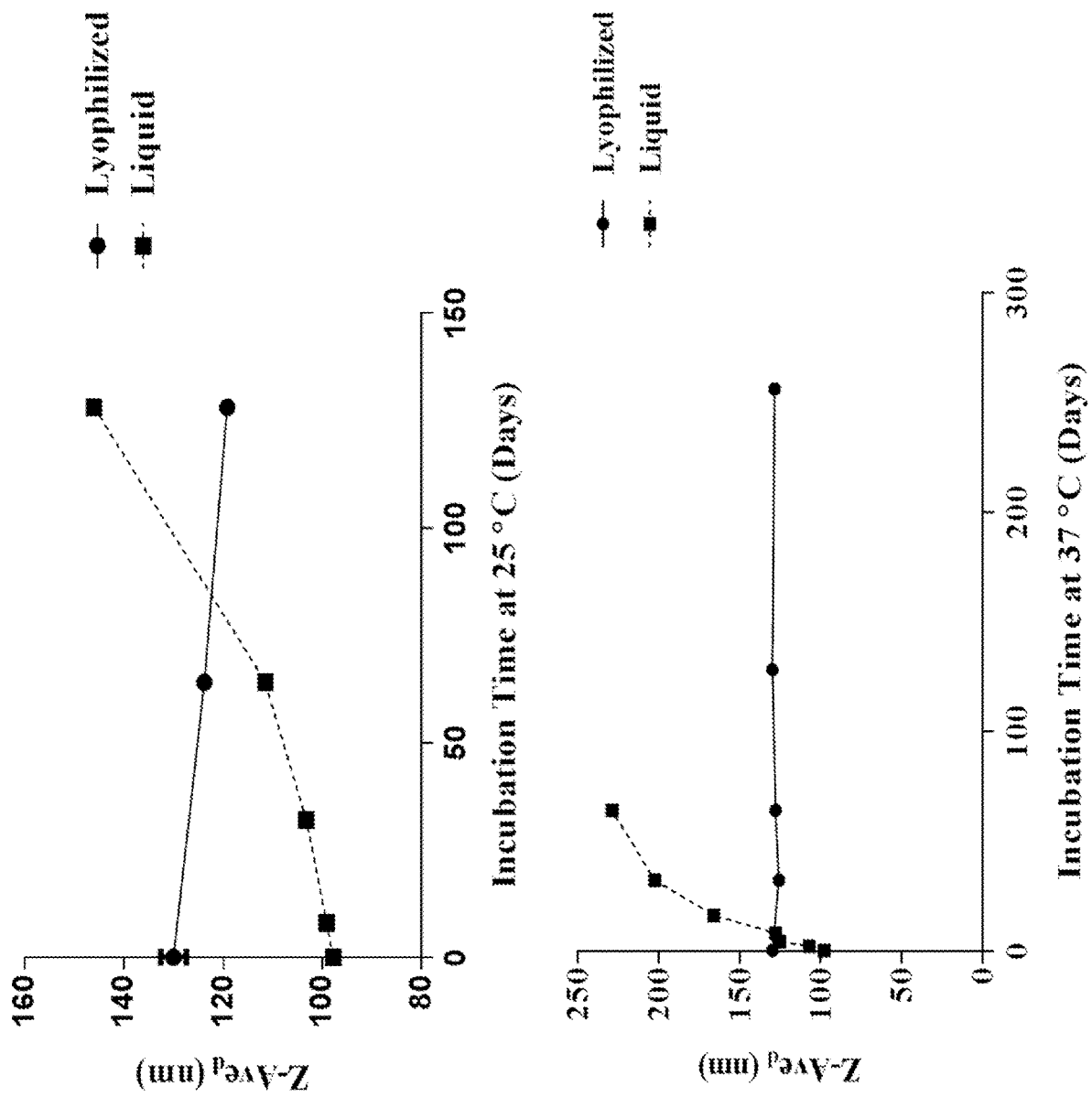
FIG. 2A) Particle size in the liquid emulsion prior to lyophilization (filled square) and reconstituted lyophilized emulsion (filled circle) when stored over time at 25° C. (top panel) or 37° C. (bottom panel).
Figure 2B:
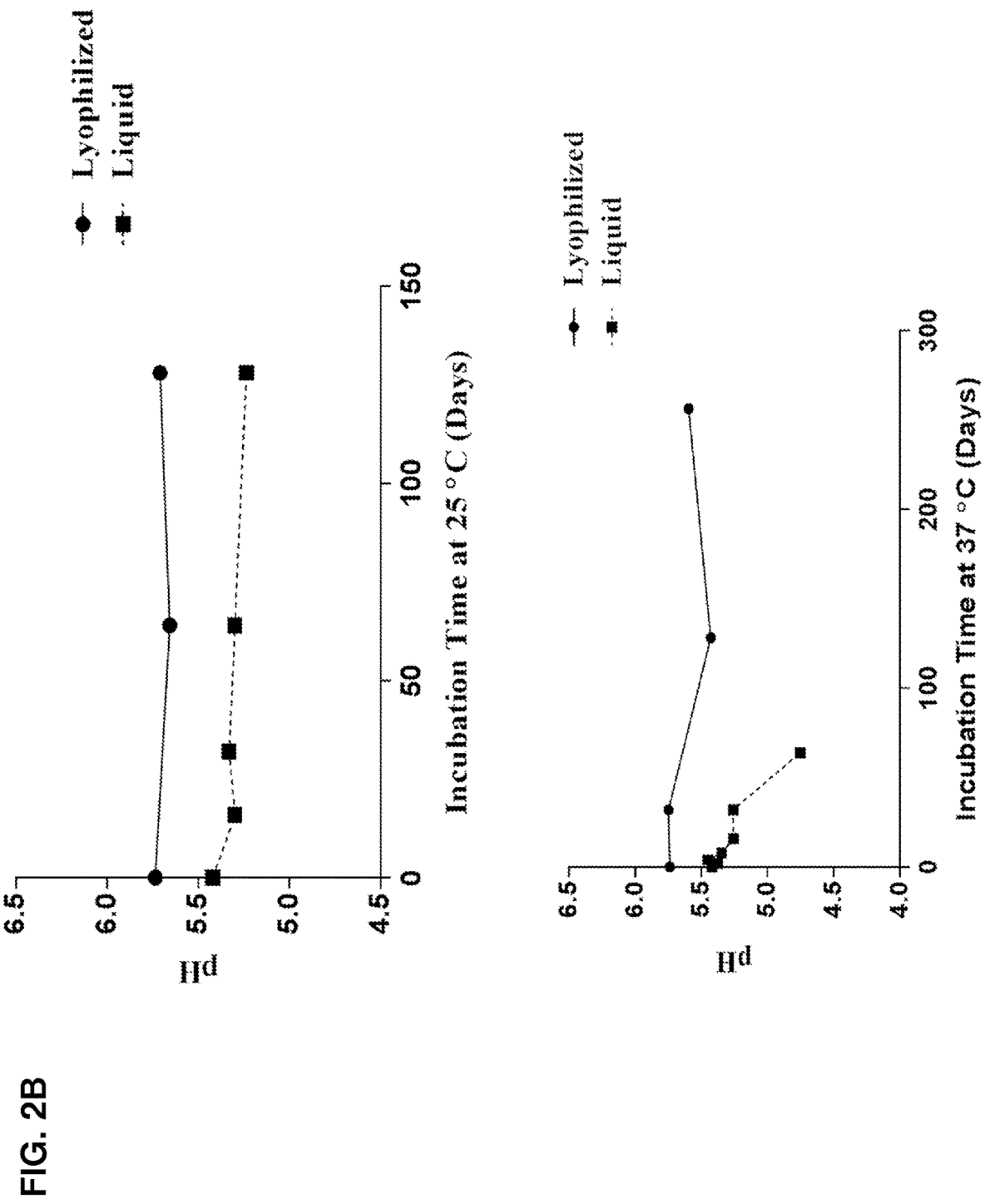
FIG. 2B) pH in liquid emulsion (filled square) and reconstituted lyophilized emulsion (filled circle) when stored over time at 25° C. (top panel) or 37° C. (bottom panel).
Figure 2C:
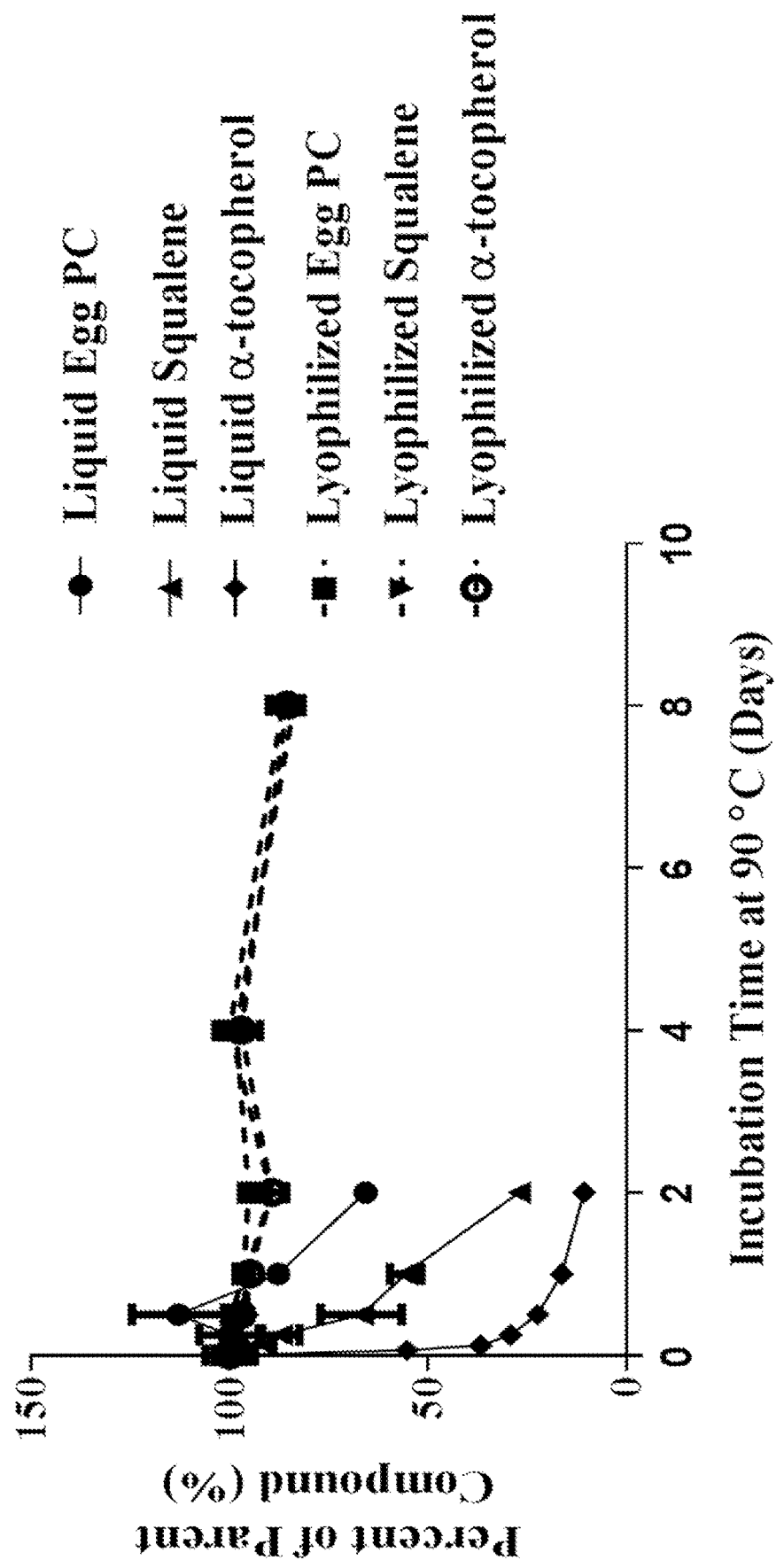
FIG. 2C) Amount of components in the emulsion when stored at an accelerated degradation condition of 90° C. over time. Percent (%) of egg-derived phosphatidylcholine (liquid egg-PC; filled circle), squalene (liquid squalene; filled triangle) and α-tocopherol (liquid α-tocopherol; filled diamond) in liquid emulsion shows rapid changes in component concentration as compared to egg-derived phosphatidylcholine (lyophilized egg-PC; filled square), squalene (lyophilized squalene; inverted filled triangle) and α-tocopherol (lyophilized α-tocopherol; empty circle) in reconstituted lyophilized emulsion.

Following the successful lyophilization and reconstitution of SE in trehalose, the stability of lyophilized and non-lyophilized SE was evaluated to determine if lyophilization improved emulsion stability. Based on reconstituted lyophilized SE particle size (FIG. 2A) and pH (FIG. 2B), the lyophilized formulation was more stable than the liquid formulation at 25° C. and 37° C. No significant changes in chemical composition were observed for liquid or reconstituted lyophilized SE at these temperatures. Lyophilization also increased chemical stability of the emulsion at the elevated temperatures necessary to induce compositional changes in the liquid formulation (FIG. 2C). Specifically, α-tocopherol, squalene, and egg-derived phosphatidylcholine (egg-PC) were all protected in a lyophilized formulation as compared to liquid formulation. Further, a separate oil phase, which would be indicative of oiling-off, was not detected. Thus because oil did not appear to redistribute within this system or enter a different phase, the particles remained as emulsions following reconstitution.

Determination of a Primary Failure Mechanism

Figure 3A:
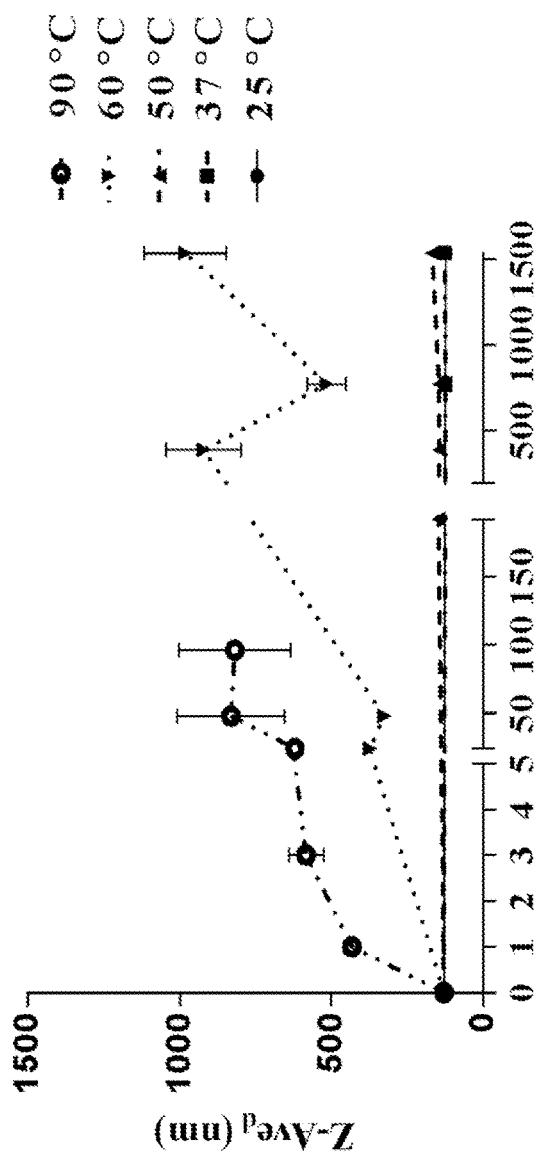
FIG. 3A) Particle size in reconstituted lyophilized emulsion stored at 25° C. (filled circle), 37° C. (filled square), 50° C. (filled triangle), 60° C. (inverted filled triangle), or 90° C. (empty circle) over time.
Figure 3B:
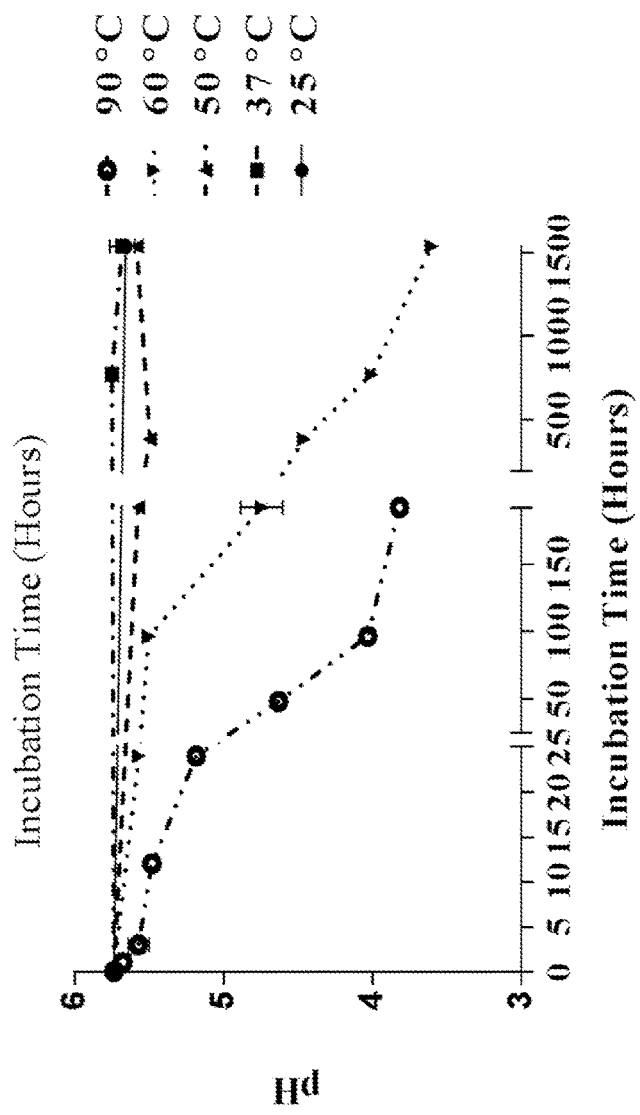
FIG. 3B) pH in reconstituted lyophilized emulsion stored at 25° C. (filled circle), 37° C. (filled square), 50° C. (filled triangle), 60° C. (inverted filled triangle), or 90° C. (empty circle) over time.
Figure 3C:
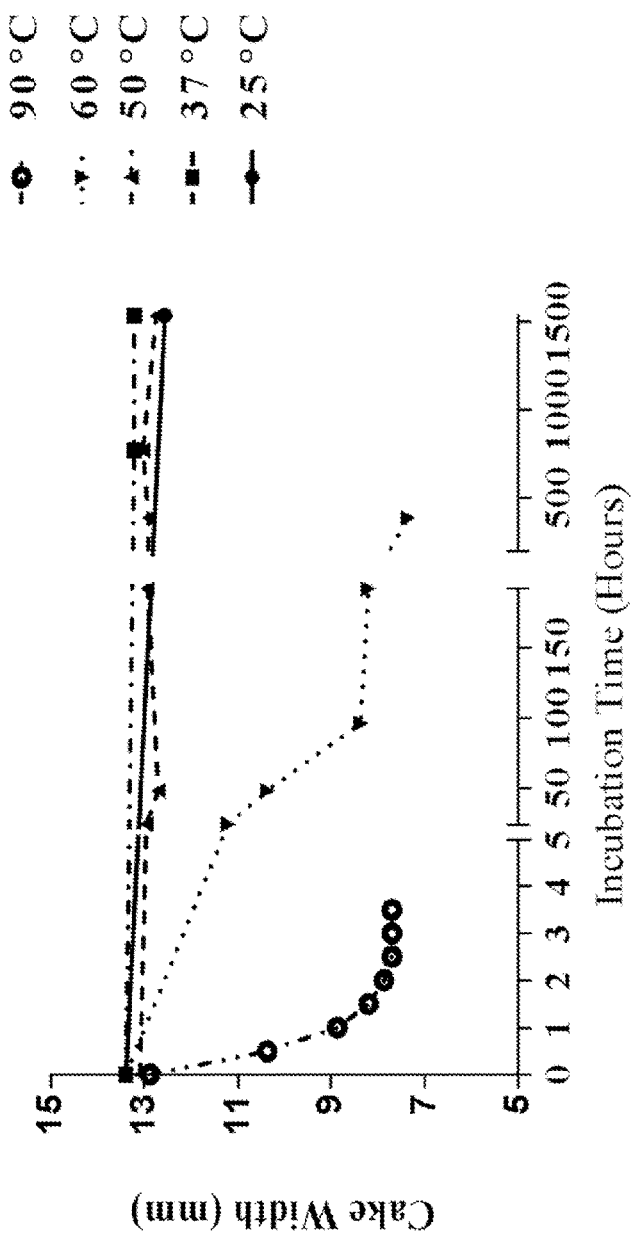
FIG. 3C) Cake width ratio in lyophilized emulsion stored at 25° C. (filled circle), 37° C. (filled square), 50° C. (filled triangle), 60° C. (inverted filled triangle), or 90° C. (empty circle) over time.
Figure 3D:
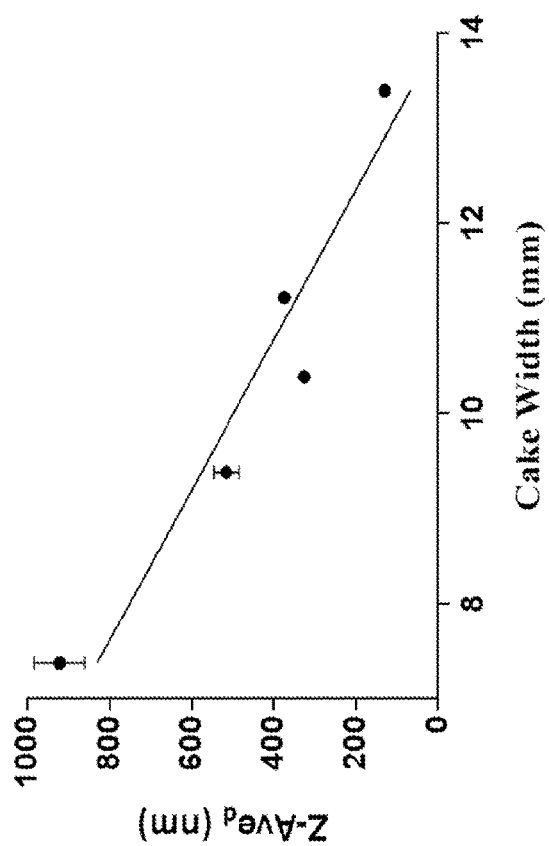
FIG. 3D) Melt-back, as measured by shrinking cake width, inversely correlated with particle size when lyophilized emulsion was stored at 60° C. under stressed stability conditions.

In order to advance the stability of lyophilized SE beyond trehalose, an investigation to determine the primary failure mechanism was conducted, with the intention of selecting future formulations that inhibit this mechanism. Lyophilized SE was stored at a range of temperatures of 25, 37, 50, 60, and 90° C. for up to 1500 hours or until the formulations had failed beyond the limits of characterization (FIG. 3). The lyophilized emulsion was much less stable above 50° C. The first observed changes were particle size growth which occurred concurrently (FIG. 3A and FIG. 3C) with cake melt-back. Large changes in pH only began to occur once the particles had failed by size (FIG. 3B), and was therefore not considered the primary failure mechanism. Thus, because emulsion component concentrations (FIG. 2C) and pH (FIG. 3B) did not change first, the mechanism was assumed not to be covalent in origin. However, cake melt-back was directly correlated with particle size growth over time (FIG. 3D). Since cake melt-back appeared to occur faster than particle size growth, cake resistance to melt-back was a critical attribute for maintaining emulsion particle size stability under stressed conditions.

Excipient Screen for SE Reconstitution

Based on the putative failure mechanism, a screen of excipients was conducted to identify compounds that maintained emulsion characteristics and were resistant to melt back (Table 1, FIG. 4). Excipients were grouped into four classes depending on cake structure and maintenance of emulsion characteristics following reconstitution. Representative data of these classes is shown in FIG. 5.

TABLE 1

Comparison of formulation characteristics between reconstituted 2% (v/v) oil SE in 5% (w/v) formulations.

| Excipient | Cake Appearance | Creaming (1 hour) | PdI | DLS Z-Average (d · nm) | Mean Zeta-Potential (mV) | pH |
|---|---|---|---|---|---|---|
| NON-LYOPHILIZED SE ||||||||
| SE (10% v/v Bulk Material) | Liquid; milky white emulsion | Negative | 0.10 | 99.7 | −8.6 | 5.5 |
| Trehalose (Pre-Lyophilized) | Liquid; milky white emulsion | Negative | 0.19 | 115.6 | −9.6 | 6.0 |
| CLASS 1: FORM CAKES, MAINTAIN EMULSIONS ||||||||
| Trehalose | White Cake | Negative | 0.21 | 136.8 | −18.9 | 5.9 |
| Dextrose | Spongiform White Cake | Negative | 0.17 | 112.6 | −18.7 | 6.1 |
| Lactose | Elegant White Cake | Negative | 0.19 | 159.3 | −19.0 | 5.9 |
| Maltose | Elegant White Cake | Negative | 0.21 | 127.3 | −21.5 | 6.2 |
| Sucrose | Spongiform White Cake | Negative | 0.22 | 115.5 | −18 | 6.1 |
| Raffinose | White Cake with Increased Volume | Negative | 0.24 | 149 | −24.2 | 5.8 |
| Mannose | Spongiform White Cake | Negative | 0.12 | 110.2 | −15 | 6.1 |
| Fructose | Spongiform White Cake | Negative | 0.11 | 121.9 | −16.8 | 5.5 |
| Lactulose | White Cake | Negative | 0.19 | 141.6 | −22 | 5.7 |
| CLASS 2: DO NOT FORM CAKES, MAINTAIN EMULSIONS ||||||||
| Ribose | No Cake, White/Bubbled Film | Negative | 0.23 | 130.8 | −11.4 | 5.2 |
| CLASS 3: FORM EXCELLENT CAKES, DISRUPT EMULSIONS ||||||||
| Dextran 40,000 | Spongiform White Cake | Positive | 0.84 | 1000+ | −27.8 | 5.5 |
| PEG 3350 | Elegant White Cake | Positive | 0.78 | 970.9 | −24.6 | 3.3 |
| Mannitol | White Cake | Positive | 0.90 | 1000+ | −19.4 | 2.9 |
| Stachyose | Elegant White Cake | Positive | 0.60 | 253.6 | −23.4 | 6.8 |
| Dipicolinic Acid (0.5%) | Elegant White Cake | Positive | 0.93 | 1000+ | −6.7 | 5.1 |
| CLASS 4: DO NOT FORM CAKES, DISRUPT EMULSIONS ||||||||
| Sorbitol | No Cake, Clear Film | Positive | 0.83 | 1000+ | −24.8 | 5.1 |
| Nicotinic Acid (0.5%) | No Cake, Thick White Film | Positive | 0.61 | 265.4 | −6.2 | 5.3 |
| Proline | No Cake, Solidified Bubbles | Positive | 0.81 | 742 | −5.5 | 4.3 |

Figure 4A:
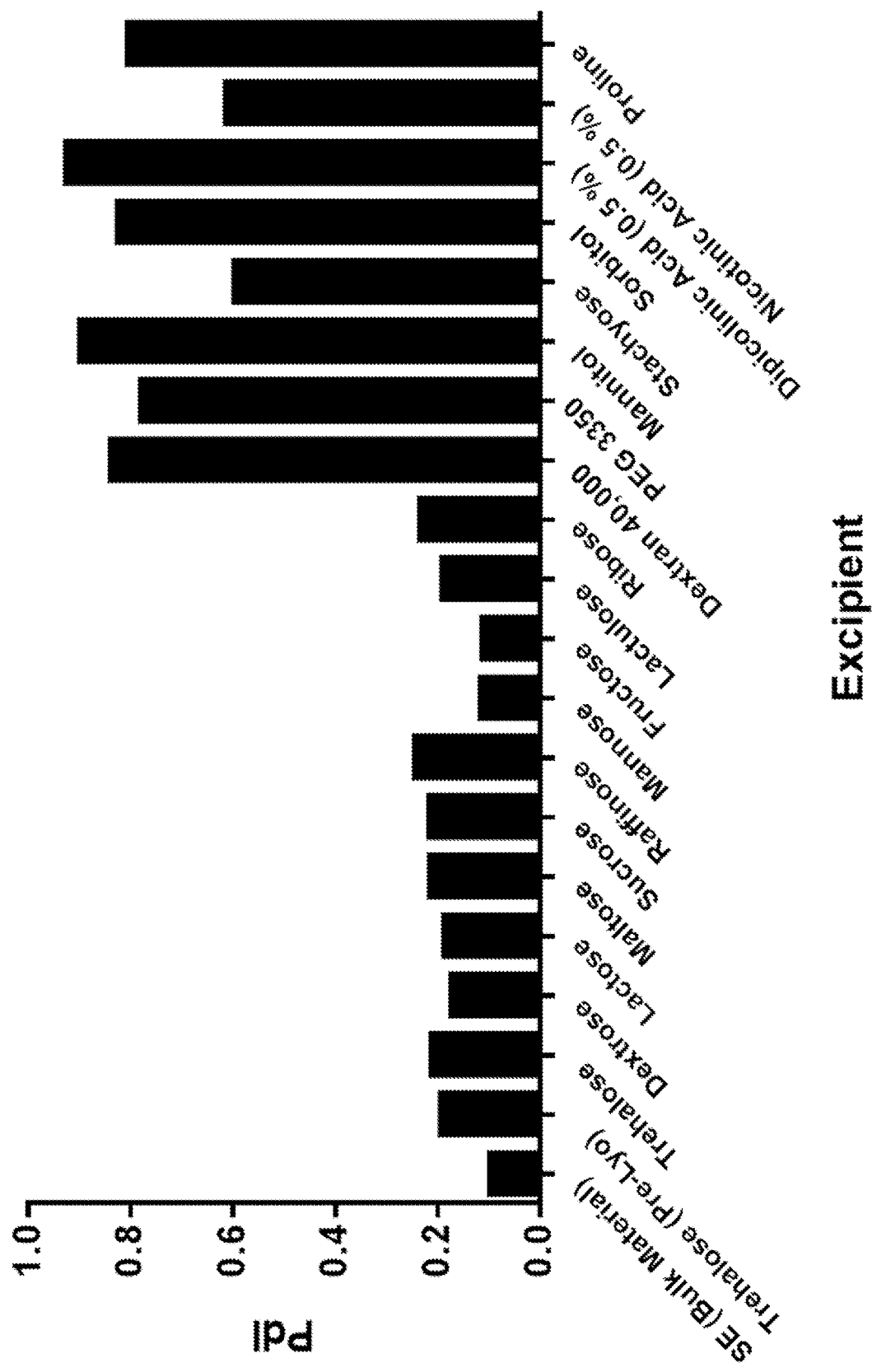
FIG. 4A) Formulation Polydispersity Index (PdI) with each excipient.
Figure 4B:
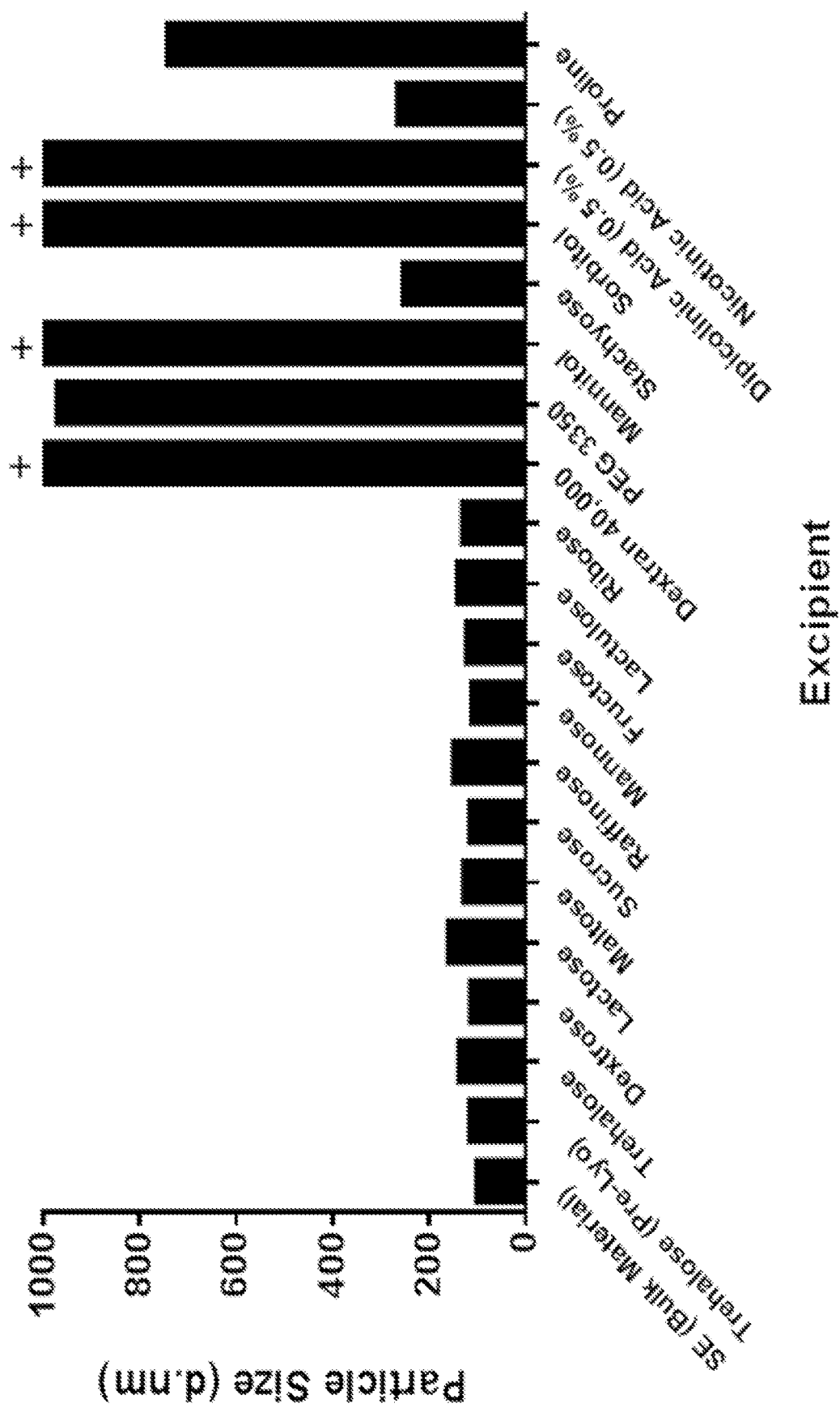
FIG. 4B) Emulsion particle size (nM) with each excipient. From left to right, SE (Bulk Material), trehalose (Pre-lyophilization), trehalose, dextrose, lactose, maltose, sucrose, raffinose, mannose, fructose, lactulose, ribose, dextran 40,000, PEG 3350, mannitol, stachyose, sorbitol, dipicolinic acid (0.5%), nicotinic acid (0.5%), and proline.
Figure 5A:
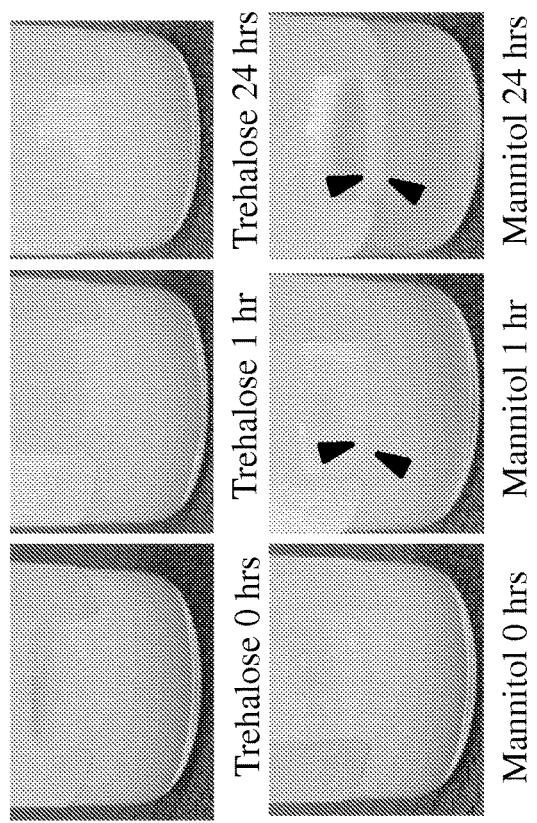
FIG. 5A) Cake images of lyophilized emulsions.

Class 1 excipients formed white cakes with a range of cake morphologies, and did not significantly change the emulsions characteristics following lyophilization (Table 1, FIG. 4A-B). This class included trehalose, dextrose, lactose, maltose, sucrose, raffinose, mannose, fructose, and lactulose. Reconstituted emulsion particle size was under 200 nm, no creaming was observed over one hour, and the PdI was less than 0.25. Zeta potentials decreased, from −9 mV to −15 to −25 mV. The pH varied from 5.4 to 6.2. The cake appearance of lyophilized SE in 5% trehalose, a representative class 1 formulation, was acceptable despite being slightly shrunken (FIG. 5A). Creaming was not observed within 24 hours (FIG. 5B), and particle size distributions remained homogenous below 150 nm (FIG. 5C).

Ribose, a class 2 excipient, did not form a cake when lyophilized and instead formed a film (FIG. 5A), but the emulsion could be reconstituted with an acceptable particle size, PdI, zeta potential, and pH (Table 1, FIG. 4A-B).

Figure 5B:
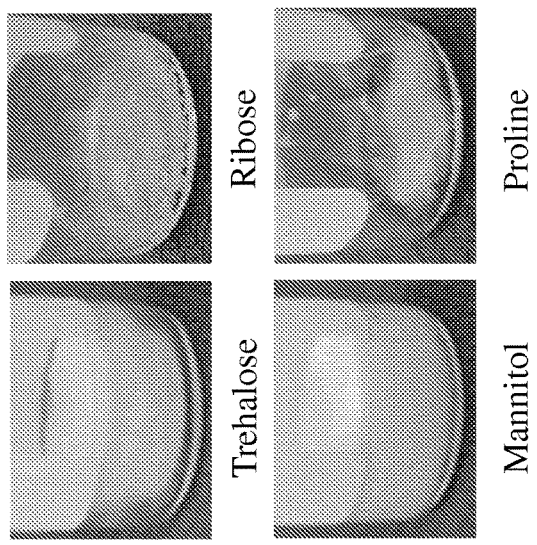
FIG. 5B) Creaming comparison between trehalose and mannitol reconstituted lyophilized formulations. Arrows indicate creaming.
Figure 5C:
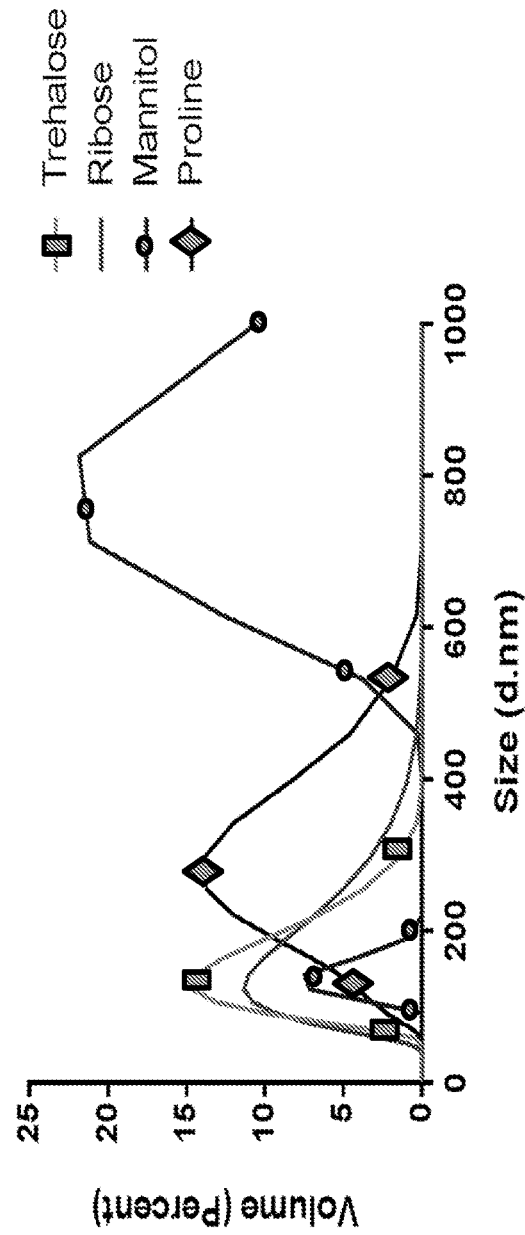
FIG. 5C) Particle size volume distributions as measured by DLS.

Excipients of class 3 formed good cakes, but disrupted the emulsion following reconstitution (Table 1, FIG. 4, and FIG. 5). Reconstituted particle sizes were above 200 nm and PdI values were large, between 0.59 and 0.93. The pH and consequently zeta potential varied widely within this group. The large change in pH observed for PEG and mannitol containing formulations happened during lyophilization. Pre-lyophilization pH was adjusted to 5.5. As expected from the large particle size and high polydispersity, class 3 excipients caused creaming following reconstitution (Table 1, FIG. 5B).

Class 4 excipients did not form cakes, and disrupted the emulsion in the same way as class 3 compounds, although instead of creaming these formulations failed to reconstitute completely (Table 1, FIG. 4, and FIG. 5). Each of these excipients resulted in large SE particles with high PdI values, and pH values between 4.3 and 5.1. Dipicolinic acid and nicotinic acid were fairly insoluble in water, meaning these formulations were generated at 10% of the mass concentration of the other formulations. This may have been a contributing factor towards poor emulsion maintenance with these excipients.

Single Excipient Structural Screen for Cake Thermostability

Figure 6A:
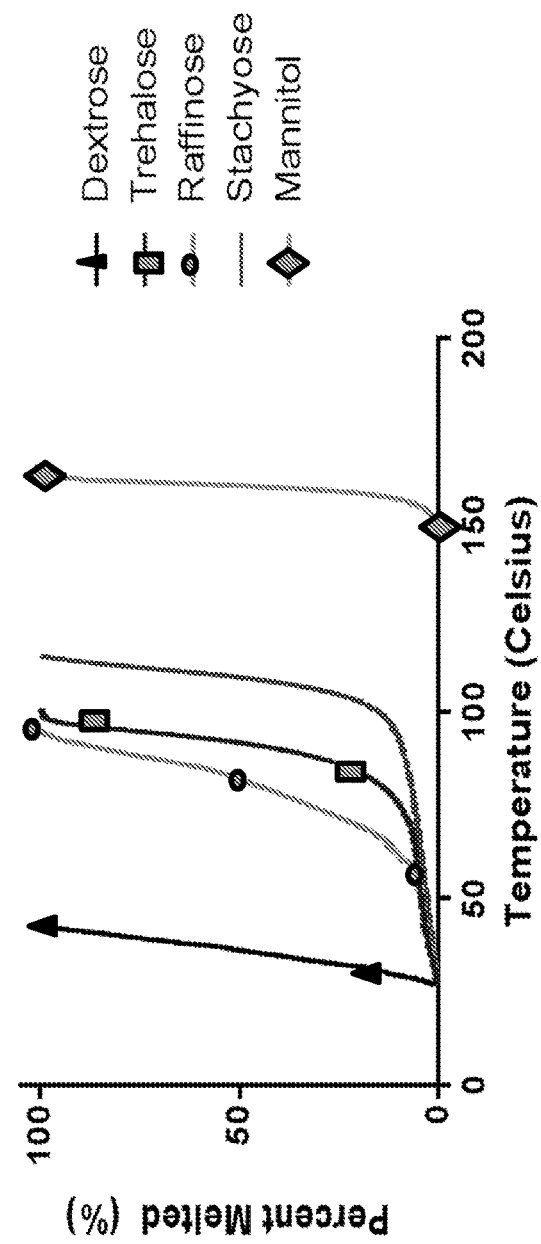
FIG. 6A) Melting point apparatus thermograms of melting transition for representative formulations.
Figure 6B:
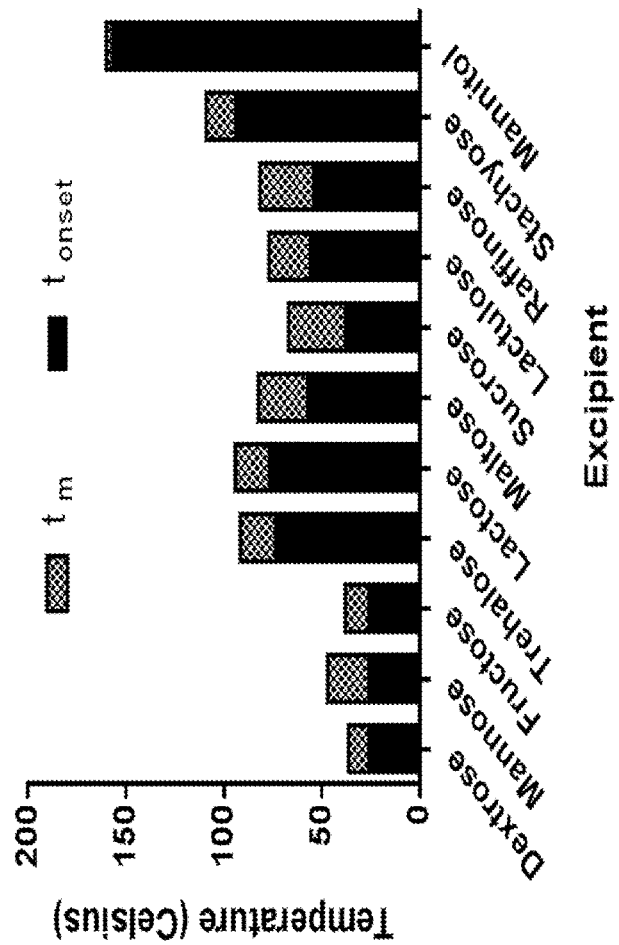
FIG. 6B) Cake onset and tm temperature within each excipient.

After identifying alternative lyophilization excipients, cake thermostability was evaluated for a selection of the cake-forming excipients. This was employed as a method of identifying excipients with higher melting points and greater resistance to melt-back (Table 2). Class 1 excipients had the lowest onset points ranging from instantaneous, meaning at or below the 27° C. starting temperature, to 78° C. The melting midpoints ranged from 36° C. to 94° C. Class 3 excipients had onset points above 90° C. and all had melting midpoints above 100° C. Mannitol demonstrated the greatest cake stability, with a narrow melting point range centered at 160.1° C. Representative cake melting thermograms are shown in FIG. 6A. Comparison of excipients based on cake onset and melting points are shown in FIG. 6B. Monomeric sugars appeared to have much lower melting points than polymeric sugar excipients.

TABLE 2

Comparison of cake melting characteristics between 2% (v/v) oil in SE in 5% (w/v) formulations.

| Excipient (5% w/v) | $t_{onset}$ (° C.) | $t_m$ (° C.) | Melting Range (° C.) 25 to 75% Intensity | Class | Sugar Polymer Length |
|---|---|---|---|---|---|
| Dextrose | Below 27 | 36.4 | 32.5-39.2 | 1 | 1 |
| Mannose | Below 27 | 47 | 40.8-50.6 | 1 | 1 |
| Fructose | Below 27 | 38.1 | 34.3-41.5 | 1 | 1 |
| Trehalose | 75 | 91.8 | 86.0-94.7 | 1 | 2 |
| Lactose | 78 | 94.4 | 89.5-97.7 | 1 | 2 |
| Maltose | 58 | 82.5 | 73.7-87.0 | 1 | 2 |
| Sucrose | 39 | 67.4 | 59.2-73.4 | 1 | 2 |
| Lactulose | 57 | 77.3 | 70.8-83.7 | 1 | 2 |
| Raffinose | 55 | 81.9 | 71.6-88.1 | 1 | 3 |
| Stachyose | 95 | 109.2 | 104.7-111.8 | 3 | 4 |
| Mannitol | 158 | 160.1 | 158.6-161.1 | 3 | NA |

Impact of Cake Thermostability on Formulation Stability

Figure 7A:
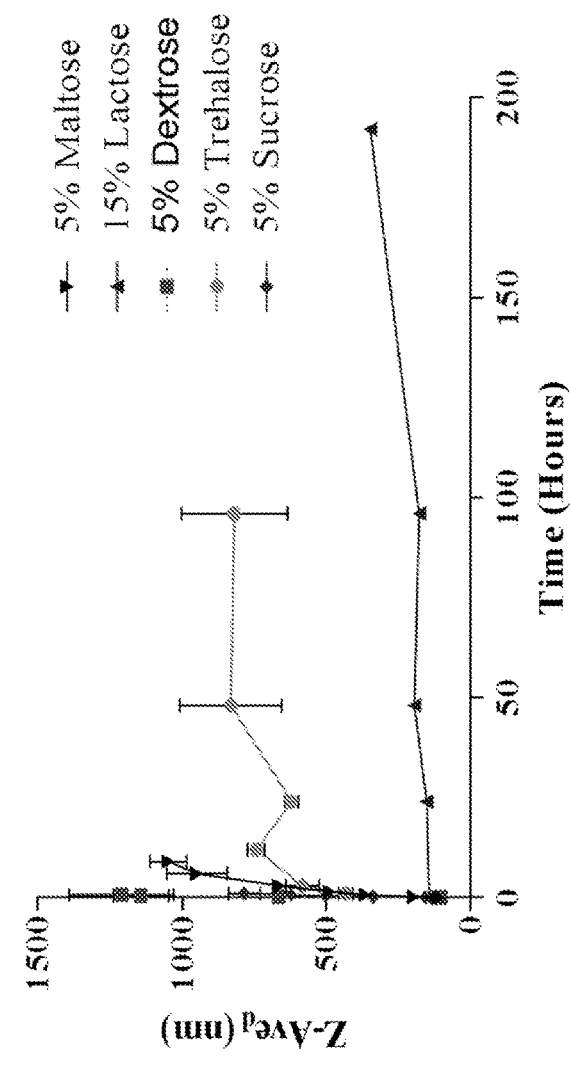
FIG. 7A) Particle size stability depends on the type of bulking agent and concentration of bulking agent used. SE in 5% dextrose (filled square), 5% sucrose (filled diamond), 5% maltose (filled inverted triangle), 5% trehalose (filled circle), and 15% lactose (filled triangle) excipients.
Figure 7B:
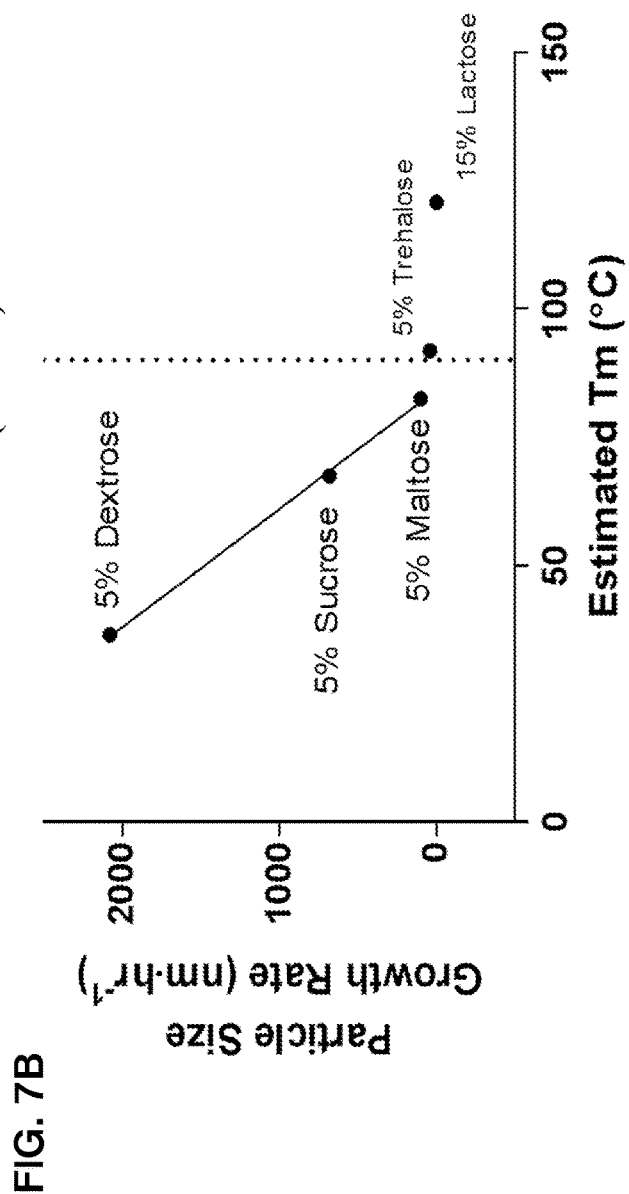
FIG. 7B) particle size growth rate correlates with transition temperature, a property of the bulking agent. Dotted line represents the stressed stability temperature of 90° C.

To evaluate the correlation between cake melting point and thermal stability, rates of particle size growth for SE in various sugars with differing melting points were evaluated at 90° C. The difference in stability between 5% formulations of dextrose, sucrose, maltose, trehalose, and a 15% lactose formulation with widely differing melting points was investigated (FIG. 7). A 15% lactose formulation was identified as having a higher melting point than 5% lactose and was selected because its melting point was well above the stress storage temperature of 90° C. Dextrose was observed to have the lowest melting point, and experienced the most rapid particle size growth (FIG. 7A). Sucrose, maltose and trehalose had intermediate melting points, and experienced intermediate melting rates. As the cake melting points increased between formulations, this particle size growth decreased, with 15% lactose having the highest melting point and lowest particle size growth rate. Additionally, a bifurcation in particle growth rate was observed (FIG. 7B) between samples with tm above and below the storage temperature, providing further evidence that cake melt-back was the primary thermal degradation failure mechanism.

Excipient Combination Screen for Cake Thermostability

Figure 8:
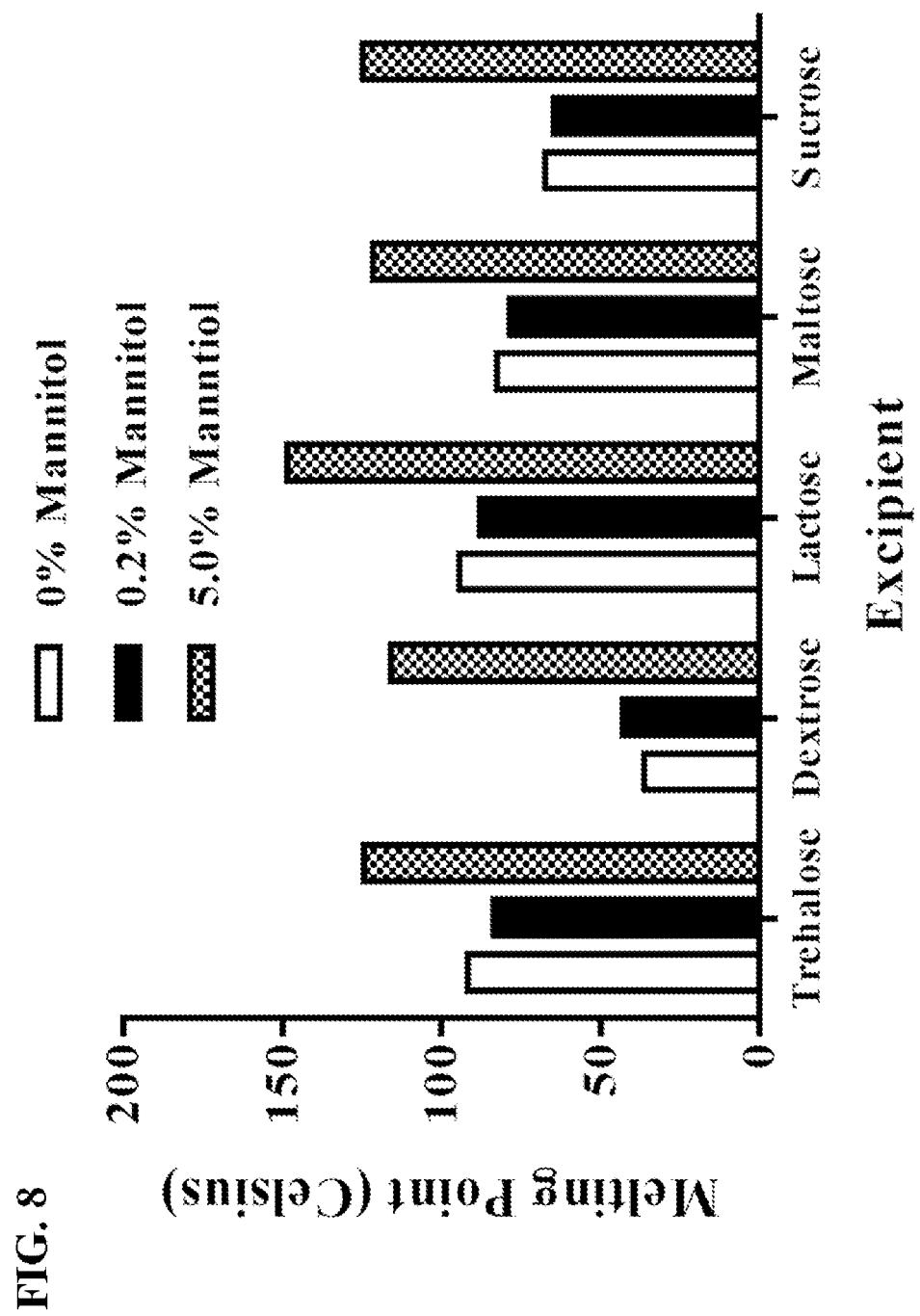
FIG. 8 shows that formulation with mannitol and class 1 excipients greatly increased cake thermostability without emulsion disruption. Comparison of cake Tm between 2% (v/v) oil SE in 5% (w/v) formulations containing trehalose, dextrose, lactose, maltose, or sucrose with either 0.2%, 5% (w/v) mannitol or no mannitol.

Due to the observation that mannitol increased cake thermostability (Table 2), various class 1 excipients were combined with mannitol in an attempt to generate formulations that maintained emulsions, but had superior cake stability (Table 3, FIG. 8). The class 1 excipients reduced emulsion particle size growth in the presence of mannitol. Addition of 0.2% w/v mannitol did not increase particle size or Tm. 5% w/v mannitol greatly increased cake Tm but also increased emulsion particle size and PdI, and concurrently decreased pH.

nol; 27:393-422). A recombinant fusion protein antigen consisting of four Mtb proteins, Rv3619, Rv1813, Rv3260, and RV2608, designated ID93 has been developed. These component proteins were identified as being recognized by human T cells from either TB-infected or BCG-immunized donors and are protective against Mtb challenge in mouse and guinea pig models when paired with an adjuvant (Bertholet et al., 2010, Sci Transl Med, 2:53ra74; Bertholet et al., 2008, J Immunol, 181:7948-7947) that induces robust TH1 responses such as the synthetic TLR4 agonist glucopyranosyl lipid adjuvant formulated in a squalene-in-water stable emulsion (GLA-SE). ID93+GLA-SE is currently undergoing Phase I safety testing in human volunteers.

Both ID93 and GLA-SE were stable for more than a year when stored under continuous cold-chain maintenance. Under these conditions no changes in protein concentration, GLA concentration, particle size, or physical appearance were observed. Stability observations were ongoing with no estimated time to degradation at 4° C. Although the stability of ID93+GLA-SE was on par with other vaccines, an increase in the vaccine thermostability to lessen the requirement for continuous cold chain maintenance was desired. One approach to improving vaccine stability at elevated temperatures was to lyophilize the antigen component of the vaccine, which is then mixed with the adjuvant at the time of usage. However this required cold-chain maintenance for the adjuvant and increased the technological burden of

TABLE 3

Comparison of cake characteristics between 2% (v/v) oil SE in 5% (w/v) formulations with either 0.2% or 0.5% (w/v) mannitol.

| Excipient (5% w/v) | Mannitol Concentration (% w/v) | $t_{onset}$ (° C.) | $t_m$ (° C.) | Melting Range (° C.) 25 to 75% Intensity | pH | PdI | DLS Z-Average (d.nm) |
|---|---|---|---|---|---|---|---|
| Trehalose | 0.2 | 64 | 83.8 | 78.5-87.1 | 6.0 | 0.19 | 138.6 |
| Trehalose | 5 | 81 | 124.4 | 111.9-136.7 | 5.3 | 0.24 | 162.4 |
| Dextrose | 0.2 | Below 27 | 43.1 | 37.4-47.3 | 5.9 | 0.18 | 114.4 |
| Dextrose | 5 | 84 | 115.9 | 106.3-121.7 | 5.0 | 0.17 | 123.8 |
| Lactose | 0.2 | 68 | 87.9 | 83.2-90.9 | 6.0 | 0.24 | 165.2 |
| Lactose | 5 | 141 | 148.6 | 146.3-150.1 | 5.2 | 0.24 | 175 |
| Maltose | 0.2 | 57 | 78.6 | 72.3-83.3 | 6.1 | 0.26 | 136.5 |
| Maltose | 5 | 83 | 121.6 | 107.4-136.4 | 5.3 | 0.25 | 154.4 |
| Sucrose | 0.2 | 42 | 64.7 | 56.8-71.0 | 6.1 | 0.20 | 110.9 |
| Sucrose | 5 | 78 | 124.7 | 113.1-129.0 | 5.3 | 0.21 | 125.9 |

Example 2: Stability of Lyophilized Adjuvanted Vaccines Against Tuberculosis

The only approved vaccine for tuberculosis (TB), *Bacillus* Calmette-Guérin (BCG), was first used in humans in 1921 and has been effective in reducing the incidence of disseminated TB in children. However, BCG has proven ineffective at preventing pulmonary TB in adolescents and adults (Checkley et al., 2011, Trends Pharmacol Sci, 32:601-606; Rowland et al., 2011, Expert Rev Vaccines, 10:645-658; Anderson et al., 2005, Nat Rev Microbiol, 3:656-662). Mathematical modeling of the impact of implementing a hypothetical new vaccine against TB with 60% efficacy predicts an 80% drop in incidence by 2050 (Abu-Raddad et al., 2009, PNAS, 106:13980-13985). Thus there is an urgent need for a new TB vaccine to either boost immunity primed by BCG or replace BCG. Protective immunity against *Mycobacterium tuberculosis* (Mtb) requires both TNF and IFN-γ production by CD4 T cells (Flynn et al., 2001, Annu Rev Immunol, 19:93-129; Cooper A. M., Annu Rev Immuvaccination. To surmount this problem a single vial of both the antigen ID93 and GLA-SE adjuvant (termed "covialed") was developed.

Materials and Methods

Sample Preparation and Lyophilization

The construction, expression, and purification of the ID93 tandem fusion protein containing the Mtb genes Rv3619, Rv1813, Rv3620, and Rv2608 have been described previously (Bertholet et al., 2010, Sci Transl Med, 2:53ra74). Briefly the ID93 fusion protein was expressed in *E. coli*, purified under denaturing conditions by chromatography on DEAE and Q Sepharose columns, and analyzed by SDS-PAGE on a 4-20% Tris glycine gel (Invitrogen). GLA (also known as PHAD) was purchased from Avanti Polar Lipids Inc. (Alabaster, Ala.). GLA-SE containing 1,2-dimyristoyl-sn-glycero-3-phosphocholine (DMPC) was formulated according to the previously described methods (Orr et al., 2013 J Control Release 172:190-200; Anderson et al., 2010 Colloids Surf B: Biointerfaces 75:123-32). Briefly, GLA-SE emulsions were produced by mixing a buffered aqueous phase (poloxamer 188 and glycerol in ammonium phosphate buffer pH 5.1) and oil phase (DMPC and GLA dispersed into squalene by sonication at 70° C.) and then microfluidizing the mixture using the Microfluidics M110P (Newton, Mass.) for 12 passes at 30,000 psi. Component concentrations in the emulsions consisted of 10% v/v squalene, 1.9% w/v phosphatidylcholine, 0.1% w/v poloxamer 188, 2.3% w/v glycerol, and 25 mM ammonium phosphate buffer. GLA-SE was diluted to the specified concentrations for use.

For analysis of GLA-SE adjuvanted vaccine, liquid and lyophilized samples were prepared with 1.5 mL fill volumes in 3 mL glass vials. Covial samples containing ID93 (5 µg/mL)+GLA-SE (50 µg/mL, 2% total oil) were prepared in 20 mM tromethamine (Tris) at pH 8.0 (Coler et al., 2011, PLoS One, 6, e16333). Separately vialed ID93 or GLA-SE were prepared at twice the concentration of covialed samples (10 µg/mL ID93 or 100 µg/mL GLA, 4% total oil GLA-SE) and mixed 1:1 prior to injection. Samples for SDS-PAGE were prepared at 100 µg/mL ID93 to facilitate analysis. Lyophilized samples also contained 5% (w/v) D-trehalose dehydrate as a stabilizer and were lyophilized using a VirTis (Gardiner, N.Y.) AdVantage 2.0 EL-85 benchtop freeze dryer. The lyophilization recipe utilized a thermal treatment schedule including a 10-hour freezing step from 4 to −40° C., and an annealing step at −15° C. The primary drying phase (at 100 mTorr) lasted 18 hours from −40° C. to 25° C. Finally, a secondary drying phase at 50 mTorr was employed at 25° C. for 9 hours. All samples were stoppered in atmospheric gas at 500 mTorr, sealed using aluminum caps, and stored at 4° C. until use. Heat stressed samples were incubated at 50° C. for 30 days and unstressed samples were stored at 4° C. prior to injection.

For analysis of SLA-SE adjuvanted vaccine, lyophilized samples were prepared with 1.5 mL fill volumes in 3 mL glass vials. Covial samples containing 2% (v/v) oil SE, 50 µg/mL SLA, 100 µg/mL ID93, 20 mM Tris pH 8.0 and 5% (w/v) trehalose were prepared. Samples were lyophilized using a VirTis (Gardiner, N.Y.) AdVantage 2.0 EL-85 benchtop freeze dryer. The lyophilization recipe utilized a thermal treatment schedule including a 10-hour freezing step from 4 to −40° C., and an annealing step at −15° C. The primary drying phase (at 100 mTorr) lasted 18 hours from −40° C. to 25° C. Finally, a secondary drying phase at 50 mTorr was employed at 25° C. for 9 hours. All samples were stoppered in atmospheric gas at 500 mTorr, sealed using aluminum caps, and stored at 4° C. until use. Heat stressed samples were incubated at 50° C. for 30 days and unstressed samples were stored at 4° C. Duplicate vials (denoted A and B) were characterized. Sample reconstitution was done with 1.5 mL filtered H2O.

Reducing SDS-PAGE

Reducing SDS-PAGE was performed using Life Technologies (Grand Island, N.Y.) NuPAGE LDS sample buffer, with 1.25% β-mercaptoethanol added, and incubated at 90° C. for 15 minutes. Samples were run at 180 V for 65 minutes using 1 µg of ID93 per lane in Life Technologies Novex 4-20% acrylamide tris-glycine precast gel cassettes. Gels were stained overnight using Life Technologies SimplyBlue SafeStain before destaining, drying, and imaging. Band intensities were compared using ImageJ software (NIH) (Schneider et al., 2012, Nat Methods, 9:671-675.

Particle Analysis

Particle size, polydispersity, and zeta potential measurements were made as described previously (Fox et al., 2008, Colloids and Surfaces B: Biointerfaces, 65:98-105) using a Malvern (Worcestershire, UK) Nano-ZS after 100 times dilution into ultrapure water filtered through a 20 nm Whatman (Maidstone, Kent, UK) Anotop plus filter. Nanoparticle tracking analysis was performed with a NanoSight LM10 (Amesbury, UK) with a 405 nm laser and a Hamamatsu Orca Flash 2.8 CMOS camera (Hamamatsu, JP). Samples were diluted 1:105 in 20-nm filtered ultrapure water in three steps. Each sample was diluted and analyzed four times, independently, to account for dilution error. Ninety seconds of video were recorded for each sample with optimized shutter and gain settings. The camera histogram gating was adjusted to maximize sensitivity. Data analysis was performed using NanoSight NTA 2.3 software (Wiltshire, UK) in standard mode.

Chemical Integrity of Adjuvant

Concentrations of squalene, DMPC, GLA and SLA were monitored using reverse-phase HPLC (RP-HPLC) as described previously (Fox et al., 2008, Colloids and Surfaces B: Biointerfaces, 65:98-105). An Agilent 1200 (Santa Clara, Calif.) and an ESA Biosciences Corona Charged Aerosol Detector (CAD; Chelmsford, Mass.) were used with a Waters (Milford, Mass.) Atlantics C18 5 µm column (4.6 mm×250 mm). Mobile phase A contained 75:15:10 (v/v/v) methanol, chloroform, and water with 20 mM ammonium acetate, and 1% acetic acid. Mobile phase B contained 50:50 (v/v) methanol and chloroform, 20 mM ammonium acetate, and 1% acetic acid. Samples were prepared by dilution (1:20) into mobile phase B, 9 µL were injected onto a 30° C. column, and elution with a gradient of 100% to 10% mobile phase A over 45 minutes was used. Standard curves were fit with a second order polynomial, as recommended by the detector manufacturer, and sample concentrations determined by interpolation.

Animals and Immunizations 6-8 week old female C57BL/6 mice were purchased from Charles River and maintained in Specific Pathogen Free conditions. After infection animals were maintained in Animal Biosafety Level 3 containment. Mice were immunized three times three weeks apart by intramuscular injection of 100 µL of the indicated vaccine preparation. For BCG immunization 5×104 CFU (Pasteur strain, Sanofi Pasteur) were injected intradermally once at the time of the first subunit immunization.

Blood Cell Counts

Peripheral blood was collected from mice (N=5/group) eighteen hours after immunization. Whole blood was stained for CD90.2 (clone 53-2.1) and CD19 (clone 6D5). Sphero AccuCount Rainbow Particles (Spherotech, Lake Forest, Ill.) were added according to the manufacturer's instructions. Cells were washed and resuspended in PBS. Up to 106 events were collected on a four laser LSRFortessa flow cytometer (BD Biosciences). Data were analyzed with FlowJo. Absolute numbers of CD19+ B cells and CD90.2+ T cells per microliter of blood were calculated according to the manufacturer's instructions.

Antibody Responses

Mouse sera (N=5/group) were prepared 21 days after immunization by collection of retro-orbital blood into microtainer serum collection tubes (VWR International, West Chester, Pa.), followed by centrifugation. Each serum sample was then analyzed by antibody capture ELISA. Briefly, ELISA plates (Nunc, Rochester, N.Y.) were coated with 1 µg/ml recombinant antigen in 0.1 M bicarbonate buffer and blocked with 1% BSA-PBS. Then, in consecutive order and following washes in PBS/Tween20, serially diluted serum samples, anti-mouse IgG, IgG1 or IgG2c-HRP (all Southern Biotech, Birmingham, Ala.) and ABTS-H2O2 (Kirkegaard and Perry Laboratories, Gaithersburg, Md.)

were added to the plates. Plates were analyzed at 405 nm (ELX808, Bio-Tek Instruments Inc, Winooski, Vt.).

Intracellular Cytokine Staining

One month after the final immunization, splenocytes were isolated from five animals per group. Red blood cells were lysed using Red Blood Cell Lysis Buffer (eBioscience) and resuspended in RPMI 1640 and 10% FBS. Cells were plated at 2×106 cells/well in 96-well plates and were stimulated for 1 hour with media or ID93 (10 μg/mL) at 37° C. GolgiPlug (BD Biosciences) was added and the cells were incubated for an additional 7 hours at 37° C. Cells were washed and surface stained with fluorochrome labeled antibodies to CD4 (clone GK1.5), CD8 (clone 53-6. 7), and CD44 (clone IM7) (BioLegend and eBioscience) in the presence of antibodies to CD16/32 (clone 2.4G2) for 20 minutes at 4° C. Cells were washed and permeabilized with Cytofix/Cytoperm (BD Biosciences) for 20 minutes at room temperature. Cells were washed twice with Perm/Wash (BD Biosciences) and stained intracellularly with fluorochrome labeled antibodies to IFN-γ (clone XMG-1.2), IL-2 (JES6-5H4), TNF (MP6-XT22), CD154 (clone MR1), IL-5 (clone TRFK5), and IL-17A (clone TC11-18H10.1) (BioLegend and eBio science) for 20 minutes at room temperature. Cells were washed and resuspended in PBS. Up to 106 events were collected on a four laser LSRFortessa flow cytometer (BD Biosciences). Data were analyzed with FlowJo. Cells were gated as singlets>lymphocytes>CD4+CD8−>CD44+>cytokine positive.

M. Tuberculosis Aerosol Challenge and Enumeration

Four weeks after the last immunization, mice (n=7/group) were aerogenically infected with M. tuberculosis H37Rv (ATCC No. 35718; American Type Culture Collection) using a GlasCol aerosol generator calibrated to deliver 50-100 bacteria into the lungs. To confirm the amount of bacteria delivered an additional three unimmunized animals per infection were euthanized one day later and bacterial burden in the lungs were enumerated. Protection was determined three weeks after challenge by harvesting the lungs from the infected mice, homogenizing the tissue in 0.1% PBS-TWEEN® 80, and plating 5-fold serial dilutions on7H10 agar plates (Molecular Toxicology) for bacterial growth. Bacterial colonies were counted after incubation at 37° C. with 5% $CO_2$ for 14-21 days.

Statistical Methods

Bacterial burdens were normalized by log 10 transformation. Statistical significance of differences in bacterial burdens, cytokine production, blood cell counts, and antibody titers were determined using one-way analysis of variance with the Bonferroni Multiple Comparison Test using Prism 5 (GraphPad Software).

Results

Physicochemical Characterization of GLA-SE Adjuvanted Vaccine Formulation

A lyophilization regimen for this covialed adjuvanted vaccine was developed. Upon lyophilization, a white, partially shrunken cake was formed, and, after reconstitution with water, the emulsion reformed and appeared similar to the pre-lyophilized emulsion (FIG. 9, top row). The potential to increase stability to heat stress by lyophilization was evaluated by incubating liquid or lyophilized ID93+GLA-SE at 50° C. for 30 days. After heat stress, no visible change in sample quality was observed (FIG. 9, bottom row) when compared to unstressed sample (FIG. 9, top row). Reconstituted samples maintained the appearance of an emulsion and lyophilized cakes did not show any further signs of collapse or discoloration.

Figure 10A:
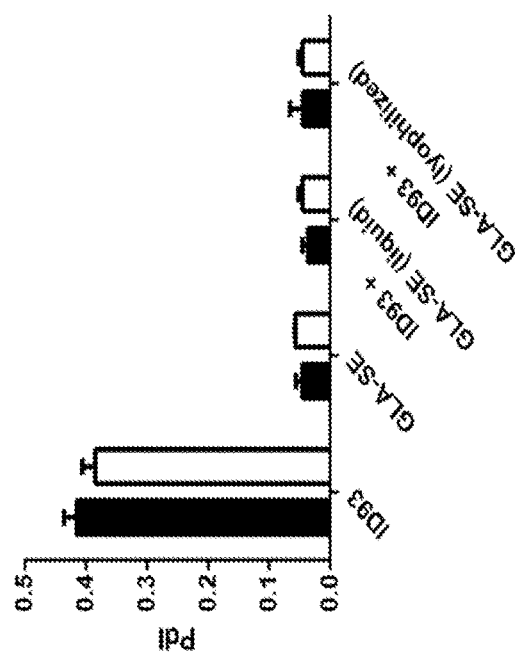
FIG. 10A) Z-Average diameter from DLS experiments, FIG. 10B) polydispersity index (PdI) from DLS experiments, FIG. 10C) Zeta potential measurements from nanoparticle tracking analysis and FIG. 10D) particle concentration measurements from nanoparticle tracking analysis. Filled bars represent unstressed samples (i.e. stored at 4° C. for 30 days) and open bars represent samples stressed at 50° C. for 30 days.
Figure 10B:
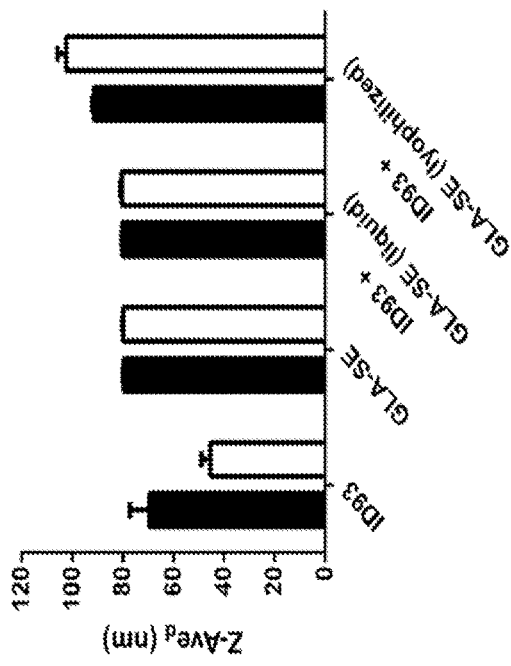
FIG. 10 shows particle characterization of liquid and reconstituted lyophilized samples containing ID93 and/or GLA-SE as indicated in the figure labels.
Figure 10C:
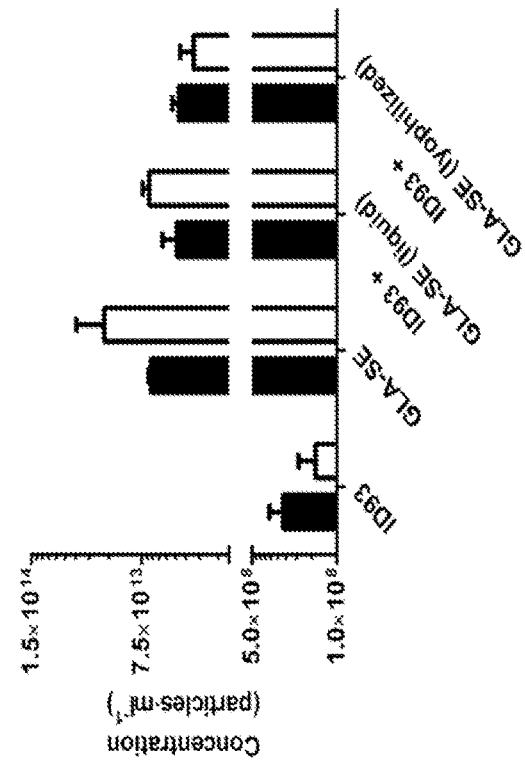
Figure 10D:
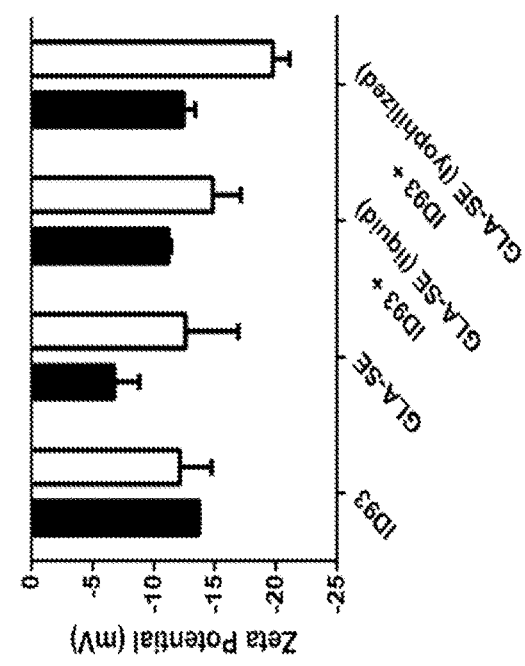

Particle characteristics are critical for effective vaccine development as particle size determines the speed and mechanism of vaccine trafficking in vivo. Maintenance of particle size below 200 nm is desirable in order to allow terminal sterile filtration of the product; in addition, particle sizes<200 nm are able to rapidly access the lymph node (Bachmann et al., 2010, Nature Rev Immunol, 10:787-796). To assess whether covialing or lyophilization and reconstitution of covialed ID93+GLA-SE altered the biophysical properties the particle size, concentration, polydispersity, and overall zeta potential of ID93, GLA-SE, covialed ID93+GLA-SE and lyophilized covial ID93+GLA-SE was examined. Measured particle characteristics after mixing were primarily reflective of the contribution of GLA-SE due to the five orders of magnitude higher particle concentration as compared to ID93. Covialing ID93 and GLA-SE did not affect the particle size relative to GLA-SE alone (80 nm in both cases) (FIG. 10A). Lyophilization and subsequent reconstitution of ID93+GLA-SE resulted in a minor increase of approximately 10 nm, within the error of the measurement. ID93 formed polydisperse aggregates with a Z-average diameter of approximately 70 nm. Heat stress of ID93 alone reduced the average particle size observed; however, this was not statistically significant (p>0.05) (FIG. 10A). Heat stress of GLA-SE alone or in combination with ID93 did not affect particle size or concentration across any of the platforms tested (FIG. 10A and FIG. 10D). GLA-SE was a highly homogenous solution as reflected by the low polydispersity value (FIG. 10B). Although the degree of polydispersity observed for ID93 was much higher, the mixture of ID93 and GLA-SE retained the overall low polydispersity characteristic of GLA-SE, reflective of the relative proportions of ID93 and GLA-SE particles. Importantly, lyophilized and reconstituted ID93+GLA-SE retained this uniform particle size. Exposure to heat stress did not affect the polydispersity of ID93, GLA-SE, or covialed ID93+GLA-SE in liquid or lyophilized formats. Both ID93 and GLA-SE have an overall negative zeta potential in the current configuration. Mixing the two resulted in an average zeta potential of −13 mV, which was unaffected by lyophilization (FIG. 10C). Upon heat stress a more negative zeta potential was seen for all GLA-SE containing samples; however, this change was only statistically significant for lyophilized ID93+GLA_SE (p<0.025). Overall lyophilization and reconstitution of ID93+GLA-SE does not alter the physicochemical characteristics when compared to non-lyophilized ID93+GLA-SE. The physicochemical characteristics of ID93, but not GLA-SE, were significantly impacted by exposure to elevated temperatures for a prolonged time.

Figure 11:
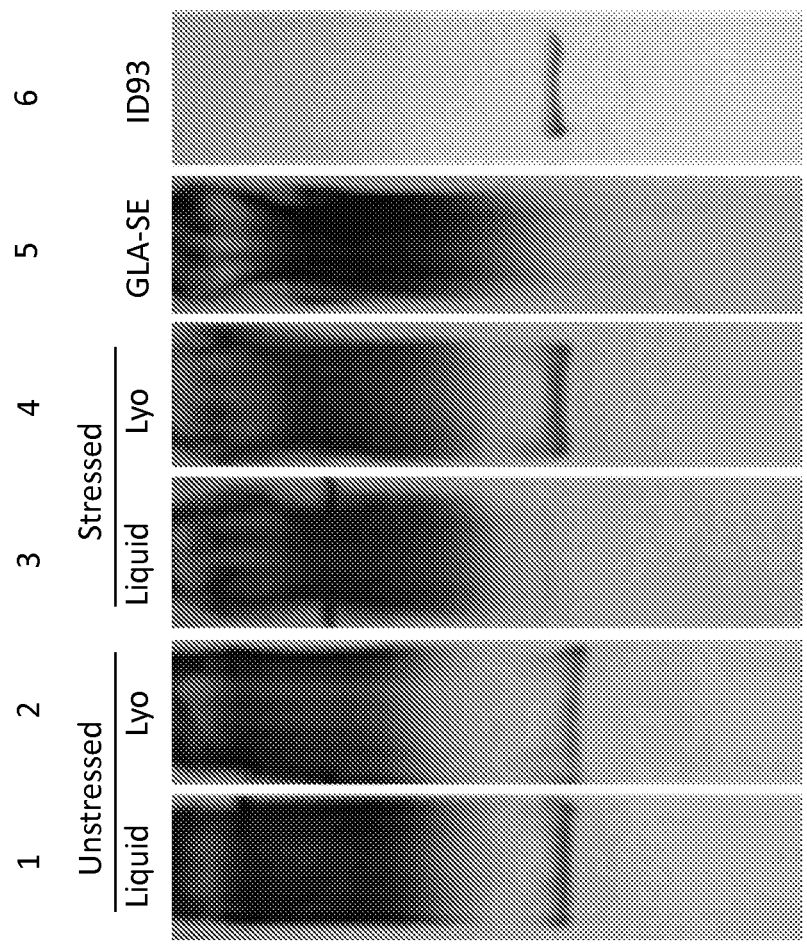
FIG. 11 shows a reducing SDS-PAGE with staining of covialed ID93+GLA-SE liquid (lanes 1 and 3) and reconstituted lyophilized samples (lanes 2 and 4). Samples were either unstressed (lanes 1 and 2) or stressed (lanes 3 and 4) at 50° C. for 30 days. Unstressed GLA-SE and ID93 are shown for comparison (lanes 5 and 6, respectively).

To assess how covialing, lyophilization and heat stress affected the chemical integrity of ID93+GLA-SE, ID93 concentration by SDS PAGE and GLA, and squalene and DMPC (the latter two were the major components of the stable emulsion) concentrations by RP-HPLC were evaluated. Samples containing 100 μg/mL ID93 were evaluated due to the inability to detect ID93 at 5 μg/mL by SDS-PAGE. Covialed samples containing 100 μg/mL and 5 μg/mL ID93 were found to behave similarly in terms of particle size, particle concentration, zeta potential, and GLA degradation profiles under liquid, lyophilized, and heat-stressed conditions. GLA-SE ran as a defuse smear, likely due to the disruption of emulsion particles by SDS, and was visible after staining. Lyophilization and reconstitution of covialed ID93+GLA-SE resulted in a 5-10% decrease in ID93 concentration, expected due to dilution upon reconstitution, indicating that substantial hydrolysis of ID93 had not occurred (FIG. 11). Upon exposure to heat stress at 50° C.

for one month there was a dramatic reduction in the ID93 present in ID93+GLA-SE. Lyophilization of ID93+GLA-SE rendered the protein resistant to this degradation with 6% and 90% of the ID93 band intensity observed after heat stress for the liquid and lyophilized samples, relative to the unstressed samples respectively (FIG. 11). Thus lyophilization of ID93+GLA-SE protected the ID93 protein from heat stress-induced degradation.

As expected, after mixing GLA-SE 1:1 with ID93, approximately half of the original concentration of GLA, DMPC, and squalene were measured, and no material was lost after lyophilization and reconstitution (FIG. 12A). Exposure of liquid GLA-SE to heat stress caused a 50% loss of GLA concentration (p<0.001). This was exacerbated by coviating with ID93 to the point that there was no detectable GLA after heat stress (FIG. 12A). This enhanced susceptibility may have been due to the more basic pH of the covialed ID93+GLA-SE compared to GLA-SE alone. This loss of GLA was ameliorated by lyophilization of the covialed ID93+GLA-SE, with ~50% of the GLA recovered after reconstitution of the heat stressed lyophilized ID93+GLA-SE (FIG. 12D). GLA was the major heat labile component of GLA-SE as neither the DMPC nor the squalene concentration was affected by heat stress (FIG. 12B-D). Taken together, these data showed that the two active components of ID93+GLA-SE were protected from heat induced degradation by lyophilization.

Overall, lyophilization of ID93+GLA-SE resulted in a white to off-white cake that retained the chemical and biophysical properties of covialed ID93+GLA-SE upon reconstitution. Exposure of ID93+GLA-SE to heat stress resulted in a significant loss of both ID93 and GLA. Lyophilization of covialed ID93+GLA-SE largely ameliorated these losses due to heat stress, indicating that this approach could reduce or eliminate the need for cold-chain maintenance of this vaccine candidate.

Vaccine Immunogenicity and Efficacy of GLA-SE Adjuvanted Vaccine Formulation

Figure 13B:
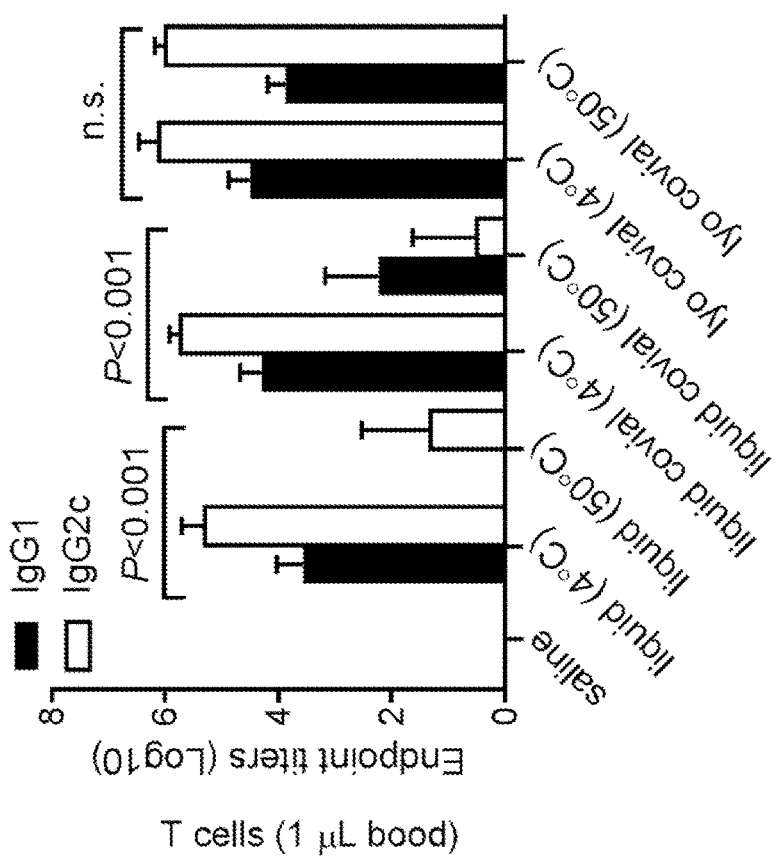
FIG. 13B) ID93-specific serum antibody titers were determined three weeks after the first immunization.
Figure 13A:
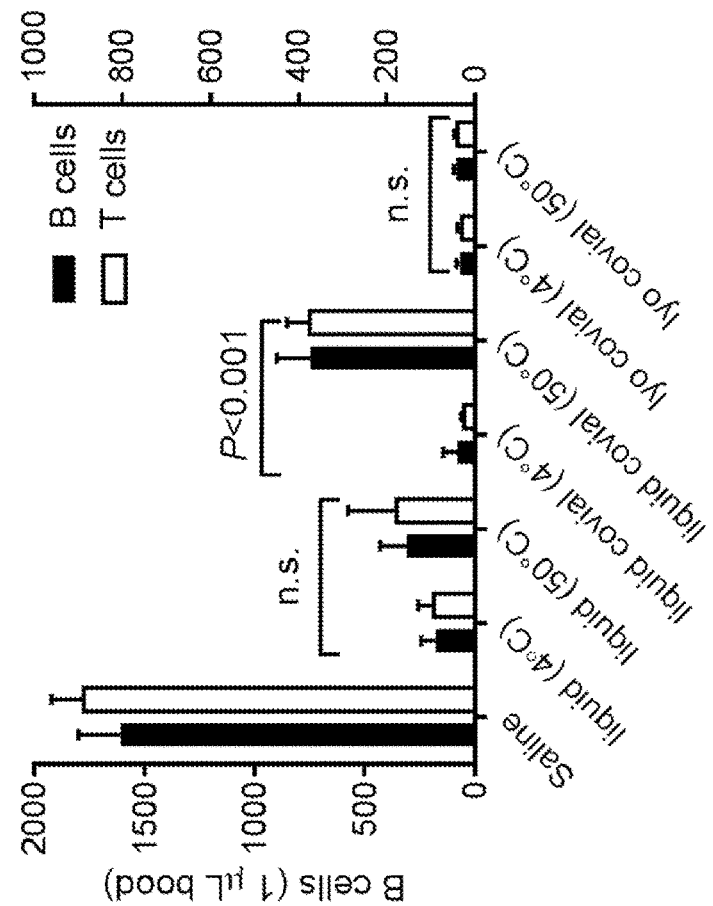
FIG. 13A) B and T cell blood counts were determined 18 hours after immunization.

To determine how heat stress affected the biological activity of ID93+GLA-SE and whether lyophilization ameliorated any detrimental effects, mice were immunized with saline or ID93+GLA-SE that was stored as separate vials of liquid antigen and adjuvant (liquid), a mixture of antigen and adjuvant (liquid covial) or co-lyophilized antigen and adjuvant (lyo covial). Immunization material was stored at either 4° C. (i.e. unstressed) or 50° C. (i.e. heat stressed) for one month prior to immunization. Following immunization there was a transient loss of circulating B and T cells from the blood as these cells homed to the draining lymph node where they encountered antigen (Shiow et al., 2006, Nature, 440: 540-544). This transient lymphopenia has been termed lymph node shutdown as lymphocytes become transiently trapped in the lymph node in a process necessary for efficient interactions between antigen presenting cells and cognate lymphocytes. The GLA-SE adjuvant augmented this effect which may in part account for its excellent adjuvant activity. Immunization with unstressed liquid ID93+GLA-SE elicited a dramatic loss of both B and T cells from the blood (FIG. 13A). Stressing the liquid ID93+GLA-SE at 50° C. for a month reduced this effect, suggesting that the activity of GLA was impaired by heat stress. Unstressed liquid covial ID93+GLA-SE induced lymph node shutdown as efficiently as the liquid vaccine, however this liquid covial material was more affected by heat stress as the degree of lymph node shutdown was markedly reduced, likely reflective of the loss of detectable GLA (FIG. 13A). Lyophilized covial ID93+GLA-SE elicited transient lymphopenia to a similar degree to the liquid material, however unlike the liquid covial material this effect was not impaired by heat stress of the lyophilized covial vaccine. These data suggested that biological activity of the GLA-SE adjuvant was susceptible to heat stress and this was exacerbated by coviating with the ID93 antigen. Importantly, lyophilization rendered coviated ID93+GLA-SE resistant to the damages of heat stress as read out by this parameter.

To more fully examine the impacts of heat stress and lyophilization on the biological activity of ID93+GLA-SE ID93-specific antibody titers following immunization were evaluated. Immunization with ID93+GLA-SE elicited a mixed IgG1, IgG2c response that is skewed towards IgG2c production. This was reflective of the IFN-γ dominated CD4 T cell responses produced by ID93+GLA-SE. Exposure to heat stress significantly impaired the ability of liquid ID93+GLA-SE to elicit measurable antibody titers (FIG. 13B). This was likely due to degradation of the ID93 protein upon heat stress (FIG. 11). Although coviating ID93+GLA-SE did not alter the magnitude of the antibody response when the vaccine was stored at 4° C., this was not sufficient to prevent loss of the antibody-inducing potential caused by heat stress. Conversely the lyophilized covial ID93+GLA-SE elicited robust antibody responses similar in magnitude and IgG1/IgG2c skewing to the liquid unstressed material and this was not impaired by heat stress (FIG. 13B).

Figure 13C:
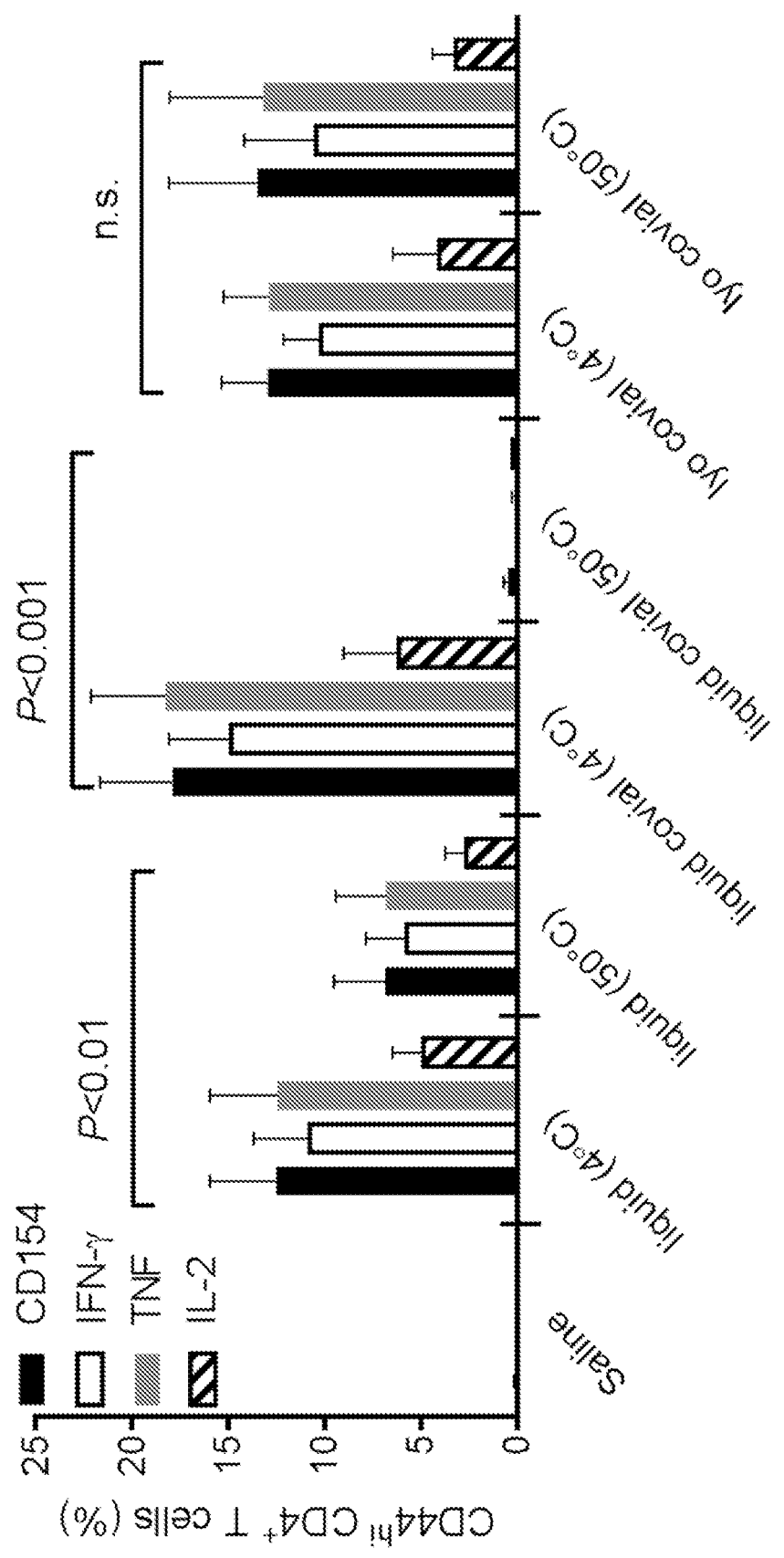
FIG. 13C) The frequency of ID93-specific CD4 T cells in the spleen were evaluated one month after the final immunization by analyzing cytokine production following in vitro restimulation with ID93.

ID93+GLA-SE protected against *M. tuberculosis* by inducing ID93-specific CD4 T cells that made IFN-γ, TNF, and IL-2 (i.e. TH1 cells). Exposure to heat stress reduced the frequency of ID93-specific TH1 cells as measured by production of any of these cytokines by almost 50% following the third immunization with liquid ID93+GLA-SE (FIG. 13C). That the TH1 response to stressed liquid ID93+GLA-SE was maintained despite degradation of the ID93 protein likely reflected the presence of immunogenic peptides and residual GLA after heat exposure. Coviating of liquid ID93+GLA-SE slightly enhanced the magnitude of the TH1 response when stored at 4° C., however exposure to heat stress completely ablated the ability of liquid univialed ID93+GLA-SE to elicit such response. Lyophilized covial ID93+GLA-SE induced TH1 responses to a level similar to that produced with liquid ID93+GLA-SE. Critically, unlike liquid or liquid covialed ID93+GLA-SE, lyophilized covial ID93+GLA-SE fully retained the ability to elicit ID93-specific TH1 cells following heat stress (FIG. 13C). It was previously determined that ID93-specific CD4 T cells elicited immunization with native ID93+GLA-SE are exclusively TH1 cells, failing to produce IL-5 (TH2) or IL-17 (TH17) upon restimulation (Orr et al, 2013, Eur J Immunol.). Coviating, lyophilization and/or exposure to heat stress did not enhance the induction of either TH2 or TH17 cells by ID93+GLA-SE as measured by detectable IL-5 or IL-17 production. Production of CD154 following stimulation has been proposed to be a generalized marker of CD4 T cell activation regardless of cytokine production (Frentsch et al, 2005, Nat Med, 11:1118:1124). In all cases CD154 expression levels closely mirrored that of both IFN-γ and TNF, further indicating that there was no deviation from the TH1 programming. Overall the early impairment lymphocyte egress from the blood (FIG. 13A) strongly correlated with the subsequent loss of both the antibody (FIG. 13B) and CD4 T cell response (FIG. 13C) to ID93+GLA-SE vaccination.

Figure 14A:
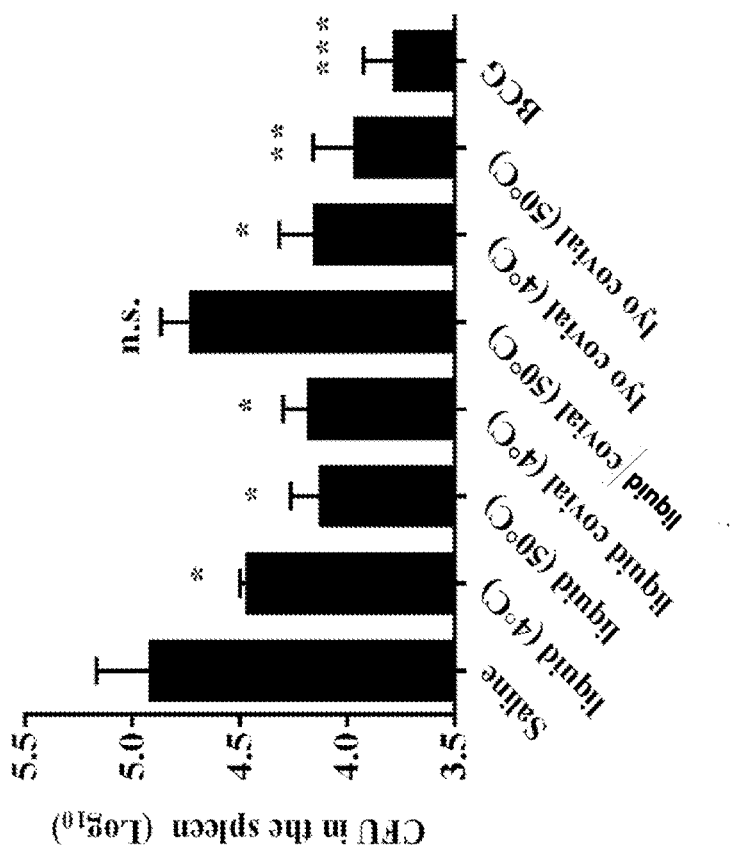
FIG. 14 shows aerosolized *M. tuberculosis* challenge and enumeration in ID93+GLA-SE immunized mice. One month after the final immunization animals were challenged with a low dose of aerosolized *M. tuberculosis*. Bacterial burden in the FIG. 14A) lung and FIG. 14B) spleen were determined three weeks later. Data displayed as mean+s.d. of N=5-7 mice/group. Data shown from one of two experiments with similar results. *, , *, and **** indicate $P<0.05$, 0.01, 0.001 and 0.0001, respectively, relative to saline. n.s. not significant relative to saline. Statistical comparisons between 4° C. and 50° C. samples are indicated.
Figure 14B:
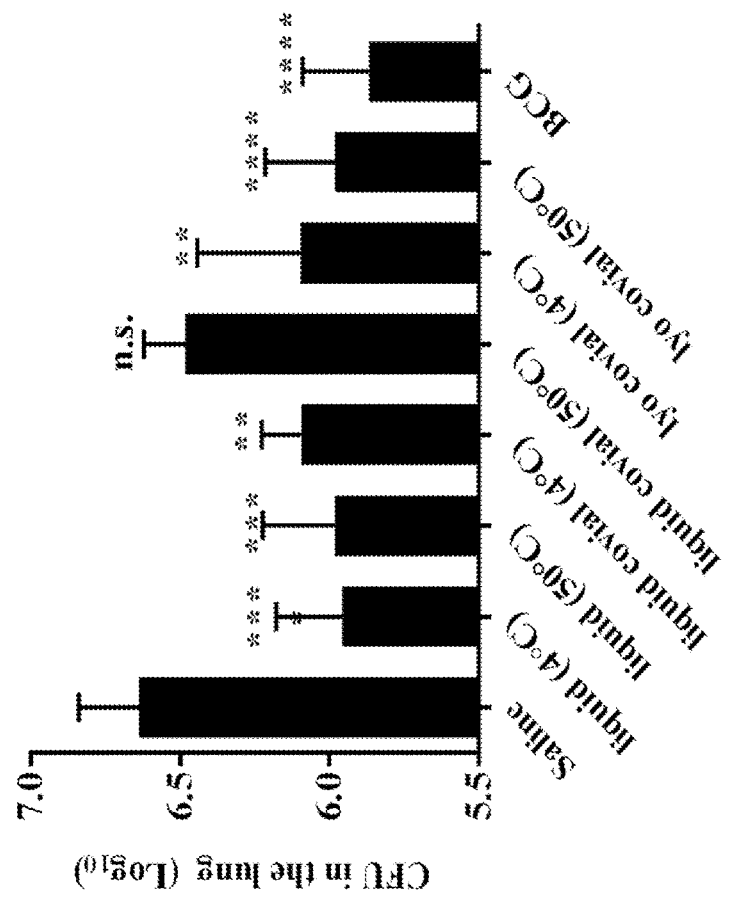

To assess how heat stress, coviating, and lyophilization affected the protective efficacy of ID93+GLA-SE, immunized mice were challenged with a low dose of aerosolized *M. tuberculosis*. Three weeks later animals immunized with liquid ID93+GLA-SE were significantly protected against *M. tuberculosis* relative to the saline immunized animals as measured by reduced bacterial burdens in the lungs and spleen (FIG. 14A and FIG. 14B). Heat stressing liquid ID93+GLA-SE separately did not impair this protective efficacy, likely reflective of the residual ID93-specific TH1 response elicited by this immunization (FIG. 13C). Covialing of ID93+GLA-SE did not impair protective efficacy when stored at 4° C., but the liquid covialed vaccine lost all protective efficacy when exposed to heat stress. Lyophilization of the covialed ID93+GLA-SE maintained protective efficacy and most importantly lyophilization of ID93+GLA-SE abrogated the loss of protective efficacy due to heat stress (FIG. 14A and FIG. 14B).

Colyophilization and reconstitution of the antigen and nanoemulsion adjuvant did not significantly alter the physicochemical characteristics of the vaccine. Upon reconstitution the concentrations of both the antigen and the TLR4 agonist GLA, as well as the squalene oil, were not substantially different than that of the starting material. Prolonged exposure to heat stress had little effect on the physical characteristics of either the liquid covialed or colyophilized vaccine; however, heat exposure led to chemical degradation of both the antigen and the TLR4 agonist, but not the squalene or phospholipid components of the adjuvant. Colyophilization partially protected against this loss of TLR4 agonist.

The loss of GLA due to heat stress was strongly predictive of the impaired immune responses and protective efficacy of the vaccine when administered to experimental animals. Although this relationship was not completely linear, the reduction in GLA in the liquid samples resulted in decreased frequencies of ID93-specific CD4 T cells after immunization. The complete loss of GLA in the heat stressed liquid covialed ID93+GLA-SE matched the loss of CD4 T cell induction. Conversely the degradation of the ID93 protein in the liquid samples had little impact on the magnitude of the CD4 T cell response. Without wishing to be bound to theory, this may likely be attributed to retention of the immunodominant peptides necessary to prime the T cell response in the heat stressed samples. On the other hand heat induced degradation of ID93 significantly impaired the magnitude of the antibody response to the vaccine. Many of the ID93-specific antibodies may be conformationally dependent. Further the residual antibody response was preferentially IgG1 indicating a loss of GLA driven IgG2c skewing. Colyophilization of ID93+GLA-SE largely prevented heat stress induced loss of ID93-specific antibody responses, indicating that the protein structure was protected by this process. This would suggest that protection of antigens against heat stress is a more critical parameter for vaccines that rely on antibody responses for protective efficacy than vaccines such as ID93+GLA-SE that rely on T cells for protective efficacy. Indeed the heat stressed separately vialed liquid vaccine retained a degree of protective efficacy against experimental challenge with aerosolized Mtb. There is a clear relationship between the ability to retain GLA concentration by lyophilization in the face of thermal stress, the retention of TH1 induction, and maintenance of protective efficacy.

Physicochemical Characterization of SLA-SE Adjuvanted Vaccine Formulation

A lyophilization regimen for covialed SLA-SE adjuvanted ID93 vaccine was developed. Upon lyophilization, a white, partially shrunken cake was formed, and, after reconstitution with water, the emulsion reformed (FIG. 15). The potential to increase stability to heat stress by lyophilization was evaluated by incubating duplicate samples (A and B) of lyophilized ID93+SLA-SE at 50° C. for 30 days. After heat stress, no visible change in sample quality was observed (FIG. 15; 30 Days, A and 30 Days, B) when compared to unstressed sample (FIG. 15; 0 Days, A and 0 Days, B). Reconstituted samples maintained the appearance of an emulsion, did not show creaming 24 hours after reconstitution, and lyophilized cakes did not show any further signs of collapse or discoloration.

To assess how covialing, lyophilization and heat stress affected the chemical integrity of ID93+SLA-SE, ID93 concentration in the reconstituted formulations was evaluated by SDS PAGE (FIG. 16). Reconstituted samples containing 1 µg/mL ID93 were loaded per lane. ID93 was observed as a 98 kDa band in all samples tested. Lyophilization and reconstitution of stressed covialed ID93+SLA-SE did not result in a substantial hydrolysis of ID93 when compared to stressed covialed ID93+SLA-SE (FIG. 16). Therefore, lyophilization of ID93+SLA-SE protected the ID93 protein from heat stress-induced degradation.

Figure 17A:
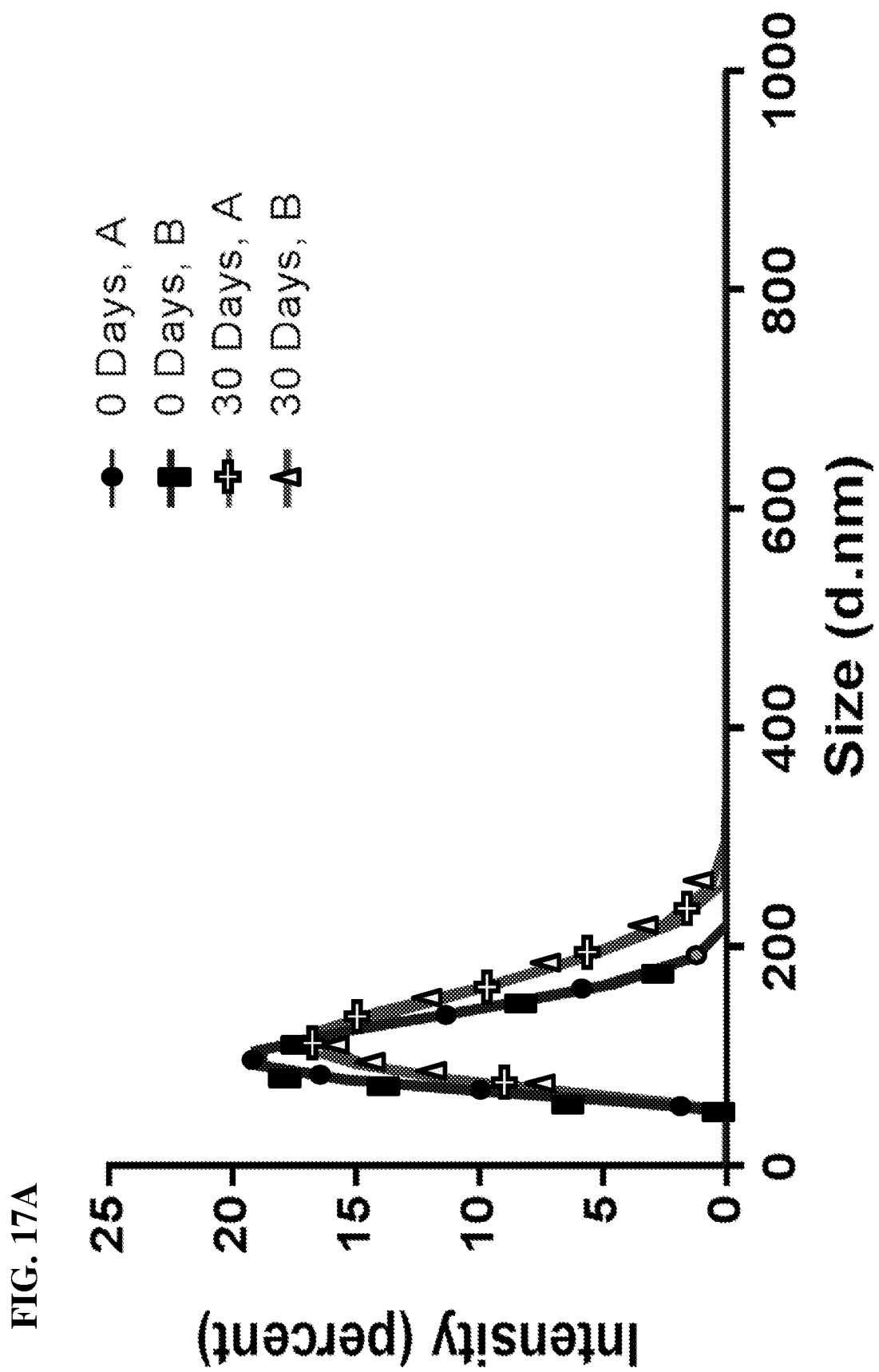
FIG. 17A) Particle size distributions (diameter) by intensity.
Figures 17B, 17C:
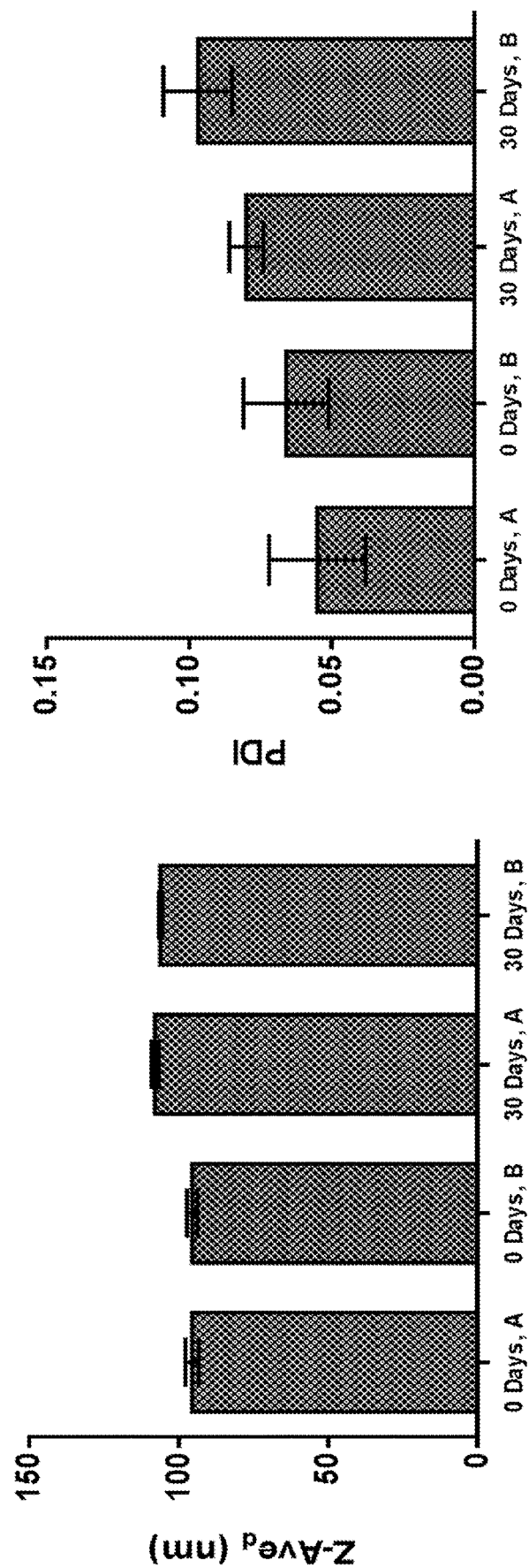
FIG. 17B) Z-average diameter.
FIG. 17C) Polydispersity Index (PdI). Error bars represent 1 standard deviation about the mean, n=4 runs.
Figure 18:
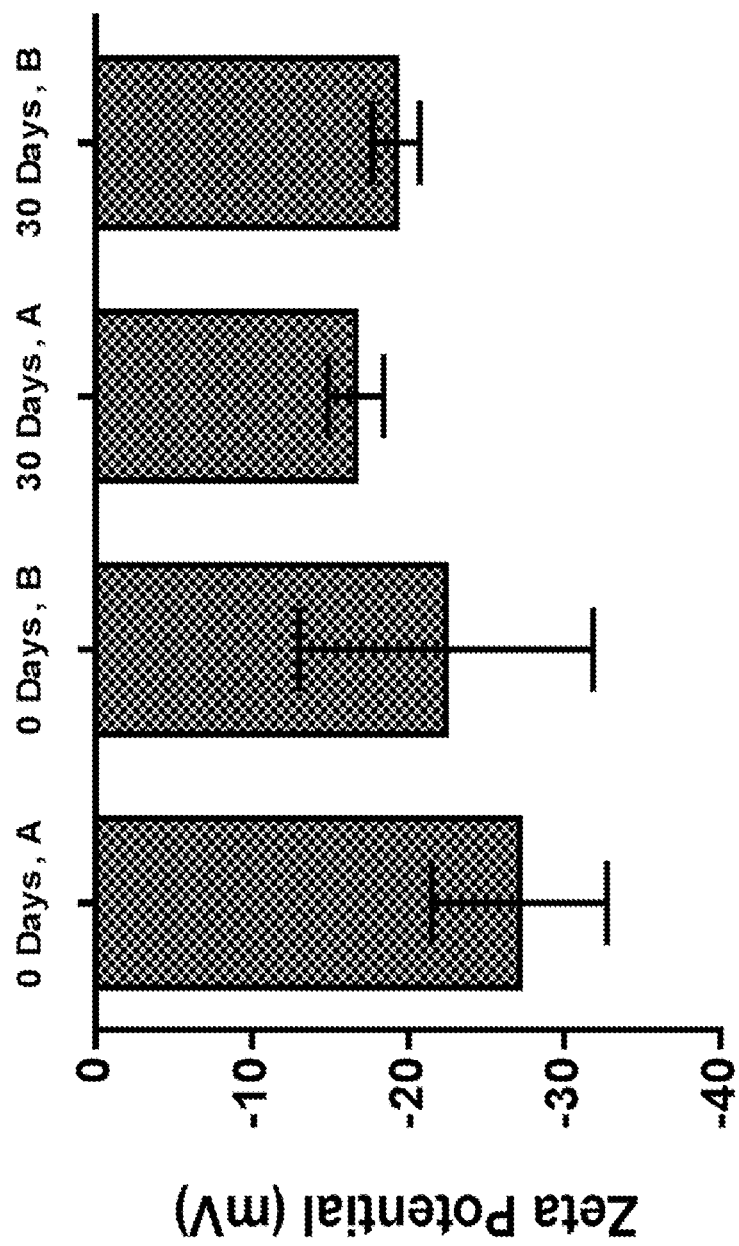
FIG. 18 shows DLS zeta potential (mV) of reconstituted ID93+SLA-SE co-lyophilized formulations. Error bars represent 1 standard deviation about the mean, n=4 runs.
Figure 19:
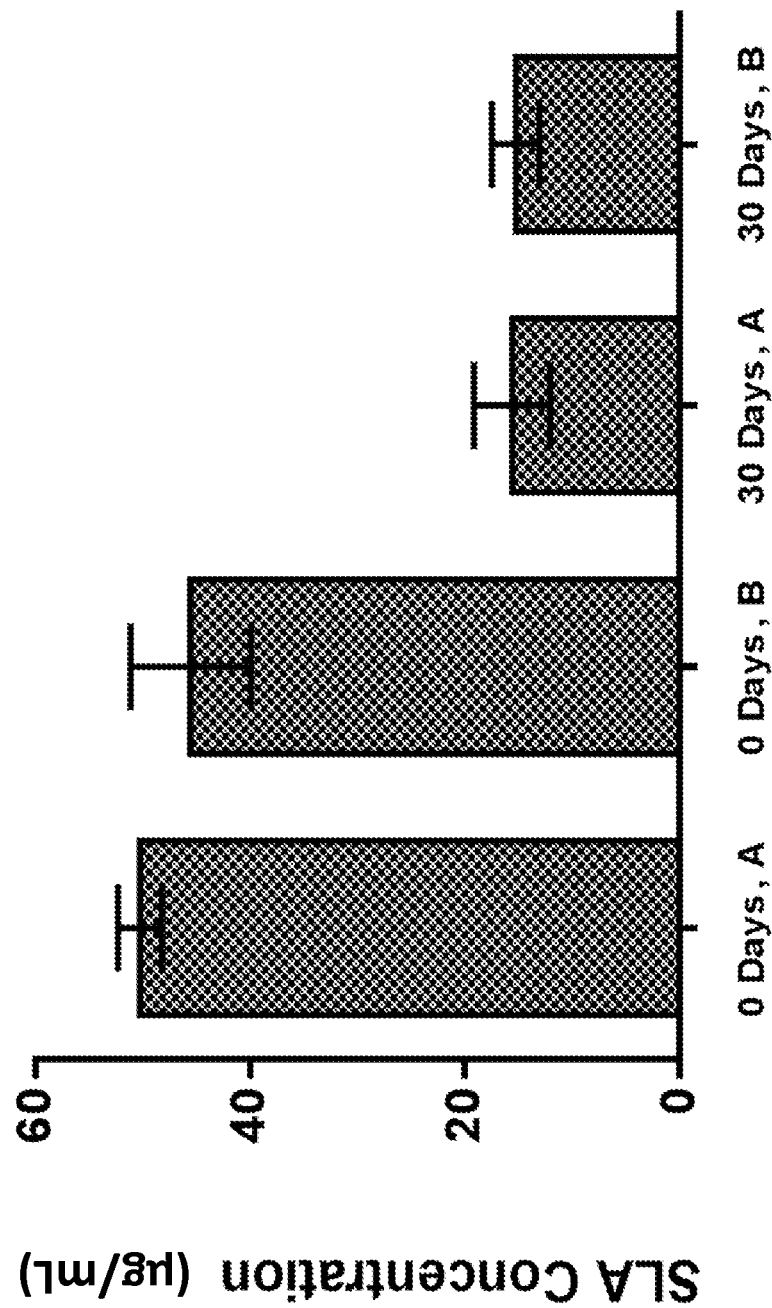
FIG. 19 shows HPLC-derived SLA concentrations (μg/mL) in reconstituted ID93+SLA-SE co-lyophilized formulations. Error bars represent 1 standard deviation about the mean, n=3 runs.

To assess whether heat stress of reconstituted lyophilized covialed ID93+SLA-SE altered the biophysical properties of the adjuvanted vaccine, the particle size, concentration, polydispersity, and overall zeta potential of lyophilized covialed ID93+SLA-SE was examined when under stressed or unstressed conditions. Heat stress of reconstituted lyophilized covialed ID93+SLA-SE did not significantly alter particle size or polydisperse aggregates (FIG. 17A-C) or zeta potential (FIG. 18) as compared to unstressed covialed ID93+SLA-SE. Similar to reconstituted lyophilized covialed ID93+GLA-SE, heat stress of reconstituted lyophilized covialed ID93+SLA-SE resulted in about ~50% recovery of SLA (FIG. 19).

Example 3: Lyophilized Vaccine Emulsion Formulation and Long Term Stability

Figure 20:
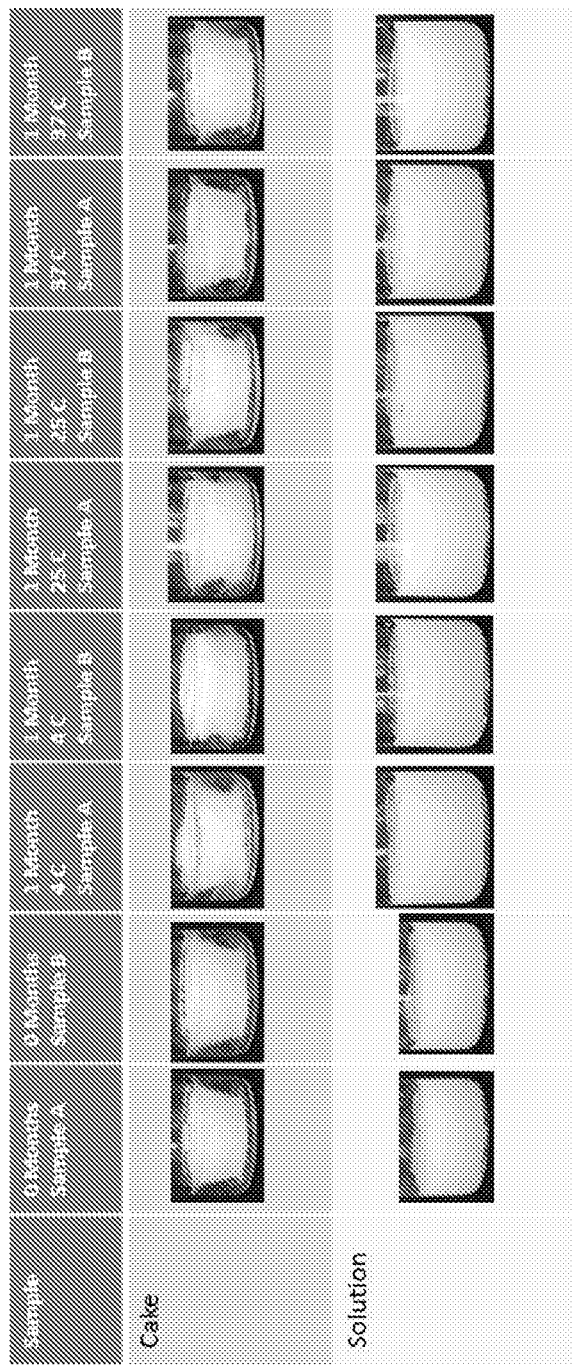
FIG. 20 shows the cake formation of duplicate lyophilized ID93+GLA-SE samples and the appearance of the emulsion following reconstitution at time zero (immediately after lyophilization) and one month post lyophilization when stored at 4° C., 25° C., and 37° C. The sample stored at 4° C. represents the control lyophilized emulsion kept under normal cold chain storage conditions of 2°-8° C. The cake appears white and slightly shrunken in appearance with no evidence of browning and the reconstituted emulsion does not cream at one hour or at 24 hours post reconstitution.
Figure 27A:
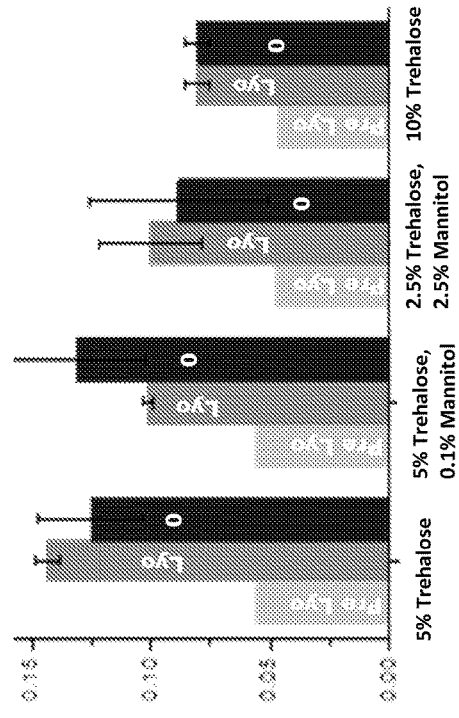
FIGS. 27A-D shows the comparison of the prelyophilized GLA-SE emulsion prior to the addition of the lyophilization components (cake forming excipients) as indicated below each set of bars as 5% Trehalose alone (no glycerol), 5% Trehalose w/v, 0.1% w/v Mannitol, 2.5% w/v Trehalose, 2.5% w/v Mannitol, 2.5% w/v Trehalose, 2.5% w/v Mannitol (labeled on the bars as Pre Lyo), the GLA-SE emulsion immediately after addition of the lyophilization components (labeled on the bars as Lyo), and post lyophilization following reconstitution (labeled as 0, or if unlabeled, the third bar in each lyophilization formulation set) for each lyophilization formulation. Initial comparison of the lyophilization formulations demonstrated no appreciable differences between the lyophilization formulations with each formulation and having the appropriate reconstituted emulsion characteristics (desired characteristics) including a particle size with Z-average diameter of less than about 200 nm, lack of appreciable aggregates as measured by polydispersity, physiologic pH, and no appreciable loss of GLA (values greater than 90% of the initial content).
Figure 27B:
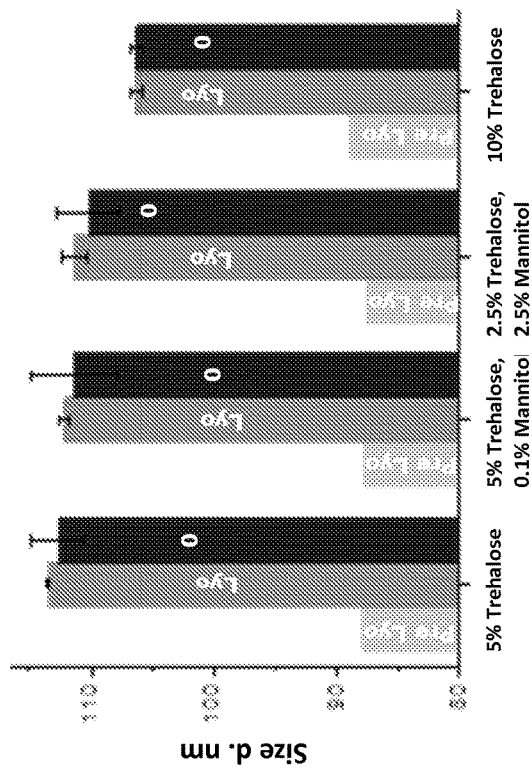
Figure 27C:
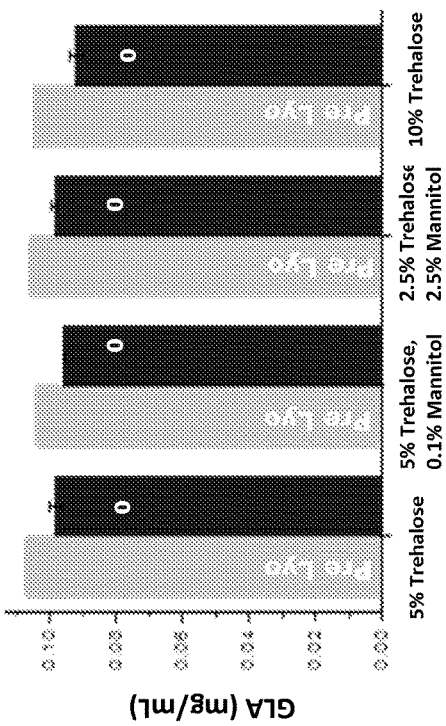
Figure 27D:
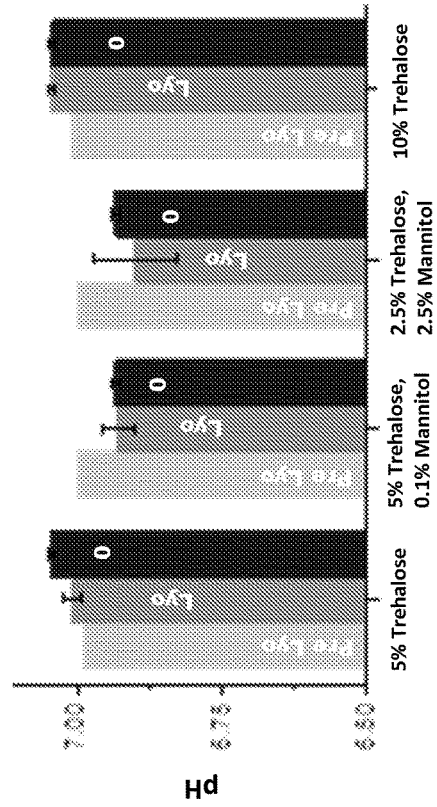
Figure 30B:
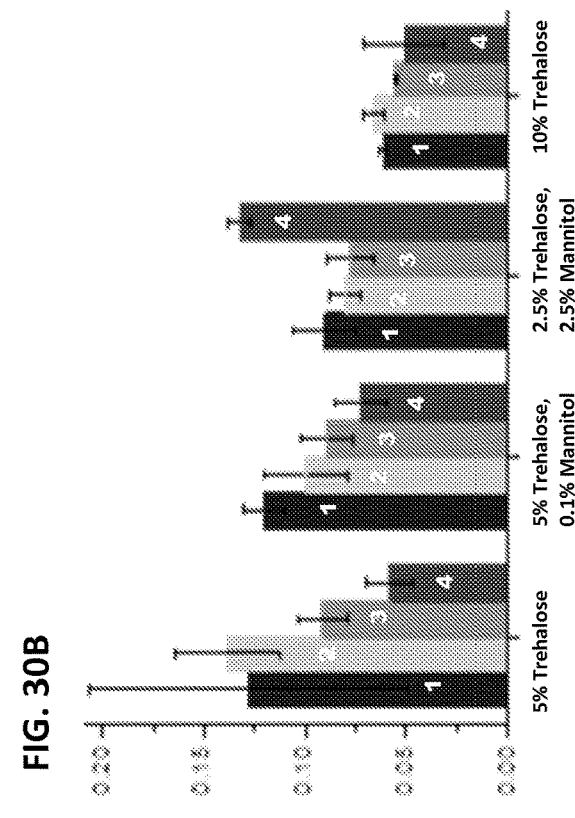
FIG. 30 shows the various single vial GLA-SE lyophilization formulations (the emulsion containing the cake forming excipients) as indicated below each set of bars as 5% Trehalose alone (no glycerol), 5% Trehalose w/v, 0.1% w/v Mannitol, 2.5% w/v Trehalose, 2.5% w/v Mannitol, 2.5% w/v Trehalose, 2.5% w/v Mannitol stored at 4° C. (bar 1), 25° C. (bar 2), 37° C. (bar 3), and 50° C. ((bar 4) for a particular formulation) for one month (1 mo). Samples were reconstituted and analyzed for particle size (Z-average diameter, nm), polydispersity (PDI) as a function of aggregation, pH, and concentration of GLA (mg/ml).
FIG. 30A) demonstrates that all 4 lyophilization formulations when stored at temperature ranging from 4° C.-50° C. displayed the desired size particle size of less than about 200 nm, FIG. 30B) demonstrates that all 4 lyophilization formulations when stored at temperature ranging from 4° C.-50° C. displayed the desired lack of appreciable aggregates as measured by polydispersity, and FIG. 30C) demonstrates that all 4 lyophilization formulations when stored at temperatures ranging from 4° C.-50° C. displayed the desired physiologic pH.
FIG. 30D) all lyophilization formulations for GLA-SE show no appreciable loss of GLA (values ranging between approximately 105%-94%) of the original concentration of GLA when stored as the lyophilized cake at temperatures ranging from 4° C.-50° C. for one month and reconstituted to form the GLA-SE emulsion.
Figure 30D:
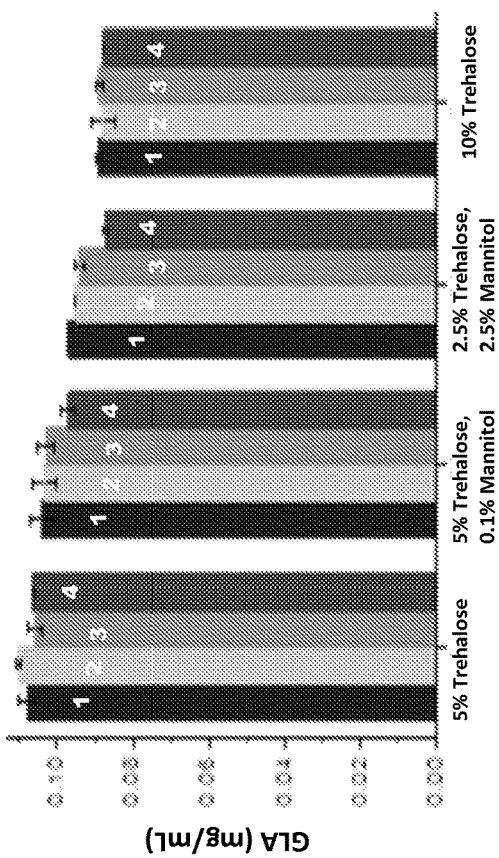
Figure 30A:
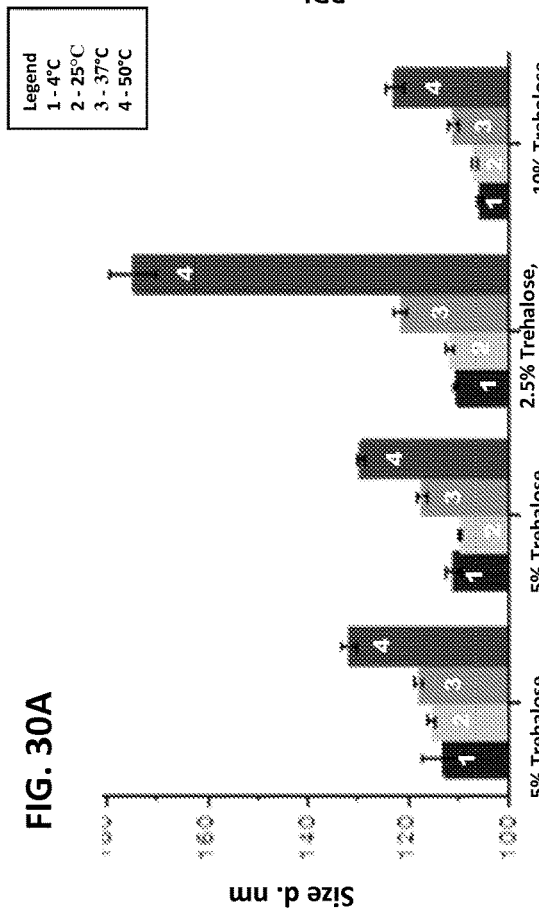
Figure 30C:
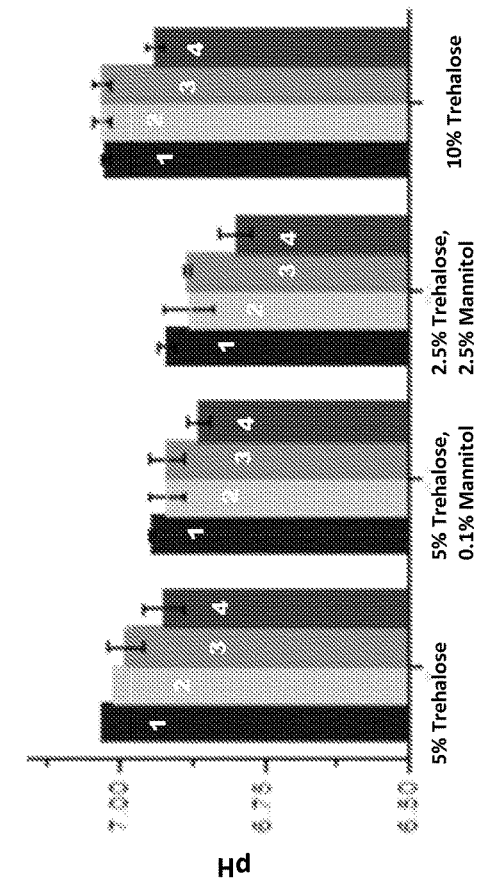

A lyophilization regimen for covialed GLA-SE adjuvanted ID93 vaccine was developed. The formulation evaluated for long term stability was the same formulation as described in Example 1, for the GLA-SE formulation which consisted of 2% v/v squalene, 0.4% w/v DMPC, 0.02% w/v poloxamer 188, 0.5% w/v glycerol, and 5 mM ammonium phosphate plus the ID 93 polypeptide lyophilized in the presence of 20 mM tromethamine and 5% w/v trehalose. Upon lyophilization, a white, partially shrunken cake was formed, and, after reconstitution with water, the emulsion reformed with no visible signs of creaming (FIG. 20). The potential to increase stability to heat stress by lyophilization was evaluated by incubating duplicate samples (A and B) of lyophilized ID93+GLA-SE at 4° C., 25° C., and 37° C. for one year.

3 Month Stability Data

Storage for three months at 4° C., 25° C., and 37° C. demonstrates no change in the appearance of the cake or the ability to form a suitable emulsion upon reconstitution compared to time zero (FIG. 21A and FIG. 21B). Lyophilized cakes did not show any further signs of collapse or discoloration, and reconstituted samples maintained the appearance of an emulsion with no creaming up to 24 hours after reconstitution.

The biophysical properties of the lyophilized adjuvanted vaccine ID93+GLA-SE, was examined at three month for samples stored 4° C., 25° C., and 37° C. in terms of particle size (Z-Aved nm), and polydispersity (PDI). At three months the formulations demonstrated no significant alteration in particle size or aggregates at any of the storage temperatures up to 37° C. (FIG. 21B).

To assess how covialing, lyophilization and heat stress affects the chemical integrity of the ID93 polypeptide, in the lyophilized emulsion stored at 4° C., 25° C., and 37° C. for three months, the reconstituted formulation was evaluated by SDS PAGE (FIG. 21C). Reconstituted samples containing 1 µg/mL ID93 were loaded per lane. ID93 was observed as a 98 kDa band in all samples tested. Lyophilization and reconstitution of ID93+GLA-SE does not result in a substantial hydrolysis of the ID93 polypeptide. Therefore, lyophilization of ID93+GLA-SE protects the ID93 protein from heat stress-induced degradation.

The chemical integrity of the SE formulation was assessed by HPLC and analyzed for DMPC and Squalene. The results in FIG. 21D demonstrate no loss or degradation of either component of the oil-in-water emulsion.

The concentration of the adjuvant in the lyophilized ID93+GLA-SE formulation stored at 4° C., 25° C., and 37° C. was assessed (FIG. 21E). The data demonstrates that there was no significant loss of GLA from the initial concentration of 50 µg/ml at any storage temperature at 3 months.

6 Month Stability Data

Storage for six months at 4° C., 25° C., or 37° C. demonstrates no change in the appearance of the cake or the ability to form a suitable emulsion upon reconstitution (FIG. 22A and FIG. 22B) compared to time zero. Lyophilized cakes does not show any further signs of collapse or discoloration, and reconstituted samples maintained the appearance of an emulsion with no creaming up to 24 hours after reconstitution.

The biophysical properties of the lyophilized adjuvanted vaccine ID93+GLA-SE, was examined at six months for the lyophilized samples stored 4° C., 25° C., and 37° C. for particle size (Z-Aved nm), and polydispersity (PDI). At six months the formulations demonstrated no significant alteration in particle size or aggregates at any of the storage temperatures up to 37° C. (FIG. 22B).

To assess how covialing, lyophilization and heat stress affects the chemical integrity of the ID93 polypeptide in the ID93+GLA-SE lyophilized formulation after storage at 4° C., 25° C., and 37° C. for six months, the reconstituted formulation was evaluated by SDS PAGE (FIG. 22C). Reconstituted samples containing 1 µg/mL ID93 were loaded per lane. ID93 was observed as a 98 kDa band in all samples tested. Lyophilization and reconstitution of ID93+ GLA-SE does not result in a substantial hydrolysis of ID93. Therefore, lyophilization of ID93+GLA-SE protects the ID93 protein from heat stress-induced degradation.

The chemical integrity of the SE formulation was assessed by HPLC and analyzed for DMPC and Squalene. The results in FIG. 22D demonstrate no loss or degradation of either component of the oil-in-water emulsion.

The concentration of the adjuvant in the lyophilized ID93+GLA-SE formulation stored at 4° C., 25° C., and 37° C. was assessed (FIG. 22E). The data demonstrates that there was no significant loss of GLA compared to the initial concentration of 50 µg/ml at storage temperatures of 4° C. or 25° C., but the 37° C. storage temperature demonstrates an approximate 50% loss of GLA at six months.

9 Month Stability Data

Storage for nine months at 4° C., 25° C., or 37° C. demonstrates no change in the appearance of the cake or the ability to form a suitable emulsion upon reconstitution (FIG. 23A and FIG. 23B) compared to time zero. Lyophilized cakes did not show any further signs of collapse or discoloration, and reconstituted samples maintained the appearance of an emulsion with no creaming up to 24 hours after reconstitution.

The biophysical properties of the lyophilized adjuvanted vaccine ID93+GLA-SE, was examined at nine months for samples stored 4° C., 25° C., and 37° C. in terms of particle size (Z-Average nm), and polydispersity (PdI). At nine months, the formulations demonstrated no significant alteration in particle size or aggregates at any of the storage temperatures up to 37° C. (FIG. 23B).

To assess how covialing, lyophilization and heat stress affects the chemical integrity of the ID93 polypeptide after storage at 4° C., 25° C., and 37° C. for nine months, the reconstituted formulation was evaluated by SDS PAGE (FIG. 23C). Reconstituted samples containing 1 µg/mL ID93 were loaded per lane. ID93 was observed as a 98 kDa band in all samples tested. Lyophilization and reconstitution of ID93+GLA-SE does not result in a substantial hydrolysis of ID93. Therefore, lyophilization of ID93+GLA-SE protects the ID93 protein from heat stress-induced degradation.

The chemical integrity of the SE formulation was assessed by HPLC and analyzed for DMPC and Squalene. The results in FIG. 23D demonstrate no loss or degradation of either component of the oil-in-water emulsion after nine months of storage.

The concentration of the adjuvant in the lyophilized ID93+GLA-SE formulation stored at 4° C., 25° C., and 37° C. was assessed (FIG. 23E). The data demonstrates that there was no significant loss of GLA compared to the initial concentration of 50 µg/ml at 4° C. or 25° C., but the 37° C. demonstrates the same approximate 69% loss of GLA at nine months as was seen at six months.

12 Month Stability Data

Storage for twelve months at 4° C., 25° C., or 37° C. demonstrates no change in the appearance of the cake or the ability to form a suitable emulsion upon reconstitution (FIG. 24A and FIG. 24B) compared to time zero. Lyophilized cakes did not show any further signs of collapse or discoloration, and reconstituted samples maintained the appearance of an emulsion with no creaming up to 24 hours after reconstitution.

The biophysical properties of the lyophilized adjuvanted vaccine ID93+GLA-SE, was examined at twelve months for samples stored 4° C., 25° C., and 37° C. in terms of particle size (Z-Aved nm), and polydispersity (PDI). At twelve months, the formulations demonstrated no significant alteration in particle size or aggregates at any of the storage temperatures up to 37° C. (FIG. 24B).

To assess how covialing, lyophilization and heat stress affects the chemical integrity of the ID93 polypeptide after storage at 4° C., 25° C., and 37° C. for twelve months, the reconstituted formulation was evaluated by SDS PAGE (FIG. 24C). Reconstituted samples containing 1 µg/mL ID93 were loaded per lane. ID93 was observed as a 98 kDa band in all samples tested. Lyophilization and reconstitution of ID93+GLA-SE does not result in a substantial hydrolysis of ID93. Therefore, lyophilization of ID93+GLA-SE protects the ID93 protein from heat stress-induced degradation at twelve months.

The concentration of the adjuvant in the lyophilized ID93+GLA-SE formulation stored at 4° C., 25° C., and 37° C. was assessed (FIG. 23E). The data demonstrates that there was no significant loss of GLA compared to the initial concentration of 50 µg/ml at 4° C. or 25° C., but the 37° C. demonstrates a 69% loss of GLA at twelve months.

Example 4: Lyophilized Vaccine Emulsion Formulation and Stability in Single and Multi-Excipient Systems with Improved Heat Stability and No Loss of Adjuvant at Higher Temperatures The lyophilized and formulated oil-in-water stable emulsions were prepared and lyophilized using the materials and according to the methods described in Example 1. Properties of the lyophilized oil-in-water stable emulsion (SE) formulation were reconstituted and characterized for melting point, moisture determination, particle size and zeta potential, chemical degradation by high performance liquid chromatography, reconstitution screen, cake stability screen, and accelerated stability characterization as described in Example 1.

Based on preliminary experiments, it was postulated that the use of glycerol as a tonicity agent may be contributing to the thermolability of the formulations of the invention at temperatures above 25° C. Investigations were conducted to determine if removal of glycerol as a tonicity agent in the formulations of the invention would provide greater thermostability at temperatures above 25° C. for longer than three months. In addition to the removal of glycerol, the percentage of biodegradeable oil, in this example squalene, was evaluated for thermostabilty and cake characterization when lyophilized in the improved 50° C. thermostabile 2.5% trehalose and 2.5% mannitol lyophilization formulations of the invention by methods described in Example 1.

The samples as described in example 1 represent the indicated percentages of squalene (from 2% to 10% v/v squalene as indicated), 0.4% w/v DMPC, 0.02% w/v poloxamer 188, 0.5% w/v glycerol, and 5 mM ammonium phosphate that either contained 0.5% w/v glycerol or were formulated with no glycerol plus or minus the 2% v/v Tris as an additional tonicity agent. The data in FIG. 25A demonstrates that the emulsion formulations with increasing concentration of squalene (2-10% v/v) and lacking the 0.5% glycerol (labeled as No Glycerol) all formed elegant cakes upon lyophilization with no shrinking of the cake or discoloration even after 30 days at 50° C. when compared to the formulations containing the 0.0.5% glycerol v\v (labeled as With Glycerol) form cakes that are slightly shrunken and depressed both immediately post lyophilization (time O days) and 30 days after storage at 50° C. Comparison of the reconstitution of the cake for creaming of the formulation demonstrated no appreciable differences.

FIG. 25B and FIG. 25C demonstrate that there is no appreciable difference in the either the particle size in for particle size (Z-Aved nm), and polydispersity (PDI) (respectively) for any of the formulations after storage at 50° C. for 30 days for any of the formulation. FIG. 25D provides evidence that the presence of 0.5% v/v glycerol does affect the stability to the adjuvant, GLA in the formulation. None of the emulsion formulations prepared with increasing biodegradable oil content (25-10%) show any loss in GLA concentration comparing the starting concentration (time zero depicted by a 0 on the bar) compared to the samples reconstituted after storage of the lyophilized vials at 50° C. for thirty days (depicted by a 1 in the bar). Emulsions lyophilized in the presence of glycerol demonstrate a 30-40% loss of GLA.

Based on this data, it is likely that vaccine formulations of the invention can be lyophilized to withstand 50° C. temperature that would produce more elegant cakes and thereby as one of ordinary skill in the art would recognize afford a greater thermostability.

Figure 26A:
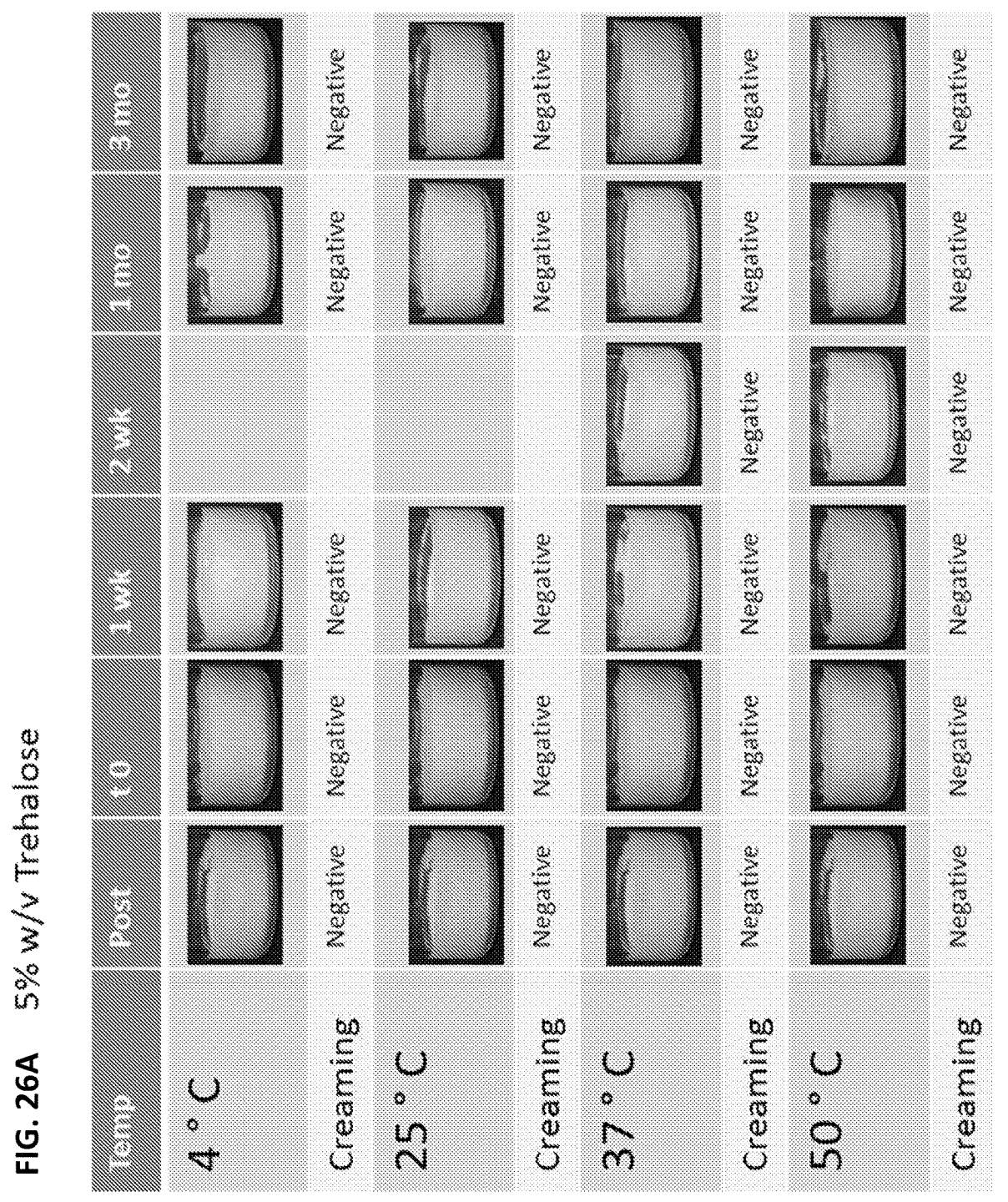

Example 5: Development and Characterization of Four Lyophilized Vaccine Emulsion Formulations and Stability in Single and Multi-Excipient Systems with Improved Heat Stability and No Loss of Adjuvant at Higher Temperatures Four lyophilization formulations were evaluated for their ability to thermoprotect the GLA-SE emulsion described herein with all formulations lacking glycerol as a tonicity agent. The formulations developed and evaluated were 5% Trehalose alone (no glycerol) (FIG. 26A), 5% Trehalose w/v, 0.1% w/v Mannitol (FIG. 26B), 2.5% w/v Trehalose, 2.5% w/v Mannitol) (FIG. 26C), and 10% w/v Trehalose (FIG. 26D) were evaluated for cake formation and appearance and creaming following reconstitution a time 0 (immediately following lyophilization), one week (1 wk), 2 weeks (2 wk), 1 month (1 mo) and 3 months (3 mo) following lyophilization for samples stored the indicated time at 4° C., 25° C., 37° C., and 50° C. as indicated. Comparison of the data indicates that all samples formed lovely white cakes with the 5% Trehalose w/v, 0.1% w/v Mannitol (FIG. 26B), 2.5% w/v Trehalose, 2.5% w/v Mannitol) (FIG. 26C) forming the most elegant cakes at all storage temperatures. The elegant cakes formed by 5% Trehalose w/v, 0.1% w/v Mannitol (FIG. 26B), 2.5% w/v Trehalose, 2.5% w/v Mannitol) (FIG. 26C) demonstrate an elegant structure as known in the art. Thus removal of glycerol as a tonicity agent from the lyophilized GLA-SE emulsions of the invention produces a more elegant cake structure that maintains its structural integrity over a range of temperatures from 4° C., 25° C., 37° C., and 50° C. when stored for one week (1 wk), 2 weeks (2 wk), 1 month (1 mo) and 3 months (3 mo) (FIG. 26A-D), The lyophilized formulations were all stored at 4° C., 25° C., 37° C., and 50° C. for one week (1 wk), 2 weeks (2 wk), 1 month (1 mo) and 3 months (3 mo) as indicated. Samples were removed form storage, reconstituted and compared for particle size (Z-Aved nm), polydispersity (PDI), pH and GLA content following reconstitution as represented in FIG. 27-31.

FIG. 27 depicts the comparison of the prelyophilized emulsion prior to the addition of the lyophilization components (labeled on the bars as Pre Lyo), the GLA-SE formulation prior to lyophilization (labeled on the bars as Lyo) and post lyophilization following reconstitution (labeled as 0) for each formulation. Initial comparison of the formulations demonstrated no appreciable differences between the lyophilization formulations with each formulation and having the appropriate reconstituted emulsion characteristics including a particle size with Z-average diameter of less than about 200 nm, lack of appreciable aggregates as measured by polydispersity, physiologic pH, and no appreciable loss of GLA.

FIG. 28 depict the various single vial lyophilization formulations stored at 4° C. (bar 1), 25° C. (bar 2), 37° C. (bar 3), and 50° C. (bar 4) for one week (1 wk). Samples were reconstituted and analyzed for particle size (Z-average diameter, nm), polydispersity (PDI) as a function of aggregation, pH, and concentration of GLA (mg/ml). The data in FIG. 28A demonstrates that all 4 lyophilization formulations when stored at temperature ranging from 4° C.-50° C. displayed the desired size particle size of less than about 200 nm (FIG. 28A), lack of appreciable aggregates as measured by polydispersity (FIG. 28B), and physiologic pH (FIG. 28C). It is noteworthy that while the average particle size for the lyophilized cakes increase at 50° C. for all formulations by roughly 40% compared to the other samples, the particle size was still within the desired less than about 200 nm. Importantly, the formulations tested all lacking glycerol demonstrated no loss of GLA after one week of storage at any temperature tested.

FIG. 29 depict the various single vial lyophilization formulations stored at 37° C. (bar 3) and 50° C. (bar 4) for two weeks (2 wk). Samples were reconstituted and analyzed for particle size (Z-average diameter, nm), polydispersity (PDI) as a function of aggregation, pH, and concentration of GLA (mg/ml). The data in FIG. 29A demonstrates that all 4 lyophilization formulations when stored at temperatures ranging from 37° C.-50° C. displayed the desired size particle size of less than about 200 nm (FIG. 28A), lack of appreciable aggregates as measured by polydispersity (FIG. 29B), and physiologic pH (FIG. 29C). It is noteworthy that while the average particle size for the lyophilized cakes increased after one week at 50° C. for all formulations by roughly 40% compared to the other samples, the particle size appeared unchanged at the second week and was still within the desired less than about 200 nm. Importantly, the formulations tested all lacking glycerol demonstrated no loss of GLA after one week of storage at any temperature tested.

FIG. 30 depict the various single vial lyophilization formulations stored at 4° C. (bar 1), 25° C. (bar 2), 37° C. (bar 3), and 50° C. (bar 4) for one month (1 mo). Samples were reconstituted and analyzed for particle size (Z-average diameter, nm), polydispersity (PDI) as a function of aggregation, pH, and concentration of GLA (mg/ml). The data in FIG. 30A demonstrates that all 4 lyophilization formulations when stored at temperature ranging from 4° C.-50° C. displayed the desired size particle size of less than about 200 nm (FIG. 30A), lack of appreciable aggregates as measured by polydispersity (FIG. 30B), and physiologic pH (FIG. 30C). The trending toward average particle size growth for the 2.5% trehalose, 2.5% mannitol formulation from 120 to 175 nm is noted, but the average particle size is still below 200 nm and the formulation does not depict any loss of GLA.

FIG. 31 depict the various single vial lyophilization formulations stored at 4° C. (bar 1), 25° C. (bar 2), 37° C. (bar 3), and 50° C. (bar 4) for one month (1 mo). Samples were reconstituted and analyzed for particle size (Z-average diameter, nm), polydispersity (PDI) as a function of aggregation, pH, and concentration of GLA (mg/ml). The data in FIG. 31A demonstrates that all 4 lyophilization formulations when stored at temperature ranging from 4° C.-50° C. displayed the desired size particle size of less than about 200 nm (FIG. 31A), lack of appreciable aggregates as measured by polydispersity (FIG. 31B), and physiologic pH (FIG. 31C). The data in this Example 5 provides for additional lead candidate formulations for the single vial lyophilization of an oil-in-water emulsion (SE) comprising an adjuvant (GLA) that when stored at temperatures for up to 50° C. for greater than or equal to one month display enhance thermostability at 50° C.

The present invention provides for a number of formulations for the single vial lyophilization of oil-in-water emulsions that are suitable for vaccine delivery of antigens, single adjuvants, multiple adjuvants or any combination thereof that have particular utility for decreasing or eliminating the need for cold chain storage making them improved formulations over the art.

SEQUENCES

ID93 fusion polypeptide with optional His tag
(SEQ ID NO: 1)
MGSSHHHHHHSSGLVPRGSHMTINYQFGDVDAHGAMIRAQAGSLEAEHQA
IISDVLTASDFWGGAGSAACQGFITQLGRNFQVIYEQANAHGQKVQAAGN
NMAQTDSAVGSSWAGTHLANGSMSEVMMSEIAGLPIPPIIHYGAIAYAPS
GASGKAWHQRTPARAEQVALEKCGDKTCKVVSRFTRCGAVAYNGSKYQGG
TGLTRRAAEDDAVNRLEGGRIVNWACNELMTSRFMTDPHAMRDMAGRFEV
HAQTVEDEARRMWASAQNISGAGWSGMAEATSLDTMTQMNQAFRNIVNML
HGVRDGLVRDANNYEQQEQASQQILSSVDINFAVLPPEVNSARIFAGAGL
GPMLAAASAWDGLAEELHAAAGSFASVTTGLAGDAWHGPASLAMTRAASP
YVGWLNTAAGQAAQAAGQARLAASAFEATLAATVSPAMVAANRTRLASLV
AANLLGQNAPAIAAAEAEYEQIWAQDVAAMFGYHSAASAVATQLAPIQEG
LQQQLQNVLAQLASGNLGSGNVGVGNIGNDNIGNANIGFGNRGDANIGIG
NIGDRNLGIGNTGNWNIGIGITGNGQIGFGKPANPDVLVVGNGGPGVTAL
VMGGTDSLLPLPNIPLLEYAARFITPVHPGYTATFLETPSQFFPFTGLNS
LTYDVSVAQGVTNLHTAIMAQLAAGNEVVVFGTSQSATIATFEMRYLQSL
PAHLRPGLDELSFTLTGNPNRPDGGILTRFGFSIPQLGFTLSGATPADAY
PTVDYAFQYDGVNDFPKYPLNVFATANAIAGILFLHSGLIALPPDLASGV
VQPVSSPDVLTTYILLPSQDLPLLVPLRAIPLLGNPLADLIQPDLRVLVE
LGYDRTAHQDVPSPFGLFPDVDWAEVAADLQQGAVQGVNDALSGLGLPPP
WQPALPRLFST ID93 fusion polypeptide
(SEQ ID NO: 2)
MTINYQFGDVDAHGAMIRAQAGSLEAEHQAIISDVLTASDFWGGAGSAAC
QGFITQLGRNFQVIYEQANAHGQKVQAAGNNMAQTDSAVGSSWAGTHLAN
GSMSEVMMSEIAGLPIPPIIHYGAIAYAPSGASGKAWHQRTPARAEQVAL
EKCGDKTCKVVSRFTRCGAVAYNGSKYQGGTGLTRRAAEDDAVNRLEGGR
IVNWACNELMTSRFMTDPHAMRDMAGRFEVHAQTVEDEARRMWASAQNIS
GAGWSGMAEATSLDTMTQMNQAFRNIVNMLHGVRDGLVRDANNYEQQEQA
SQQILSSVDINFAVLPPEVNSARIFAGAGLGPMLAAASAWDGLAEELHAA
AGSFASVTTGLAGDAWHGPASLAMTRAASPYVGWLNTAAGQAAQAAGQAR
LAASAFEATLAATVSPAMVAANRTRLASLVAANLLGQNAPAIAAAEAEYE
QIWAQDVAAMFGYHSAASAVATQLAPIQEGLQQQLQNVLAQLASGNLGSG
NVGVGNIGNDNIGNANIGFGNRGDANIGIGNIGDRNLGIGNTGNWNIGIG
ITGNGQIGFGKPANPDVLVVGNGGPGVTALVMGGTDSLLPLPNIPLLEYA
ARFITPVHPGYTATFLETPSQFFPFTGLNSLTYDVSVAQGVTNLHTAIMA
QLAAGNEVVVFGTSQSATIATFEMRYLQSLPAHLRPGLDELSFTLTGNPN
RPDGGILTRFGFSIPQLGFTLSGATPADAYPTVDYAFQYDGVNDFPKYPL
NVFATANAIAGILFLHSGLIALPPDLASGVVQPVSSPDVLTTYILLPSQD
LPLLVPLRAIPLLGNPLADLIQPDLRVLVELGYDRTAHQDVPSPFGLFPD
VDWAEVAADLQQGAVQGVNDALSGLGLPPPWQPALPRLFST ID83 fusion polypeptide with optional His tag
(SEQ ID NO: 3)
MGSSHHHHHHSSGLVPRGSHMGTHLANGSMSEVMMSEIAGLPIPPIIHYG
AIAYAPSGASGKAWHQRTPARAEQVALEKCGDKTCKVVSRFTRCGAVAYN
GSKYQGGTGLTRRAAEDDAVNRLEGGRIVNWACNELMTSRFMTDPHAMRD
MAGRFEVHAQTVEDEARRMWASAQNISGAGWSGMAEATSLDTMTQMNQAF
RNIVNMLHGVRDGLVRDANNYEQQEQASQQILSSVDINFAVLPPEVNSAR
IFAGAGLGPMLAAASAWDGLAEELHAAAGSFASVTTGLAGDAWHGPASLA
MTRAASPYVGWLNTAAGQAAQAAGQARLAASAFEATLAATVSPAMVAANR
TRLASLVAANLLGQNAPAIAAAEAEYEQIWAQDVAAMFGYHSAASAVATQ
LAPIQEGLQQQLQNVLAQLASGNLGSGNVGVGNIGNDNIGNANIGFGNRG
DANIGIGNIGDRNLGIGNTGNWNIGIGITGNGQIGFGKPANPDVLVVGNG
GPGVTALVMGGTDSLLPLPNIPLLEYAARFITPVHPGYTATFLETPSQFF
PFTGLNSLTYDVSVAQGVTNLHTAIMAQLAAGNEVVVFGTSQSATIATFE
MRYLQSLPAHLRPGLDELSFTLTGNPNRPDGGILTRFGFSIPQLGFTLSG
ATPADAYPTVDYAFQYDGVNDFPKYPLNVFATANAIAGILFLHSGLIALP
PDLASGVVQPVSSPDVLTTYILLPSQDLPLLVPLRAIPLLGNPLADLIQP
DLRVLVELGYDRTAHQDVPSPFGLFPDVDWAEVAADLQQGAVQGVNDALS
GLGLPPPWQPALPRLFST ID83 fusion polypeptide
(SEQ ID NO: 4)
HLANGSMSEVMMSEIAGLPIPPIIHYGAIAYAPSGASGKAWHQRTPARAE
QVALEKCGDKTCKVVSRFTRCGAVAYNGSKYQGGTGLTRRAAEDDAVNRL
EGGRIVNWACNELMTSRFMTDPHAMRDMAGRFEVHAQTVEDEARRMWASA
QNISGAGWSGMAEATSLDTMTQMNQAFRNIVNMLHGVRDGLVRDANNYEQ
QEQASQQILSSVDINFAVLPPEVNSARIFAGAGLGPMLAAASAWDGLAEE
LHAAAGSFASVTTGLAGDAWHGPASLAMTRAASPYVGWLNTAAGQAAQAA
GQARLAASAFEATLAATVSPAMVAANRTRLASLVAANLLGQNAPAIAAAE
AEYEQIWAQDVAAMFGYHSAASAVATQLAPIQEGLQQQLQNVLAQLASGN
LGSGNVGVGNIGNDNIGNANIGFGNRGDANIGIGNIGDRNLGIGNTGNWN
IGIGITGNGQIGFGKPANPDVLVVGNGGPGVTALVMGGTDSLLPLPNIPL

| SEQUENCES |
|---|
| LEYAARFITPVHPGYTATFLETPSQFFPFTGLNSLTYDVSVAQGVTNLHT<br>AIMAQLAAGNEVVVFGTSQSATIATFEMRYLQSLPAHLRPGLDELSFTLT<br>GNPNRPDGGILTRFGFSIPQLGFTLSGATPADAYPTVDYAFQYDGVNDFP<br>KYPLNVFATANAIAGILFLHSGLIALPPDLASGVVQPVSSPDVLTTYILL<br>PSQDLPLLVPLRAIPLLGNPLADLIQPDLRVLVELGYDRTAHQDVPSPFG<br>LFPDVDWAEVAADLQQGAVQGVNDALSGLGLPPPWQPALPRLFST |

Rv1813

(SEQ ID NO: 5)
MITNLRRRTAMAAAGLGAALGLGILLVPTVDAHLANGSMSEVMMSEIAGL
PIPPIIHYGAIAYAPSGASGKAWHQRTPARAEQVALEKCGDKTCKVVSRF
TRCGAVAYNGSKYQGGTGLTRRAAEDDAVNRLEGGRIVNWACN

Rv3620

(SEQ ID NO: 6)
MTSRFMTDPHAMRDMAGRFEVHAQTVEDEARRMWASAQNISGAGWSGMAE
ATSLDTMTQMNQAFRNIVNMLHGVRDGLVRDANNYEQQEQASQQILSS

| SEQUENCES |
|---|

Rv2608

(SEQ ID NO: 7)
MNFAVLPPEVNSARIFAGAGLGPMLAAASAWDGLAEELHAAAGSFASVTT
GLAGDAWHGPASLAMTRAASPYVGWLNTAAGQAAQAAGQARLAASAFEAT
LAATVSPAMVAANRTRLASLVAANLLGQNAPAIAAAEAEYEQIWAQDVAA
MFGYHSAASAVATQLAPIQEGLQQQLQNVLAQLASGNLGSGNVGVGNIGN
DNIGNANIGFGNRGDANIGIGNIGDRNLGIGNTGNWNIGIGITGNGQIGF
GKPANPDVLVVGNGGPGVTALVMGGTDSLLPLPNIPLLEYAARFITPVHP
GYTATFLETPSQFFPFTGLNSLTYDVSVAQGVTNLHTAIMAQLAAGNEVV
VFGTSQSATIATFEMRYLQSLPAHLRPGLDELSFTLTGNPNRPDGGILTR
FGFSIPQLGFTLSGATPADAYPTVDYAFQYDGVNDFPKYPLNVFATANAI
AGILFLHSGLIALPPDLASGVVQPVSSPDVLTTYILLPSQDLPLLVPLRA
IPLLGNPLADLIQPDLRVLVELGYDRTAHQDVPSPFGLFPDVDWAEVAAD
LQQGAVQGVNDALSGLGLPPPWQPALPRLF

Rv3619

(SEQ ID NO: 8)
MTINYQFGDVDAHGAMIRAQAGSLEAEHQAIISDVLTASDFWGGAGSAAC
QGFITQLGRNFQVIYEQANAHGQKVQAAGNNMAQTDSAVGSSWA

---

What is claimed is:

1. A thermostable lyophilized vaccine composition comprising:
   a metabolizable oil;
   a cake-forming excipient, wherein the cake-forming excipient is (1) a combination of mannitol and trehalose or (2) a trehalose; and
   an adjuvant, wherein the adjuvant is a TLR4 agonist, wherein the composition is formed by lyophilization of an oil-in-water emulsion formulation, does not comprise glycerol, does not contain liposomes, does not contain alum, is in the form of a cake, forms an oil-in-water emulsion upon reconstitution, and is thermostable at a temperature between about 8° C. to about 60° C. for at least 10 months.

2. The composition of claim 1, wherein the cake-forming excipient is trehalose which is at a concentration of about 10% (w/v) in the oil-in-water emulsion formulation.

3. The composition of claim 1, wherein the cake-forming excipient is trehalose which is at a concentration of about 5% (w/v) in the oil-in-water emulsion formulation.

4. The composition of claim 1, wherein the composition is formed by lyophilization of an oil-in water emulsion formulation, wherein the cake-forming excipient is a combination of mannitol and trehalose, wherein the mannitol in the oil-in water emulsion formulation is at a concentration of about 0.1% (w/v) and trehalose in the oil-in water emulsion formulation is at a concentration of about 5% (w/v).

5. The composition of claim 1, wherein the composition is formed by lyophilization of an oil-in water emulsion formulation, wherein the cake-forming excipient is a combination of mannitol and trehalose, and wherein the mannitol in the oil-in water emulsion formulation is at a concentration of about 2.5% (w/v) and trehalose in the oil-in water emulsion formulation is at a concentration of about 2.5% (w/v).

6. The composition of claim 1 wherein the composition is thermostable for at least 12 months.

7. The composition of claim 1 wherein the composition is thermostable at about 25° C. for at least 10 months.

8. The composition of claim 1 wherein the composition is thermostable at about 37° C. for at least 10 months.

9. The composition of claim 1 wherein the composition is thermostable at about 50° C. for at least 10 months.

10. The composition of claim 1 wherein the composition is in the form of an elegant cake.

11. The composition of claim 1 wherein the cake does not exhibit browning by visual inspection when stored at temperature between about 8° C. to about 60° C. for at least 1 month.

12. The composition of claim 1, wherein the thermostability of the composition is determined prior to reconstitution of the composition.

13. The composition of claim 12, wherein the cake does not exhibit shrinking, cracking and/or browning.

14. The composition of claim 1, wherein the thermostability is determined following reconstitution of the composition.

15. The composition of claim 14, wherein thermostability is determined by inspection of the oil-in-water emulsion formed upon reconstitution for creaming.

16. The composition of claim 1, wherein thermostability is determined by assay of the components of the oil-in-water emulsion formed upon reconstitution.

17. The composition of claim 1, wherein the oil-in-water emulsion formed upon reconstitution has a particle size with a Z-average diameter of less than about 200 nm.

18. The composition of claim 1, further comprising an antigen.

19. The composition of claim 18, wherein the antigen is a polypeptide, a nucleic acid encoding a polypeptide, or a pathogen.

20. The composition of claim 1, wherein the metabolizable oil is squalene, synthetic squalene, grape seed oil, olive oil, or a synthetic isoprenoid.

21. The composition of claim 1, wherein the TLR4 agonist is MPL, 3d-MPL, or synthetic GLA.

22. The composition of claim 21, wherein the synthetic GLA has the following structure:

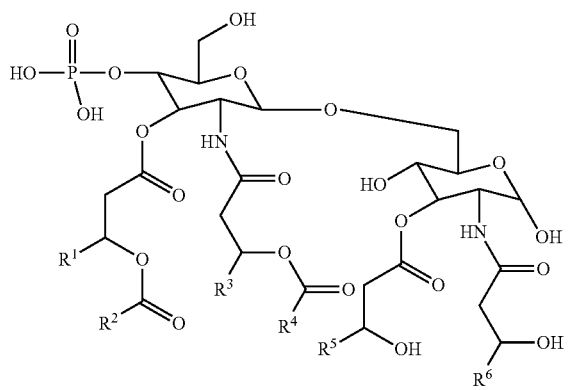

wherein $R^1$, $R^3$, $R^5$, and $R^6$ are $C_{11}$-$C_{20}$ alkyl; and $R^2$ and $R^4$ are $C_9$-$C_{20}$ alkyl.

23. The composition of claim 22, wherein $R^1$, $R^3$, $R^5$ and $R^6$ are $C_{11}$ alkyl; and $R^2$ and $R^4$ are $C_9$ alkyl.

24. The composition of claim 1, wherein the metabolizable oil is squalene, synthetic squalene, grape seed oil, olive oil or a synthetic isoprenoid.

25. The composition of claim 1, further comprising 1,2-dimyristoy 1-sn-glycero-3-phosphocholine (DMPC), 1-palmitoyl-2-oleoyl-sn-glycerol-3-phsphocholine (POPC), 1,2-dioleoyl-sn-glycero-3-phosphocholine (DOPC), egg phosphatidylcholine (PC), lecithin, a polysorbate surfactant, or a combination thereof.

26. The composition of claim 1, further comprising a surfactant.

27. The composition of claim 26, wherein the surfactant is poloxomer 188.

28. The composition of claim 1, further comprising an antioxidant.

29. The composition of claim 28, wherein the antioxidant is vitamin E.

30. A single vial comprising the thermostable lyophilized vaccine of claim 1, wherein the composition is contained in the vial.

31. A method of storing the thermostable lyophilized vaccine composition of claim 1 at between about 25° C. to about 60° C. for at least 10 months.

32. A method for generating the thermostable lyophilized vaccine composition of claim 1, comprising the step of lyophilizing an oil-in-water emulsion to form the thermostable lyophilized vaccine composition, wherein the oil-in-water emulsion prior to lyophilization comprises the metabolizable oil and the cake-forming excipient.

33. A method of stimulating an immune response in a subject comprising: (a) reconstituting the thermostable lyophilized vaccine composition of claim 1 into an oil-in-water emulsion, wherein the composition is in the form of a cake and (b) administering the emulsion to the subject, thereby stimulating an immune response in the subject.

34. The composition of claim 1, and wherein the adjuvant concentration in the oil-in-water emulsion formed upon reconstitution exhibits no more than about 25% breakdown of the adjuvant concentration in the oil-in-water emulsion formulation prior to lyophilization.

35. The composition of claim 18, wherein the antigen concentration in the oil-in-water emulsion formed upon reconstitution exhibits no more than about 25% breakdown of the antigen concentration in the oil-in-water emulsion formulation prior to lyophilization.

36. A thermostable lyophilized vaccine composition comprising:
- a metabolizable oil;
- a cake-forming excipient, wherein the cake-forming excipient is (1) a combination of mannitol trehalose or (2) trehalose; and
- an adjuvant, wherein the adjuvant is a TLR4 agonist,
- wherein the composition is formed by lyophilization of an oil-in-water emulsion formulation, does not comprise glycerol, does not contain liposomes, is in the form of a cake, forms an oil-in-water emulsion upon reconstitution, and is thermostable at a temperature of about 50° C. for at least 10 months.

37. The composition of claim 36, wherein the cake-forming excipient is trehalose which is at a concentration of about 10% (w/v) in the oil-in-water emulsion formulation.

38. The composition of claim 36, wherein the cake-forming excipient is trehalose which is at a concentration of about 5% (w/v) in the oil-in-water emulsion formulation.

39. The composition of claim 36, wherein the composition is formed by lyophilization of an oil-in water emulsion formulation, wherein the cake-forming excipient is a combination of mannitol and trehalose, wherein the mannitol in the oil-in water emulsion formulation is at a concentration of about 0.1% (w/v) and trehalose in the oil-in water emulsion formulation is at a concentration of about 5% (w/v).

40. The composition of claim 36, wherein the composition is formed by lyophilization of an oil-in water emulsion formulation, wherein the cake-forming excipient is a combination of mannitol and trehalose, and wherein the mannitol in the oil-in water emulsion formulation is at a concentration of about 2.5% (w/v) and trehalose in the oil-in water emulsion formulation is at a concentration of about 2.5% (w/v).

41. The composition of claim 36, wherein the cake does not exhibit browning by visual inspection after storage.

42. A thermostable lyophilized vaccine composition comprising:
- a metabolizable oil, wherein the metabolizable oil is squalene;
- 1,2-dimyristoyl-sn-glycero-3-phosphocholine (DMPC);
- a cake-forming excipient, wherein the cake-forming excipient is (1) a combination of mannitol and trehalose or (2) trehalose; and
- an adjuvant, wherein the adjuvant is glucopyranosyl lipid adjuvant (GLA),
- wherein the composition is in the form of a cake, is formed by lyophilization of an oil-in-water emulsion formulation, and the oil-in-water emulsion formulation does not comprise glycerol, wherein the composition is thermostable at a temperature between 8° C. to 60° C. for at least 10 months.

43. The composition of claim 42, wherein the composition is thermostable at a temperature of about 50° C. for at least 10 months.

44. The composition of claim 42, wherein the cake-forming excipient comprises at least about 5% (w/v) trehalose.

* * * * *

UNITED STATES PATENT AND TRADEMARK OFFICE
CERTIFICATE OF CORRECTION

| | | |
|---|---|---|
| PATENT NO. | : 11,801,223 B2 | Page 1 of 1 |
| APPLICATION NO. | : 15/108773 | |
| DATED | : October 31, 2023 | |
| INVENTOR(S) | : Christopher B. Fox et al. | |

It is certified that error appears in the above-identified patent and that said Letters Patent is hereby corrected as shown below:

In the Specification

Column 1 Line 12 insert:
--STATEMENT OF GOVERNMENT INTEREST
This invention was made with government support under HHSN272200800045C awarded by the National Institute of Health. The government has certain rights in the invention.--

Signed and Sealed this
Twenty-seventh Day of May, 2025

Coke Morgan Stewart
*Acting Director of the United States Patent and Trademark Office*